US011547765B2

(12) United States Patent
Xiao et al.

(10) Patent No.: US 11,547,765 B2
(45) Date of Patent: Jan. 10, 2023

(54) OPTIMIZED MINI-DYSTROPHIN GENES AND EXPRESSION CASSETTES AND THEIR USE

(71) Applicants: The University of North Carolina at Chapel Hill, Chapel Hill, NC (US); Bamboo Therapeutics, Inc., Chapel Hill, NC (US)

(72) Inventors: Xiao Xiao, Chapel Hill, NC (US); Juan Li, Chapel Hill, NC (US); Chunping Qiao, Chapel Hill, NC (US); Scott W. J. McPhee, Chapel Hill, NC (US); Richard J. Samulski, Hillsborough, NC (US); Maritza McIntyre, Rockville, MD (US)

(73) Assignees: The University of North Carolina at Chapel Hill, Chapel Hill, NC (US); Bamboo Therapeutics, Inc., Chapel Hill, NC (US)

(*) Notice: Subject to any disclaimer, the term of this patent is extended or adjusted under 35 U.S.C. 154(b) by 0 days.

(21) Appl. No.: 16/787,938

(22) Filed: Feb. 11, 2020

(65) Prior Publication Data

US 2020/0376141 A1 Dec. 3, 2020

Related U.S. Application Data

(63) Continuation of application No. 15/628,268, filed on Jun. 20, 2017, now abandoned.

(60) Provisional application No. 62/352,675, filed on Jun. 21, 2016, provisional application No. 62/516,449, filed on Jun. 7, 2017.

(51) Int. Cl.

| | |
|---|---|
| ***A61K 48/00*** | (2006.01) |
| ***C07K 14/47*** | (2006.01) |
| ***A61K 38/17*** | (2006.01) |
| ***A61K 45/06*** | (2006.01) |
| ***C07K 14/78*** | (2006.01) |
| ***C12N 15/86*** | (2006.01) |

(52) U.S. Cl.

CPC ...... *A61K 48/0058* (2013.01); *A61K 38/1709* (2013.01); *A61K 45/06* (2013.01); *C07K 14/4708* (2013.01); *C07K 14/78* (2013.01); *C12N 15/86* (2013.01); *A01K 2217/075* (2013.01); *A01K 2227/10* (2013.01); *A01K 2227/105* (2013.01); *A01K 2267/0306* (2013.01); *C12N 2750/14143* (2013.01); *C12N 2800/22* (2013.01); *C12N 2830/008* (2013.01)

(58) Field of Classification Search

CPC ................ A61K 48/0058; A61K 45/06; A61K 38/1709; C12N 15/86; C12N 2830/008; C12N 2800/22; C12N 2750/14143; A01K 2227/10; A01K 2217/075

See application file for complete search history.

(56) References Cited

U.S. PATENT DOCUMENTS

| | | | |
|---|---|---|---|
| 6,057,158 | A | 5/2000 | Chamberlain et al. |
| 6,063,622 | A | 5/2000 | Chamberlain et al. |
| 6,083,750 | A | 7/2000 | Chamberlain et al. |
| 6,812,339 | B1 | 11/2004 | Venter et al. |
| 7,001,761 | B2 | 2/2006 | Xiao |
| 7,112,668 | B2 | 9/2006 | Rastelli et al. |
| 7,172,893 | B2 | 2/2007 | Rabinowitz et al. |
| 7,510,867 | B2 | 3/2009 | Xiao |
| 7,745,391 | B2 | 6/2010 | Mintz et al. |
| 7,771,993 | B2 | 8/2010 | Stedman et al. |
| 7,906,111 | B2 | 3/2011 | Wilson et al. |
| 8,586,006 | B2 | 11/2013 | Hood et al. |
| 9,061,059 | B2 | 6/2015 | Chakraborty et al. |
| 9,089,604 | B2 | 7/2015 | Chakraborty et al. |
| 9,220,755 | B2 | 12/2015 | Chakraborty et al. |
| 2006/0073586 | A1 | 4/2006 | Xiao |
| 2009/0004743 | A1 | 1/2009 | Ferrari et al. |
| 2009/0181380 | A1 | 7/2009 | Belouchi et al. |
| 2010/0120628 | A1 | 5/2010 | Belouchi et al. |
| 2010/0144538 | A1 | 6/2010 | Belouchi et al. |
| 2011/0097761 | A1 | 4/2011 | Chamberlain et al. |
| 2011/0183924 | A1 | 7/2011 | Mintz et al. |
| 2013/0136729 | A1 | 5/2013 | French et al. |
| 2014/0010861 | A1 | 1/2014 | Bancel et al. |
| 2014/0171485 | A1 | 6/2014 | Bancel et al. |
| 2014/0200264 | A1 | 7/2014 | Bancel et al. |
| 2014/0206755 | A1 | 7/2014 | Bancel et al. |
| 2014/0234255 | A1 | 8/2014 | Lai et al. |
| 2014/0255467 | A1 | 9/2014 | Bancel et al. |
| 2014/0255468 | A1 | 9/2014 | Bancel et al. |
| 2014/0303093 | A1 | 10/2014 | Ervasti et al. |
| 2015/0044277 | A1 | 2/2015 | Bancel et al. |

(Continued)

FOREIGN PATENT DOCUMENTS

| | | |
|---|---|---|
| EP | 1716227 | 11/2006 |
| EP | 1303617 | 9/2007 |

(Continued)

OTHER PUBLICATIONS

"Office Action corresponding to Indonesian Application No. PID201900102 dated Nov. 25, 2020."

"Office Action corresponding to Russian Application No. 2019101208 dated Nov. 6, 2020".

Arnau, Jose , et al., "Reprint of: Current strategies for the use of affinity tags and tag removal for the purification of recombinant proteins", Protein Expression and Purification 48:1-13 (2005).

Berry, Marla J., et al., "Substitution of Cysteine for Selenocysteine in Type I Iodothyronine Deiodinase Reduces the Catalytic Efficiency of the Protein but Enhances its Translation", Endocrinology 131(4),1848-1852 (1992).

(Continued)

*Primary Examiner* — Olga N Chernyshev

(74) *Attorney, Agent, or Firm* — Myers Bigel, P.A.

(57) ABSTRACT

This invention relates to polynucleotides encoding mini-dystrophin proteins, viral vectors comprising the same, and methods of using the same for delivery of mini-dystrophin to a cell or a subject.

46 Claims, 66 Drawing Sheets

Specification includes a Sequence Listing.

(56) References Cited

U.S. PATENT DOCUMENTS

| | | | | |
|---|---|---|---|---|
| 2015/0246950 | A1 | 9/2015 | Acharjee | |
| 2017/0368198 | A1* | 12/2017 | Xiao .................. | A61K 38/1709 |
| 2018/0148488 | A1 | 5/2018 | Chamberlain et al. | |

FOREIGN PATENT DOCUMENTS

| | | |
|---|---|---|
| EP | 1366160 | 7/2008 |
| EP | 1287125 | 7/2009 |
| EP | 1668143 | 3/2013 |
| JP | 11318467 | 11/1999 |
| JP | 2019525740 A | 9/2019 |
| WO | 2000/28004 | 5/2000 |
| WO | 2001/83695 | 11/2001 |
| WO | 2002/06495 | 1/2002 |
| WO | 2002/29056 | 4/2002 |
| WO | 2002/081517 | 10/2002 |
| WO | 2005/071059 | 8/2005 |
| WO | 2008/088895 | 7/2008 |
| WO | 2013/151665 | 10/2013 |
| WO | 2015/197232 | 12/2015 |
| WO | 2015/197869 | 12/2015 |

OTHER PUBLICATIONS

Burns, William R., et al., "A high molecular weight-melanoma associated antigen-specific chimeric antigen receptor redirects lymphocytes to target human melanomas", Cancer Res. 70(8):3027-3033 (Apr. 15, 2010).

Richman, Sarah A., et al., "High-Affinity GD2-specific CAR T Cells Induce Fatal Encephalitis in a Preclinical Neuroblastoma Model", Cancer Immunol. Res. 6(1):36-46 (Jan. 2018).

Duan "Systemic AAV micro-dystrophin gene therapy for Duchenne muscular dystrophy", Molecular Therapy 26(10):2337-2356 (2018).

"Precision Genetic Medicine for Neuromuscular Diseases: 23rd International Congress of the World Muscle Society", Sarepta Therapeutics (2018) (27 pages).

"Translarna: Assessment report for initial marketing authorization application", European Medicines Agency: Science Medicines Health (2014) (106 pages).

"Translarna: Summary of Product Characteristics", European Medicines Agency (39 pages) (2014).

Aatsma-Rus et al. "Circulating Biomarkers for Duchenne Muscular Dystrophy", Journal of Neuromuscular Diseases 2:S49-S58 (2015).

Anderson et al. "Deflazacort But Not Prednisone Improves Both Muscle Repair and Fiber Growth in Diaphragm and Limb Muscle in Vivo in the MDX Dystrophic Mouse", Muscle & Nerve 19:1576-1585 (1996).

Anonymous: "The DMD mutations database The dystrophin gene", Dec. 24, 2015 (Dec. 24, 2015), XP055401365, Retrieved from the Internet: URL:https://web.archive.org/web/20151224134431/http://www.umd.be/DMD/W_DMD/gene.html (16 pages).

Athanasopoulos et al. "Codon Optimization of the Microdystrophin Gene for Duchene Muscular Dystrophy Gene Therapy", Duan (ed.), Muscle Gene Therapy: Methods and Protocols, Methods in Molecular Biology, vol. 709:21-37 (2011).

Beenakker et al. "Functional ability and muscle force in healthy children and ambulant Duchenne muscular dystrophy patients", European Journal of Paediatric Neurology 9:387-393 (2005).

Bello et al. "DMD genotypes and loss of ambulation in the CINRG Duchenne Natural History Study", Neurology 87:401-409 (2016).

Bhanu Munil Koppanati "In Utero Delivery of AAV Vectors for Efficient Treatment of Muscle Disorders", Doctoral Thesis, University of Pittsburgh (2009) (138 pages).

Bhasin et al. "Molecular Extensibility of Mini-dystrophins and a Dystrophin Rod Construct", J. Mol. Biol. 352:795-806 (2005).

Bowies et al. "Phase 1 Gene Therapy for Duchenne Muscular Dystrophy Using a Translational Optimized AAV Vector", Molecular Therapy 20(2):443-455 (2012).

Bushby et al. "Ataluren Treatment of Patients With Nonsense Mutation Dystrophinopathy", Muscle Nerve 50:477-487 (2014).

Bushby et al. "Diagnosis and management of Duchenne muscular dystrophy, part 1: diagnosis, and pharmacological and psychosocial management", Lancet Neurol 9:77-93 (2010).

Campbell et al. "Myostatin inhibitor in DMD", Muscle & Nerve pp. 1-20, 41-42 (22 pages) (2016).

Cao et al. "Persistent Dystrophin Expression in the Skeletal Muscle of mdx Mice by Using a Tissue Specific Promoter", 53rd Annual Meeting of the Orthopaedic Research Society Poster No. 0424 (1 page) (2007).

Chen et al. "Functional Impairment of Circulating Angiogenic Cells for Treatment of Myocardial Infarction Is Differentially Driven by Both Advanced Age and Coronary Artery Disease, and Is Improved or Further Impaired by Modulating Nitric Oxide Synthase Expression", Molecular Therapy 21(1):S142 (2013).

Choi et al. "Optimization of AAV expression cassettes to improve packaging capacity and transgene expression in neurons", Molecular Brain 7:17 (2014) (10 pages).

Cirak at al. "Exon skipping and dystrophin restoration in patients with Duchenne muscular dystrophy after systemic phosphorodiamidate morpholino oligomer treatment: an open-label, phase 2, dose-escalation study", Lancet 378:595-605 (2011).

Dayton et al. "The advent of AAV9 expands applications for brain and spinal cord gene delivery", Expert Opin Biol Ther. 12(6):757-766 (2012).

Duan "Muscle Gene Therapy: Methods and Protocols", Methods in Molecular Biology 709 (382 pages) (2011).

Finkel et al. "Phase 2a Study of Ataluren-Mediated Dystrophin Production in Patients with Nonsense Mutation Duchenne Muscular Dystrophy", PLOS One 8(12):e81302 (2013).

Gao et al. "Clades of Adeno-Associated Viruses Are Widely Disseminated in Human Tissues", Journal of Virology 78(12):6381-5388 (2004).

GenBanK Accession No. NM_004006.1, *Homo sapiens* dystrophin, Jun. 10, 1999 (10 pages).

Gray et al. "Production of Recombinant Adeno-Associated Viral Vectors and Use in In Vitro and In Vivo Administration", Curr Protoc Neurosci. Oct. 2011 ; Chapter: Unit4.17. doi:10.1002/0471142301.ns0417s57 (36 pages).

Griggs et al. "Prednisone in Duchenne Dystrophy", Arch Neurol 48:383-388 (1991).

Guiraud et al. "Pharmacological advances for treatment in Duchenne muscular dystrophy", Current Opinion in Pharmacology 34:36-48 (2017).

Harper et al. "Modular flexibility of dystrophin: Implications for gene therapy of Duchenne muscular dystrophy", Nature Medicine 8(3):253-261 (2002).

Hauser at al. "Analysis of Muscle Creatine Kinase Regulatory Elements in Recombinant Adenoviral Vectors", Molecular Therapy 2(1):16-25 (2000).

Henricson et al. "The 6-Minute Walk Test and Person-Reported Outcomes in Boys with Duchenne Muscular Dystrophy and Typically Developing Controls:Longitudinal Comparisons and Clinically-Meaningful Changes Over One Year", PLOS Currents Muscular Dystrophy Jul. 8, 2013 . Edition 1. doi:10.1371/currents.md.9e17658b007eb79fcd6f723089f79e06.

Highlights of Prescribing Information Emflaza™ (deflazacort) tablets, for oral use Emflaza™ (deflazacort) oral suspension Initial U.S. Approval: 2017.

Highlights of Prescribing Information: Dosage Forms and Strengths Exondys 51® safely and effectively. Exondys 51 (eteplirsen) injection, for intravenous use initial U.S. Approval: 2016.

Huchet et al. "Exhaustive characterizatIon of the newly developed Duchenne muscular dystrophy rat model: a unique animal model for DMD which mimics the human disease at both the muscular and the cardiac levels", Abstracts 2017/Neuromuscular Disorders 27:S247 (2017).

International Preliminary Report on Patentability corresponding to International Application No. PCT/IB2017/053656 dated Jan. 3, 2019.

International Search Report corresponding to International Application No. PCT/IB2017/053656 dated Sep. 29, 2017.

Jaynes et al. "The Muscle Creatine Kinase Gene Is Regulated by Multiple Upstream Elements, Including a Muscle-Specific Enhancer", Molecular and Cellular Biology 8(1):62-70 (1988).

(56) References Cited

OTHER PUBLICATIONS

Kinalt et al. "Local restoration of dystrophin expression with the morpholino oligomer AVI-4658 in Duchenne muscular dystrophy: a single-blind, placebo-controlled; dose-escalation, proof-of-concept study", Lancet Neurol 8:918-928 (2009).
Koenig et al. "Detailed Analysis of the Repeat Domain of Dystrophin Reveals Four Potential Hinge Segments That May Confer Flexibility", The Journal of Biological Chemistry 265(8):4560-4566 (1990).
Koenig et al. "The Complete Sequence of Dystroprin Predicts a Rod-Shaped Cytoskeletal Protein", Cell. 63:219-228 (1988).
Kornegay et al. "Pharmacologic Management of Duchenne Muscular Dystrophy: Target Identification and Preclinical Trials", ILAR Journal 55(1):119-149 (2014).
Kornegay et al. "Widespread Muscle Espression of an AAV9 Human Mini-dystrophin Vector After Intravenous Injection in Neonatal Dystrophin-deficient Dogs", Molecular Therapy 18(8):1501-1508 (2010).
Larcher et al. "Characterization of Dystrophin Deficient Rats: A New Model for Duchenne Muscular Dystrophy", PLOS One 9(10)e110371 (2014) (13 pages).
Larkindale et al. "Duchenne Regulatory Science Consortium Meeting on Disease Progression Modeling for Duchenne Muscular Dystrophy", PLOS Currents Muscular Dystrophy Jan. 12, 2017 . Edition 1. doi: 10.1371/currents.md.83071bbd728982f2f1073f4950e03586 (11 pages).
Le Guiner et al. "Long term miorodystrophin gene therapy is effective in a canine model of Duchenne muscular dystrophy", Nature Communications | 8:16105 | DOI: 10.1038/ncomms16105 |www.nature.com/naturecommunications (15 pages) (2017).
Li et al. "Hydrodynamic Limb Vein Injection of AAV9 Results in Regional and Systemic Long-Term Expression of Minidystrophin in Young Adult GRMD Dogs", Molecular Therapy 17(1):S278 (2009).
Lu et al. "Strength and Functional Measurement for Patients with Muscular Dystropy", Muscular Dystrophy Chp. 17 pp. 321-330 (2012).
Mann et al. "Antisense-induced exon skipping and synthesis of dystrophin in the mdx mouse", PNAS 98(1):42-47 (2001).
Manning et al. "What has the mdx mouse model of duchenne muscular dystrophy contributed to our understanding of this disease?", J Muscle Res Cell Motil 36:155-167 (2015).
McCourt et al. "In vitro stability of therapeutically relevant, internally truncated dystrophins", Skeletal Muscle (2015) (11 pages).
McDonald et al. "The 6-Minute Walk Test and Other Endpoints in Duchenne Muscular Dystrophy: Longitudinal Natural History Observations Over 48 Weeks From a Multicenter Study", Muscle Nerve 48:343-356 (2013).
McDonald et al. "The 6-Minute Walk Test as a New Outcome Measure in Duchenne Muscular Dystrophy", Muscle Nerve 41:500-510 (2010).
Mendell "Safety Study of Mini-dystrophin Gene to Treat Duchenne Muscular Dystrophy", ClinicalTrials.gov NCT00428935, dated Feb. 5, 2013, (5 pages).
Mendell et al. "Dystrophin Immunity in Duchenne's Muscular Dystrophy", N Engl J Med 363:1429-1437 (2010).
Mendell at al. "Gene therapy for muscular dystrophy: Lessons learned and path forward", Neuroscience Letters 527:90-99 (2012).
Mendell at al. "Longitudinal Effect of Eteplirsen versus Historical Control on Ambulation in Duchenne Muscular Dystrophy", Ann Neurol 79:257-271 (2016).
Morris et al. "An Epitope Structure for the C-Terminal Domain of Dystrophin and Utrophin", Biochemistry 37:11117-11127 (1998).
Nadarajah et al. "Serum matrix metalloproteinase-9 (MMP-9) as a biomarker for monitoring disease progression in Duchenne muscular dystrophy (DMD)", Neuromuscular Disorders 21:569-578 (2011).
Nakamura et al. "Mammalian Models of Duchenne Muscular Dystrophy: Pathological Characteristics and Therapeutic Applications", Journal of Biomedicine and Biotechnology vol. 2011 (8 pages) (2011).
Nguyen et al. "DOT1L regulates dystrophin expression and is critical for cardiac function", Genes & Development 25:263-274 (2011).
Office Action corresponding to Taiwanese Application No. 106120618 dated Oct. 7, 2019.
Ogura et al. "Therapeutic potential of matrix metalloproteinases in Duchenne muscular dystrophy", Frontiers in Cell and Developmental Biology 2(11):1-11 (2014).
Peltz et al. "Ataluren as an agent for therapeutic nonsense supression", Annu Rev Med. 64:407-425 (2013).
Petkova et al. "In vivo analysis of dystrophin (re-) expression in DmdEGFP and DmdEGFP-mdx reporter mice", Abstracts 2017/ Neuromuscular Disorders 27:S186 (2017).
Porrua et al. "Transcription Termination: Variations on Common Themes", Trends in Genetics 32(8):508-522 (2016).
Proudfoot "Ending the message: poly(A) signals then and now", Genes & Development 25:1770-1782 (2011).
Qiao et al. "Spliceosome-Mediated RNA Trans-Splicing for Muscular Dystrophies", Molecular Therapy 15(1):S55 (2007).
Reay et al. "Effect of Nuclear Factor ?B Inhibition on Serotype 9 Adeno-Associated Viral (AAV9) Minidystrophin Gene Transfer to the mdx Mouse", Mol Med 18:466-476 (2012).
Rodrigues et al. "Current Translational Research and Murine Models For Duchenne Muscular Dystrophy", Journal of Neuromuscular Diseases 3:29-48 (2016).
Salva et al. "Design of Tissue-specific Regulatory Cassettes for High-level rAAV-mediated Expression in Skeletal and Cardiac Muscle", Molecular Therapy 15(2):320-329 (2007).
Shield et al. "E-Box Sites and a Proximal Regulatory Region of the Muscle Creatine Kinase Gene Differentially Regulate Expression in Diverse Skeletal Muscles and Cardiac Muscle of Transgenic Mice", Molecular and Cellular Biology 16(9):5058-5068 (1996).
Sternberg et al. "Identification of Upstream Intragenic Regulatory Elements That Confer Cell-Type-Restricted and Differentiation-Specific Expression on the Muscle Creatine Kinase Gene", Molecular and Cellular Biology 8(7):2896-2909 (1988).
Tang et al. "AAV-directed muscular dystrophy gene therapy", Expert Opin. Biol. Ther. 10(3):395-408 (2010).
Tang et al. "Gene Therapy Combined with NF-kappaB lnhibition for Duchenne Muscular Dystrophy ", University of Pittsburgh (3 pages) ORS 2013 Annual Meeting, Poster No. 0626.
Trollet et al. "Gene therapy for muscular dystrophy: current progress and future prospects", Expert Opin. Biol. Ther. 9(7):849-866 (2009).
Uniprot Accession No. GB5B864. naked mole rat dystrophin, Dec. 14, 2011 (2 pages).
Uniprot Accession No. P11532, human dystrophin, Oct. 1, 1989 (2 pages).
Wang et al. "A canine minidystrophin is functional and therapeutic in mdx mice", Gene Therapy 15:1099-1106 (2008).
Wang et al. "Adeno-associated virus vector carrying human minidystrophin genes effectively ameliorates muscular dystrophy in mdx mouse model", PNAS 97(25):13714-13719 (2000).
Wang et al. "Construction and analysis of compact muscle-specific promoters for AAV vectors", Gene Therapy 15:1489-1499 (2008).
Wang et al. "Systemic Human Minidystrophin Gene Transfer Improves Functions and Life Span of Dystrophin and Dystrophin/Utrophin-Deficient Mice", J Orthop Res 27:421-426 (2009).
Watchko et al. "Adeno-Associated Virus Vector-Mediated in dystrophin Gene Therapy Improves Dystrophic Muscle Contractile Function in mdx Mice", Human Gene Therapy 13:1451-1460 (2002).
Wells "Tracking progress: an update on animal models for Duchenne muscular dystrophy", The Company of Biologists Ltd: Disease Models & Mechanisms 11:1-3 (2018).
Werling et al. "Systematic Comparison and Validation of Quantitative Real-Time PCR Methods for the Quantitation of Adeno-Associated Viral Products", Human Gene Therapy Methods 25:82-92 (2015).
Willcocks et al. "Multicenter Prospective Longitudinal Study of Magnetic Resonance Biomarkers in a Large Duchenne Muscular Dystroplhy Cohort", Ann Neurol 79-535-547 (2016).
Willmann et al. "Mammalian animal models for Duchenne muscular dystrophy", Neuromuscular Disorders 19:241-249 (2009).

(56) References Cited

OTHER PUBLICATIONS

Wright et al. "Consider Muscle Disease in Children with Elevated Transaminase",J Am Board Fam Med 25:536-540 (2012).
Written Opinion of the International Searching Authority corresponding to International Application No. PCT/IB2017/053656 dated Sep. 29, 2017.
Xiao et al., Production Production of High-Titer Recombinant Adena-Associated Virus Vectors in the Absence of Helper Adenovirus, (Mar. 1998), Journal of Virology 72(3) :2224-2232.
Yuasa et al. "Injection of a recombinant AAV serotype 2 into canine skeletal muscles evokes strong immune responses against transgene products", Gene Therapy 14:1249-1260 (2007).
Yue et al. "Safe and bodywide muscle transduction in young adult Duchenne muscular dystrophy dogs with adeno-associated virus", Human Molecular Genetics 24(20):5880-5890 (2015).
Zhang et al., Novel Mini-Dystrophin Gene Dual Adena-Associated Virus Vectors Restore Neuronal Nitric Oxide Synthase Expression at the Sarcolemma, (Jan. 2012), Human Gene Therapy 23:98-103.
Zhu et al. "Serum Enzyme Profiles Differentiate Five Types of Muscular Dystrophy", Hindawi Publishing Corporation: Disease Markers vol. 2015 (7 pages).
"Office Action corresponding to Colombian Application No. NC2019/0000395 dated Jun. 28, 2021".
"Office Action corresponding to Indonesian Application No. PID201900102 dated Jun. 22, 2021".
"Examination Report corresponding to Australian Application No. 2017281983 dated Apr. 8, 2021".
"Office Action corresponding to Japanese Application No. 2020-187024 dated Oct. 11, 2021".
"Office Action corresponding to Argentinian Application No. 20170101711 dated Nov. 11, 2021".
"Office Action corresponding to Chinese Application No. 201780050809.7 dated Oct. 22, 2021".
"Office Action corresponding to Colombian Application No. NC2019/0000395 dated Nov. 25, 2021".
"Office Action corresponding to Saudi Arabian Application No. 518400823 dated Mar. 10, 2022".
"Office Action corresponding to Israeli Application No. 263,199 dated Mar. 26, 2022".
"Office Action corresponding to Australian Application No. 2017281983 dated Apr. 4, 2022".
"Office Action corresponding to Japanese Application No. 2020-187024 dated Jul. 12, 2022".
"Office Action corresponding to Mexican Application No. MX/a/2018/015921 dated Mar. 16, 2022".
Hu, Peiqi, et al., "Prevention of Skeletal and Cardiac Dysfunction in Dystrophin/Utrophin Double KO Mice by Systemic Delivery of AAV9-Minidystrophin", Molecular Therapy 17(Supplement 1):S362 (May 2009).
Kang, Robert, et al., "A Novel AAV Vector-based Combinatorial Gene Therapy Ameliorates Spine Abnormalities in a Severe DMD Murine Model", ORS 2015 Annual Meeting Poster No. 1573 (4 pages).
Li, Juan, et al., "Long-Term (2-8 years) Body-Wide Expression of AAV9-Minidystrophin Gene in Golden Retriever Muscular Dystrophy Dogs After Regional Limb Vein Injection", Molecular Therapy 24(Supplement 1):S284 (May 2016) 1 page.
Li, Juan, et al., "Efficient Long-Term Bodywide Expression of an AAV9-Minidystraphin in the Muscle and Heart of Young Adult GRMD Dogs after Intravascular Injection without Immune Suppression", Molecular Therapy 19 (Supplement 1):S21 (May 2011) 1 page.
Li, Juan, et al., "Muscle Force Improvement by Long-Term Systemic Expression of an AAV9 Minidystrophin after Delivery in Young Adult GRMD Dogs without Immune Suppression", Molecular Therapy 20(Supplement 1):S69 (May 2012) 1 page.
Qiao, Chunping, et al., "Dobutamine Stress Enhances Echocardiography Detection in mdx Mouse Heart and Reveals Therapeutic Benefits by Minidystrophin Gene Therapy", Molecular Therapy 21 (Supplement 1):S142 (May 2013)1 page.
Tang, Ying, et al., "Gene Therapy Combined with NF-kappaB Inhibition for Duchenne Muscular Dystrophy", Molecular Therapy 21 (Supplement 1):S111 (May 2013) 1 page.
Yuan, Zhenhua, et al., "A Versatile Adeno-Associated Virus Vector Producer Cell Line Method for Scalable Vector Production of Different Serotypes", Human Gene Therapy 22:613-624 (May 2011).
"Office Action corresponding to Korean Application No. 10-2018-7037062 dated Sep. 5, 2022".
"Office Action corresponding to Brazilian Application No. 112018076394-2 dated Nov. 16, 2022".
"Office Action corresponding to Saudia Arabian Application No. 518400623 dated Oct. 27, 2022".

* cited by examiner

H&E STAINING OF CRYOSECTIONS (8μm) OF TIBIALIS ANTERIOR MUSCLES, 10X MAGNIFICATION.

LEFT HINDLIMB (NON-INJECTED SIDE) CRANIAL SARTORIUS MUSCLE

NORMAL DOG | DMD DOG | DMD DOG + MINIDYS

NORMAL DOG | DMD DOG | DMD DOG + MINIDYS

```
                        1                                                           60
Δ3990          (1)  MVWWEEVEDCYEREDVQKKTFTKWVNAQFSKFGKQHIENLFSDLQDGRRLLDLLEGLTGQ
Dys3978        (1)  MLWWEEVEDCYEREDVQKKTFTKWVNAQFSKFGKQHIENLFSDLQDGRRLLDLLEGLTGQ
                    61                                                         120
Δ3990         (61)  KLPKEKGSTRVHALNNVNKALRVLQNNNVDLVNIGSTDIVDGNHKLTLGLIWNIILHWQV
Dys3978       (61)  KLPKEKGSTRVHALNNVNKALRVLQNNNVDLVNIGSTDIVDGNHKLTLGLIWNIILHWQV
                    121                                                        180
Δ3990        (121)  KNVMKNIMAGLQQTNSEKILLSWVRQSTRNYPQVNVINFTTSWSDGLALNALIHSHRPDL
Dys3978      (121)  KNVMKNIMAGLQQTNSEKILLSWVRQSTRNYPQVNVINFTTSWSDGLALNALIHSHRPDL
                    181                                                        240
Δ3990        (181)  FDWNSVVCQQSATQRLEHAFNIARYQLGIEKLLDPEDVDTTYPDKKSILMYITSLFQVLP
Dys3978      (181)  FDWNSVVCQQSATQRLEHAFNIARYQLGIEKLLDPEDVDTTYPDKKSILMYITSLFQVLP
                    241                                                        300
Δ3990        (241)  QQVSIEAIQEVEMLPRPPKVTKEEHFQLHHQMHYSQQITVSLAQGYERTSSPKPRFKSYA
Dys3978      (241)  QQVSIEAIQEVEMLPRPPKVTKEEHFQLHHQMHYSQQITVSLAQGYERTSSPKPRFKSYA
                    301                                                        360
Δ3990        (301)  YTQAAYVTTSDPTRSPFPSQHLEAPEDKSFGSSLMESEVNLDRYQTALEEVLSWLLSAED
Dys3978      (301)  YTQAAYVTTSDPTRSPFPSQHLEAPEDKSFGSSLMESEVNLDRYQTALEEVLSWLLSAED
                    361                                                        420
Δ3990        (361)  TLQAQGEISNDVEVVKDQFHTHEGYMMDLTAHQGRVGNILQLGSKLIGTGKLSEDEETEV
Dys3978      (361)  TLQAQGEISNDVEVVKDQFHTHEGYMMDLTAHQGRVGNILQLGSKLIGTGKLSEDEETEV
                    421                                                        480
Δ3990        (421)  QEQMNLLNSRWECLRVASMEKQSNLHRVLMDLQNQKLKELNDWLTKTEERTRKMEEEPLG
Dys3978      (421)  QEQMNLLNSRWECLRVASMEKQSNLHRVLMDLQNQKLKELNDWLTKTEERTRKMEEEPLG
```

FIG. 55A

```
                  481                                                          540
Δ3990     (481) PDLEDLKRQVQQHKVLQEDLEQEQVRVNSLTHMVVVVDESSGDHATAALEEQLKVLGDRW
Dys3978   (481) PDLEDLKRQVQQHKVLQEDLEQEQVRVNSLTHMVVVVDESSGDHATAALEEQLKVLGDRW
                  541                                                          600
Δ3990     (541) ANICRWTEDRWVLLQDQPDLAPGLTTIGASPTQTVTLVTQPVVTKETAISKLEMPSSLML
Dys3978   (541) ANICRWTEDRWVLLQDQPDLAPGLTTIGASPTQTVTLVTQPVVTKETAISKLEMPSSLML
                  601                                                          660
Δ3990     (601) EVPTHRLLQQFPLDLEKFLAWLTEAETTANVLQDATRKERLLEDSKGVKELMKQWQDLQG
Dys3978   (601) EVPTHRLLQQFPLDLEKFLAWLTEAETTANVLQDATRKERLLEDSKGVKELMKQWQDLQG
                  661                                                          720
Δ3990     (661) EIEAHTDVYHNLDENSQKILRSLEGSDDAVLLQRRLDNMNFKWSELRKKSLNIRSHLEAS
Dys3978   (661) EIEAHTDVYHNLDENSQKILRSLEGSDDAVLLQRRLDNMNFKWSELRKKSLNIRSHLEAS
                  721                                                          780
Δ3990     (721) SDQWKRLHLSLQELLVWLQLKDDELSRQAPIGGDFPAVQKQNDVHRAFKRELKTKEPVIM
Dys3978   (721) SDQWKRLHLSLQELLVWLQLKDDELSRQAPIGGDFPAVQKQNDVHRAFKRELKTKEPVIM
                  781                                                          840
Δ3990     (781) STLETVRIFLTEQPLEGLEKLYQEPRELPPEERAQNVTRLLRKQAEEVNTEWEKLNLHSA
Dys3978   (781) STLETVRIFLTEQPLEGLEKLYQEPRELPPEERAQNVTRLLRKQAEEVNTEWEKLNLHSA
                  841                                                          900
Δ3990     (841) DWQRKIDETLERLQELQEATDELDLKLRQAEVIKGSWQPVGDLLIDSLQDHLEKVKALRG
Dys3978   (841) DWQRKIDETLERLQELQEATDELDLKLRQAEVIKGSWQPVGDLLIDSLQDHLEKVKALRG
                  901                                                          960
Δ3990     (901) EIAPLKENVSHVNDLARQLTTLGIQLSPYNLSTLEDLNTRWKLLQVAVEDRVRQLHEAHR
Dys3978   (901) EIAPLKENVSHVNDLARQLTTLGIQLSPYNLSTLEDLNTRWKLLQVAVEDRVRQLHEAHR
```

FIG. 55B

```
                   961                                                          1020
Δ3990      (961)   DFGPASQHFLSTSVQGPWERAISPNKVPYYINHETQTTCWDHPKMTELYQSLADLNNVRF
Dys3978    (961)   DFGPASQHFLSTSVQGPWERAISPNKVPYYINHETQTTCWDHPKMTELYQSLADLNNVRF
                   1021                                                         1080
Δ3990     (1021)   SAYRTAMKLRRLQKALCLDLLSLSAACDALDQHNLKQNDQPMDILQIINCLTTIYDRLEQ
Dys3978   (1021)   SAYRTAMKLRRLQKALCLDLLSLSAACDALDQHNLKQNDQPMDILQIINCLTTIYDRLEQ
                   1081                                                         1140
Δ3990     (1081)   EHNNLVNVPLCVDMCLNWLLNVYDTGRTGRIRVLSFKTGIISLCKAHLEDKYRYLFKQVA
Dys3978   (1081)   EHNNLVNVPLCVDMCLNWLLNVYDTGRTGRIRVLSFKTGIISLCKAHLEDKYRYLFKQVA
                   1141                                                         1200
Δ3990     (1141)   SSTGFCDQRRLGLLLHDSIQIPRQLGEVASFGGSNIEPSVRSCFQFANNKPEIEAALFLD
Dys3978   (1141)   SSTGFCDQRRLGLLLHDSIQIPRQLGEVASFGGSNIEPSVRSCFQFANNKPEIEAALFLD
                   1201                                                         1260
Δ3990     (1201)   WMRLEPQSMVWLPVLHRVAAAETAKHQAKCNICKECPIIGFRYRSLKHFNYDICQSCFFS
Dys3978   (1201)   WMRLEPQSMVWLPVLHRVAAAETAKHQAKCNICKECPIIGFRYRSLKHFNYDICQSCFFS
                   1261                                                         1320
Δ3990     (1261)   GRVAKGHKMHYPMVEYCTPTTSGEDVRDFAKVLKNKFRTKRYFAKHPRMGYLPVQTVLEG
Dys3978   (1261)   GRVAKGHKMHYPMVEYCTPTTSGEDVRDFAKVLKNKFRTKRYFAKHPRMGYLPVQTVLEG
                   1321
Δ3990     (1321)   DNMETPDTM    SEQ ID NO:27
Dys3978   (1321)   DNMET····    SEQ ID NO:7
```

FIG. 55C

```
                          1                                                          60
Wildtype Δ3990      (1)   ATGGTTTGGTGGGAAGAAGTAGAGGACTGTTATGAAAGAGAAGATGTTCAAAAGAAAACA
Hopti-Dys3978       (1)   ATGCTTTGGTGGGAGGAAGTGGAGGACTGCTACGAGAGAGAGGACGTGCAGAAGAAAACC

                          61                                                        120
Wildtype Δ3990     (61)   TTCACAAAATGGGTAAATGCACAATTTTCTAAGTTTGGGAAGCAGCATATTGAGAACCTC
Hopti-Dys3978      (61)   TTCACCAAGTGGGTGAACGCCCAGTTCAGCAAGTTCGGCAAGCAGCACATCGAGAACCTG

                          121                                                       180
Wildtype Δ3990    (121)   TTCAGTGACCTACAGGATGGGAGGCGCCTCCTAGACCTCCTCGAAGGCCTGACAGGGCAA
Hopti-Dys3978     (121)   TTCAGCGACCTGCAGGATGGCAGGAGACTGCTGGACCTGCTGGAGGGCCTGACCGGCCAG

                          181                                                       240
Wildtype Δ3990    (181)   AAACTGCCAAAAGAAAAAGGATCCACAAGAGTTCATGCCCTGAACAATGTCAACAAGGCA
Hopti-Dys3978     (181)   AAGCTGCCCAAGGAGAAGGGCAGCACCAGAGTGCACGCCCTGAACAACGTGAACAAGGCC

                          241                                                       300
Wildtype Δ3990    (241)   CTGCGGGTTTTGCAGAACAATAATGTTGATTTAGTGAATATTGGAAGTACTGACATCGTA
Hopti-Dys3978     (241)   CTGAGAGTGCTGCAGAACAACAACGTGGACCTGGTGAACATCGGCAGCACCGACATCGTG

                          301                                                       360
Wildtype Δ3990    (301)   GATGGAAATCATAAACTGACTCTTGGTTTGATTTGGAATATAATCCTCCACTGGCAGGTC
Hopti-Dys3978     (301)   GACGGCAACCACAAGCTGACCCTGGGCCTGATCTGGAACATCATCCTGCACTGGCAGGTG

                          361                                                       420
Wildtype Δ3990    (361)   AAAAATGTAATGAAAAATATCATGGCTGGATTGCAACAAACCAACAGTGAAAAGATTCTC
Hopti-Dys3978     (361)   AAGAACGTGATGAAGAACATCATGGCCGGCCTGCAGCAGACCAACAGCGAGAAGATCCTG

                          421                                                       480
Wildtype Δ3990    (421)   CTGAGCTGGGTCCGACAATCAACTCGTAATTATCCACAGGTTAATGTAATCAACTTCACC
Hopti-Dys3978     (421)   CTGAGCTGGGTGAGGCAGAGCACCAGAAACTACCCCCAGGTGAACGTGATCAACTTCACC
```

FIG. 56A

```
                              481                                                         540
Wildtype Δ3990      (481)  ACCAGCTGGTCTGATGGCCTGGCTTTGAATGCTCTCATCCATAGTCATAGGCCAGACCTA
Hopti-Dys3978       (481)  ACCTCCTGGAGCGACGGCCTGGCCCTGAACGCCCTGATCCACAGCCACAGACCCGACCTG

                              541                                                         600
Wildtype Δ3990      (541)  TTTGACTGGAATAGTGTGGTTTGCCAGCAGTCAGCCACACAACGACTGGAACATGCATTC
Hopti-Dys3978       (541)  TTCGACTGGAACAGCGTGGTGTGTCAGCAGAGCGCCACCCAGAGACTGGAGCACGCCTTC

                              601                                                         660
Wildtype Δ3990      (601)  AACATCGCCAGATATCAATTAGGCATAGAGAAACTACTCGATCCTGAAGATGTTGATACC
Hopti-Dys3978       (601)  AACATCGCCAGATACCAGCTGGGCATCGAGAAGCTGCTGGACCCCGAGGACGTGGACACC

                              661                                                         720
Wildtype Δ3990      (661)  ACCTATCCAGATAAGAAGTCCATCTTAATGTACATCACATCACTCTTCCAAGTTTTGCCT
Hopti-Dys3978       (661)  ACCTACCCCGACAAGAAAAGCATCCTCATGTACATTACCAGCCTGTTCCAGGTGCTGCCC

                              721                                                         780
Wildtype Δ3990      (721)  CAACAAGTGAGCATTGAAGCCATCCAGGAAGTGGAAATGTTGCCAAGGCCACCTAAAGTG
Hopti-Dys3978       (721)  CAGCAGGTGTCCATCGAGGCCATCCAGGAAGTGGAAATGCTGCCCAGGCCCCCCAAAGTG

                              781                                                         840
Wildtype Δ3990      (781)  ACTAAAGAAGAACATTTTCAGTTACATCATCAAATGCACTATTCTCAACAGATCACGGTC
Hopti-Dys3978       (781)  ACCAAGGAGGAGCACTTCCAGCTGCACCACCAGATGCACTACAGCCAGCAGATCACAGTG

                              841                                                         900
Wildtype Δ3990      (841)  AGTCTAGCACAGGGATATGAGAGAACTTCTTCCCCTAAGCCTCGATTCAAGAGCTATGCC
Hopti-Dys3978       (841)  AGCCTGGCCCAGGGCTATGAGAGAACCAGCAGCCCCAAGCCCAGATTCAAGAGCTACGCC

                              901                                                         960
Wildtype Δ3990      (901)  TACACACAGGCTGCTTATGTCACCACCTCTGACCCTACACGGAGCCCATTTCCTTCACAG
Hopti-Dys3978       (901)  TACACCCAGGCCGCCTACGTGACCACCTCCGACCCCACCAGAAGCCCCTTCCCCAGCCAG
```

FIG. 56B

```
                              961                                                        1020
Wildtype Δ3990        (961)  CATTTGGAAGCTCCTGAAGACAAGTCATTTGGCAGTTCATTGATGGAGAGTGAAGTAAAC
Hopti-Dys3978         (961)  CACCTGGAGGCCCCCGAGGACAAGAGCTTCGGCAGCAGCCTGATGGAGAGCGAAGTGAAC

                              1021                                                       1080
Wildtype Δ3990       (1021)  CTGGACCGTTATCAAACAGCTTTAGAAGAAGTATTATCGTGGCTTCTTTCTGCTGAGGAC
Hopti-Dys3978        (1021)  CTGGACAGATACCAGACCGCCCTGGAGGAAGTGCTGTCCTGGCTGCTGAGCGCCGAGGAC

                              1081                                                       1140
Wildtype Δ3990       (1081)  ACATTGCAAGCACAAGGAGAGATTTCTAATGATGTGGAAGTGGTGAAAGACCAGTTTCAT
Hopti-Dys3978        (1081)  ACCCTGCAGGCCCAGGGCGAGATCAGCAACGACGTGGAAGTGGTGAAGGACCAGTTCCAC

                              1141                                                       1200
Wildtype Δ3990       (1141)  ACTCATGAGGGGTACATGATGGATTTGACAGCCCATCAGGGCCGGGTTGGTAATATTCTA
Hopti-Dys3978        (1141)  ACCCACGAGGGCTACATGATGGATCTGACCGCCCACCAGGGCAGAGTGGGCAATATCCTG

                              1201                                                       1260
Wildtype Δ3990       (1201)  CAATTGGGAAGTAAGCTGATTGGAACAGGAAAATTATCAGAAGATGAAGAAACTGAAGTA
Hopti-Dys3978        (1201)  CAGCTGGGCAGCAAGCTGATCGGCACCGGCAAGCTGAGCGAGGACGAGGAGACCGAAGTG

                              1261                                                       1320
Wildtype Δ3990       (1261)  CAAGAGCAGATGAATCTCCTAAATTCAAGATGGGAATGCCTCAGGGTAGCTAGCATGGAA
Hopti-Dys3978        (1261)  CAGGAGCAGATGAACCTGCTGAACAGCAGATGGGAGTGCCTGAGAGTGGCCAGCATGGAG

                              1321                                                       1380
Wildtype Δ3990       (1321)  AAACAAAGCAATTTACATAGAGTTTTAATGGATCTCCAGAATCAGAAACTGAAAGAGTTG
Hopti-Dys3978        (1321)  AAGCAGAGCAACCTGCACAGAGTGCTGATGGACCTGCAGAACCAGAAGCTGAAGGAGCTG

                              1381                                                       1440
Wildtype Δ3990       (1381)  AATGACTGGCTAACAAAAACAGAAGAAAGAACAAGGAAAATGGAGGAAGAGCCTCTTGGA
Hopti-Dys3978        (1381)  AACGACTGGCTGACCAAGACCGAGGAGCGGACCAGAAAGATGGAGGAGGAGCCCCTGGGC
```

FIG. 56C 1441 1500
Wildtype Δ3990 (1441) CCTGATCTTGAAGACCTAAAACGCCAAGTACAACAACATAAGGTGCTTCAAGAAGATCTA
Hopti-Dys3978 (1441) CCCGACCTGGAGGACCTGAAGAGACAGGTGCAGCAGCACAAAGTGCTGCAGGAGGACCTG 1501 1560
Wildtype Δ3990 (1501) GAACAAGAACAAGTCAGGGTCAATTCTCTCACTCACATGGTGGTGGTAGTTGATGAATCT
Hopti-Dys3978 (1501) GAGCAGGAGCAGGTGCGCGTGAACAGCCTGACCCACATGGTGGTGGTCGTGGACGAGAGC 1561 1620
Wildtype Δ3990 (1561) AGTGGAGATCACGCAACTGCTGCTTTGGAAGAACAACTTAAGGTATTGGGAGATCGATGG
Hopti-Dys3978 (1561) AGCGGCGACCACGCCACAGCCGCCCTGGAAGAGCAGCTGAAAGTGCTGGGCGACAGATGG 1621 1680
Wildtype Δ3990 (1621) GCAAACATCTGTAGATGGACAGAAGACCGCTGGGTTCTTTTACAAGACCAGCCTGACCTA
Hopti-Dys3978 (1621) GCCAATATTTGTAGGTGGACCGAGGACAGATGGGTGCTGCTGCAGGACCAGCCCGACCTG 1681 1740
Wildtype Δ3990 (1681) GCTCCTGGACTGACCACTATTGGAGCCTCTCCTACTCAGACTGTTACTCTGGTGACACAA
Hopti-Dys3978 (1681) GCCCCTGGCCTGACCACCATCGGCGCCAGCCCCACCCAGACCGTGACCCTGGTGACCCAG 1741 1800
Wildtype Δ3990 (1741) CCTGTGGTTACTAAGGAAACTGCCATCTCCAAACTAGAAATGCCATCTTCCTTGATGTTG
Hopti-Dys3978 (1741) CCCGTGGTGACAAAGGAGACCGCCATCAGCAAGCTGGAGATGCCCAGCTCCCTGATGCTG 1801 1860
Wildtype Δ3990 (1801) GAGGTACCTACTCATAGATTACTGCAACAGTTCCCCCTGGACCTGGAAAAGTTTCTTGCC
Hopti-Dys3978 (1801) GAAGTGCCCACCCACCGCCTGCTCCAGCAGTTCCCCCTGGACCTGGAGAAGTTCCTGGCC 1861 1920
Wildtype Δ3990 (1861) TGGCTTACAGAAGCTGAAACAACTGCCAATGTCCTACAGGATGCTACCCGTAAGGAAAGG
Hopti-Dys3978 (1861) TGGCTGACCGAGGCCGAAACCACCGCCAATGTGCTCCAGGACGCCACTAGAAAGGAGAGG

FIG. 56D

```
                              1921                                                        1980
Wildtype Δ3990     (1921)  CTCCTAGAAGACTCCAAGGGAGTAAAAGAGCTGATGAAACAATGGCAAGACCTCCAAGGT
Hopti-Dys3978      (1921)  CTGCTGGAGGACAGCAAGGGCGTGAAAGAGCTGATGAAGCAGTGGCAGGATCTGCAGGGC

                              1981                                                        2040
Wildtype Δ3990     (1981)  GAAATTGAAGCTCACACAGATGTTTATCACAACCTGGATGAAAACAGCCAAAAAATCCTG
Hopti-Dys3978      (1981)  GAAATCGAGGCCCACACCGACGTGTACCACAACCTGGACGAGAACAGCCAGAAGATTCTG

                              2041                                                        2100
Wildtype Δ3990     (2041)  AGATCCCTGGAAGGTTCCGATGATGCAGTCCTGTTACAAAGACGTTTGGATAACATGAAC
Hopti-Dys3978      (2041)  AGGAGCCTGGAGGGCAGCGACGACGCCGTCCTGCTCCAGAGGAGGCTGGACAACATGAAC

                              2101                                                        2160
Wildtype Δ3990     (2101)  TTCAAGTGGAGTGAACTTCGGAAAAAGTCTCTCAACATTAGGTCCCATTTGGAAGCCAGT
Hopti-Dys3978      (2101)  TTCAAGTGGAGCGAGCTGCGGAAGAAGAGCCTGAACATCCGGAGCCACCTGGAAGCCAGC

                              2161                                                        2220
Wildtype Δ3990     (2161)  TCTGACCAGTGGAAGCGTCTGCACCTTTCTCTGCAGGAACTTCTGGTGTGGCTACAGCTG
Hopti-Dys3978      (2161)  AGCGACCAGTGGAAGAGACTGCACCTGAGCCTGCAGGAGCTGCTGGTGTGGCTGCAGCTG

                              2221                                                        2280
Wildtype Δ3990     (2221)  AAAGATGATGAATTAAGCCGGCAGGCACCTATTGGAGGCGACTTTCCAGCAGTTCAGAAG
Hopti-Dys3978      (2221)  AAGGACGACGAGCTGAGCAGACAGGCCCCCATCGGCGGCGACTTCCCCGCCGTGCAGAAG

                              2281                                                        2340
Wildtype Δ3990     (2281)  CAGAACGATGTACATAGGGCCTTCAAGAGGGAATTGAAAACTAAAGAACCTGTAATCATG
Hopti-Dys3978      (2281)  CAGAACGACGTGCACCGGGCCTTCAAGAGGGAGCTGAAAACCAAGGAACCCGTGATCATG

                              2341                                                        2400
Wildtype Δ3990     (2341)  AGTACTCTTGAGACTGTACGAATATTTCTGACAGAGCAGCCTTTGGAAGGACTAGAGAAA
Hopti-Dys3978      (2341)  AGCACCCTGGAGACAGTGCGGATCTTCCTGACCGAGCAGCCCCTGGAGGGACTGGAGAAG
```

FIG. 56E

```
                              2401                                                        2460
Wildtype Δ3990       (2401)   CTCTACCAGGAGCCCAGAGAGCTGCCTCCTGAGGAGAGAGCCCAGAATGTCACTCGGCTT
Hopti-Dys3978        (2401)   CTGTACCAGGAGCCCAGAGAGCTGCCCCCCGAGGAGAGAGCCCAGAACGTGACCAGGCTG

                              2461                                                        2520
Wildtype Δ3990       (2461)   CTACGAAAGCAGGCTGAGGAGGTCAATACTGAGTGGGAAAAATTGAACCTGCACTCCGCT
Hopti-Dys3978        (2461)   CTGAGAAAGCAGGCCGAGGAAGTGAATACCGAGTGGGAGAAGCTGAATCTGCACAGCGCC

                              2521                                                        2580
Wildtype Δ3990       (2521)   GACTGGCAGAGAAAAATAGATGAGACCCTTGAAAGACTCCAGGAACTTCAAGAGGCCACG
Hopti-Dys3978        (2521)   GACTGGCAGAGAAAGATCGACGAGACCCTGGAGAGACTCCAGGAACTGCAGGAAGCCACC

                              2581                                                        2640
Wildtype Δ3990       (2581)   GATGAGCTGGACCTCAAGCTGCGCCAAGCTGAGGTGATCAAGGGATCCTGGCAGCCCGTG
Hopti-Dys3978        (2581)   GACGAGCTGGACCTGAAGCTGAGACAGGCCGAAGTGATCAAGGGCAGCTGGCAGCCTGTG

                              2641                                                        2700
Wildtype Δ3990       (2641)   GGCGATCTCCTCATTGACTCTCTCCAAGATCACCTCGAGAAAGTCAAGGCACTTCGAGGA
Hopti-Dys3978        (2641)   GGCGATCTGCTGATCGACTCCCTGCAGGATCACCTGGAGAAAGTGAAGGCCCTGCGGGGC

                              2701                                                        2760
Wildtype Δ3990       (2701)   GAAATTGCGCCTCTGAAAGAGAACGTGAGCCACGTCAATGACCTTGCTCGCCAGCTTACC
Hopti-Dys3978        (2701)   GAGATCGCCCCCCTGAAGGAGAATGTGAGCCACGTGAACGACCTGGCCAGACAGCTGACC

                              2761                                                        2820
Wildtype Δ3990       (2761)   ACTTTGGGCATTCAGCTCTCACCGTATAACCTCAGCACTCTGGAAGACCTGAACACCAGA
Hopti-Dys3978        (2761)   ACCCTGGGCATCCAGCTGAGCCCCTACAACCTGAGCACACTGGAGGATCTGAACACCCGG

                              2821                                                        2880
Wildtype Δ3990       (2821)   TGGAAGCTTCTGCAGGTGGCCGTCGAGGACCGAGTCAGGCAGCTGCATGAAGCCCACAGG
Hopti-Dys3978        (2821)   TGGAAACTGCTGCAGGTGGCCGTGGAGGATAGAGTGAGGCAGCTGCACGAAGCCCACAGA
```

FIG. 56F

```
                                  2881                                                        2940
Wildtype Δ3990        (2881)  GACTTTGGTCCAGCATCTCAGCACTTTCTTTCCACGTCTGTCCAGGGTCCCTGGGAGAGA
Hopti-Dys3978         (2881)  GACTTCGGCCCTGCCTCCCAGCACTTCCTGAGCACCAGCGTGCAGGGCCCCTGGGAGAGA

                                  2941                                                        3000
Wildtype Δ3990        (2941)  GCCATCTCGCCAAACAAAGTGCCCTACTATATCAACCACGAGACTCAAACAACTTGCTGG
Hopti-Dys3978         (2941)  GCCATCTCCCCCAACAAAGTGCCCTACTACATCAACCACGAGACCCAGACCACCTGCTGG

                                  3001                                                        3060
Wildtype Δ3990        (3001)  GACCATCCCAAAATGACAGAGCTCTACCAGTCTTTAGCTGACCTGAATAATGTCAGATTC
Hopti-Dys3978         (3001)  GACCACCCTAAGATGACCGAGCTGTATCAGAGCCTGGCCGACCTGAACAATGTGCGGTTC

                                  3061                                                        3120
Wildtype Δ3990        (3061)  TCAGCTTATAGGACTGCCATGAAACTCCGAAGACTGCAGAAGGCCCTTTGCTTGGATCTC
Hopti-Dys3978         (3061)  AGCGCCTACAGAACCGCCATGAAGCTGCGGAGACTGCAGAAGGCCCTGTGCCTGGATCTG

                                  3121                                                        3180
Wildtype Δ3990        (3121)  TTGAGCCTGTCAGCTGCATGTGATGCCTTGGACCAGCACAACCTCAAGCAAAATGACCAG
Hopti-Dys3978         (3121)  CTGAGCCTGAGCGCCGCCTGCGACGCCCTGGACCAGCACAACCTGAAGCAGAATGACCAG

                                  3181                                                        3240
Wildtype Δ3990        (3181)  CCCATGGATATCCTGCAGATTATTAATTGTTTGACCACTATTTATGACCGCCTGGAGCAA
Hopti-Dys3978         (3181)  CCCATGGACATCCTGCAGATCATCAACTGCCTGACCACAATCTACGACCGGCTGGAACAG

                                  3241                                                        3300
Wildtype Δ3990        (3241)  GAGCACAACAATTTGGTCAACGTCCCTCTCTGCGTGGATATGTGTCTGAACTGGCTGCTG
Hopti-Dys3978         (3241)  GAGCACAACAACCTGGTGAATGTGCCCCTGTGCGTGGACATGTGCCTGAATTGGCTGCTG

                                  3301                                                        3360
Wildtype Δ3990        (3301)  AATGTTTATGATACGGGACGAACAGGGAGGATCCGTGTCCTGTCTTTTAAAACTGGCATC
Hopti-Dys3978         (3301)  AACGTGTACGACACCGGCAGGACCGGCAGAATCCGCGTGCTGAGCTTCAAGACCGGCATC
```

FIG. 56G

```
                                 3361                                                       3420
Wildtype Δ3990          (3361)   ATTTCCCTGTGTAAAGCACATTTGGAAGACAAGTACAGATACCTTTTCAAGCAAGTGGCA
Hopti-Dys3978           (3361)   ATCAGCCTGTGCAAGGCCCACCTGGAGGATAAGTACCGCTACCTGTTCAAGCAGGTGGCC

                                 3421                                                       3480
Wildtype Δ3990          (3421)   AGTTCAACAGGATTTTGTGACCAGCGCAGGCTGGGCCTCCTTCTGCATGATTCTATCCAA
Hopti-Dys3978           (3421)   AGCAGCACCGGCTTCTGCGATCAGAGGAGACTGGGCCTGCTGCTGCACGATAGCATCCAG

                                 3481                                                       3540
Wildtype Δ3990          (3481)   ATTCCAAGACAGTTGGGTGAAGTTGCATCCTTTGGGGGCAGTAACATTGAGCCAAGTGTC
Hopti-Dys3978           (3481)   ATCCCTAGGCAGCTGGGCGAAGTGGCCAGCTTTGGCGGCAGCAACATCGAGCCCTCTGTG

                                 3541                                                       3600
Wildtype Δ3990          (3541)   CGGAGCTGCTTCCAATTTGCTAATAATAAGCCAGAGATCGAAGCGGCCCTCTTCCTAGAC
Hopti-Dys3978           (3541)   AGGAGCTGCTTCCAGTTCGCCAACAACAAGCCCGAGATCGAGGCCGCCCTGTTCCTGGAC

                                 3601                                                       3660
Wildtype Δ3990          (3601)   TGGATGAGACTGGAACCCCAGTCCATGGTGTGGCTGCCCGTCCTGCACAGAGTGGCTGCT
Hopti-Dys3978           (3601)   TGGATGAGGCTGGAGCCTCAGAGCATGGTGTGGCTGCCTGTGCTGCACAGAGTGGCCGCC

                                 3661                                                       3720
Wildtype Δ3990          (3661)   GCAGAAACTGCCAAGCATCAGGCCAAATGTAACATCTGCAAAGAGTGTCCAATCATTGGA
Hopti-Dys3978           (3661)   GCCGAGACCGCCAAGCACCAGGCCAAGTGCAATATCTGCAAGGAGTGCCCCATCATCGGC

                                 3721                                                       3780
Wildtype Δ3990          (3721)   TTCAGGTACAGGAGTCTAAAGCACTTTAATTATGACATCTGCCAAAGCTGCTTTTTTTCT
Hopti-Dys3978           (3721)   TTCCGGTACAGGAGCCTGAAGCACTTCAACTACGACATCTGCCAGAGCTGCTTTTTCAGC

                                 3781                                                       3840
Wildtype Δ3990          (3781)   GGTCGAGTTGCAAAAGGCCATAAAATGCACTATCCCATGGTGGAATATTGCACTCCGACT
Hopti-Dys3978           (3781)   GGCAGAGTGGCCAAGGGCCACAAAATGCACTACCCCATGGTGGAGTACTGCACCCCCACC
```

FIG. 56H

```
                           3841                                                      3900
Wildtype Δ3990     (3841) ACATCAGGAGAAGATGTTCGAGACTTTGCCAAGGTACTAAAAACAAATTTCGAACCAAA
Hopti-Dys3978      (3841) ACCTCCGGCGAGGATGTGAGAGACTTCGCCAAAGTGCTGAAGAATAAGTTCCGGACCAAG

                           3901                                                      3960
Wildtype Δ3990     (3901) AGGTATTTTGCGAAGCATCCCCGAATGGGCTACCTGCCAGTGCAGACTGTCTTAGAGGGG
Hopti-Dys3978      (3901) CGGTACTTTGCCAAGCACCCCAGGATGGGCTACCTGCCCGTGCAGACCGTGCTGGAAGGC

                           3961
Wildtype Δ3990     (3961) GACAACATGGAAACTCCCGACACAATGTAG    SEQ ID NO:28
Hopti-Dys3978      (3961) GACAACATGGAGACC············TGA    SEQ ID NO:1
```

FIG. 56I

SEQUENCE LISTING

<160> NUMBER OF SEQ ID NOS: 28

<210> SEQ ID NO 1
<211> LENGTH: 3978
<212> TYPE: DNA
<213> ORGANISM: Artificial Sequence
<220> FEATURE:
<223> OTHER INFORMATION: Hopti-Dys3978 gene

<400> SEQUENCE: 1

```
atgctttggt gggaggaagt ggaggactgc tacgagagag aggacgtgca gaagaaaacc     60
ttcaccaagt gggtgaacgc ccagttcagc aagttcggca agcagcacat cgagaacctg    120
ttcagcgacc tgcaggatgg caggagactg ctggacctgc tggagggcct gaccggccag    180
aagctgccca aggagaaggg cagcaccaga gtgcacgccc tgaacaacgt gaacaaggcc    240
ctgagagtgc tgcagaacaa caacgtggac ctggtgaaca tcggcagcac cgacatcgtg    300
gacggcaacc acaagctgac cctgggcctg atctggaaca tcatcctgca ctggcaggtg    360
aagaacgtga tgaagaacat catggccggc ctgcagcaga ccaacagcga gaagatcctg    420
ctgagctggg tgaggcagag caccagaaac taccccccagg tgaacgtgat caacttcacc    480
acctcctgga gcgacggcct ggccctgaac gccctgatcc acagccacag acccgacctg    540
ttcgactgga acagcgtggt gtgtcagcag agcgccaccc agagactgga gcacgccttc    600
aacatcgcca gataccagct gggcatcgag aagctgctgg accccgagga cgtggacacc    660
acctaccccg acaagaaaag catcctcatg tacattacca gcctgttcca ggtgctgccc    720
cagcaggtgt ccatcgaggc catccaggaa gtggaaatgc tgcccaggcc ccccaaagtg    780
accaaggagg agcacttcca gctgcaccac cagatgcact acagccagca gatcacagtg    840
agcctggccc agggctatga gagaaccagc agccccaagc ccagattcaa gagctacgcc    900
tacacccagg ccgcctacgt gaccacctcc gaccccacca gaagcccctt ccccagccag    960
cacctggagg cccccgagga caagagcttc ggcagcagcc tgatggagag cgaagtgaac   1020
ctggacagat accagaccgc cctggaggaa gtgctgtcct ggctgctgag cgccgaggac   1080
accctgcagg cccagggcga gatcagcaac gacgtggaag tggtgaagga ccagttccac   1140
acccacgagg gctacatgat ggatctgacc gcccaccagg gcagagtggg caatatcctg   1200
cagctgggca gcaagctgat cggcaccggc aagctgagcg aggacgagga gaccgaagtg   1260
caggagcaga tgaacctgct gaacagcaga tgggagtgcc tgagagtggc cagcatggag   1320
aagcagagca acctgcacag agtgctgatg gacctgcaga accagaagct gaaggagctg   1380
aacgactggc tgaccaagac cgaggagcgg accagaaaga tggaggagga gcccctgggc   1440
cccgacctgg aggacctgaa gagacaggtg cagcagcaca aagtgctgca ggaggacctg   1500
gagcaggagc aggtgcgcgt gaacagcctg acccacatgg tggtggtcgt ggacgagagc   1560
agcggcgacc acgccacagc cgccctggaa gagcagctga aagtgctggg cgacagatgg   1620
gccaatattt gtaggtggac cgaggacaga tgggtgctgc tgcaggacca gcccgacctg   1680
gcccctggcc tgaccaccat cggcgccagc cccacccaga ccgtgaccct ggtgacccag   1740
cccgtggtga caaaggagac cgccatcagc aagctggaga tgcccagctc cctgatgctg   1800
gaagtgccca cccaccgcct gctccagcag ttccccctgg acctggagaa gttcctggcc   1860
tggctgaccg aggccgaaac caccgccaat gtgctccagg acgccactag aaaggagagg   1920
```

-continued

```
ctgctggagg acagcaaggg cgtgaaagag ctgatgaagc agtggcagga tctgcagggc   1980

gaaatcgagg cccacaccga cgtgtaccac aacctggacg agaacagcca gaagattctg   2040

aggagcctgg agggcagcga cgacgccgtc ctgctccaga ggaggctgga caacatgaac   2100

ttcaagtgga gcgagctgcg gaagaagagc ctgaacatcc ggagccacct ggaagccagc   2160

agcgaccagt ggaagagact gcacctgagc ctgcaggagc tgctggtgtg gctgcagctg   2220

aaggacgacg agctgagcag acaggccccc atcggcggcg acttccccgc cgtgcagaag   2280

cagaacgacg tgcaccgggc cttcaagagg gagctgaaaa ccaaggaacc cgtgatcatg   2340

agcaccctgg agacagtgcg gatcttcctg accgagcagc ccctggaggg actggagaag   2400

ctgtaccagg agcccagaga gctgcccccc gaggagagag cccagaacgt gaccaggctg   2460

ctgagaaagc aggccgagga agtgaatacc gagtgggaga agctgaatct gcacagcgcc   2520

gactggcaga gaaagatcga cgagaccctg gagagactcc aggaactgca ggaagccacc   2580

gacgagctgg acctgaagct gagacaggcc gaagtgatca agggcagctg gcagcctgtg   2640

ggcgatctgc tgatcgactc cctgcaggat cacctggaga aagtgaaggc cctgcggggc   2700

gagatcgccc ccctgaagga gaatgtgagc cacgtgaacg acctggccag acagctgacc   2760

accctgggca tccagctgag cccctacaac ctgagcacac tggaggatct gaacacccgg   2820

tggaaactgc tgcaggtggc cgtggaggat agagtgaggc agctgcacga agcccacaga   2880

gacttcggcc ctgcctccca gcacttcctg agcaccagcg tgcagggccc ctgggagaga   2940

gccatctccc ccaacaaagt gccctactac atcaaccacg agacccagac cacctgctgg   3000

gaccacccta agatgaccga gctgtatcag agcctggccg acctgaacaa tgtgcggttc   3060

agcgcctaca gaaccgccat gaagctgcgg agactgcaga aggccctgtg cctggatctg   3120

ctgagcctga gcgccgcctg cgacgccctg gaccagcaca acctgaagca gaatgaccag   3180

cccatggaca tcctgcagat catcaactgc ctgaccacaa tctacgaccg gctggaacag   3240

gagcacaaca acctggtgaa tgtgcccctg tgcgtggaca tgtgcctgaa ttggctgctg   3300

aacgtgtacg acaccggcag gaccggcaga atccgcgtgc tgagcttcaa gaccggcatc   3360

atcagcctgt gcaaggccca cctggaggat aagtaccgct acctgttcaa gcaggtggcc   3420

agcagcaccg gcttctgcga tcagaggaga ctgggcctgc tgctgcacga tagcatccag   3480

atccctaggc agctgggcga agtggccagc tttggcggca gcaacatcga gccctctgtg   3540

aggagctgct tccagttcgc caacaacaag cccgagatcg aggccgccct gttcctggac   3600

tggatgaggc tggagcctca gagcatggtg tggctgcctg tgctgcacag agtggccgcc   3660

gccgagaccg ccaagcacca ggccaagtgc aatatctgca aggagtgccc catcatcggc   3720

ttccggtaca ggagcctgaa gcacttcaac tacgacatct gccagagctg ctttttcagc   3780

ggcagagtgg ccaagggcca caaaatgcac taccccatgg tggagtactg cacccccacc   3840

acctccggcg aggatgtgag agacttcgcc aaagtgctga agaataagtt ccggaccaag   3900

cggtactttg ccaagcaccc caggatgggc tacctgcccg tgcagaccgt gctggaaggc   3960

gacaacatgg agacctga                                                  3978
```

```
<210> SEQ ID NO 2
<211> LENGTH: 3837
<212> TYPE: DNA
<213> ORGANISM: Artificial Sequence
<220> FEATURE:
<223> OTHER INFORMATION: Hopti-Dys3837 gene

<400> SEQUENCE: 2
```

```
atgctttggt gggaggaagt ggaggactgc tacgagagag aggacgtgca gaagaaaacc     60
ttcaccaagt gggtgaacgc ccagttcagc aagttcggca agcagcacat cgagaacctg    120
ttcagcgacc tgcaggatgg caggagactg ctggacctgc tggagggcct gaccggccag    180
aagctgccca aggagaaggg cagcaccaga gtgcacgccc tgaacaacgt gaacaaggcc    240
ctgagagtgc tgcagaacaa caacgtggac ctggtgaaca tcggcagcac cgacatcgtg    300
gacggcaacc acaagctgac cctgggcctg atctggaaca tcatcctgca ctggcaggtg    360
aagaacgtga tgaagaacat catggccggc ctgcagcaga ccaacagcga gaagatcctg    420
ctgagctggg tgaggcagag caccagaaac tacccccagg tgaacgtgat caacttcacc    480
acctcctgga gcgacggcct ggccctgaac gccctgatcc acagccacag acccgacctg    540
ttcgactgga acagcgtggt gtgtcagcag agcgccaccc agagactgga gcacgccttc    600
aacatcgcca gataccagct gggcatcgag aagctgctgg accccgagga cgtggacacc    660
acctaccccg acaagaaaag catcctcatg tacattacca gcctgttcca ggtgctgccc    720
cagcaggtgt ccatcgaggc catccaggaa gtggaaatgc tgcccaggcc ccccaaagtg    780
accaaggagg agcacttcca gctgcaccac cagatgcact acagccagca gatcacagtg    840
agcctggccc agggctatga gagaaccagc agccccaagc ccagattcaa gagctacgcc    900
tacacccagg ccgcctacgt gaccacctcc gaccccacca gaagcccctt ccccagccag    960
cacctggagg cccccgagga caagagcttc ggcagcagcc tgatggagag cgaagtgaac   1020
ctggacagat accagaccgc cctggaggaa gtgctgtcct ggctgctgag cgccgaggac   1080
accctgcagg cccagggcga gatcagcaac gacgtggaag tggtgaagga ccagttccac   1140
acccacgagg gctacatgat ggatctgacc gcccaccagg gcagagtggg caatatcctg   1200
cagctgggca gcaagctgat cggcaccggc aagctgagcg aggacgagga gaccgaagtg   1260
caggagcaga tgaacctgct gaacagcaga tgggagtgcc tgagagtggc cagcatggag   1320
aagcagagca acctgcacag agtgctgatg gacctgcaga accagaagct gaaggagctg   1380
aacgactggc tgaccaagac cgaggagcgg accagaaaga tggaggagga gcccctgggc   1440
cccgacctgg aggacctgaa gagacaggtg cagcagcaca aagtgctgca ggaggacctg   1500
gagcaggagc aggtgcgcgt gaacagcctg acccacatgg tggtggtcgt ggacgagagc   1560
agcggcgacc acgccacagc cgccctggaa gagcagctga aagtgctggg cgacagatgg   1620
gccaatattt gtaggtggac cgaggacaga tgggtgctgc tgcaggacac ccaccgcctg   1680
ctccagcagt tcccccctgga cctggagaag ttcctggcct ggctgaccga ggccgaaacc   1740
accgccaatg tgctccagga cgccactaga aaggagaggc tgctggagga cagcaagggc   1800
gtgaaagagc tgatgaagca gtggcaggat ctgcagggcg aaatcgaggc ccacaccgac   1860
gtgtaccaca acctggacga gaacagccag aagattctga ggagcctgga gggcagcgac   1920
gacgccgtcc tgctccagag gaggctggac aacatgaact tcaagtggag cgagctgcgg   1980
aagaagagcc tgaacatccg gagccacctg gaagccagca gcgaccagtg gaagagactg   2040
cacctgagcc tgcaggagct gctggtgtgg ctgcagctga aggacgacga gctgagcaga   2100
caggccccca tcggcggcga cttccccgcc gtgcagaagc agaacgacgt gcaccgggcc   2160
ttcaagaggg agctgaaaac caaggaaccc gtgatcatga gcaccctgga gacagtgcgg   2220
atcttcctga ccgagcagcc cctggaggga ctggagaagc tgtaccagga gcccagagag   2280
ctgccccccg aggagagagc ccagaacgtg accaggctgc tgagaaagca ggccgaggaa   2340
```

gtgaataccg agtgggagaa gctgaatctg cacagcgccg actggcagag aaagatcgac 2400
gagaccctgg agagactcca ggaactgcag gaagccaccg acgagctgga cctgaagctg 2460
agacaggccg aagtgatcaa gggcagctgg cagcctgtgg gcgatctgct gatcgactcc 2520
ctgcaggatc acctggagaa agtgaaggcc ctgcggggcg agatcgcccc cctgaaggag 2580
aatgtgagcc acgtgaacga cctggccaga cagctgacca ccctgggcat ccagctgagc 2640
ccctacaacc tgagcacact ggaggatctg aacacccggt ggaaactgct gcaggtggcc 2700
gtggaggata gagtgaggca gctgcacgaa gcccacagag acttcggccc tgcctcccag 2760
cacttcctga gcaccagcgt gcagggcccc tgggagagag ccatctcccc caacaaagtg 2820
ccctactaca tcaaccacga gacccagacc acctgctggg accaccctaa gatgaccgag 2880
ctgtatcaga gcctggccga cctgaacaat gtgcggttca gcgcctacag aaccgccatg 2940
aagctgcgga gactgcagaa ggccctgtgc ctggatctgc tgagcctgag cgccgcctgc 3000
gacgccctgg accagcacaa cctgaagcag aatgaccagc ccatggacat cctgcagatc 3060
atcaactgcc tgaccacaat ctacgaccgg ctggaacagg agcacaacaa cctggtgaat 3120
gtgcccctgt gcgtggacat gtgcctgaat tggctgctga acgtgtacga caccggcagg 3180
accggcagaa tccgcgtgct gagcttcaag accggcatca tcagcctgtg caaggcccac 3240
ctggaggata agtaccgcta cctgttcaag caggtggcca gcagcaccgg cttctgcgat 3300
cagaggagac tgggcctgct gctgcacgat agcatccaga tccctaggca gctgggcgaa 3360
gtggccagct ttggcggcag caacatcgag ccctctgtga ggagctgctt ccagttcgcc 3420
aacaacaagc ccgagatcga ggccgccctg ttcctggact ggatgaggct ggagcctcag 3480
agcatggtgt ggctgcctgt gctgcacaga gtggccgccg ccgagaccgc caagcaccag 3540
gccaagtgca atatctgcaa ggagtgcccc atcatcggct tccggtacag gagcctgaag 3600
cacttcaact acgacatctg ccagagctgc tttttcagcg gcagagtggc caagggccac 3660
aaaatgcact accccatggt ggagtactgc acccccacca cctccggcga ggatgtgaga 3720
gacttcgcca aagtgctgaa gaataagttc cggaccaagc ggtactttgc caagcacccc 3780
aggatgggct acctgcccgt gcagaccgtg ctggaaggcg acaacatgga gacctga 3837

<210> SEQ ID NO 3
<211> LENGTH: 3978
<212> TYPE: DNA
<213> ORGANISM: Artificial Sequence
<220> FEATURE:
<223> OTHER INFORMATION: Copti-Dys3978 gene

<400> SEQUENCE: 3
atgctttggt gggaggaagt ggaggactgc tacgagcggg aggacgtgca gaagaaaacc 60
ttcaccaagt gggtgaacgc ccagttcagc aagttcggca agcagcacat cgagaacctg 120
ttcagcgacc tgcaggacgg caggcggctg ctggacctcc tggaaggcct gaccggccag 180
aagctgccca aagagaaggg cagcaccagg gtgcacgccc tgaacaacgt gaacaaggcc 240
ctgagggtgc tgcagaacaa caacgtggac ctggtgaaca tcggcagcac cgacatcgtg 300
gacggcaacc acaagctgac cctgggcctg atctggaaca tcatcctgca ctggcaggtc 360
aagaacgtga tgaagaacat catggccggc ctgcagcaga ccaacagcga gaagatcctg 420
ctgtcctggg tgcggcagag caccaggaac tacccccagg tcaacgtgat caacttcacc 480
acctcttgga gcgacggcct ggccctgaac gccctgatcc acagccacag gcccgacctg 540
ttcgactgga acagcgtggt gtgccagcag agcgccaccc agaggctgga acacgccttc 600

-continued

```
aacatcgcca gataccagct gggcatcgag aagctgctgg atcccgagga cgtggacacc    660
acctaccccg acaagaaaag catcctcatg tacatcacca gcctgttcca ggtgctgccc    720
cagcaggtgt ccatcgaggc catccaggaa gtggagatgc tgcccaggcc ccccaaggtc    780
accaaagagg aacacttcca gctgcaccac cagatgcact acagccagca gatcaccgtg    840
agcctggccc agggctacga gaggaccagc agccccaagc ccaggttcaa gagctacgcc    900
tacacccagg ccgcctacgt gaccacctcc gaccccacca ggtcccccctt ccccagccag    960
catctcgaag cccccgagga caagagcttc ggcagcagcc tgatggaaag cgaggtgaac   1020
ctggacagat accagaccgc cctggaagaa gtgctgtctt ggctgctgtc cgccgaggac   1080
accctgcagg cccagggcga gatcagcaac gacgtggagg tcgtgaagga ccagttccac   1140
acccacgagg gctacatgat ggacctgacc gcccaccagg gcagagtggg caacatcctg   1200
cagctgggca gcaagctgat cggcaccggc aagctgtccg aggacgagga aaccgaggtg   1260
caggaacaga tgaacctgct gaacagcaga tgggagtgcc tgagggtggc cagcatggaa   1320
aagcagagca acctgcacag ggtgctgatg gatctgcaga accagaagct caaagagctg   1380
aacgactggc tgaccaagac cgaggaaagg acccggaaga tggaagagga acccctgggc   1440
cccgatctcg aagatctgaa gaggcaggtg cagcagcaca aggtgctgca ggaagatctc   1500
gaacaggaac aggtccgggt caacagcctg acccacatgg tcgtggtggt ggacgagagc   1560
agcggcgacc acgccaccgc tgccctggaa gagcagctga aggtgctggg cgacagatgg   1620
gccaacatct gccggtggac cgaggacaga tgggtcctcc tgcaggacca gcccgacctg   1680
gcccctggcc tgacaaccat cggcgccagc ccccacccaga ccgtgaccct ggtgacccag   1740
cccgtggtga ccaaagagac cgccatcagc aagctggaaa tgcccagctc cctgatgctg   1800
gaagtgccca cccacaggct cctccagcag ttccccctgg acctggaaaa gttcctggcc   1860
tggctgaccg aggccgagac caccgccaac gtgctgcagg acgccaccag gaaagagagg   1920
ctgctggaag atagcaaggg cgtgaaagag ctgatgaagc agtggcagga cctgcagggg   1980
gagattgagg cccacaccga cgtgtaccac aacctggacg agaacagcca gaaaatcctg   2040
agaagcctgg aaggcagcga cgacgccgtg ctgctgcaga ggcggctgga caacatgaac   2100
ttcaagtgga gcgagctgag gaagaagagc ctgaacatca ggtcccatct ggaagccagc   2160
agcgaccagt ggaagaggct gcacctgagc ctgcaggaac tgctcgtctg gctgcagctg   2220
aaagacgacg agctgtccag gcaggccccc atcggcggcg acttccccgc cgtgcagaaa   2280
cagaacgacg tgcacagggc cttcaagcgg gagctgaaaa ccaaagagcc cgtgatcatg   2340
agcaccctgg aaaccgtgag gatcttcctg accgagcagc cctggaaggg actggaaaag   2400
ctgtaccagg aacccagaga gctgcccccc gaggaacggg cccagaacgt gaccaggctg   2460
ctgagaaagc aggccgagga agtgaacacc gagtgggaga agctgaacct gcactccgcc   2520
gactggcaga ggaagatcga cgagaccctg gaaaggctcc aggaactgca ggaagccacc   2580
gacgagctgg acctgaagct gagacaggcc gaggtgatca agggcagctg gcagcccgtg   2640
ggcgacctgc tgatcgactc cctgcaggat cacctggaaa aagtgaaggc cctgcggggc   2700
gagatcgccc ccctgaaaga gaacgtcagc cacgtcaacg acctggccag gcagctgacc   2760
accctgggca tccagctgtc cccctacaac ctgtccaccc tggaagatct gaacacaagg   2820
tggaagctgc tgcaggtggc cgtggaggac agagtgaggc agctgcacga ggcccacagg   2880
gacttcggcc ctgcctccca gcacttcctg agcaccagcg tgcagggccc ctgggagagg   2940
```

-continued

```
gccatctccc ccaacaaggt gccctactac atcaaccacg agacccagac cacctgctgg   3000

gaccacccta agatgaccga gctgtaccag tccctggccg acctgaacaa tgtgcggttc   3060

agcgcctacc ggaccgccat gaagctgagg cggctgcaga aagccctgtg cctggatctg   3120

ctgtccctga gcgccgcctg cgacgccctg gaccagcaca acctgaagca gaacgaccag   3180

cccatggata tcctgcagat catcaactgt ctgaccacca tctacgacag gctggaacag   3240

gaacacaaca acctggtcaa cgtgcccctg tgcgtggaca tgtgcctgaa ctggctgctg   3300

aacgtgtacg acaccggcag gaccggccgg atcagggtgc tgtccttcaa gaccggcatc   3360

atcagcctgt gcaaggccca cctggaagat aagtaccgct acctgttcaa gcaggtggcc   3420

agctctaccg gcttctgcga ccagcggagg ctgggcctgc tgctgcacga cagcatccag   3480

atcccccggc agctgggcga ggtggcctcc ttcggcggca gcaacatcga gcccagcgtg   3540

cggagctgct tccagttcgc caacaacaag cccgagatcg aggccgccct gttcctggac   3600

tggatgcggc tggaacccca gagcatggtc tggctgcccg tgctgcacag agtggctgcc   3660

gccgagaccg ccaagcacca ggccaagtgc aacatctgca aagagtgccc catcatcggc   3720

ttcaggtaca gaagcctgaa gcacttcaac tacgacatct gccagagctg tttcttcagc   3780

ggcagggtgg ccaagggcca caaaatgcac taccccatgg tggagtactg cacccccacc   3840

acctccggcg aggacgtgag ggacttcgcc aaggtgctga agaataagtt ccggaccaag   3900

cggtacttcg ccaaacaccc caggatgggc tacctgcccg tgcagaccgt gctggaaggc   3960

gacaacatgg aaacctga                                                 3978
```

<210> SEQ ID NO 4
<211> LENGTH: 606
<212> TYPE: DNA
<213> ORGANISM: Artificial Sequence
<220> FEATURE:
<223> OTHER INFORMATION: hCK promoter

<400> SEQUENCE: 4

```
gaattcggta ccccactacg ggtttaggct gcccatgtaa ggaggcaagg cctggggaca     60

cccgagatgc ctggttataa ttaacccaga catgtggctg cccccccccc ccccaacacc    120

tgctgcctct aaaaataacc ctgtccctgg tggatcccct gcatgcgaag atcttcgaac    180

aaggctgtgg gggactgagg gcaggctgta acaggcttgg gggccagggc ttatacgtgc    240

ctgggactcc caaagtatta ctgttccatg ttcccggcga agggccagct gtcccccgcc    300

agctagactc agcacttagt ttaggaacca gtgagcaagt cagcccttgg ggcagcccat    360

acaaggccat ggggctgggc aagctgcacg cctgggtccg ggggtgggcac ggtgcccggg    420

caacgagctg aaagctcatc tgctctcagg ggcccctccc tggggacagc ccctcctggc    480

tagtcacacc ctgtaggctc ctctatataa cccaggggca caggggctgc cctcattcta    540

ccaccacctc cacagcacag acagacactc aggagccagc cagcgtcgag cggccgatcc    600

gccacc                                                               606
```

<210> SEQ ID NO 5
<211> LENGTH: 759
<212> TYPE: DNA
<213> ORGANISM: Artificial Sequence
<220> FEATURE:
<223> OTHER INFORMATION: hCKplus promoter

<400> SEQUENCE: 5

```
gaattcggta ccccactacg ggtctaggct gcccatgtaa ggaggcaagg cctggggaca     60
```

cccgagatgc ctggttataa ttaaccccaa cacctgctgc cccccccccc ccaacacctg 120
ctgcctctaa aaataaccct gtccctggtg gatcccctgc atgccccact acgggtttag 180
gctgcccatg taaggaggca aggcctgggg acacccgaga tgcctggtta taattaaccc 240
agacatgtgg ctgccccccc cccccccaac acctgctgcc tctaaaaata accctgtccc 300
tggtggatcc cctgcatgcg aagatcttcg aacaaggctg tgggggactg agggcaggct 360
gtaacaggct tgggggccag ggcttatacg tgcctgggac tcccaaagta ttactgttcc 420
atgttcccgg cgaagggcca gctgtccccc gccagctaga ctcagcactt agtttaggaa 480
ccagtgagca agtcagccct tggggcagcc catacaaggc catggggctg ggcaagctgc 540
acgcctgggt ccggggtggg cacggtgccc gggcaacgag ctgaaagctc atctgctctc 600
aggggcccct ccctggggac agcccctcct ggctagtcac accctgtagg ctcctctata 660
taacccaggg gcacaggggc tgccctcatt ctaccaccac ctccacagca cagacagaca 720
ctcaggagcc agccagcgtc gagcggccga tccgccacc 759

<210> SEQ ID NO 6
<211> LENGTH: 67
<212> TYPE: DNA
<213> ORGANISM: Artificial Sequence
<220> FEATURE:
<223> OTHER INFORMATION: Synthetic polyA

<400> SEQUENCE: 6
tgaggagctc gagaggccta ataaagagct cagatgcatc gatcagagtg tgttggtttt 60
ttgtgtg 67

<210> SEQ ID NO 7
<211> LENGTH: 1325
<212> TYPE: PRT
<213> ORGANISM: Artificial Sequence
<220> FEATURE:
<223> OTHER INFORMATION: Dys3978 protein

<400> SEQUENCE: 7

Met Leu Trp Trp Glu Glu Val Glu Asp Cys Tyr Glu Arg Glu Asp Val
1 5 10 15

Gln Lys Lys Thr Phe Thr Lys Trp Val Asn Ala Gln Phe Ser Lys Phe
20 25 30

Gly Lys Gln His Ile Glu Asn Leu Phe Ser Asp Leu Gln Asp Gly Arg
35 40 45

Arg Leu Leu Asp Leu Leu Glu Gly Leu Thr Gly Gln Lys Leu Pro Lys
50 55 60

Glu Lys Gly Ser Thr Arg Val His Ala Leu Asn Asn Val Asn Lys Ala
65 70 75 80

Leu Arg Val Leu Gln Asn Asn Asn Val Asp Leu Val Asn Ile Gly Ser
85 90 95

Thr Asp Ile Val Asp Gly Asn His Lys Leu Thr Leu Gly Leu Ile Trp
100 105 110

Asn Ile Ile Leu His Trp Gln Val Lys Asn Val Met Lys Asn Ile Met
115 120 125

Ala Gly Leu Gln Gln Thr Asn Ser Glu Lys Ile Leu Leu Ser Trp Val
130 135 140

Arg Gln Ser Thr Arg Asn Tyr Pro Gln Val Asn Val Ile Asn Phe Thr
145 150 155 160

-continued

```
Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Gln Pro Asp Leu
545                 550                 555                 560

Ala Pro Gly Leu Thr Thr Ile Gly Ala Ser Pro Thr Gln Thr Val Thr
                565                 570                 575

Leu Val Thr Gln Pro Val Val Thr Lys Glu Thr Ala Ile Ser Lys Leu
```

-continued

```
            580                 585                 590

Glu Met Pro Ser Ser Leu Met Leu Glu Val Pro Thr His Arg Leu Leu
        595                 600                 605

Gln Gln Phe Pro Leu Asp Leu Glu Lys Phe Leu Ala Trp Leu Thr Glu
    610                 615                 620

Ala Glu Thr Thr Ala Asn Val Leu Gln Asp Ala Thr Arg Lys Glu Arg
625                 630                 635                 640

Leu Leu Glu Asp Ser Lys Gly Val Lys Glu Leu Met Lys Gln Trp Gln
                645                 650                 655

Asp Leu Gln Gly Glu Ile Glu Ala His Thr Asp Val Tyr His Asn Leu
            660                 665                 670

Asp Glu Asn Ser Gln Lys Ile Leu Arg Ser Leu Glu Gly Ser Asp Asp
        675                 680                 685

Ala Val Leu Leu Gln Arg Arg Leu Asp Asn Met Asn Phe Lys Trp Ser
    690                 695                 700

Glu Leu Arg Lys Lys Ser Leu Asn Ile Arg Ser His Leu Glu Ala Ser
705                 710                 715                 720

Ser Asp Gln Trp Lys Arg Leu His Leu Ser Leu Gln Glu Leu Leu Val
                725                 730                 735

Trp Leu Gln Leu Lys Asp Asp Glu Leu Ser Arg Gln Ala Pro Ile Gly
            740                 745                 750

Gly Asp Phe Pro Ala Val Gln Lys Gln Asn Asp Val His Arg Ala Phe
        755                 760                 765

Lys Arg Glu Leu Lys Thr Lys Glu Pro Val Ile Met Ser Thr Leu Glu
    770                 775                 780

Thr Val Arg Ile Phe Leu Thr Glu Gln Pro Leu Glu Gly Leu Glu Lys
785                 790                 795                 800

Leu Tyr Gln Glu Pro Arg Glu Leu Pro Pro Glu Glu Arg Ala Gln Asn
                805                 810                 815

Val Thr Arg Leu Leu Arg Lys Gln Ala Glu Glu Val Asn Thr Glu Trp
            820                 825                 830

Glu Lys Leu Asn Leu His Ser Ala Asp Trp Gln Arg Lys Ile Asp Glu
        835                 840                 845

Thr Leu Glu Arg Leu Gln Glu Leu Gln Glu Ala Thr Asp Glu Leu Asp
    850                 855                 860

Leu Lys Leu Arg Gln Ala Glu Val Ile Lys Gly Ser Trp Gln Pro Val
865                 870                 875                 880

Gly Asp Leu Leu Ile Asp Ser Leu Gln Asp His Leu Glu Lys Val Lys
                885                 890                 895

Ala Leu Arg Gly Glu Ile Ala Pro Leu Lys Glu Asn Val Ser His Val
            900                 905                 910

Asn Asp Leu Ala Arg Gln Leu Thr Thr Leu Gly Ile Gln Leu Ser Pro
        915                 920                 925

Tyr Asn Leu Ser Thr Leu Glu Asp Leu Asn Thr Arg Trp Lys Leu Leu
    930                 935                 940

Gln Val Ala Val Glu Asp Arg Val Arg Gln Leu His Glu Ala His Arg
945                 950                 955                 960

Asp Phe Gly Pro Ala Ser Gln His Phe Leu Ser Thr Ser Val Gln Gly
                965                 970                 975

Pro Trp Glu Arg Ala Ile Ser Pro Asn Lys Val Pro Tyr Tyr Ile Asn
            980                 985                 990

His Glu Thr Gln Thr Thr Cys Trp  Asp His Pro Lys Met  Thr Glu Leu
        995                 1000                1005
```

Tyr Gln Ser Leu Ala Asp Leu Asn Asn Val Arg Phe Ser Ala Tyr
1010 1015 1020

Arg Thr Ala Met Lys Leu Arg Arg Leu Gln Lys Ala Leu Cys Leu
1025 1030 1035

Asp Leu Leu Ser Leu Ser Ala Ala Cys Asp Ala Leu Asp Gln His
1040 1045 1050

Asn Leu Lys Gln Asn Asp Gln Pro Met Asp Ile Leu Gln Ile Ile
1055 1060 1065

Asn Cys Leu Thr Thr Ile Tyr Asp Arg Leu Glu Gln Glu His Asn
1070 1075 1080

Asn Leu Val Asn Val Pro Leu Cys Val Asp Met Cys Leu Asn Trp
1085 1090 1095

Leu Leu Asn Val Tyr Asp Thr Gly Arg Thr Gly Arg Ile Arg Val
1100 1105 1110

Leu Ser Phe Lys Thr Gly Ile Ile Ser Leu Cys Lys Ala His Leu
1115 1120 1125

Glu Asp Lys Tyr Arg Tyr Leu Phe Lys Gln Val Ala Ser Ser Thr
1130 1135 1140

Gly Phe Cys Asp Gln Arg Arg Leu Gly Leu Leu Leu His Asp Ser
1145 1150 1155

Ile Gln Ile Pro Arg Gln Leu Gly Glu Val Ala Ser Phe Gly Gly
1160 1165 1170

Ser Asn Ile Glu Pro Ser Val Arg Ser Cys Phe Gln Phe Ala Asn
1175 1180 1185

Asn Lys Pro Glu Ile Glu Ala Ala Leu Phe Leu Asp Trp Met Arg
1190 1195 1200

Leu Glu Pro Gln Ser Met Val Trp Leu Pro Val Leu His Arg Val
1205 1210 1215

Ala Ala Ala Glu Thr Ala Lys His Gln Ala Lys Cys Asn Ile Cys
1220 1225 1230

Lys Glu Cys Pro Ile Ile Gly Phe Arg Tyr Arg Ser Leu Lys His
1235 1240 1245

Phe Asn Tyr Asp Ile Cys Gln Ser Cys Phe Phe Ser Gly Arg Val
1250 1255 1260

Ala Lys Gly His Lys Met His Tyr Pro Met Val Glu Tyr Cys Thr
1265 1270 1275

Pro Thr Thr Ser Gly Glu Asp Val Arg Asp Phe Ala Lys Val Leu
1280 1285 1290

Lys Asn Lys Phe Arg Thr Lys Arg Tyr Phe Ala Lys His Pro Arg
1295 1300 1305

Met Gly Tyr Leu Pro Val Gln Thr Val Leu Glu Gly Asp Asn Met
1310 1315 1320

Glu Thr
1325

<210> SEQ ID NO 8
<211> LENGTH: 1278
<212> TYPE: PRT
<213> ORGANISM: Artificial Sequence
<220> FEATURE:
<223> OTHER INFORMATION: Dys3837 protein

<400> SEQUENCE: 8

Met Leu Trp Trp Glu Glu Val Glu Asp Cys Tyr Glu Arg Glu Asp Val
1 5 10 15

```
Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430
```

-continued

```
Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Thr His Arg Leu
545                 550                 555                 560

Leu Gln Gln Phe Pro Leu Asp Leu Glu Lys Phe Leu Ala Trp Leu Thr
                565                 570                 575

Glu Ala Glu Thr Thr Ala Asn Val Leu Gln Asp Ala Thr Arg Lys Glu
            580                 585                 590

Arg Leu Leu Glu Asp Ser Lys Gly Val Lys Glu Leu Met Lys Gln Trp
        595                 600                 605

Gln Asp Leu Gln Gly Glu Ile Glu Ala His Thr Asp Val Tyr His Asn
    610                 615                 620

Leu Asp Glu Asn Ser Gln Lys Ile Leu Arg Ser Leu Glu Gly Ser Asp
625                 630                 635                 640

Asp Ala Val Leu Leu Gln Arg Arg Leu Asp Asn Met Asn Phe Lys Trp
                645                 650                 655

Ser Glu Leu Arg Lys Lys Ser Leu Asn Ile Arg Ser His Leu Glu Ala
            660                 665                 670

Ser Ser Asp Gln Trp Lys Arg Leu His Leu Ser Leu Gln Glu Leu Leu
        675                 680                 685

Val Trp Leu Gln Leu Lys Asp Asp Glu Leu Ser Arg Gln Ala Pro Ile
    690                 695                 700

Gly Gly Asp Phe Pro Ala Val Gln Lys Gln Asn Asp Val His Arg Ala
705                 710                 715                 720

Phe Lys Arg Glu Leu Lys Thr Lys Glu Pro Val Ile Met Ser Thr Leu
                725                 730                 735

Glu Thr Val Arg Ile Phe Leu Thr Glu Gln Pro Leu Glu Gly Leu Glu
            740                 745                 750

Lys Leu Tyr Gln Glu Pro Arg Glu Leu Pro Pro Glu Glu Arg Ala Gln
        755                 760                 765

Asn Val Thr Arg Leu Leu Arg Lys Gln Ala Glu Glu Val Asn Thr Glu
    770                 775                 780

Trp Glu Lys Leu Asn Leu His Ser Ala Asp Trp Gln Arg Lys Ile Asp
785                 790                 795                 800

Glu Thr Leu Glu Arg Leu Gln Glu Leu Gln Glu Ala Thr Asp Glu Leu
                805                 810                 815

Asp Leu Lys Leu Arg Gln Ala Glu Val Ile Lys Gly Ser Trp Gln Pro
            820                 825                 830

Val Gly Asp Leu Leu Ile Asp Ser Leu Gln Asp His Leu Glu Lys Val
        835                 840                 845

Lys Ala Leu Arg Gly Glu Ile Ala Pro Leu Lys Glu Asn Val Ser His
```

```
    850                 855                 860

Val Asn Asp Leu Ala Arg Gln Leu Thr Thr Leu Gly Ile Gln Leu Ser
865                 870                 875                 880

Pro Tyr Asn Leu Ser Thr Leu Glu Asp Leu Asn Thr Arg Trp Lys Leu
                885                 890                 895

Leu Gln Val Ala Val Glu Asp Arg Val Arg Gln Leu His Glu Ala His
            900                 905                 910

Arg Asp Phe Gly Pro Ala Ser Gln His Phe Leu Ser Thr Ser Val Gln
        915                 920                 925

Gly Pro Trp Glu Arg Ala Ile Ser Pro Asn Lys Val Pro Tyr Tyr Ile
    930                 935                 940

Asn His Glu Thr Gln Thr Thr Cys Trp Asp His Pro Lys Met Thr Glu
945                 950                 955                 960

Leu Tyr Gln Ser Leu Ala Asp Leu Asn Asn Val Arg Phe Ser Ala Tyr
                965                 970                 975

Arg Thr Ala Met Lys Leu Arg Arg Leu Gln Lys Ala Leu Cys Leu Asp
            980                 985                 990

Leu Leu Ser Leu Ser Ala Ala Cys  Asp Ala Leu Asp Gln  His Asn Leu
        995                 1000                1005

Lys Gln  Asn Asp Gln Pro Met  Asp Ile Leu Gln Ile  Ile Asn Cys
    1010                1015                1020

Leu Thr  Thr Ile Tyr Asp Arg  Leu Glu Gln Glu His  Asn Asn Leu
    1025                1030                1035

Val Asn  Val Pro Leu Cys Val  Asp Met Cys Leu Asn  Trp Leu Leu
    1040                1045                1050

Asn Val  Tyr Asp Thr Gly Arg  Thr Gly Arg Ile Arg  Val Leu Ser
    1055                1060                1065

Phe Lys  Thr Gly Ile Ile Ser  Leu Cys Lys Ala His  Leu Glu Asp
    1070                1075                1080

Lys Tyr  Arg Tyr Leu Phe Lys  Gln Val Ala Ser Ser  Thr Gly Phe
    1085                1090                1095

Cys Asp  Gln Arg Arg Leu Gly  Leu Leu Leu His Asp  Ser Ile Gln
    1100                1105                1110

Ile Pro  Arg Gln Leu Gly Glu  Val Ala Ser Phe Gly  Gly Ser Asn
    1115                1120                1125

Ile Glu  Pro Ser Val Arg Ser  Cys Phe Gln Phe Ala  Asn Asn Lys
    1130                1135                1140

Pro Glu  Ile Glu Ala Ala Leu  Phe Leu Asp Trp Met  Arg Leu Glu
    1145                1150                1155

Pro Gln  Ser Met Val Trp Leu  Pro Val Leu His Arg  Val Ala Ala
    1160                1165                1170

Ala Glu  Thr Ala Lys His Gln  Ala Lys Cys Asn Ile  Cys Lys Glu
    1175                1180                1185

Cys Pro  Ile Ile Gly Phe Arg  Tyr Arg Ser Leu Lys  His Phe Asn
    1190                1195                1200

Tyr Asp  Ile Cys Gln Ser Cys  Phe Phe Ser Gly Arg  Val Ala Lys
    1205                1210                1215

Gly His  Lys Met His Tyr Pro  Met Val Glu Tyr Cys  Thr Pro Thr
    1220                1225                1230

Thr Ser  Gly Glu Asp Val Arg  Asp Phe Ala Lys Val  Leu Lys Asn
    1235                1240                1245

Lys Phe  Arg Thr Lys Arg Tyr  Phe Ala Lys His Pro  Arg Met Gly
    1250                1255                1260
```

Tyr Leu Pro Val Gln Thr Val Leu Glu Gly Asp Asn Met Glu Thr
1265 1270 1275

<210> SEQ ID NO 9
<211> LENGTH: 4953
<212> TYPE: DNA
<213> ORGANISM: Artificial Sequence
<220> FEATURE:
<223> OTHER INFORMATION: AAV vector genome with Hopti-Dys3978 gene

<400> SEQUENCE: 9
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tgaattcggt accccactac gggtttaggc 180
tgcccatgta aggaggcaag gcctggggac acccgagatg cctggttata attaacccag 240
acatgtggct gccccccccc cccccaacac ctgctgcctc taaaaataac cctgtccctg 300
gtggatcccc tgcatgcgaa gatcttcgaa caaggctgtg ggggactgag ggcaggctgt 360
aacaggcttg ggggccaggg cttatacgtg cctgggactc ccaaagtatt actgttccat 420
gttcccggcg aagggccagc tgtcccccgc cagctagact cagcacttag tttaggaacc 480
agtgagcaag tcagcccttg gggcagccca tacaaggcca tggggctggg caagctgcac 540
gcctgggtcc ggggtgggca cggtgcccgg gcaacgagct gaaagctcat ctgctctcag 600
gggcccctcc ctggggacag cccctcctgg ctagtcacac cctgtaggct cctctatata 660
acccaggggc acaggggctg ccctcattct accaccacct ccacagcaca gacagacact 720
caggagccag ccagcgtcga gcggccgatc cgccaccatg ctttggtggg aggaagtgga 780
ggactgctac gagagagagg acgtgcagaa gaaaaccttc accaagtggg tgaacgccca 840
gttcagcaag ttcggcaagc agcacatcga gaacctgttc agcgacctgc aggatggcag 900
gagactgctg gacctgctgg agggcctgac cggccagaag ctgcccaagg agaagggcag 960
caccagagtg cacgccctga acaacgtgaa caaggccctg agagtgctgc agaacaacaa 1020
cgtggacctg gtgaacatcg gcagcaccga catcgtggac ggcaaccaca agctgaccct 1080
gggcctgatc tggaacatca tcctgcactg gcaggtgaag aacgtgatga agaacatcat 1140
ggccggcctg cagcagacca acagcgagaa gatcctgctg agctgggtga ggcagagcac 1200
cagaaactac ccccaggtga acgtgatcaa cttcaccacc tcctggagcg acggcctggc 1260
cctgaacgcc ctgatccaca gccacagacc cgacctgttc gactggaaca gcgtggtgtg 1320
tcagcagagc gccacccaga gactggagca cgccttcaac atcgccagat accagctggg 1380
catcgagaag ctgctggacc ccgaggacgt ggacaccacc taccccgaca agaaaagcat 1440
cctcatgtac attaccagcc tgttccaggt gctgccccag caggtgtcca tcgaggccat 1500
ccaggaagtg gaaatgctgc ccaggccccc caaagtgacc aaggaggagc acttccagct 1560
gcaccaccag atgcactaca gccagcagat cacagtgagc ctggcccagg gctatgagag 1620
aaccagcagc cccaagccca gattcaagag ctacgcctac acccaggccg cctacgtgac 1680
cacctccgac cccaccagaa gccccttccc cagccagcac ctggaggccc ccgaggacaa 1740
gagcttcggc agcagcctga tggagagcga agtgaacctg gacagatacc agaccgccct 1800
ggaggaagtg ctgtcctggc tgctgagcgc cgaggacacc ctgcaggccc agggcgagat 1860
cagcaacgac gtggaagtgg tgaaggacca gttccacacc cacgagggct acatgatgga 1920
tctgaccgcc caccagggca gagtgggcaa tatcctgcag ctgggcagca agctgatcgg 1980
caccggcaag ctgagcgagg acgaggagac cgaagtgcag gagcagatga acctgctgaa 2040
cagcagatgg gagtgcctga gagtggccag catggagaag cagagcaacc tgcacagagt 2100
gctgatggac ctgcagaacc agaagctgaa ggagctgaac gactggctga ccaagaccga 2160
ggagcggacc agaaagatgg aggaggagcc cctgggcccc gacctggagg acctgaagag 2220
acaggtgcag cagcacaaag tgctgcagga ggacctggag caggagcagg tgcgcgtgaa 2280
cagcctgacc cacatggtgg tggtcgtgga cgagagcagc ggcgaccacg ccacagccgc 2340
cctggaagag cagctgaaag tgctgggcga cagatgggcc aatatttgta ggtggaccga 2400
ggacagatgg gtgctgctgc aggaccagcc cgacctggcc cctggcctga ccaccatcgg 2460
cgccagcccc acccagaccg tgaccctggt gacccagccc gtggtgacaa aggagaccgc 2520
catcagcaag ctggagatgc ccagctccct gatgctggaa gtgcccaccc accgcctgct 2580
ccagcagttc cccctggacc tggagaagtt cctggcctgg ctgaccgagg ccgaaaccac 2640
cgccaatgtg ctccaggacg ccactagaaa ggagaggctg ctggaggaca gcaagggcgt 2700
gaaagagctg atgaagcagt ggcaggatct gcagggcgaa atcgaggccc acaccgacgt 2760
gtaccacaac ctggacgaga acagccagaa gattctgagg agcctggagg gcagcgacga 2820
cgccgtcctg ctccagagga ggctggacaa catgaacttc aagtggagcg agctgcggaa 2880
gaagagcctg aacatccgga gccacctgga agccagcagc gaccagtgga agagactgca 2940
cctgagcctg caggagctgc tggtgtggct gcagctgaag gacgacgagc tgagcagaca 3000
ggcccccatc ggcggcgact tccccgccgt gcagaagcag aacgacgtgc accgggcctt 3060
caagagggag ctgaaaacca aggaacccgt gatcatgagc accctggaga cagtgcggat 3120
cttcctgacc gagcagcccc tggagggact ggagaagctg taccaggagc ccagagagct 3180
gcccccccgag gagagagccc agaacgtgac caggctgctg agaaagcagg ccgaggaagt 3240
gaataccgag tgggagaagc tgaatctgca cagcgccgac tggcagagaa agatcgacga 3300
gaccctggag agactccagg aactgcagga agccaccgac gagctggacc tgaagctgag 3360
acaggccgaa gtgatcaagg gcagctggca gcctgtgggc gatctgctga tcgactccct 3420
gcaggatcac ctggagaaag tgaaggccct gcggggcgag atcgcccccc tgaaggagaa 3480
tgtgagccac gtgaacgacc tggccagaca gctgaccacc ctgggcatcc agctgagccc 3540
ctacaacctg agcacactgg aggatctgaa cacccggtgg aaactgctgc aggtggccgt 3600
ggaggataga gtgaggcagc tgcacgaagc ccacagagac ttcggccctg cctcccagca 3660
cttcctgagc accagcgtgc agggcccctg ggagagagcc atctccccca acaaagtgcc 3720
ctactacatc aaccacgaga cccagaccac ctgctgggac caccctaaga tgaccgagct 3780
gtatcagagc ctggccgacc tgaacaatgt gcggttcagc gcctacagaa ccgccatgaa 3840
gctgcggaga ctgcagaagg ccctgtgcct ggatctgctg agcctgagcg ccgcctgcga 3900
cgccctggac cagcacaacc tgaagcagaa tgaccagccc atggacatcc tgcagatcat 3960
caactgcctg accacaatct acgaccggct ggaacaggag cacaacaacc tggtgaatgt 4020
gcccctgtgc gtggacatgt gcctgaattg gctgctgaac gtgtacgaca ccggcaggac 4080
cggcagaatc cgcgtgctga gcttcaagac cggcatcatc agcctgtgca aggcccacct 4140
ggaggataag taccgctacc tgttcaagca ggtggccagc agcaccggct tctgcgatca 4200
gaggagactg ggcctgctgc tgcacgatag catccagatc cctaggcagc tgggcgaagt 4260
ggccagcttt ggcggcagca acatcgagcc ctctgtgagg agctgcttcc agttcgccaa 4320
caacaagccc gagatcgagg ccgccctgtt cctggactgg atgaggctgg agcctcagag 4380
catggtgtgg ctgcctgtgc tgcacagagt ggccgccgcc gagaccgcca agcaccaggc 4440
caagtgcaat atctgcaagg agtgccccat catcggcttc cggtacagga gcctgaagca 4500
cttcaactac gacatctgcc agagctgctt tttcagcggc agagtggcca agggccacaa 4560
aatgcactac cccatggtgg agtactgcac ccccaccacc tccggcgagg atgtgagaga 4620
cttcgccaaa gtgctgaaga ataagttccg gaccaagcgg tactttgcca agcaccccag 4680
gatgggctac ctgcccgtgc agaccgtgct ggaaggcgac aacatggaga cctgatgagg 4740
agctcgagag gcctaataaa gagctcagat gcatcgatca gagtgtgttg gtttttgtg 4800 tgagatctag gaacccctag tgatggagtt ggccactccc tctctgcgcg ctcgctcgct 4860
cactgaggcc gcccgggcaa agcccgggcg tcgggcgacc tttggtcgcc cggcctcagt 4920
gagcgagcga gcgcgcagag agggagtggc caa 4953

<210> SEQ ID NO 10
<211> LENGTH: 4812
<212> TYPE: DNA
<213> ORGANISM: Artificial Sequence
<220> FEATURE:
<223> OTHER INFORMATION: AAV vector genome with Hopti-Dys3837 gene

<400> SEQUENCE: 10
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tgaattcggt accccactac gggtttaggc 180
tgcccatgta aggaggcaag gcctggggac acccgagatg cctggttata attaacccag 240
acatgtggct gccccccccc cccccaacac ctgctgcctc taaaaataac cctgtccctg 300
gtggatcccc tgcatgcgaa gatcttcgaa caaggctgtg gggactgag ggcaggctgt 360 aacaggcttg ggggccaggg cttatacgtg cctgggactc ccaaagtatt actgttccat 420
gttcccggcg aagggccagc tgtcccccgc cagctagact cagcacttag tttaggaacc 480
agtgagcaag tcagcccttg gggcagccca tacaaggcca tggggctggg caagctgcac 540
gcctgggtcc ggggtgggca cggtgcccgg gcaacgagct gaaagctcat ctgctctcag 600
gggcccctcc ctggggacag cccctcctgg ctagtcacac cctgtaggct cctctatata 660
acccaggggc acaggggctg ccctcattct accaccacct ccacagcaca gacagacact 720
caggagccag ccagcgtcga gcggccgatc cgccaccatg ctttggtggg aggaagtgga 780
ggactgctac gagagagagg acgtgcagaa gaaaaccttc accaagtggg tgaacgccca 840
gttcagcaag ttcggcaagc agcacatcga gaacctgttc agcgacctgc aggatggcag 900
gagactgctg gacctgctgg agggcctgac cggccagaag ctgcccaagg agaagggcag 960
caccagagtg cacgccctga acaacgtgaa caaggccctg agagtgctgc agaacaacaa 1020
cgtggacctg gtgaacatcg gcagcaccga catcgtggac ggcaaccaca agctgaccct 1080
gggcctgatc tggaacatca tcctgcactg gcaggtgaag aacgtgatga agaacatcat 1140
ggccggcctg cagcagacca acagcgagaa gatcctgctg agctgggtga ggcagagcac 1200
cagaaactac ccccaggtga acgtgatcaa cttcaccacc tcctggagcg acggcctggc 1260
cctgaacgcc ctgatccaca gccacagacc cgacctgttc gactggaaca gcgtggtgtg 1320
tcagcagagc gccacccaga gactggagca cgccttcaac atcgccagat accagctggg 1380
catcgagaag ctgctggacc ccgaggacgt ggacaccacc taccccgaca agaaaagcat 1440

-continued

```
cctcatgtac attaccagcc tgttccaggt gctgccccag caggtgtcca tcgaggccat   1500
ccaggaagtg gaaatgctgc ccaggccccc caaagtgacc aaggaggagc acttccagct   1560
gcaccaccag atgcactaca gccagcagat cacagtgagc ctggcccagg gctatgagag   1620
aaccagcagc cccaagccca gattcaagag ctacgcctac acccaggccg cctacgtgac   1680
cacctccgac cccaccagaa gccccttccc cagccagcac ctggaggccc ccgaggacaa   1740
gagcttcggc agcagcctga tggagagcga agtgaacctg gacagatacc agaccgccct   1800
ggaggaagtg ctgtcctggc tgctgagcgc cgaggacacc ctgcaggccc agggcgagat   1860
cagcaacgac gtggaagtgg tgaaggacca gttccacacc cacgagggct acatgatgga   1920
tctgaccgcc caccagggca gagtgggcaa tatcctgcag ctgggcagca agctgatcgg   1980
caccggcaag ctgagcgagg acgaggagac cgaagtgcag gagcagatga acctgctgaa   2040
cagcagatgg gagtgcctga gagtggccag catggagaag cagagcaacc tgcacagagt   2100
gctgatggac ctgcagaacc agaagctgaa ggagctgaac gactggctga ccaagaccga   2160
ggagcggacc agaaagatgg aggaggagcc cctgggcccc gacctggagg acctgaagag   2220
acaggtgcag cagcacaaag tgctgcagga ggacctggag caggagcagg tgcgcgtgaa   2280
cagcctgacc cacatggtgg tggtcgtgga cgagagcagc ggcgaccacg ccacagccgc   2340
cctggaagag cagctgaaag tgctgggcga cagatgggcc aatatttgta ggtggaccga   2400
ggacagatgg gtgctgctgc aggacaccca ccgcctgctc cagcagttcc ccctggacct   2460
ggagaagttc ctggcctggc tgaccgaggc cgaaaccacc gccaatgtgc tccaggacgc   2520
cactagaaag gagaggctgc tggaggacag caagggcgtg aaagagctga tgaagcagtg   2580
gcaggatctg cagggcgaaa tcgaggccca caccgacgtg taccacaacc tggacgagaa   2640
cagccagaag attctgagga gcctggaggg cagcgacgac gccgtcctgc tccagaggag   2700
gctggacaac atgaacttca agtggagcga gctgcggaag aagagcctga acatccggag   2760
ccacctggaa gccagcagcg accagtggaa gagactgcac ctgagcctgc aggagctgct   2820
ggtgtggctg cagctgaagg acgacgagct gagcagacag gcccccatcg gcggcgactt   2880
ccccgccgtg cagaagcaga acgacgtgca ccgggccttc aagagggagc tgaaaaccaa   2940
ggaacccgtg atcatgagca ccctggagac agtgcggatc ttcctgaccg agcagcccct   3000
ggagggactg gagaagctgt accaggagcc cagagagctg ccccccgagg agagagccca   3060
gaacgtgacc aggctgctga gaaagcaggc cgaggaagtg aataccgagt gggagaagct   3120
gaatctgcac agcgccgact ggcagagaaa gatcgacgag accctggaga gactccagga   3180
actgcaggaa gccaccgacg agctggacct gaagctgaga caggccgaag tgatcaaggg   3240
cagctggcag cctgtgggcg atctgctgat cgactccctg caggatcacc tggagaaagt   3300
gaaggccctg cggggcgaga tcgcccccct gaaggagaat gtgagccacg tgaacgacct   3360
ggccagacag ctgaccaccc tgggcatcca gctgagcccc tacaacctga gcacactgga   3420
ggatctgaac acccggtgga aactgctgca ggtggccgtg gaggatagag tgaggcagct   3480
gcacgaagcc cacagagact tcggccctgc ctcccagcac ttcctgagca ccagcgtgca   3540
gggcccctgg gagagagcca tctcccccaa caaagtgccc tactacatca accacgagac   3600
ccagaccacc tgctgggacc accctaagat gaccgagctg tatcagagcc tggccgacct   3660
gaacaatgtg cggttcagcg cctacagaac cgccatgaag ctgcggagac tgcagaaggc   3720
cctgtgcctg gatctgctga gcctgagcgc cgcctgcgac gccctggacc agcacaacct   3780
```

gaagcagaat gaccagccca tggacatcct gcagatcatc aactgcctga ccacaatcta 3840
cgaccggctg gaacaggagc acaacaacct ggtgaatgtg cccctgtgcg tggacatgtg 3900
cctgaattgg ctgctgaacg tgtacgacac cggcaggacc ggcagaatcc gcgtgctgag 3960
cttcaagacc ggcatcatca gcctgtgcaa ggcccacctg gaggataagt accgctacct 4020
gttcaagcag gtggccagca gcaccggctt ctgcgatcag aggagactgg gcctgctgct 4080
gcacgatagc atccagatcc ctaggcagct gggcgaagtg gccagctttg gcggcagcaa 4140
catcgagccc tctgtgagga gctgcttcca gttcgccaac aacaagcccg agatcgaggc 4200
cgccctgttc ctggactgga tgaggctgga gcctcagagc atggtgtggc tgcctgtgct 4260
gcacagagtg gccgccgccg agaccgccaa gcaccaggcc aagtgcaata tctgcaagga 4320
gtgccccatc atcggcttcc ggtacaggag cctgaagcac ttcaactacg acatctgcca 4380
gagctgcttt ttcagcggca gagtggccaa gggccacaaa atgcactacc ccatggtgga 4440
gtactgcacc cccaccacct ccggcgagga tgtgagagac ttcgccaaag tgctgaagaa 4500
taagttccgg accaagcggt actttgccaa gcaccccagg atgggctacc tgcccgtgca 4560
gaccgtgctg gaaggcgaca acatggagac ctgatgagga gctcgagagg cctaataaag 4620
agctcagatg catcgatcag agtgtgttgg ttttttgtgt gagatctagg aacccctagt 4680
gatggagttg gccactccct ctctgcgcgc tcgctcgctc actgaggccg cccgggcaaa 4740
gcccgggcgt cgggcgacct ttggtcgccc ggcctcagtg agcgagcgag cgcgcagaga 4800
gggagtggcc aa 4812

<210> SEQ ID NO 11
<211> LENGTH: 4965
<212> TYPE: DNA
<213> ORGANISM: Artificial Sequence
<220> FEATURE:
<223> OTHER INFORMATION: AAV vector genome with Hopti-Dys3837 gene

<400> SEQUENCE: 11
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctagatc tgaattcggt accccactac gggtctaggc 180
tgcccatgta aggaggcaag gcctggggac acccgagatg cctggttata attaacccca 240
acacctgctg cccccccccc cccaacacct gctgcctcta aaaataaccc tgtccctggt 300
ggatcccctg catgccccac tacgggttta ggctgcccat gtaaggaggc aaggcctggg 360
gacacccgag atgcctggtt ataattaacc cagacatgtg gctgcccccc cccccccaa 420 cacctgctgc ctctaaaaat aaccctgtcc ctggtggatc ccctgcatgc gaagatcttc 480
gaacaaggct gtgggggact gagggcaggc tgtaacaggc ttgggggcca gggcttatac 540
gtgcctggga ctcccaaagt attactgttc catgttcccg gcgaagggcc agctgtcccc 600
cgccagctag actcagcact tagtttagga accagtgagc aagtcagccc ttggggcagc 660
ccatacaagg ccatggggct gggcaagctg cacgcctggg tccggggtgg gcacggtgcc 720
cgggcaacga gctgaaagct catctgctct caggggcccc tccctgggga cagcccctcc 780
tggctagtca caccctgtag gctcctctat ataacccagg ggcacagggg ctgccctcat 840
tctaccacca cctccacagc acagacagac actcaggagc cagccagcgt cgagcggccg 900
atccgccacc atgctttggt gggaggaagt ggaggactgc tacgagagag aggacgtgca 960
gaagaaaacc ttcaccaagt gggtgaacgc ccagttcagc aagttcggca agcagcacat 1020

-continued

```
cgagaacctg ttcagcgacc tgcaggatgg caggagactg ctggacctgc tggagggcct   1080
gaccggccag aagctgccca aggagaaggg cagcaccaga gtgcacgccc tgaacaacgt   1140
gaacaaggcc ctgagagtgc tgcagaacaa caacgtggac ctggtgaaca tcggcagcac   1200
cgacatcgtg gacggcaacc acaagctgac cctgggcctg atctggaaca tcatcctgca   1260
ctggcaggtg aagaacgtga tgaagaacat catggccggc ctgcagcaga ccaacagcga   1320
gaagatcctg ctgagctggg tgaggcagag caccagaaac tacccccagg tgaacgtgat   1380
caacttcacc acctcctgga gcgacggcct ggccctgaac gccctgatcc acagccacag   1440
acccgacctg ttcgactgga acagcgtggt gtgtcagcag agcgccaccc agagactgga   1500
gcacgccttc aacatcgcca gataccagct gggcatcgag aagctgctgg accccgagga   1560
cgtggacacc acctaccccg acaagaaaag catcctcatg tacattacca gcctgttcca   1620
ggtgctgccc cagcaggtgt ccatcgaggc catccaggaa gtggaaatgc tgcccaggcc   1680
ccccaaagtg accaaggagg agcacttcca gctgcaccac cagatgcact acagccagca   1740
gatcacagtg agcctggccc agggctatga gagaaccagc agccccaagc ccagattcaa   1800
gagctacgcc tacacccagg ccgcctacgt gaccacctcc gaccccacca gaagcccctt   1860
ccccagccag cacctggagg cccccgagga caagagcttc ggcagcagcc tgatggagag   1920
cgaagtgaac ctggacagat accagaccgc cctggaggaa gtgctgtcct ggctgctgag   1980
cgccgaggac accctgcagg cccagggcga gatcagcaac gacgtggaag tggtgaagga   2040
ccagttccac acccacgagg gctacatgat ggatctgacc gcccaccagg gcagagtggg   2100
caatatcctg cagctgggca gcaagctgat cggcaccggc aagctgagcg aggacgagga   2160
gaccgaagtg caggagcaga tgaacctgct gaacagcaga tgggagtgcc tgagagtggc   2220
cagcatggag aagcagagca acctgcacag agtgctgatg gacctgcaga accagaagct   2280
gaaggagctg aacgactggc tgaccaagac cgaggagcgg accagaaaga tggaggagga   2340
gcccctgggc cccgacctgg aggacctgaa gagacaggtg cagcagcaca aagtgctgca   2400
ggaggacctg gagcaggagc aggtgcgcgt gaacagcctg acccacatgg tggtggtcgt   2460
ggacgagagc agcggcgacc acgccacagc cgccctggaa gagcagctga aagtgctggg   2520
cgacagatgg gccaatattt gtaggtggac cgaggacaga tgggtgctgc tgcaggacac   2580
ccaccgcctg ctccagcagt tcccccctgga cctggagaag ttcctggcct ggctgaccga   2640
ggccgaaacc accgccaatg tgctccagga cgccactaga aaggagaggc tgctggagga   2700
cagcaagggc gtgaaagagc tgatgaagca gtggcaggat ctgcagggcg aaatcgaggc   2760
ccacaccgac gtgtaccaca acctggacga gaacagccag aagattctga ggagcctgga   2820
gggcagcgac gacgccgtcc tgctccagag gaggctggac aacatgaact tcaagtggag   2880
cgagctgcgg aagaagagcc tgaacatccg gagccacctg gaagccagca gcgaccagtg   2940
gaagagactg cacctgagcc tgcaggagct gctggtgtgg ctgcagctga aggacgacga   3000
gctgagcaga caggccccca tcggcggcga cttccccgcc gtgcagaagc agaacgacgt   3060
gcaccgggcc ttcaagaggg agctgaaaac caaggaaccc gtgatcatga gcaccctgga   3120
gacagtgcgg atcttcctga ccgagcagcc cctggaggga ctggagaagc tgtaccagga   3180
gcccagagag ctgccccccg aggagagagc ccagaacgtg accaggctgc tgagaaagca   3240
ggccgaggaa gtgaataccg agtgggagaa gctgaatctg cacagcgccg actggcagag   3300
aaagatcgac gagaccctgg agagactcca ggaactgcag gaagccaccg acgagctgga   3360
```

```
cctgaagctg agacaggccg aagtgatcaa gggcagctgg cagcctgtgg gcgatctgct   3420

gatcgactcc ctgcaggatc acctggagaa agtgaaggcc ctgcggggcg agatcgcccc   3480

cctgaaggag aatgtgagcc acgtgaacga cctggccaga cagctgacca ccctgggcat   3540

ccagctgagc ccctacaacc tgagcacact ggaggatctg aacacccggt ggaaactgct   3600

gcaggtggcc gtggaggata gagtgaggca gctgcacgaa gcccacagag acttcggccc   3660

tgcctcccag cacttcctga gcaccagcgt gcagggcccc tgggagagag ccatctcccc   3720

caacaaagtg ccctactaca tcaaccacga gacccagacc acctgctggg accaccctaa   3780

gatgaccgag ctgtatcaga gcctggccga cctgaacaat gtgcggttca gcgcctacag   3840

aaccgccatg aagctgcgga gactgcagaa ggccctgtgc ctggatctgc tgagcctgag   3900

cgccgcctgc gacgccctgg accagcacaa cctgaagcag aatgaccagc ccatggacat   3960

cctgcagatc atcaactgcc tgaccacaat ctacgaccgg ctggaacagg agcacaacaa   4020

cctggtgaat gtgcccctgt gcgtggacat gtgcctgaat tggctgctga acgtgtacga   4080

caccggcagg accggcagaa tccgcgtgct gagcttcaag accggcatca tcagcctgtg   4140

caaggcccac ctggaggata agtaccgcta cctgttcaag caggtggcca gcagcaccgg   4200

cttctgcgat cagaggagac tgggcctgct gctgcacgat agcatccaga tccctaggca   4260

gctgggcgaa gtggccagct ttggcggcag caacatcgag ccctctgtga ggagctgctt   4320

ccagttcgcc aacaacaagc ccgagatcga ggccgccctg ttcctggact ggatgaggct   4380

ggagcctcag agcatggtgt ggctgcctgt gctgcacaga gtggccgccg ccgagaccgc   4440

caagcaccag gccaagtgca atatctgcaa ggagtgcccc atcatcggct tccggtacag   4500

gagcctgaag cacttcaact acgacatctg ccagagctgc tttttcagcg gcagagtggc   4560

caagggccac aaaatgcact accccatggt ggagtactgc acccccacca cctccggcga   4620

ggatgtgaga gacttcgcca aagtgctgaa gaataagttc cggaccaagc ggtactttgc   4680

caagcacccc aggatgggct acctgcccgt gcagaccgtg ctggaaggcg acaacatgga   4740

gacctgatga ggagctcgag aggcctaata aagagctcag atgcatcgat cagagtgtgt   4800

tggtttttttg tgtgagatct aggaacccct agtgatggag ttggccactc cctctctgcg   4860

cgctcgctcg ctcactgagg ccgcccgggc aaagcccggg cgtcgggcga cctttggtcg   4920

cccggcctca gtgagcgagc gagcgcgcag agagggagtg gccaa                4965
```

<210> SEQ ID NO 12
<211> LENGTH: 4955
<212> TYPE: DNA
<213> ORGANISM: Artificial Sequence
<220> FEATURE:
<223> OTHER INFORMATION: AAV vector genome with Copti-Dys3978 gene

<400> SEQUENCE: 12

```
ttggccactc cctctctgcg cgctcgctcg ctcactgagg ccgggcgacc aaaggtcgcc     60

cgacgcccgg gctttgcccg ggcggcctca gtgagcgagc gagcgcgcag agagggagtg    120

gccaactcca tcactagggg ttcctcagat ctgaattcgg taccccacta cgggtttagg    180

ctgcccatgt aaggaggcaa ggcctgggga cacccgagat gcctggttat aattaaccca    240

gacatgtggc tgcccccccc ccccccaaca cctgctgcct ctaaaaataa ccctgtccct    300

ggtggatccc ctgcatgcga agatcttcga acaaggctgt gggggactga gggcaggctg    360

taacaggctt gggggccagg gcttatacgt gcctgggact cccaaagtat tactgttcca    420

tgttcccggc gaagggccag ctgtccccccg ccagctagac tcagcactta gtttaggaac    480
```

cagtgagcaa gtcagccctt ggggcagccc atacaaggcc atggggctgg gcaagctgca 540
cgcctgggtc cggggtgggc acggtgcccg ggcaacgagc tgaaagctca tctgctctca 600
ggggcccctc cctggggaca gcccctcctg gctagtcaca ccctgtaggc tcctctatat 660
aacccagggg cacaggggct gccctcattc taccaccacc tccacagcac agacagacac 720
tcaggagcca gccagcgtcg agcggccgcc accatgcttt ggtgggagga agtggaggac 780
tgctacgagc gggaggacgt gcagaagaaa accttcacca agtgggtgaa cgcccagttc 840
agcaagttcg gcaagcagca catcgagaac ctgttcagcg acctgcagga cggcaggcgg 900
ctgctggacc tcctggaagg cctgaccggc cagaagctgc ccaaagagaa gggcagcacc 960
agggtgcacg ccctgaacaa cgtgaacaag gccctgaggg tgctgcagaa caacaacgtg 1020
gacctggtga acatcggcag caccgacatc gtggacggca accacaagct gaccctgggc 1080
ctgatctgga acatcatcct gcactggcag gtcaagaacg tgatgaagaa catcatggcc 1140
ggcctgcagc agaccaacag cgagaagatc ctgctgtcct gggtgcggca gagcaccagg 1200
aactacccc aggtcaacgt gatcaacttc accacctctt ggagcgacgg cctggccctg 1260
aacgccctga tccacagcca caggcccgac ctgttcgact ggaacagcgt ggtgtgccag 1320
cagagcgcca cccagaggct ggaacacgcc ttcaacatcg ccagatacca gctgggcatc 1380
gagaagctgc tggatcccga ggacgtggac accacctacc ccgacaagaa aagcatcctc 1440
atgtacatca ccagcctgtt ccaggtgctg ccccagcagg tgtccatcga ggccatccag 1500
gaagtggaga tgctgcccag gcccccccaag gtcaccaaag aggaacactt ccagctgcac 1560
caccagatgc actacagcca gcagatcacc gtgagcctgg cccagggcta cgagaggacc 1620
agcagcccca agcccaggtt caagagctac gcctacaccc aggccgccta cgtgaccacc 1680
tccgacccca ccaggtcccc cttccccagc cagcatctcg aagcccccga ggacaagagc 1740
ttcggcagca gcctgatgga aagcgaggtg aacctggaca gataccagac cgccctggaa 1800
gaagtgctgt cttggctgct gtccgccgag gacaccctgc aggcccaggg cgagatcagc 1860
aacgacgtgg aggtcgtgaa ggaccagttc cacacccacg agggctacat gatggacctg 1920
accgcccacc agggcagagt gggcaacatc ctgcagctgg gcagcaagct gatcggcacc 1980
ggcaagctgt ccgaggacga ggaaaccgag gtgcaggaac agatgaacct gctgaacagc 2040
agatgggagt gcctgagggt ggccagcatg gaaaagcaga gcaacctgca cagggtgctg 2100
atggatctgc agaaccagaa gctcaaagag ctgaacgact ggctgaccaa gaccgaggaa 2160
aggacccgga agatggaaga ggaacccctg ggccccgatc tcgaagatct gaagaggcag 2220
gtgcagcagc acaaggtgct gcaggaagat ctcgaacagg aacaggtccg ggtcaacagc 2280
ctgacccaca tggtcgtggt ggtggacgag agcagcggcg accacgccac cgctgccctg 2340
gaagagcagc tgaaggtgct gggcgacaga tgggccaaca tctgccggtg gaccgaggac 2400
agatgggtcc tcctgcagga ccagcccgac ctggcccctg gcctgacaac catcggcgcc 2460
agccccaccc agaccgtgac cctggtgacc cagcccgtgg tgaccaaaga gaccgccatc 2520
agcaagctgg aaatgcccag ctccctgatg ctggaagtgc ccacccacag gctcctccag 2580
cagttccccc tggacctgga aaagttcctg gcctggctga ccgaggccga gaccaccgcc 2640
aacgtgctgc aggacgccac caggaaagag aggctgctgg aagatagcaa gggcgtgaaa 2700
gagctgatga agcagtggca ggacctgcag ggggagattg aggcccacac cgacgtgtac 2760
cacaacctgg acgagaacag ccagaaaatc ctgagaagcc tggaaggcag cgacgacgcc 2820

-continued gtgctgctgc agaggcggct ggacaacatg aacttcaagt ggagcgagct gaggaagaag 2880
agcctgaaca tcaggtccca tctggaagcc agcagcgacc agtggaagag gctgcacctg 2940
agcctgcagg aactgctcgt ctggctgcag ctgaaagacg acgagctgtc caggcaggcc 3000
cccatcggcg gcgacttccc cgccgtgcag aaacagaacg acgtgcacag ggccttcaag 3060
cgggagctga aaaccaaaga gcccgtgatc atgagcaccc tggaaaccgt gaggatcttc 3120
ctgaccgagc agcccctgga aggactggaa aagctgtacc aggaacccag agagctgccc 3180
cccgaggaac gggcccagaa cgtgaccagg ctgctgagaa agcaggccga ggaagtgaac 3240
accgagtggg agaagctgaa cctgcactcc gccgactggc agaggaagat cgacgagacc 3300
ctggaaaggc tccaggaact gcaggaagcc accgacgagc tggacctgaa gctgagacag 3360
gccgaggtga tcaagggcag ctggcagccc gtgggcgacc tgctgatcga ctccctgcag 3420
gatcacctgg aaaaagtgaa ggccctgcgg ggcgagatcg ccccccctgaa agagaacgtc 3480 agccacgtca acgacctggc caggcagctg accaccctgg gcatccagct gtccccctac 3540
aacctgtcca ccctggaaga tctgaacaca aggtggaagc tgctgcaggt ggccgtggag 3600
gacagagtga ggcagctgca cgaggcccac agggacttcg gccctgcctc ccagcacttc 3660
ctgagcacca gcgtgcaggg cccctgggag agggccatct cccccaacaa ggtgccctac 3720
tacatcaacc acgagaccca gaccacctgc tgggaccacc ctaagatgac cgagctgtac 3780
cagtccctgg ccgacctgaa caatgtgcgg ttcagcgcct accggaccgc catgaagctg 3840
aggcggctgc agaaagccct gtgcctggat ctgctgtccc tgagcgccgc ctgcgacgcc 3900
ctggaccagc acaacctgaa gcagaacgac cagcccatgg atatcctgca gatcatcaac 3960
tgtctgacca ccatctacga caggctggaa caggaacaca acaacctggt caacgtgccc 4020
ctgtgcgtgg acatgtgcct gaactggctg ctgaacgtgt acgacaccgg caggaccggc 4080
cggatcaggg tgctgtcctt caagaccggc atcatcagcc tgtgcaaggc ccacctggaa 4140
gataagtacc gctacctgtt caagcaggtg gccagctcta ccggcttctg cgaccagcgg 4200
aggctgggcc tgctgctgca cgacagcatc cagatccccc ggcagctggg cgaggtggcc 4260
tccttcggcg gcagcaacat cgagcccagc gtgcggagct gcttccagtt cgccaacaac 4320
aagcccgaga tcgaggccgc cctgttcctg gactggatgc ggctggaacc ccagagcatg 4380
gtctggctgc ccgtgctgca cagagtggct gccgccgaga ccgccaagca ccaggccaag 4440
tgcaacatct gcaaagagtg ccccatcatc ggcttcaggt acagaagcct gaagcacttc 4500
aactacgaca tctgccagag ctgtttcttc agcggcaggg tggccaaggg ccacaaaatg 4560
cactacccca tggtggagta ctgcaccccc accacctccg gcgaggacgt gagggacttc 4620
gccaaggtgc tgaagaataa gttccggacc aagcggtact tcgccaaaca ccccaggatg 4680
ggctacctgc ccgtgcagac cgtgctggaa ggcgacaaca tggaaacctg ataacacgcg 4740
tcgactcgag aggcctaata aagagctcag atgcatcgat cagagtgtgt tggtttttg 4800 tgtgagatct aggaacccct agtgatggag ttggccactc cctctctgcg cgctcgctcg 4860
ctcactgagg ccgcccgggc aaagcccggg cgtcgggcga cctttggtcg cccggcctca 4920
gtgagcgagc gagcgcgcag agagggagtg gccaa 4955

<210> SEQ ID NO 13
<211> LENGTH: 736
<212> TYPE: PRT
<213> ORGANISM: adeno-associated virus 9

<400> SEQUENCE: 13

-continued

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415
```

-continued

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 14
<211> LENGTH: 145
<212> TYPE: DNA
<213> ORGANISM: adeno-associated virus 2

<400> SEQUENCE: 14
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcct 145

<210> SEQ ID NO 15
<211> LENGTH: 145
<212> TYPE: DNA
<213> ORGANISM: adeno-associated virus 2

<400> SEQUENCE: 15
aggaacccct agtgatggag ttggccactc cctctctgcg cgctcgctcg ctcactgagg 60
ccgcccgggc aaagcccggg cgtcgggcga cctttggtcg cccggcctca gtgagcgagc 120
gagcgcgcag agagggagtg gccaa 145

<210> SEQ ID NO 16
<211> LENGTH: 577
<212> TYPE: DNA
<213> ORGANISM: Artificial Sequence
<220> FEATURE:
<223> OTHER INFORMATION: Synthetic enhancer and promoter

<400> SEQUENCE: 16
ccactacggg tctaggctgc ccatgtaagg aggcaaggcc tggggacacc cgagatgcct 60
ggttataatt aacccagaca tgtggctgcc cccccccccc ccaacacctg ctgcctctaa 120
aaataaccct gtccctggtg gatcccctgc atgcgaagat cttcgaacaa ggctgtgggg 180
gactgagggc aggctgtaac aggcttgggg gccagggctt atacgtgcct gggactccca 240
aagtattact gttccatgtt cccggcgaag ggccagctgt cccccgccag ctagactcag 300
cacttagttt aggaaccagt gagcaagtca gcccttgggg cagcccatac aaggccatgg 360
ggctgggcaa gctgcacgcc tgggtccggg gtgggcacgg tgcccgggca acgagctgaa 420
agctcatctg ctctcagggg cccctccctg ggacagcccc tcctggcta gtcacaccct 480 gtaggctcct ctatataacc caggggcaca ggggctgccc tcattctacc accacctcca 540
cagcacagac agacactcag gagccagcca gcgtcga 577

<210> SEQ ID NO 17
<211> LENGTH: 54
<212> TYPE: DNA
<213> ORGANISM: Artificial Sequence
<220> FEATURE:
<223> OTHER INFORMATION: Synthetic transcription terminator

<400> SEQUENCE: 17
aggcctaata aagagctcag atgcatcgat cagagtgtgt tggtttttg tgtg 54

<210> SEQ ID NO 18
<211> LENGTH: 4955
<212> TYPE: DNA
<213> ORGANISM: Artificial Sequence
<220> FEATURE:
<223> OTHER INFORMATION: AAV vector genome with Hopti-Dys3978 gene

<400> SEQUENCE: 18
ttggccactc cctctctgcg cgctcgctcg ctcactgagg ccgggcgacc aaaggtcgcc 60
cgacgcccgg gctttgcccg ggcggcctca gtgagcgagc gagcgcgcag agagggagtg 120
gccaactcca tcactagggg ttcctcagat ctgaattcgg taccccacta cgggtctagg 180
ctgcccatgt aaggaggcaa ggcctgggga cacccgagat gcctggttat aattaaccca 240
gacatgtggc tgcccccccc cccccaaca cctgctgcct ctaaaaataa ccctgtccct 300
ggtggatccc ctgcatgcga agatcttcga acaaggctgt gggggactga gggcaggctg 360
taacaggctt gggggccagg gcttatacgt gcctgggact cccaaagtat tactgttcca 420
tgttcccggc gaagggccag ctgtcccccg ccagctagac tcagcactta gtttaggaac 480
cagtgagcaa gtcagccctt ggggcagccc atacaaggcc atggggctgg gcaagctgca 540

-continued

```
cgcctgggtc cggggtgggc acggtgcccg ggcaacgagc tgaaagctca tctgctctca    600
ggggcccctc cctggggaca gcccctcctg gctagtcaca ccctgtaggc tcctctatat    660
aacccagggg cacaggggct gccctcattc taccaccacc tccacagcac agacagacac    720
tcaggagcca gccagcgtcg agcggccgat ccgccaccat gctttggtgg gaggaagtgg    780
aggactgcta cgagagagag gacgtgcaga agaaaacctt caccaagtgg gtgaacgccc    840
agttcagcaa gttcggcaag cagcacatcg agaacctgtt cagcgacctg caggatggca    900
ggagactgct ggacctgctg gagggcctga ccggccagaa gctgcccaag gagaagggca    960
gcaccagagt gcacgccctg aacaacgtga acaaggccct gagagtgctg cagaacaaca   1020
acgtggacct ggtgaacatc ggcagcaccg acatcgtgga cggcaaccac aagctgaccc   1080
tgggcctgat ctggaacatc atcctgcact ggcaggtgaa gaacgtgatg aagaacatca   1140
tggccggcct gcagcagacc aacagcgaga agatcctgct gagctgggtg aggcagagca   1200
ccagaaacta cccccaggtg aacgtgatca acttcaccac ctcctggagc gacggcctgg   1260
ccctgaacgc cctgatccac agccacagac ccgacctgtt cgactggaac agcgtggtgt   1320
gtcagcagag cgccacccag agactggagc acgccttcaa catcgccaga taccagctgg   1380
gcatcgagaa gctgctggac cccgaggacg tggacaccac ctaccccgac aagaaaagca   1440
tcctcatgta cattaccagc ctgttccagg tgctgcccca gcaggtgtcc atcgaggcca   1500
tccaggaagt ggaaatgctg cccaggcccc ccaaagtgac caaggaggag cacttccagc   1560
tgcaccacca gatgcactac agccagcaga tcacagtgag cctggcccag ggctatgaga   1620
gaaccagcag ccccaagccc agattcaaga gctacgccta cacccaggcc gcctacgtga   1680
ccacctccga ccccaccaga agccccttcc ccagccagca cctggaggcc cccgaggaca   1740
agagcttcgg cagcagcctg atggagagcg aagtgaacct ggacagatac cagaccgccc   1800
tggaggaagt gctgtcctgg ctgctgagcg ccgaggacac cctgcaggcc cagggcgaga   1860
tcagcaacga cgtggaagtg gtgaaggacc agttccacac ccacgagggc tacatgatgg   1920
atctgaccgc ccaccagggc agagtgggca atatcctgca gctgggcagc aagctgatcg   1980
gcaccggcaa gctgagcgag gacgaggaga ccgaagtgca ggagcagatg aacctgctga   2040
acagcagatg ggagtgcctg agagtggcca gcatggagaa gcagagcaac ctgcacagag   2100
tgctgatgga cctgcagaac cagaagctga aggagctgaa cgactggctg accaagaccg   2160
aggagcggac cagaaagatg gaggaggagc ccctgggccc cgacctggag gacctgaaga   2220
gacaggtgca gcagcacaaa gtgctgcagg aggacctgga gcaggagcag gtgcgcgtga   2280
acagcctgac ccacatggtg gtggtcgtgg acgagagcag cggcgaccac gccacagccg   2340
ccctggaaga gcagctgaaa gtgctgggcg acagatgggc caatatttgt aggtggaccg   2400
aggacagatg ggtgctgctg caggaccagc ccgacctggc ccctggcctg accaccatcg   2460
gcgccagccc cacccagacc gtgaccctgg tgacccagcc cgtggtgaca aaggagaccg   2520
ccatcagcaa gctggagatg cccagctccc tgatgctgga agtgcccacc caccgcctgc   2580
tccagcagtt ccccctggac ctggagaagt tcctggcctg gctgaccgag gccgaaacca   2640
ccgccaatgt gctccaggac gccactagaa aggagaggct gctggaggac agcaagggcg   2700
tgaaagagct gatgaagcag tggcaggatc tgcagggcga aatcgaggcc cacaccgacg   2760
tgtaccacaa cctggacgag aacagccaga agattctgag gagcctggag ggcagcgacg   2820
acgccgtcct gctccagagg aggctggaca acatgaactt caagtggagc gagctgcgga   2880
agaagagcct gaacatccgg agccacctgg aagccagcag cgaccagtgg aagagactgc   2940
```

```
acctgagcct gcaggagctg ctggtgtggc tgcagctgaa ggacgacgag ctgagcagac   3000

aggcccccat cggcggcgac ttccccgccg tgcagaagca gaacgacgtg caccgggcct   3060

tcaagaggga gctgaaaacc aaggaacccg tgatcatgag caccctggag acagtgcgga   3120

tcttcctgac cgagcagccc ctggagggac tggagaagct gtaccaggag cccagagagc   3180

tgcccccga ggagagagcc cagaacgtga ccaggctgct gagaaagcag gccgaggaag    3240

tgaataccga gtgggagaag ctgaatctgc acagcgccga ctggcagaga aagatcgacg   3300

agaccctgga gagactccag gaactgcagg aagccaccga cgagctggac ctgaagctga   3360

gacaggccga agtgatcaag ggcagctggc agcctgtggg cgatctgctg atcgactccc   3420

tgcaggatca cctggagaaa gtgaaggccc tgcggggcga gatcgccccc ctgaaggaga   3480

atgtgagcca cgtgaacgac ctggccagac agctgaccac cctgggcatc cagctgagcc   3540

cctacaacct gagcacactg gaggatctga acacccggtg gaaactgctg caggtggccg   3600

tggaggatag agtgaggcag ctgcacgaag cccacagaga cttcggccct gcctcccagc   3660

acttcctgag caccagcgtg cagggcccct gggagagagc catctccccc aacaaagtgc   3720

cctactacat caaccacgag acccagacca cctgctggga ccaccctaag atgaccgagc   3780

tgtatcagag cctggccgac ctgaacaatg tgcggttcag cgcctacaga accgccatga   3840

agctgcggag actgcagaag gccctgtgcc tggatctgct gagcctgagc gccgcctgcg   3900

acgccctgga ccagcacaac ctgaagcaga atgaccagcc catggacatc ctgcagatca   3960

tcaactgcct gaccacaatc tacgaccggc tggaacagga gcacaacaac ctggtgaatg   4020

tgcccctgtg cgtggacatg tgcctgaatt ggctgctgaa cgtgtacgac accggcagga   4080

ccggcagaat ccgcgtgctg agcttcaaga ccggcatcat cagcctgtgc aaggcccacc   4140

tggaggataa gtaccgctac ctgttcaagc aggtggccag cagcaccggc ttctgcgatc   4200

agaggagact gggcctgctg ctgcacgata gcatccagat ccctaggcag ctgggcgaag   4260

tggccagctt tggcggcagc aacatcgagc cctctgtgag gagctgcttc cagttcgcca   4320

acaacaagcc cgagatcgag gccgccctgt tcctggactg gatgaggctg gagcctcaga   4380

gcatggtgtg gctgcctgtg ctgcacagag tggccgccgc cgagaccgcc aagcaccagg   4440

ccaagtgcaa tatctgcaag gagtgcccca tcatcggctt ccggtacagg agcctgaagc   4500

acttcaacta cgacatctgc cagagctgct ttttcagcgg cagagtggcc aagggccaca   4560

aaatgcacta ccccatggtg gagtactgca cccccaccac ctccggcgag gatgtgagag   4620

acttcgccaa agtgctgaag aataagttcc ggaccaagcg gtactttgcc aagcacccca   4680

ggatgggcta cctgcccgtg cagaccgtgc tggaaggcga caacatggag acctgatgag   4740

gagctcgaga ggcctaataa agagctcaga tgcatcgatc agagtgtgtt ggttttttgt   4800

gtgagatctg aggaacccct agtgatggag ttggccactc cctctctgcg cgctcgctcg   4860

ctcactgagg ccgcccgggc aaagcccggg cgtcgggcga cctttggtcg cccggcctca   4920

gtgagcgagc gagcgcgcag agagggagtg gccaa                              4955
```

<210> SEQ ID NO 19
<211> LENGTH: 23
<212> TYPE: DNA
<213> ORGANISM: Artificial Sequence
<220> FEATURE:
<223> OTHER INFORMATION: Primer

<400> SEQUENCE: 19
ccaacaaagt gccctactac atc 23

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ggttgtgctg gtccagggcg t 21

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
ccgagctgta tcagagcctg gcc 23

<210> SEQ ID NO 22
<211> LENGTH: 21
<212> TYPE: DNA
<213> ORGANISM: Artificial Sequence
<220> FEATURE:
<223> OTHER INFORMATION: Primer

<400> SEQUENCE: 22
gcgaaagtgg aaaagccaag t 21

<210> SEQ ID NO 23
<211> LENGTH: 24
<212> TYPE: DNA
<213> ORGANISM: Artificial Sequence
<220> FEATURE:
<223> OTHER INFORMATION: Primer

<400> SEQUENCE: 23
gccacatcaa caggactctt gtag 24

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
caaagcctaa aagacagcgg caagttgaat 30

<210> SEQ ID NO 25
<211> LENGTH: 3685
<212> TYPE: PRT
<213> ORGANISM: Homo sapiens

<400> SEQUENCE: 25

Met Leu Trp Trp Glu Glu Val Glu Asp Cys Tyr Glu Arg Glu Asp Val
1 5 10 15

Gln Lys Lys Thr Phe Thr Lys Trp Val Asn Ala Gln Phe Ser Lys Phe
20 25 30

Gly Lys Gln His Ile Glu Asn Leu Phe Ser Asp Leu Gln Asp Gly Arg
35 40 45

-continued

```
Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
```

-continued 465 470 475 480

Pro Asp Leu Glu Asp Leu Lys Arg Gln Val Gln Gln His Lys Val Leu
485 490 495

Gln Glu Asp Leu Glu Gln Glu Gln Val Arg Val Asn Ser Leu Thr His
500 505 510

Met Val Val Val Val Asp Glu Ser Ser Gly Asp His Ala Thr Ala Ala
515 520 525

Leu Glu Glu Gln Leu Lys Val Leu Gly Asp Arg Trp Ala Asn Ile Cys
530 535 540

Arg Trp Thr Glu Asp Arg Trp Val Leu Leu Gln Asp Ile Leu Leu Lys
545 550 555 560

Trp Gln Arg Leu Thr Glu Glu Gln Cys Leu Phe Ser Ala Trp Leu Ser
565 570 575

Glu Lys Glu Asp Ala Val Asn Lys Ile His Thr Thr Gly Phe Lys Asp
580 585 590

Gln Asn Glu Met Leu Ser Ser Leu Gln Lys Leu Ala Val Leu Lys Ala
595 600 605

Asp Leu Glu Lys Lys Lys Gln Ser Met Gly Lys Leu Tyr Ser Leu Lys
610 615 620

Gln Asp Leu Leu Ser Thr Leu Lys Asn Lys Ser Val Thr Gln Lys Thr
625 630 635 640

Glu Ala Trp Leu Asp Asn Phe Ala Arg Cys Trp Asp Asn Leu Val Gln
645 650 655

Lys Leu Glu Lys Ser Thr Ala Gln Ile Ser Gln Ala Val Thr Thr Thr
660 665 670

Gln Pro Ser Leu Thr Gln Thr Thr Val Met Glu Thr Val Thr Thr Val
675 680 685

Thr Thr Arg Glu Gln Ile Leu Val Lys His Ala Gln Glu Glu Leu Pro
690 695 700

Pro Pro Pro Pro Gln Lys Lys Arg Gln Ile Thr Val Asp Ser Glu Ile
705 710 715 720

Arg Lys Arg Leu Asp Val Asp Ile Thr Glu Leu His Ser Trp Ile Thr
725 730 735

Arg Ser Glu Ala Val Leu Gln Ser Pro Glu Phe Ala Ile Phe Arg Lys
740 745 750

Glu Gly Asn Phe Ser Asp Leu Lys Glu Lys Val Asn Ala Ile Glu Arg
755 760 765

Glu Lys Ala Glu Lys Phe Arg Lys Leu Gln Asp Ala Ser Arg Ser Ala
770 775 780

Gln Ala Leu Val Glu Gln Met Val Asn Glu Gly Val Asn Ala Asp Ser
785 790 795 800

Ile Lys Gln Ala Ser Glu Gln Leu Asn Ser Arg Trp Ile Glu Phe Cys
805 810 815

Gln Leu Leu Ser Glu Arg Leu Asn Trp Leu Glu Tyr Gln Asn Asn Ile
820 825 830

Ile Ala Phe Tyr Asn Gln Leu Gln Gln Leu Glu Gln Met Thr Thr Thr
835 840 845

Ala Glu Asn Trp Leu Lys Ile Gln Pro Thr Thr Pro Ser Glu Pro Thr
850 855 860

Ala Ile Lys Ser Gln Leu Lys Ile Cys Lys Asp Glu Val Asn Arg Leu
865 870 875 880

Ser Gly Leu Gln Pro Gln Ile Glu Arg Leu Lys Ile Gln Ser Ile Ala
885 890 895

```
Leu Lys Glu Lys Gly Gln Gly Pro Met Phe Leu Asp Ala Asp Phe Val
            900                 905                 910

Ala Phe Thr Asn His Phe Lys Gln Val Phe Ser Asp Val Gln Ala Arg
        915                 920                 925

Glu Lys Glu Leu Gln Thr Ile Phe Asp Thr Leu Pro Pro Met Arg Tyr
    930                 935                 940

Gln Glu Thr Met Ser Ala Ile Arg Thr Trp Val Gln Gln Ser Glu Thr
945                 950                 955                 960

Lys Leu Ser Ile Pro Gln Leu Ser Val Thr Asp Tyr Glu Ile Met Glu
                965                 970                 975

Gln Arg Leu Gly Glu Leu Gln Ala Leu Gln Ser Ser Leu Gln Glu Gln
            980                 985                 990

Gln Ser Gly Leu Tyr Tyr Leu Ser  Thr Thr Val Lys Glu  Met Ser Lys
        995                 1000                 1005

Lys Ala  Pro Ser Glu Ile Ser  Arg Lys Tyr Gln Ser  Glu Phe Glu
    1010                 1015                 1020

Glu Ile  Glu Gly Arg Trp Lys  Lys Leu Ser Ser Gln  Leu Val Glu
    1025                 1030                 1035

His Cys  Gln Lys Leu Glu Glu  Gln Met Asn Lys Leu  Arg Lys Ile
    1040                 1045                 1050

Gln Asn  His Ile Gln Thr Leu  Lys Lys Trp Met Ala  Glu Val Asp
    1055                 1060                 1065

Val Phe  Leu Lys Glu Glu Trp  Pro Ala Leu Gly Asp  Ser Glu Ile
    1070                 1075                 1080

Leu Lys  Lys Gln Leu Lys Gln  Cys Arg Leu Leu Val  Ser Asp Ile
    1085                 1090                 1095

Gln Thr  Ile Gln Pro Ser Leu  Asn Ser Val Asn Glu  Gly Gly Gln
    1100                 1105                 1110

Lys Ile  Lys Asn Glu Ala Glu  Pro Glu Phe Ala Ser  Arg Leu Glu
    1115                 1120                 1125

Thr Glu  Leu Lys Glu Leu Asn  Thr Gln Trp Asp His  Met Cys Gln
    1130                 1135                 1140

Gln Val  Tyr Ala Arg Lys Glu  Ala Leu Lys Gly Gly  Leu Glu Lys
    1145                 1150                 1155

Thr Val  Ser Leu Gln Lys Asp  Leu Ser Glu Met His  Glu Trp Met
    1160                 1165                 1170

Thr Gln  Ala Glu Glu Glu Tyr  Leu Glu Arg Asp Phe  Glu Tyr Lys
    1175                 1180                 1185

Thr Pro  Asp Glu Leu Gln Lys  Ala Val Glu Glu Met  Lys Arg Ala
    1190                 1195                 1200

Lys Glu  Glu Ala Gln Gln Lys  Glu Ala Lys Val Lys  Leu Leu Thr
    1205                 1210                 1215

Glu Ser  Val Asn Ser Val Ile  Ala Gln Ala Pro Pro  Val Ala Gln
    1220                 1225                 1230

Glu Ala  Leu Lys Lys Glu Leu  Glu Thr Leu Thr Thr  Asn Tyr Gln
    1235                 1240                 1245

Trp Leu  Cys Thr Arg Leu Asn  Gly Lys Cys Lys Thr  Leu Glu Glu
    1250                 1255                 1260

Val Trp  Ala Cys Trp His Glu  Leu Leu Ser Tyr Leu  Glu Lys Ala
    1265                 1270                 1275

Asn Lys  Trp Leu Asn Glu Val  Glu Phe Lys Leu Lys  Thr Thr Glu
    1280                 1285                 1290
```

Asn Ile Pro Gly Gly Ala Glu Glu Ile Ser Glu Val Leu Asp Ser
1295 1300 1305

Leu Glu Asn Leu Met Arg His Ser Glu Asp Asn Pro Asn Gln Ile
1310 1315 1320

Arg Ile Leu Ala Gln Thr Leu Thr Asp Gly Gly Val Met Asp Glu
1325 1330 1335

Leu Ile Asn Glu Glu Leu Glu Thr Phe Asn Ser Arg Trp Arg Glu
1340 1345 1350

Leu His Glu Glu Ala Val Arg Arg Gln Lys Leu Leu Glu Gln Ser
1355 1360 1365

Ile Gln Ser Ala Gln Glu Thr Glu Lys Ser Leu His Leu Ile Gln
1370 1375 1380

Glu Ser Leu Thr Phe Ile Asp Lys Gln Leu Ala Ala Tyr Ile Ala
1385 1390 1395

Asp Lys Val Asp Ala Ala Gln Met Pro Gln Glu Ala Gln Lys Ile
1400 1405 1410

Gln Ser Asp Leu Thr Ser His Glu Ile Ser Leu Glu Glu Met Lys
1415 1420 1425

Lys His Asn Gln Gly Lys Glu Ala Ala Gln Arg Val Leu Ser Gln
1430 1435 1440

Ile Asp Val Ala Gln Lys Lys Leu Gln Asp Val Ser Met Lys Phe
1445 1450 1455

Arg Leu Phe Gln Lys Pro Ala Asn Phe Glu Gln Arg Leu Gln Glu
1460 1465 1470

Ser Lys Met Ile Leu Asp Glu Val Lys Met His Leu Pro Ala Leu
1475 1480 1485

Glu Thr Lys Ser Val Glu Gln Glu Val Val Gln Ser Gln Leu Asn
1490 1495 1500

His Cys Val Asn Leu Tyr Lys Ser Leu Ser Glu Val Lys Ser Glu
1505 1510 1515

Val Glu Met Val Ile Lys Thr Gly Arg Gln Ile Val Gln Lys Lys
1520 1525 1530

Gln Thr Glu Asn Pro Lys Glu Leu Asp Glu Arg Val Thr Ala Leu
1535 1540 1545

Lys Leu His Tyr Asn Glu Leu Gly Ala Lys Val Thr Glu Arg Lys
1550 1555 1560

Gln Gln Leu Glu Lys Cys Leu Lys Leu Ser Arg Lys Met Arg Lys
1565 1570 1575

Glu Met Asn Val Leu Thr Glu Trp Leu Ala Ala Thr Asp Met Glu
1580 1585 1590

Leu Thr Lys Arg Ser Ala Val Glu Gly Met Pro Ser Asn Leu Asp
1595 1600 1605

Ser Glu Val Ala Trp Gly Lys Ala Thr Gln Lys Glu Ile Glu Lys
1610 1615 1620

Gln Lys Val His Leu Lys Ser Ile Thr Glu Val Gly Glu Ala Leu
1625 1630 1635

Lys Thr Val Leu Gly Lys Lys Glu Thr Leu Val Glu Asp Lys Leu
1640 1645 1650

Ser Leu Leu Asn Ser Asn Trp Ile Ala Val Thr Ser Arg Ala Glu
1655 1660 1665

Glu Trp Leu Asn Leu Leu Leu Glu Tyr Gln Lys His Met Glu Thr
1670 1675 1680

Phe Asp Gln Asn Val Asp His Ile Thr Lys Trp Ile Ile Gln Ala

-continued

```
    1685                1690                1695

Asp Thr  Leu Leu Asp Glu Ser  Glu Lys Lys Lys Pro  Gln Gln Lys
    1700                1705                1710

Glu Asp  Val Leu Lys Arg Leu  Lys Ala Glu Leu Asn  Asp Ile Arg
    1715                1720                1725

Pro Lys  Val Asp Ser Thr Arg  Asp Gln Ala Ala Asn  Leu Met Ala
    1730                1735                1740

Asn Arg  Gly Asp His Cys Arg  Lys Leu Val Glu Pro  Gln Ile Ser
    1745                1750                1755

Glu Leu  Asn His Arg Phe Ala  Ala Ile Ser His Arg  Ile Lys Thr
    1760                1765                1770

Gly Lys  Ala Ser Ile Pro Leu  Lys Glu Leu Glu Gln  Phe Asn Ser
    1775                1780                1785

Asp Ile  Gln Lys Leu Leu Glu  Pro Leu Glu Ala Glu  Ile Gln Gln
    1790                1795                1800

Gly Val  Asn Leu Lys Glu Glu  Asp Phe Asn Lys Asp  Met Asn Glu
    1805                1810                1815

Asp Asn  Glu Gly Thr Val Lys  Glu Leu Leu Gln Arg  Gly Asp Asn
    1820                1825                1830

Leu Gln  Gln Arg Ile Thr Asp  Glu Arg Lys Arg Glu  Glu Ile Lys
    1835                1840                1845

Ile Lys  Gln Gln Leu Leu Gln  Thr Lys His Asn Ala  Leu Lys Asp
    1850                1855                1860

Leu Arg  Ser Gln Arg Arg Lys  Lys Ala Leu Glu Ile  Ser His Gln
    1865                1870                1875

Trp Tyr  Gln Tyr Lys Arg Gln  Ala Asp Asp Leu Leu  Lys Cys Leu
    1880                1885                1890

Asp Asp  Ile Glu Lys Lys Leu  Ala Ser Leu Pro Glu  Pro Arg Asp
    1895                1900                1905

Glu Arg  Lys Ile Lys Glu Ile  Asp Arg Glu Leu Gln  Lys Lys Lys
    1910                1915                1920

Glu Glu  Leu Asn Ala Val Arg  Arg Gln Ala Glu Gly  Leu Ser Glu
    1925                1930                1935

Asp Gly  Ala Ala Met Ala Val  Glu Pro Thr Gln Ile  Gln Leu Ser
    1940                1945                1950

Lys Arg  Trp Arg Glu Ile Glu  Ser Lys Phe Ala Gln  Phe Arg Arg
    1955                1960                1965

Leu Asn  Phe Ala Gln Ile His  Thr Val Arg Glu Glu  Thr Met Met
    1970                1975                1980

Val Met  Thr Glu Asp Met Pro  Leu Glu Ile Ser Tyr  Val Pro Ser
    1985                1990                1995

Thr Tyr  Leu Thr Glu Ile Thr  His Val Ser Gln Ala  Leu Leu Glu
    2000                2005                2010

Val Glu  Gln Leu Leu Asn Ala  Pro Asp Leu Cys Ala  Lys Asp Phe
    2015                2020                2025

Glu Asp  Leu Phe Lys Gln Glu  Glu Ser Leu Lys Asn  Ile Lys Asp
    2030                2035                2040

Ser Leu  Gln Gln Ser Ser Gly  Arg Ile Asp Ile Ile  His Ser Lys
    2045                2050                2055

Lys Thr  Ala Ala Leu Gln Ser  Ala Thr Pro Val Glu  Arg Val Lys
    2060                2065                2070

Leu Gln  Glu Ala Leu Ser Gln  Leu Asp Phe Gln Trp  Glu Lys Val
    2075                2080                2085
```

-continued

```
Asn Lys  Met Tyr Lys Asp Arg  Gln Gly Arg Phe Asp  Arg Ser Val
    2090                 2095                 2100

Glu Lys  Trp Arg Arg Phe His  Tyr Asp Ile Lys Ile  Phe Asn Gln
    2105                 2110                 2115

Trp Leu  Thr Glu Ala Glu Gln  Phe Leu Arg Lys Thr  Gln Ile Pro
    2120                 2125                 2130

Glu Asn  Trp Glu His Ala Lys  Tyr Lys Trp Tyr Leu  Lys Glu Leu
    2135                 2140                 2145

Gln Asp  Gly Ile Gly Gln Arg  Gln Thr Val Val Arg  Thr Leu Asn
    2150                 2155                 2160

Ala Thr  Gly Glu Glu Ile Ile  Gln Gln Ser Ser Lys  Thr Asp Ala
    2165                 2170                 2175

Ser Ile  Leu Gln Glu Lys Leu  Gly Ser Leu Asn Leu  Arg Trp Gln
    2180                 2185                 2190

Glu Val  Cys Lys Gln Leu Ser  Asp Arg Lys Lys Arg  Leu Glu Glu
    2195                 2200                 2205

Gln Lys  Asn Ile Leu Ser Glu  Phe Gln Arg Asp Leu  Asn Glu Phe
    2210                 2215                 2220

Val Leu  Trp Leu Glu Glu Ala  Asp Asn Ile Ala Ser  Ile Pro Leu
    2225                 2230                 2235

Glu Pro  Gly Lys Glu Gln Gln  Leu Lys Glu Lys Leu  Glu Gln Val
    2240                 2245                 2250

Lys Leu  Leu Val Glu Glu Leu  Pro Leu Arg Gln Gly  Ile Leu Lys
    2255                 2260                 2265

Gln Leu  Asn Glu Thr Gly Gly  Pro Val Leu Val Ser  Ala Pro Ile
    2270                 2275                 2280

Ser Pro  Glu Glu Gln Asp Lys  Leu Glu Asn Lys Leu  Lys Gln Thr
    2285                 2290                 2295

Asn Leu  Gln Trp Ile Lys Val  Ser Arg Ala Leu Pro  Glu Lys Gln
    2300                 2305                 2310

Gly Glu  Ile Glu Ala Gln Ile  Lys Asp Leu Gly Gln  Leu Glu Lys
    2315                 2320                 2325

Lys Leu  Glu Asp Leu Glu Glu  Gln Leu Asn His Leu  Leu Leu Trp
    2330                 2335                 2340

Leu Ser  Pro Ile Arg Asn Gln  Leu Glu Ile Tyr Asn  Gln Pro Asn
    2345                 2350                 2355

Gln Glu  Gly Pro Phe Asp Val  Gln Glu Thr Glu Ile  Ala Val Gln
    2360                 2365                 2370

Ala Lys  Gln Pro Asp Val Glu  Glu Ile Leu Ser Lys  Gly Gln His
    2375                 2380                 2385

Leu Tyr  Lys Glu Lys Pro Ala  Thr Gln Pro Val Lys  Arg Lys Leu
    2390                 2395                 2400

Glu Asp  Leu Ser Ser Glu Trp  Lys Ala Val Asn Arg  Leu Leu Gln
    2405                 2410                 2415

Glu Leu  Arg Ala Lys Gln Pro  Asp Leu Ala Pro Gly  Leu Thr Thr
    2420                 2425                 2430

Ile Gly  Ala Ser Pro Thr Gln  Thr Val Thr Leu Val  Thr Gln Pro
    2435                 2440                 2445

Val Val  Thr Lys Glu Thr Ala  Ile Ser Lys Leu Glu  Met Pro Ser
    2450                 2455                 2460

Ser Leu  Met Leu Glu Val Pro  Ala Leu Ala Asp Phe  Asn Arg Ala
    2465                 2470                 2475
```

-continued

Trp Thr Glu Leu Thr Asp Trp Leu Ser Leu Leu Asp Gln Val Ile
2480 2485 2490

Lys Ser Gln Arg Val Met Val Gly Asp Leu Glu Asp Ile Asn Glu
2495 2500 2505

Met Ile Ile Lys Gln Lys Ala Thr Met Gln Asp Leu Glu Gln Arg
2510 2515 2520

Arg Pro Gln Leu Glu Glu Leu Ile Thr Ala Ala Gln Asn Leu Lys
2525 2530 2535

Asn Lys Thr Ser Asn Gln Glu Ala Arg Thr Ile Ile Thr Asp Arg
2540 2545 2550

Ile Glu Arg Ile Gln Asn Gln Trp Asp Glu Val Gln Glu His Leu
2555 2560 2565

Gln Asn Arg Arg Gln Gln Leu Asn Glu Met Leu Lys Asp Ser Thr
2570 2575 2580

Gln Trp Leu Glu Ala Lys Glu Glu Ala Glu Gln Val Leu Gly Gln
2585 2590 2595

Ala Arg Ala Lys Leu Glu Ser Trp Lys Glu Gly Pro Tyr Thr Val
2600 2605 2610

Asp Ala Ile Gln Lys Lys Ile Thr Glu Thr Lys Gln Leu Ala Lys
2615 2620 2625

Asp Leu Arg Gln Trp Gln Thr Asn Val Asp Val Ala Asn Asp Leu
2630 2635 2640

Ala Leu Lys Leu Leu Arg Asp Tyr Ser Ala Asp Asp Thr Arg Lys
2645 2650 2655

Val His Met Ile Thr Glu Asn Ile Asn Ala Ser Trp Arg Ser Ile
2660 2665 2670

His Lys Arg Val Ser Glu Arg Glu Ala Ala Leu Glu Glu Thr His
2675 2680 2685

Arg Leu Leu Gln Gln Phe Pro Leu Asp Leu Glu Lys Phe Leu Ala
2690 2695 2700

Trp Leu Thr Glu Ala Glu Thr Thr Ala Asn Val Leu Gln Asp Ala
2705 2710 2715

Thr Arg Lys Glu Arg Leu Leu Glu Asp Ser Lys Gly Val Lys Glu
2720 2725 2730

Leu Met Lys Gln Trp Gln Asp Leu Gln Gly Glu Ile Glu Ala His
2735 2740 2745

Thr Asp Val Tyr His Asn Leu Asp Glu Asn Ser Gln Lys Ile Leu
2750 2755 2760

Arg Ser Leu Glu Gly Ser Asp Asp Ala Val Leu Leu Gln Arg Arg
2765 2770 2775

Leu Asp Asn Met Asn Phe Lys Trp Ser Glu Leu Arg Lys Lys Ser
2780 2785 2790

Leu Asn Ile Arg Ser His Leu Glu Ala Ser Ser Asp Gln Trp Lys
2795 2800 2805

Arg Leu His Leu Ser Leu Gln Glu Leu Leu Val Trp Leu Gln Leu
2810 2815 2820

Lys Asp Asp Glu Leu Ser Arg Gln Ala Pro Ile Gly Gly Asp Phe
2825 2830 2835

Pro Ala Val Gln Lys Gln Asn Asp Val His Arg Ala Phe Lys Arg
2840 2845 2850

Glu Leu Lys Thr Lys Glu Pro Val Ile Met Ser Thr Leu Glu Thr
2855 2860 2865

Val Arg Ile Phe Leu Thr Glu Gln Pro Leu Glu Gly Leu Glu Lys

-continued

```
    2870                2875                2880

Leu Tyr  Gln Glu Pro Arg Glu  Leu Pro Pro Glu Glu  Arg Ala Gln
    2885                2890                2895

Asn Val  Thr Arg Leu Leu Arg  Lys Gln Ala Glu Glu  Val Asn Thr
    2900                2905                2910

Glu Trp  Glu Lys Leu Asn Leu  His Ser Ala Asp Trp  Gln Arg Lys
    2915                2920                2925

Ile Asp  Glu Thr Leu Glu Arg  Leu Gln Glu Leu Gln  Glu Ala Thr
    2930                2935                2940

Asp Glu  Leu Asp Leu Lys Leu  Arg Gln Ala Glu Val  Ile Lys Gly
    2945                2950                2955

Ser Trp  Gln Pro Val Gly Asp  Leu Leu Ile Asp Ser  Leu Gln Asp
    2960                2965                2970

His Leu  Glu Lys Val Lys Ala  Leu Arg Gly Glu Ile  Ala Pro Leu
    2975                2980                2985

Lys Glu  Asn Val Ser His Val  Asn Asp Leu Ala Arg  Gln Leu Thr
    2990                2995                3000

Thr Leu  Gly Ile Gln Leu Ser  Pro Tyr Asn Leu Ser  Thr Leu Glu
    3005                3010                3015

Asp Leu  Asn Thr Arg Trp Lys  Leu Leu Gln Val Ala  Val Glu Asp
    3020                3025                3030

Arg Val  Arg Gln Leu His Glu  Ala His Arg Asp Phe  Gly Pro Ala
    3035                3040                3045

Ser Gln  His Phe Leu Ser Thr  Ser Val Gln Gly Pro  Trp Glu Arg
    3050                3055                3060

Ala Ile  Ser Pro Asn Lys Val  Pro Tyr Tyr Ile Asn  His Glu Thr
    3065                3070                3075

Gln Thr  Thr Cys Trp Asp His  Pro Lys Met Thr Glu  Leu Tyr Gln
    3080                3085                3090

Ser Leu  Ala Asp Leu Asn Asn  Val Arg Phe Ser Ala  Tyr Arg Thr
    3095                3100                3105

Ala Met  Lys Leu Arg Arg Leu  Gln Lys Ala Leu Cys  Leu Asp Leu
    3110                3115                3120

Leu Ser  Leu Ser Ala Ala Cys  Asp Ala Leu Asp Gln  His Asn Leu
    3125                3130                3135

Lys Gln  Asn Asp Gln Pro Met  Asp Ile Leu Gln Ile  Ile Asn Cys
    3140                3145                3150

Leu Thr  Thr Ile Tyr Asp Arg  Leu Glu Gln Glu His  Asn Asn Leu
    3155                3160                3165

Val Asn  Val Pro Leu Cys Val  Asp Met Cys Leu Asn  Trp Leu Leu
    3170                3175                3180

Asn Val  Tyr Asp Thr Gly Arg  Thr Gly Arg Ile Arg  Val Leu Ser
    3185                3190                3195

Phe Lys  Thr Gly Ile Ile Ser  Leu Cys Lys Ala His  Leu Glu Asp
    3200                3205                3210

Lys Tyr  Arg Tyr Leu Phe Lys  Gln Val Ala Ser Ser  Thr Gly Phe
    3215                3220                3225

Cys Asp  Gln Arg Arg Leu Gly  Leu Leu Leu His Asp  Ser Ile Gln
    3230                3235                3240

Ile Pro  Arg Gln Leu Gly Glu  Val Ala Ser Phe Gly  Gly Ser Asn
    3245                3250                3255

Ile Glu  Pro Ser Val Arg Ser  Cys Phe Gln Phe Ala  Asn Asn Lys
    3260                3265                3270
```

```
Pro Glu  Ile Glu Ala Ala Leu  Phe Leu Asp Trp Met  Arg Leu Glu
    3275                 3280                 3285

Pro Gln  Ser Met Val Trp Leu  Pro Val Leu His Arg  Val Ala Ala
    3290                 3295                 3300

Ala Glu  Thr Ala Lys His Gln  Ala Lys Cys Asn Ile  Cys Lys Glu
    3305                 3310                 3315

Cys Pro  Ile Ile Gly Phe Arg  Tyr Arg Ser Leu Lys  His Phe Asn
    3320                 3325                 3330

Tyr Asp  Ile Cys Gln Ser Cys  Phe Phe Ser Gly Arg  Val Ala Lys
    3335                 3340                 3345

Gly His  Lys Met His Tyr Pro  Met Val Glu Tyr Cys  Thr Pro Thr
    3350                 3355                 3360

Thr Ser  Gly Glu Asp Val Arg  Asp Phe Ala Lys Val  Leu Lys Asn
    3365                 3370                 3375

Lys Phe  Arg Thr Lys Arg Tyr  Phe Ala Lys His Pro  Arg Met Gly
    3380                 3385                 3390

Tyr Leu  Pro Val Gln Thr Val  Leu Glu Gly Asp Asn  Met Glu Thr
    3395                 3400                 3405

Pro Val  Thr Leu Ile Asn Phe  Trp Pro Val Asp Ser  Ala Pro Ala
    3410                 3415                 3420

Ser Ser  Pro Gln Leu Ser His  Asp Asp Thr His Ser  Arg Ile Glu
    3425                 3430                 3435

His Tyr  Ala Ser Arg Leu Ala  Glu Met Glu Asn Ser  Asn Gly Ser
    3440                 3445                 3450

Tyr Leu  Asn Asp Ser Ile Ser  Pro Asn Glu Ser Ile  Asp Asp Glu
    3455                 3460                 3465

His Leu  Leu Ile Gln His Tyr  Cys Gln Ser Leu Asn  Gln Asp Ser
    3470                 3475                 3480

Pro Leu  Ser Gln Pro Arg Ser  Pro Ala Gln Ile Leu  Ile Ser Leu
    3485                 3490                 3495

Glu Ser  Glu Glu Arg Gly Glu  Leu Glu Arg Ile Leu  Ala Asp Leu
    3500                 3505                 3510

Glu Glu  Glu Asn Arg Asn Leu  Gln Ala Glu Tyr Asp  Arg Leu Lys
    3515                 3520                 3525

Gln Gln  His Glu His Lys Gly  Leu Ser Pro Leu Pro  Ser Pro Pro
    3530                 3535                 3540

Glu Met  Met Pro Thr Ser Pro  Gln Ser Pro Arg Asp  Ala Glu Leu
    3545                 3550                 3555

Ile Ala  Glu Ala Lys Leu Leu  Arg Gln His Lys Gly  Arg Leu Glu
    3560                 3565                 3570

Ala Arg  Met Gln Ile Leu Glu  Asp His Asn Lys Gln  Leu Glu Ser
    3575                 3580                 3585

Gln Leu  His Arg Leu Arg Gln  Leu Leu Glu Gln Pro  Gln Ala Glu
    3590                 3595                 3600

Ala Lys  Val Asn Gly Thr Thr  Val Ser Ser Pro Ser  Thr Ser Leu
    3605                 3610                 3615

Gln Arg  Ser Asp Ser Ser Gln  Pro Met Leu Leu Arg  Val Val Gly
    3620                 3625                 3630

Ser Gln  Thr Ser Asp Ser Met  Gly Glu Glu Asp Leu  Leu Ser Pro
    3635                 3640                 3645

Pro Gln  Asp Thr Ser Thr Gly  Leu Glu Glu Val Met  Glu Gln Leu
    3650                 3655                 3660
```

-continued

```
Asn Asn  Ser Phe Pro Ser Ser  Arg Gly Arg Asn Thr  Pro Gly Lys
    3665                 3670                 3675

Pro Met  Arg Glu Asp Thr Met
    3680                 3685


<210> SEQ ID NO 26
<211> LENGTH: 3978
<212> TYPE: DNA
<213> ORGANISM: Artificial Sequence
<220> FEATURE:
<223> OTHER INFORMATION: Non-codon optimized Dys3978 gene

<400> SEQUENCE: 26

atgctttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaaatgt tgccaaggcc acctaaagtg    780

actaaagaag aacattttca gttacatcat caaatgcact attctcaaca gatcacggtc    840

agtctagcac agggatatga gagaacttct tcccctaagc ctcgattcaa gagctatgcc    900

tacacacagg ctgcttatgt caccacctct gaccctacac ggagcccatt tccttcacag    960

catttggaag ctcctgaaga caagtcattt ggcagttcat tgatggagag tgaagtaaac   1020

ctggaccgtt atcaaacagc tttagaagaa gtattatcgt ggcttctttc tgctgaggac   1080

acattgcaag cacaaggaga gatttctaat gatgtggaag tggtgaaaga ccagtttcat   1140

actcatgagg ggtacatgat ggatttgaca gcccatcagg gccgggttgg taatattcta   1200

caattgggaa gtaagctgat tggaacagga aaattatcag aagatgaaga aactgaagta   1260

caagagcaga tgaatctcct aaattcaaga tgggaatgcc tcagggtagc tagcatggaa   1320

aaacaaagca atttacatag agttttaatg gatctccaga atcagaaact gaaagagttg   1380

aatgactggc taacaaaaac agaagaaaga acaaggaaaa tggaggaaga gcctcttgga   1440

cctgatcttg aagacctaaa acgccaagta caacaacata aggtgcttca agaagatcta   1500

gaacaagaac aagtcagggt caattctctc actcacatgg tggtggtagt tgatgaatct   1560

agtggagatc acgcaactgc tgctttggaa gaacaactta aggtattggg agatcgatgg   1620

gcaaacatct gtagatggac agaagaccgc tgggttcttt tacaagacca gcctgaccta   1680

gctcctggac tgaccactat tggagcctct cctactcaga ctgttactct ggtgacacaa   1740

cctgtggtta ctaaggaaac tgccatctcc aaactagaaa tgccatcttc cttgatgttg   1800

gaggtaccta ctcatagatt actgcaacag ttccccctgg acctggaaaa gtttcttgcc   1860

tggcttacag aagctgaaac aactgccaat gtcctacagg atgctacccg taaggaaagg   1920
```

```
ctcctagaag actccaaggg agtaaaagag ctgatgaaac aatggcaaga cctccaaggt   1980
gaaattgaag ctcacacaga tgtttatcac aacctggatg aaaacagcca aaaaatcctg   2040
agatccctgg aaggttccga tgatgcagtc ctgttacaaa gacgtttgga taacatgaac   2100
ttcaagtgga gtgaacttcg gaaaaagtct ctcaacatta ggtcccattt ggaagccagt   2160
tctgaccagt ggaagcgtct gcacctttct ctgcaggaac ttctggtgtg gctacagctg   2220
aaagatgatg aattaagccg gcaggcacct attggaggcg actttccagc agttcagaag   2280
cagaacgatg tacatagggc cttcaagagg gaattgaaaa ctaaagaacc tgtaatcatg   2340
agtactcttg agactgtacg aatatttctg acagagcagc ctttggaagg actagagaaa   2400
ctctaccagg agcccagaga gctgcctcct gaggagagag cccagaatgt cactcggctt   2460
ctacgaaagc aggctgagga ggtcaatact gagtgggaaa aattgaacct gcactccgct   2520
gactggcaga gaaaaataga tgagaccctt gaaagactcc aggaacttca agaggccacg   2580
gatgagctgg acctcaagct gcgccaagct gaggtgatca agggatcctg gcagcccgtg   2640
ggcgatctcc tcattgactc tctccaagat cacctcgaga aagtcaaggc acttcgagga   2700
gaaattgcgc ctctgaaaga gaacgtgagc cacgtcaatg accttgctcg ccagcttacc   2760
actttgggca ttcagctctc accgtataac ctcagcactc tggaagacct gaacaccaga   2820
tggaagcttc tgcaggtggc cgtcgaggac cgagtcaggc agctgcatga agcccacagg   2880
gactttggtc cagcatctca gcactttctt tccacgtctg tccagggtcc ctgggagaga   2940
gccatctcgc caaacaaagt gccctactat atcaaccacg agactcaaac aacttgctgg   3000
gaccatccca aaatgacaga gctctaccag tctttagctg acctgaataa tgtcagattc   3060
tcagcttata ggactgccat gaaactccga agactgcaga aggccctttg cttggatctc   3120
ttgagcctgt cagctgcatg tgatgccttg gaccagcaca acctcaagca aaatgaccag   3180
cccatggata tcctgcagat tattaattgt ttgaccacta tttatgaccg cctggagcaa   3240
gagcacaaca atttggtcaa cgtccctctc tgcgtggata tgtgtctgaa ctggctgctg   3300
aatgtttatg atacgggacg aacagggagg atccgtgtcc tgtcttttaa aactggcatc   3360
atttccctgt gtaaagcaca tttggaagac aagtacagat accttttcaa gcaagtggca   3420
agttcaacag gattttgtga ccagcgcagg ctgggcctcc ttctgcatga ttctatccaa   3480
attccaagac agttgggtga agttgcatcc tttgggggca gtaacattga gccaagtgtc   3540
cggagctgct tccaatttgc taataataag ccagagatcg aagcggccct cttcctagac   3600
tggatgagac tggaacccca gtccatggtg tggctgcccg tcctgcacag agtggctgct   3660
gcagaaactg ccaagcatca ggccaaatgt aacatctgca aagagtgtcc aatcattgga   3720
ttcaggtaca ggagtctaaa gcactttaat tatgacatct gccaaagctg cttttttttct  3780
ggtcgagttg caaaaggcca taaaatgcac tatcccatgg tggaatattg cactccgact   3840
acatcaggag aagatgttcg agactttgcc aaggtactaa aaaacaaatt tcgaaccaaa   3900
aggtattttg cgaagcatcc ccgaatgggc tacctgccag tgcagactgt cttagagggg   3960
gacaacatgg aaacttag                                                3978
```

<210> SEQ ID NO 27
<211> LENGTH: 1329
<212> TYPE: PRT
<213> ORGANISM: Artificial Sequence
<220> FEATURE:
<223> OTHER INFORMATION: Delta3990 protein

<400> SEQUENCE: 27

Met Val Trp Trp Glu Glu Val Glu Asp Cys Tyr Glu Arg Glu Asp Val
1               5                   10                  15

Gln Lys Lys Thr Phe Thr Lys Trp Val Asn Ala Gln Phe Ser Lys Phe
            20                  25                  30

Gly Lys Gln His Ile Glu Asn Leu Phe Ser Asp Leu Gln Asp Gly Arg
        35                  40                  45

Arg Leu Leu Asp Leu Leu Glu Gly Leu Thr Gly Gln Lys Leu Pro Lys
    50                  55                  60

Glu Lys Gly Ser Thr Arg Val His Ala Leu Asn Asn Val Asn Lys Ala
65                  70                  75                  80

Leu Arg Val Leu Gln Asn Asn Asn Val Asp Leu Val Asn Ile Gly Ser
                85                  90                  95

Thr Asp Ile Val Asp Gly Asn His Lys Leu Thr Leu Gly Leu Ile Trp
            100                 105                 110

Asn Ile Ile Leu His Trp Gln Val Lys Asn Val Met Lys Asn Ile Met
        115                 120                 125

Ala Gly Leu Gln Gln Thr Asn Ser Glu Lys Ile Leu Leu Ser Trp Val
    130                 135                 140

Arg Gln Ser Thr Arg Asn Tyr Pro Gln Val Asn Val Ile Asn Phe Thr
145                 150                 155                 160

Thr Ser Trp Ser Asp Gly Leu Ala Leu Asn Ala Leu Ile His Ser His
                165                 170                 175

Arg Pro Asp Leu Phe Asp Trp Asn Ser Val Val Cys Gln Gln Ser Ala
            180                 185                 190

Thr Gln Arg Leu Glu His Ala Phe Asn Ile Ala Arg Tyr Gln Leu Gly
        195                 200                 205

Ile Glu Lys Leu Leu Asp Pro Glu Asp Val Asp Thr Thr Tyr Pro Asp
    210                 215                 220

Lys Lys Ser Ile Leu Met Tyr Ile Thr Ser Leu Phe Gln Val Leu Pro
225                 230                 235                 240

Gln Gln Val Ser Ile Glu Ala Ile Gln Glu Val Glu Met Leu Pro Arg
                245                 250                 255

Pro Pro Lys Val Thr Lys Glu Glu His Phe Gln Leu His His Gln Met
            260                 265                 270

His Tyr Ser Gln Gln Ile Thr Val Ser Leu Ala Gln Gly Tyr Glu Arg
        275                 280                 285

Thr Ser Ser Pro Lys Pro Arg Phe Lys Ser Tyr Ala Tyr Thr Gln Ala
    290                 295                 300

Ala Tyr Val Thr Thr Ser Asp Pro Thr Arg Ser Pro Phe Pro Ser Gln
305                 310                 315                 320

His Leu Glu Ala Pro Glu Asp Lys Ser Phe Gly Ser Ser Leu Met Glu
                325                 330                 335

Ser Glu Val Asn Leu Asp Arg Tyr Gln Thr Ala Leu Glu Glu Val Leu
            340                 345                 350

Ser Trp Leu Leu Ser Ala Glu Asp Thr Leu Gln Ala Gln Gly Glu Ile
        355                 360                 365

Ser Asn Asp Val Glu Val Val Lys Asp Gln Phe His Thr His Glu Gly
    370                 375                 380

Tyr Met Met Asp Leu Thr Ala His Gln Gly Arg Val Gly Asn Ile Leu
385                 390                 395                 400

Gln Leu Gly Ser Lys Leu Ile Gly Thr Gly Lys Leu Ser Glu Asp Glu
                405                 410                 415

-continued

```
Glu Thr Glu Val Gln Glu Gln Met Asn Leu Leu Asn Ser Arg Trp Glu
            420                 425                 430

Cys Leu Arg Val Ala Ser Met Glu Lys Gln Ser Asn Leu His Arg Val
        435                 440                 445

Leu Met Asp Leu Gln Asn Gln Lys Leu Lys Glu Leu Asn Asp Trp Leu
    450                 455                 460

Thr Lys Thr Glu Glu Arg Thr Arg Lys Met Glu Glu Glu Pro Leu Gly
465                 470                 475                 480

Pro Asp Leu Glu Asp Leu Lys Arg Gln Val Gln Gln His Lys Val Leu
                485                 490                 495

Gln Glu Asp Leu Glu Gln Glu Gln Val Arg Val Asn Ser Leu Thr His
            500                 505                 510

Met Val Val Val Val Asp Glu Ser Ser Gly Asp His Ala Thr Ala Ala
        515                 520                 525

Leu Glu Glu Gln Leu Lys Val Leu Gly Asp Arg Trp Ala Asn Ile Cys
    530                 535                 540

Arg Trp Thr Glu Asp Arg Trp Val Leu Leu Gln Asp Gln Pro Asp Leu
545                 550                 555                 560

Ala Pro Gly Leu Thr Thr Ile Gly Ala Ser Pro Thr Gln Thr Val Thr
                565                 570                 575

Leu Val Thr Gln Pro Val Val Thr Lys Glu Thr Ala Ile Ser Lys Leu
            580                 585                 590

Glu Met Pro Ser Ser Leu Met Leu Glu Val Pro Thr His Arg Leu Leu
        595                 600                 605

Gln Gln Phe Pro Leu Asp Leu Glu Lys Phe Leu Ala Trp Leu Thr Glu
    610                 615                 620

Ala Glu Thr Thr Ala Asn Val Leu Gln Asp Ala Thr Arg Lys Glu Arg
625                 630                 635                 640

Leu Leu Glu Asp Ser Lys Gly Val Lys Glu Leu Met Lys Gln Trp Gln
                645                 650                 655

Asp Leu Gln Gly Glu Ile Glu Ala His Thr Asp Val Tyr His Asn Leu
            660                 665                 670

Asp Glu Asn Ser Gln Lys Ile Leu Arg Ser Leu Glu Gly Ser Asp Asp
        675                 680                 685

Ala Val Leu Leu Gln Arg Arg Leu Asp Asn Met Asn Phe Lys Trp Ser
    690                 695                 700

Glu Leu Arg Lys Lys Ser Leu Asn Ile Arg Ser His Leu Glu Ala Ser
705                 710                 715                 720

Ser Asp Gln Trp Lys Arg Leu His Leu Ser Leu Gln Glu Leu Leu Val
                725                 730                 735

Trp Leu Gln Leu Lys Asp Asp Glu Leu Ser Arg Gln Ala Pro Ile Gly
            740                 745                 750

Gly Asp Phe Pro Ala Val Gln Lys Gln Asn Asp Val His Arg Ala Phe
        755                 760                 765

Lys Arg Glu Leu Lys Thr Lys Glu Pro Val Ile Met Ser Thr Leu Glu
    770                 775                 780

Thr Val Arg Ile Phe Leu Thr Glu Gln Pro Leu Glu Gly Leu Glu Lys
785                 790                 795                 800

Leu Tyr Gln Glu Pro Arg Glu Leu Pro Pro Glu Glu Arg Ala Gln Asn
                805                 810                 815

Val Thr Arg Leu Leu Arg Lys Gln Ala Glu Glu Val Asn Thr Glu Trp
            820                 825                 830
```

```
Glu Lys Leu Asn Leu His Ser Ala Asp Trp Gln Arg Lys Ile Asp Glu
        835                 840                 845

Thr Leu Glu Arg Leu Gln Glu Leu Gln Glu Ala Thr Asp Glu Leu Asp
    850                 855                 860

Leu Lys Leu Arg Gln Ala Glu Val Ile Lys Gly Ser Trp Gln Pro Val
865                 870                 875                 880

Gly Asp Leu Leu Ile Asp Ser Leu Gln Asp His Leu Glu Lys Val Lys
                885                 890                 895

Ala Leu Arg Gly Glu Ile Ala Pro Leu Lys Glu Asn Val Ser His Val
            900                 905                 910

Asn Asp Leu Ala Arg Gln Leu Thr Thr Leu Gly Ile Gln Leu Ser Pro
        915                 920                 925

Tyr Asn Leu Ser Thr Leu Glu Asp Leu Asn Thr Arg Trp Lys Leu Leu
    930                 935                 940

Gln Val Ala Val Glu Asp Arg Val Arg Gln Leu His Glu Ala His Arg
945                 950                 955                 960

Asp Phe Gly Pro Ala Ser Gln His Phe Leu Ser Thr Ser Val Gln Gly
                965                 970                 975

Pro Trp Glu Arg Ala Ile Ser Pro Asn Lys Val Pro Tyr Tyr Ile Asn
            980                 985                 990

His Glu Thr Gln Thr Thr Cys Trp  Asp His Pro Lys Met  Thr Glu Leu
        995                 1000                1005

Tyr Gln  Ser Leu Ala Asp Leu  Asn Asn Val Arg Phe  Ser Ala Tyr
    1010                1015                1020

Arg Thr  Ala Met Lys Leu Arg  Arg Leu Gln Lys Ala  Leu Cys Leu
    1025                1030                1035

Asp Leu  Leu Ser Leu Ser Ala  Ala Cys Asp Ala Leu  Asp Gln His
    1040                1045                1050

Asn Leu  Lys Gln Asn Asp Gln  Pro Met Asp Ile Leu  Gln Ile Ile
    1055                1060                1065

Asn Cys  Leu Thr Thr Ile Tyr  Asp Arg Leu Glu Gln  Glu His Asn
    1070                1075                1080

Asn Leu  Val Asn Val Pro Leu  Cys Val Asp Met Cys  Leu Asn Trp
    1085                1090                1095

Leu Leu  Asn Val Tyr Asp Thr  Gly Arg Thr Gly Arg  Ile Arg Val
    1100                1105                1110

Leu Ser  Phe Lys Thr Gly Ile  Ile Ser Leu Cys Lys  Ala His Leu
    1115                1120                1125

Glu Asp  Lys Tyr Arg Tyr Leu  Phe Lys Gln Val Ala  Ser Ser Thr
    1130                1135                1140

Gly Phe  Cys Asp Gln Arg Arg  Leu Gly Leu Leu Leu  His Asp Ser
    1145                1150                1155

Ile Gln  Ile Pro Arg Gln Leu  Gly Glu Val Ala Ser  Phe Gly Gly
    1160                1165                1170

Ser Asn  Ile Glu Pro Ser Val  Arg Ser Cys Phe Gln  Phe Ala Asn
    1175                1180                1185

Asn Lys  Pro Glu Ile Glu Ala  Ala Leu Phe Leu Asp  Trp Met Arg
    1190                1195                1200

Leu Glu  Pro Gln Ser Met Val  Trp Leu Pro Val Leu  His Arg Val
    1205                1210                1215

Ala Ala  Ala Glu Thr Ala Lys  His Gln Ala Lys Cys  Asn Ile Cys
    1220                1225                1230

Lys Glu  Cys Pro Ile Ile Gly  Phe Arg Tyr Arg Ser  Leu Lys His
```

```
    1235                1240                1245

Phe Asn  Tyr Asp Ile Cys Gln  Ser Cys Phe Phe Ser  Gly Arg Val
    1250                1255                1260

Ala Lys  Gly His Lys Met His  Tyr Pro Met Val Glu  Tyr Cys Thr
    1265                1270                1275

Pro Thr  Thr Ser Gly Glu Asp  Val Arg Asp Phe Ala  Lys Val Leu
    1280                1285                1290

Lys Asn  Lys Phe Arg Thr Lys  Arg Tyr Phe Ala Lys  His Pro Arg
    1295                1300                1305

Met Gly  Tyr Leu Pro Val Gln  Thr Val Leu Glu Gly  Asp Asn Met
    1310                1315                1320

Glu Thr  Pro Asp Thr Met
    1325


<210> SEQ ID NO 28
<211> LENGTH: 3990
<212> TYPE: DNA
<213> ORGANISM: Artificial Sequence
<220> FEATURE:
<223> OTHER INFORMATION: Delta3990 gene

<400> SEQUENCE: 28

atggtttggt gggaagaagt agaggactgt tatgaaagag aagatgttca aaagaaaaca     60

ttcacaaaat gggtaaatgc acaattttct aagtttggga agcagcatat tgagaacctc    120

ttcagtgacc tacaggatgg gaggcgcctc ctagacctcc tcgaaggcct gacagggcaa    180

aaactgccaa aagaaaaagg atccacaaga gttcatgccc tgaacaatgt caacaaggca    240

ctgcgggttt tgcagaacaa taatgttgat ttagtgaata ttggaagtac tgacatcgta    300

gatggaaatc ataaactgac tcttggtttg atttggaata taatcctcca ctggcaggtc    360

aaaaatgtaa tgaaaaatat catggctgga ttgcaacaaa ccaacagtga aaagattctc    420

ctgagctggg tccgacaatc aactcgtaat tatccacagg ttaatgtaat caacttcacc    480

accagctggt ctgatggcct ggctttgaat gctctcatcc atagtcatag gccagaccta    540

tttgactgga atagtgtggt ttgccagcag tcagccacac aacgactgga acatgcattc    600

aacatcgcca gatatcaatt aggcatagag aaactactcg atcctgaaga tgttgatacc    660

acctatccag ataagaagtc catcttaatg tacatcacat cactcttcca agttttgcct    720

caacaagtga gcattgaagc catccaggaa gtggaaatgt tgccaaggcc acctaaagtg    780

actaaagaag aacattttca gttacatcat caaatgcact attctcaaca gatcacggtc    840

agtctagcac agggatatga gagaacttct tcccctaagc ctcgattcaa gagctatgcc    900

tacacacagg ctgcttatgt caccacctct gaccctacac ggagcccatt tccttcacag    960

catttggaag ctcctgaaga caagtcattt ggcagttcat tgatggagag tgaagtaaac   1020

ctggaccgtt atcaaacagc tttagaagaa gtattatcgt ggcttctttc tgctgaggac   1080

acattgcaag cacaaggaga gatttctaat gatgtggaag tggtgaaaga ccagtttcat   1140

actcatgagg ggtacatgat ggatttgaca gcccatcagg gccgggttgg taatattcta   1200

caattgggaa gtaagctgat tggaacagga aaattatcag aagatgaaga aactgaagta   1260

caagagcaga tgaatctcct aaattcaaga tgggaatgcc tcagggtagc tagcatggaa   1320

aaacaaagca atttacatag agttttaatg gatctccaga atcagaaact gaaagagttg   1380

aatgactggc taacaaaaac agaagaaaga acaaggaaaa tggaggaaga gcctcttgga   1440

cctgatcttg aagacctaaa acgccaagta caacaacata aggtgcttca agaagatcta   1500
```

-continued

```
gaacaagaac aagtcagggt caattctctc actcacatgg tggtggtagt tgatgaatct   1560
agtggagatc acgcaactgc tgctttggaa gaacaactta aggtattggg agatcgatgg   1620
gcaaacatct gtagatggac agaagaccgc tgggttcttt tacaagacca gcctgaccta   1680
gctcctggac tgaccactat tggagcctct cctactcaga ctgttactct ggtgacacaa   1740
cctgtggtta ctaaggaaac tgccatctcc aaactagaaa tgccatcttc cttgatgttg   1800
gaggtaccta ctcatagatt actgcaacag ttccccctgg acctggaaaa gtttcttgcc   1860
tggcttacag aagctgaaac aactgccaat gtcctacagg atgctacccg taaggaaagg   1920
ctcctagaag actccaaggg agtaaaagag ctgatgaaac aatggcaaga cctccaaggt   1980
gaaattgaag ctcacacaga tgtttatcac aacctggatg aaaacagcca aaaaatcctg   2040
agatccctgg aaggttccga tgatgcagtc ctgttacaaa gacgtttgga taacatgaac   2100
ttcaagtgga gtgaacttcg gaaaaagtct ctcaacatta ggtcccattt ggaagccagt   2160
tctgaccagt ggaagcgtct gcacctttct ctgcaggaac ttctggtgtg gctacagctg   2220
aaagatgatg aattaagccg gcaggcacct attggaggcg actttccagc agttcagaag   2280
cagaacgatg tacatagggc cttcaagagg gaattgaaaa ctaaagaacc tgtaatcatg   2340
agtactcttg agactgtacg aatatttctg acagagcagc ctttggaagg actagagaaa   2400
ctctaccagg agcccagaga gctgcctcct gaggagagag cccagaatgt cactcggctt   2460
ctacgaaagc aggctgagga ggtcaatact gagtgggaaa aattgaacct gcactccgct   2520
gactggcaga gaaaaataga tgagaccctt gaaagactcc aggaacttca agaggccacg   2580
gatgagctgg acctcaagct gcgccaagct gaggtgatca agggatcctg gcagcccgtg   2640
ggcgatctcc tcattgactc tctccaagat cacctcgaga aagtcaaggc acttcgagga   2700
gaaattgcgc ctctgaaaga gaacgtgagc cacgtcaatg accttgctcg ccagcttacc   2760
actttgggca ttcagctctc accgtataac ctcagcactc tggaagacct gaacaccaga   2820
tggaagcttc tgcaggtggc cgtcgaggac cgagtcaggc agctgcatga agcccacagg   2880
gactttggtc cagcatctca gcactttctt tccacgtctg tccagggtcc ctgggagaga   2940
gccatctcgc caaacaaagt gccctactat atcaaccacg agactcaaac aacttgctgg   3000
gaccatccca aaatgacaga gctctaccag tctttagctg acctgaataa tgtcagattc   3060
tcagcttata ggactgccat gaaactccga agactgcaga aggccctttg cttggatctc   3120
ttgagcctgt cagctgcatg tgatgccttg gaccagcaca acctcaagca aaatgaccag   3180
cccatggata tcctgcagat tattaattgt ttgaccacta tttatgaccg cctggagcaa   3240
gagcacaaca atttggtcaa cgtccctctc tgcgtggata tgtgtctgaa ctggctgctg   3300
aatgtttatg atacgggacg aacagggagg atccgtgtcc tgtcttttaa aactggcatc   3360
atttccctgt gtaaagcaca tttggaagac aagtacagat accttttcaa gcaagtggca   3420
agttcaacag gattttgtga ccagcgcagg ctgggcctcc ttctgcatga ttctatccaa   3480
attccaagac agttgggtga agttgcatcc tttgggggca gtaacattga gccaagtgtc   3540
cggagctgct tccaatttgc taataataag ccagagatcg aagcggccct cttcctagac   3600
tggatgagac tggaacccca gtccatggtg tggctgcccg tcctgcacag agtggctgct   3660
gcagaaactg ccaagcatca ggccaaatgt aacatctgca aagagtgtcc aatcattgga   3720
ttcaggtaca ggagtctaaa gcactttaat tatgacatct gccaaagctg ctttttttct   3780
ggtcgagttg caaaaggcca taaaatgcac tatcccatgg tggaatattg cactccgact   3840
```

-continued

```
acatcaggag aagatgttcg agactttgcc aaggtactaa aaaacaaatt tcgaaccaaa   3900

aggtattttg cgaagcatcc ccgaatgggc tacctgccag tgcagactgt cttagagggg   3960

gacaacatgg aaactcccga cacaatgtag                                    3990
```

OPTIMIZED MINI-DYSTROPHIN GENES AND EXPRESSION CASSETTES AND THEIR USE

STATEMENT OF PRIORITY

This application is a continuation of and claims priority to U.S. patent application Ser. No. 15/628,268, filed on Jun. 20, 2017, which claims the benefit of U.S. Provisional Application Ser. No. 62/352,675, filed on Jun. 21, 2016, and U.S. Provisional Application Ser. No. 62/516,449, filed on Jun. 7, 2017, the contents of each of which are incorporated herein by reference in their entirety.

STATEMENT REGARDING FEDERALLY SPONSORED RESEARCH OR DEVELOPMENT

This invention was made with government support under Grant Nos. AR050595, AR056394, and AR056953 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-784CT_ST25.txt, 138,054 bytes in size, generated on Feb. 11, 2020 and filed via EFS-Web, is provided in lieu of a paper copy. This Sequence Listing is hereby incorporated by reference into the specification for its disclosures.

FIELD OF THE INVENTION

This invention relates to polynucleotides encoding mini-dystrophin proteins, viral vectors comprising the same, and methods of using the same for delivery of mini-dystrophin to a cell or a subject.

BACKGROUND OF THE INVENTION

Duchenne muscular dystrophy (DMD) is a severe, x-linked, progressive neuromuscular disease affecting approximately one in 3,600 to 9200 live male births. The disorder is caused by frame shift mutations in the dystrophin gene abolishing the expression of the dystrophin protein. Due to the lack of the dystrophin protein, skeletal muscle, and ultimately heart and respiratory muscles (e.g., intercostal muscles and diaphragm), degenerate causing premature death. Progressive weakness and muscle atrophy begins in childhood, starting in the lower legs and pelvis before spreading into the upper arms. Other symptoms include loss of certain reflexes, waddling gait, frequent falls, difficulty rising from a sitting or lying position, difficulty climbing stairs, changes to overall posture, impaired breathing, and cardiomyopathy. Many children are unable to run rapidly or jump. The atrophied muscles, in particular the calf muscles (and, less commonly, muscles in the buttocks, shoulders, and arms), may be enlarged by an accumulation of fat and connective tissue, causing them to look larger and healthier than they actually are (called pseudohypertrophy). Bone thinning and scoliosis are common. Ultimately, independent ambulation is lost, and a wheelchair becomes necessary, in most cases between 12 to 15 years of age. As the disease progresses, the muscles in the diaphragm that assist in breathing and coughing become weaker. Affected individuals experience breathing difficulties, respiratory infections, and swallowing problems. Almost all DMD patients will develop cardiomyopathy. Pneumonia compounded by cardiac involvement is the most frequent cause of death, which frequently occurs before the third decade.

Becker muscular dystrophy (BMD) has less severe symptoms than DMD, but still leads to premature death. Compared to DMD, BMD is characterized by later-onset skeletal muscle weakness. Whereas DMD patients are wheelchair dependent before age 13, those with BMD lose ambulation and require a wheelchair after age 16. BMD patients also exhibit preservation of neck flexor muscle strength, unlike their counterparts with DMD. Despite milder skeletal muscle involvement, heart failure from DMD-associated dilated cardiomyopathy (DCM) is a common cause of morbidity and the most common cause of death in BMD, which occurs on average in the mid-40s.

Dystrophin is a cytoplasmic protein encoded by the dmd gene, and functions to link cytoskeletal actin filaments to membrane proteins. Normally, the dystrophin protein, located primarily in skeletal and cardiac muscles, with smaller amounts expressed in the brain, acts as a shock absorber during muscle fiber contraction by linking the actin of the contractile apparatus to the layer of connective tissue that surrounds each muscle fiber. In muscle, dystrophin is localized at the cytoplasmic face of the sarcolemma membrane.

First identified in 1987, the dmd gene is the largest known human gene at approximately 2.5 Mb. The gene is located on the X chromosome at position Xp21 and contains 79 exons. The most common mutations that cause DMD or BMD are large deletion mutations of one or more exons (60-70%), but duplication mutations (5-10%), and single nucleotide variants, (including small deletions or insertions, single-base changes, and splice site changes accounting for approximately 25%-35% of pathogenic variants in males with DMD and about 10%-20% of males with BMD) can also cause pathogenic dystrophin variants.

In DMD, mutations often lead to a frame shift resulting in a premature stop codon and a truncated, non-functional or unstable protein. Nonsense point mutations can also result in premature termination codons with the same result. While mutations causing DMD can affect any exon, exons 2-20 and 45-55 are common hotspots for large deletion and duplication mutations. In frame deletions result in the less severe Becker muscular dystrophy (BMD), in which patients express a truncated, partially functional dystrophin.

Full-length dystrophin is a large (427 kDa) protein comprising a number of subdomains that contribute to its function. These subdomains include, in order from the amino-terminus toward the carboxy-terminus, the N-terminal actin-binding domain, a central so-called "rod" domain, a cysteine-rich domain and lastly a carboxy-terminal domain or region. The rod domain is comprised of 4 proline-rich hinge domains (abbreviated H), and 24 spectrin-like repeats (abbreviated R) in the following order: a first hinge domain (H1), 3 spectrin-like repeats (R1, R2, R3), a second hinge domain (H2), 16 more spectrin-like repeats (R4, R5, R6, R7, R8, R9, R10, R11, R12, R13, R14, R15, R16, R17, R18, R19), a third hinge domain (H3), 5 more spectrin-like repeats (R20, R21, R22, R23, R24), and finally a fourth hinge domain (H4). Subdomains toward the carboxy-terminus of the protein are involved in connecting to the dystrophin-associated glycoprotein complex (DGC), a large protein complex that forms a critical link between the cytoskeleton and the extra-cellular matrix.

No treatment definitively halts or reverses progression of DMD. Treatment with corticosteroids is the current standard of care, but this merely slows progression by a year or two. A number of new drugs for DMD have recently been approved by regulators. These include ataluren, which causes read-through of premature stop codons, and eteplirsen, which causes skipping of exon 51, generating an internally deleted partially functional dystrophin. However, the mechanism of action of these drugs is not expected to help all DMD patients, and further evidence is required to definitively demonstrate their clinical efficacy in DMD.

With advances over the last 10-15 years in use of adeno-associated virus (AAV) mediated gene therapy to potentially treat a variety of rare diseases, there has been renewed hope and interest that AAV could be used to treat DMD and less severe dystrophinopathies (i.e., other muscle diseases associated with mutations in the dmd gene). Due to limits on payload size of AAV vectors, attention has focused on creating micro- or mini-dystrophins, smaller versions of dystrophin that eliminate non-essential subdomains while maintaining at least some function of the full-length protein. AAV-mediated mini-dystrophin gene therapy has shown promise in mdx mice, an animal model for DMD, with widespread expression in muscle and evidence of improved muscle function (See, e.g., Wang et al., *J. Orthop. Res.* 27:421 (2009)). When related experiments using a micro-dystrophin vector were attempted in the GRMD DMD dog model, however, powerful immunosuppressant drugs were required to achieve significant transduction of muscle cells (Yuasa et al., *Gene Ther.* 14:1249 (2007)). Similarly, when human DMD patients were treated with AAV vectors designed to express a mini-dystrophin, minimal protein was detected in only two of the six patients, whereas a T-cell response against the mini-dystrophin protein was stimulated in three (Bowles, et al., Mol Ther. 20(2):443-455 (2012)).

Thus, there exists a need in the art for AAV vectors encoding mini-dystrophins that can be expressed at high levels in transduced cells of subjects with DMD while minimizing immune responses to the mini-dystrophin protein.

SUMMARY OF THE INVENTION

Disclosed and exemplified herein are mini-dystrophin proteins, codon-optimized genes for expressing such mini-dystrophin proteins, AAV vectors for transducing cells with such genes, and methods of prevention and treatment using such AAV vectors, in particular for preventing and treating dystrophinopathies in subjects in need thereof. In some of these embodiments, AAV vectors of the disclosure are capable of guiding production of significant levels of mini-dystrophin in transduced cells while causing no or only muted immune response against the mini-dystrophin protein.

Certain non-limiting embodiments (E) of the inventions of the disclosure are set forth below. These and related embodiments are described in further detail in the Detailed Description, including the Examples and Drawings.

E1. A mini-dystrophin protein comprising, consisting essentially of, or consisting of the N-terminus, the Actin Binding Domain (ABD), hinge H1, rods R1 and R2, hinge H3, rods R22, R23, and R24, hinge H4, the cysteine-rich (CR) domain, and a portion of the carboxy-terminal (CT) domain of wildtype human muscle dystrophin protein (SEQ ID NO:25), wherein the CT domain does not comprise the last three amino acid residues at the carboxy-terminus of wild-type dystrophin protein.

E2. The mini-dystrophin protein of E1, wherein the N-terminus and Actin Binding Domain (ABD) together comprise, consist essentially of, or consist of amino acid numbers 1-240 from SEQ ID NO:25; hinge H1 comprises, consists essentially of, or consists of amino acid numbers 253-327 from SEQ ID NO:25; rod R1 comprises, consists essentially of, or consists of amino acid numbers 337-447 from SEQ ID NO:25; rod R2 comprises, consists essentially of, or consists of amino acid numbers 448-556 from SEQ ID NO:25; hinge H3 comprises, consists essentially of, or consists of amino acid numbers 2424-2470 from SEQ ID NO:25; rod R22 comprises, consists essentially of, or consists of amino acid numbers 2687-2802 from SEQ ID NO:25; rod R23 comprises, consists essentially of, or consists of amino acid numbers 2803-2931 from SEQ ID NO:25; rod R24 comprises, consists essentially of, or consists of amino acid numbers 2932-3040 from SEQ ID NO:25; hinge H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the portion of the CT domain comprises, consists essentially of, or consists of amino acid numbers 3300-3408 from SEQ ID NO:25.

E3. The mini-dystrophin protein of any one of E1 and E2, wherein the mini-dystrophin protein comprises, consists essentially of, or consists of the amino acid sequence of SEQ ID NO:7.

E4. A mini-dystrophin protein comprising, consisting essentially of, or consisting of the N-terminus, the Actin Binding Domain (ABD), hinge H1, rods R1, R2, R22, R23, and R24, hinge H4, the cysteine-rich (CR) domain, and a portion of the carboxy-terminal (CT) domain of wildtype human muscle dystrophin protein (SEQ ID NO:25), wherein the CT domain does not comprise the last three amino acid residues at the carboxy-terminus of wildtype dystrophin protein.

E5. The mini-dystrophin protein of E4 wherein the N-terminus and Actin Binding Domain (ABD) together comprise, consist essentially of, or consist of amino acid numbers 1-240 from SEQ ID NO:25; hinge H1 comprises, consists essentially of, or consists of amino acid numbers 253-327 from SEQ ID NO:25; rod R1 comprises, consists essentially of, or consists of amino acid numbers 337-447 from SEQ ID NO:25; rod R2 comprises, consists essentially of, or consists of amino acid numbers 448-556 from SEQ ID NO:25; rod R22 comprises, consists essentially of, or consists of amino acid numbers 2687-2802 from SEQ ID NO:25; rod R23 comprises, consists essentially of, or consists of amino acid numbers 2803-2931 from SEQ ID NO:25; rod R24 comprises, consists essentially of, or consists of amino acid numbers 2932-3040 from SEQ ID NO:25; hinge H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the portion of the CT domain comprises, consists essentially of, or consists of amino acid numbers 3300-3408 from SEQ ID NO:25.

E6. The mini-dystrophin protein of any one of E4 and E5, wherein the mini-dystrophin protein comprises, consists essentially of, or consists of the amino acid sequence of SEQ ID NO:8.

E7. A polynucleotide encoding the mini-dystrophin protein of E1-E3.

E8. A polynucleotide encoding the mini-dystrophin protein of E4-E6.

E9. The polynucleotide of any one of E7 and E8, wherein the nucleobase sequence thereof is assembled from the coding sequence of the native wildtype gene encoding full-length human muscle dystrophin, an example of which is provided by NCBI Reference Sequence NM_004006.2.

E10. The polynucleotide of E9, wherein the nucleobase sequence thereof is provided by SEQ ID NO:26.

E11. The polynucleotide of any one of E7-E10, wherein the nucleobase sequence is codon-optimized.

E12. The polynucleotide of E11, wherein the codon-optimization decreases or increases the GC content compared to the wildtype sequence.

E13. The polynucleotide of E11, wherein the codon-optimization decreases or increases the number of CpG dinucleotides compared to the wildtype sequence.

E14. The polynucleotide of E11, wherein the codon-optimization eliminates one or more cryptic splice sites.

E15. The polynucleotide of E11, wherein the codon-optimization eliminates one or more ribosome entry sites other than the one at the start of the coding sequence for the mini-dystrophin protein.

E16. The polynucleotide of E11, wherein the codon-optimization substitutes one or more rare codons for codons that occur with higher frequency in the type and/or species of cell in which the mini-dystrophin gene is intended to be expressed.

E17. The polynucleotide of E12, wherein the codon-optimization increases the GC content compared to wildtype and increases the level of gene expression by at least 50%, 100%, 150%, 200%, 250%, 300%, 350%, 400%, 450%, 500%, 550%, 600%, 650%, 700%, 750%, 800%, 900%, 1000%, or more.

E18. The polynucleotide of E12, wherein the codon-optimization increases the GC content compared to wildtype at least 5%, 10%, 15%, 20%, 25%, 30%, 35%, 40%, 45%, 50%, 55%, 60%, 65%, 70%, 75%, 80%, 85%, 90%, 95%, 100%, or more.

E19. The polynucleotide of E12, wherein the GC content is about or at least 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, or more.

E20. The polynucleotide of E13, wherein the codon-optimization decreases or increases the number of CpG dinucleotides compared to the wildtype by about or at least 5%, 10%, 15%, 20%, 25%, 30%, 35%, 40%, 45%, 50%, 55%, 60%, or more.

E21. The polynucleotide of E20, wherein the number of CpG dinucleotides, if reduced, is reduced in an amount sufficient to fully or partially suppress the silencing of gene expression due to the methylation of CpG motifs.

E22. The polynucleotide of E11, wherein the codon-optimization increases the codon adaptation index (CAI) of the mini-dystrophin gene in reference to highly expressed human genes to a value that is at least 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99.

E23. The polynucleotide of any one of E11-E22, wherein the nucleobase sequence is human codon-optimized.

E24. The polynucleotide of any one of E11-E22, wherein the nucleobase sequence is canine codon-optimized.

E25. The polynucleotide of E23, wherein the human codon-optimized sequence is provided by SEQ ID NO:1, or a nucleobase sequence at least 90%, 91%, 92%, 93%, 94%, 95%, 96%, 97%, 98%, 99%, or 99.5% identical thereto.

E26. The polynucleotide of E23, wherein the human codon-optimized sequence is provided by SEQ ID NO:2, or a nucleobase sequence at least 90%, 91%, 92%, 93%, 94%, 95%, 96%, 97%, 98%, 99%, or 99.5% identical thereto.

E27. The polynucleotide of E24, wherein the canine codon-optimized sequence is provided by SEQ ID NO:3, or a nucleobase sequence at least 90%, 91%, 92%, 93%, 94%, 95%, 96%, 97%, 98%, 99%, or 99.5% identical thereto.

E28. A vector comprising the polynucleotide of any of any one of E7-E27.

E29. The vector of E28, wherein the polynucleotide is operably linked to a genetic control region.

E30. The vector of E29, wherein the genetic control region is a promoter.

E31. The vector of E30, wherein the promoter is muscle-specific in being more active in muscle cells compared to other types of cells, such as liver cells.

E32. The vector of any one of E30-E31, wherein the genetic control region further includes an enhancer.

E33. The vector of any one of E30-E32, wherein the promoter, and enhancer if present, is from a muscle creatine kinase (CK) gene.

E34. The vector of E33, wherein the CK gene is from mouse or human.

E35. The vector of E33, wherein the genetic control region is the mouse CK7 enhancer and promoter.

E36. The vector of any one of E29-E36, wherein the genetic control region comprises the nucleobase sequence selected from the group SEQ ID NO:4, SEQ ID NO:5, and SEQ ID NO:16.

E37. The vector of any one of E28-E36, wherein the polynucleotide is operably linked to a transcription terminator region.

E38. The vector of E37, wherein the transcription terminator region comprises the nucleobase sequence of SEQ ID NO:6 or SEQ ID NO:17.

E39. The vector of any one of E28-E38, wherein the vector is an AAV viral vector genome and comprises flanking AAV inverted terminal repeats (ITRs).

E40. The vector of E39, wherein the ITRs are both AAV2 ITRs.

E41. The vector of any one of E39 and E40, wherein the nucleobase sequence of the vector is provided by a nucleobase sequence selected from the group SEQ ID NO:9, SEQ ID NO:10, SEQ ID NO:11, SEQ ID NO:12, and SEQ ID NO:18.

E42. A recombinant AAV (rAAV) particle comprising an AAV capsid and the vector of any one of E39-E41.

E43. The rAAV particle of E42, wherein the AAV capsid is the AAV9 capsid.

E44. A rAAV particle, comprising an AAV capsid having tropism for striated muscle and a vector genome for expressing a human mini-dystrophin protein.

E45. The rAAV particle of E44, wherein the AAV capsid is from the AAV9 serotype.

E46. The rAAV particle of any one of E44 and E45, wherein the vector genome comprises a human codon-optimized nucleic acid sequence encoding the human mini-dystrophin protein.

E47. The rAAV particle of any one of E44-E46, wherein the human mini-dystrophin protein comprises the following subdomains or portions thereof from full-length human muscle dystrophin protein in order from N-terminus to C-terminus: N-terminal domain, Actin-Binding Domain (ABD), hinge H1, rod R1, rod R2, hinge H3, rod R22, rod R23, rod R24, hinge H4, the Cysteine-Rich (CR) Domain, and a portion of the carboxy-terminal (CT) domain, wherein the portion of the CT domain does not include the last 3 amino acids from dystrophin.

E48. The rAAV particle of any one of E44-E47, wherein the human mini-dystrophin protein comprises the amino acid sequence of SEQ ID NO:7.

E49. The rAAV particle of any one of E44-E46, wherein the human mini-dystrophin protein comprises the following subdomains or portions thereof from full-length human muscle dystrophin protein in order from N-terminus to C-terminus: N-terminal domain, Actin-Binding Domain (ABD), hinge H1, rod R1, rod R2, rod R22, rod R23, rod R24, hinge H4, the Cysteine-Rich (CR) Domain, and a portion of the carboxy-terminal (CT) domain, wherein the portion of the CT domain does not include the last 3 amino acids from dystrophin.

E50. The rAAV particle of any one of E44-E46, and E49, wherein the human mini-dystrophin protein comprises the amino acid sequence of SEQ ID NO:8.

E51. The rAAV particle of any one of E44-E47, wherein the human codon-optimized nucleic acid sequence encoding the human mini-dystrophin protein comprises the nucleic acid sequence of SEQ ID NO:1.

E52. The rAAV particle of any one of E44-E46, E49, and E50, wherein the human codon-optimized nucleic acid sequence encoding the human mini-dystrophin protein comprises the nucleic acid sequence of SEQ ID NO:3.

E53. The rAAV particle of any one of E44-E52, wherein the vector genome further comprises AAV inverted terminal repeats (ITRs) flanking the codon-optimized nucleic acid sequence.

E54. The rAAV particle of E53, wherein the AAV ITRs are AAV2 ITRs.

E55. The rAAV particle of any one of E44-E54, wherein the vector genome further comprises a muscle-specific transcriptional regulatory element operably linked with the human codon optimized nucleic acid sequence.

E56. The rAAV particle of E55, wherein the muscle-specific transcriptional regulatory element is positioned between the 5' AAV2 ITR and the human codon-optimized nucleic acid sequence.

E57. The rAAV particle of any one of E55 and E56, wherein the muscle-specific transcriptional regulatory element is derived from the human or mouse creatine kinase (CK) gene.

E58. The rAAV particle of any one of E55-E57, wherein the muscle-specific transcriptional regulatory element comprises an enhancer and a promoter.

E59. The rAAV particle of any one of E55-E58, wherein the muscle-specific transcriptional regulatory element is the mouse CK7 enhancer and promoter.

E60. The rAAV particle of any one of E55-E59, wherein the muscle-specific transcriptional regulatory element comprises the nucleic acid sequence of SEQ ID NO:16.

E61. The rAAV particle of any one of E44-E60, wherein the vector genome further comprises a transcription termination sequence positioned between the codon-optimized nucleic acid sequence and the 3' AAV2 ITR.

E62. The rAAV particle of E61, wherein the transcription termination sequence comprises a polyadenylation signal.

E63. The rAAV particle of any one of E44-E62, wherein the vector genome comprises in 5' to 3' order: a first AAV2 ITR, a muscle-specific transcriptional regulatory element operably linked to a human codon-optimized nucleic acid sequence encoding a human mini-dystrophin protein, a transcription termination sequence, and a second AAV2 ITR.

E64. The rAAV particle of E63, wherein the muscle-specific transcriptional regulatory element comprises the nucleic acid sequence of SEQ ID NO:16.

E65. The rAAV particle of embodiments E63 or E64, wherein the human codon-optimized nucleic acid sequence comprises the nucleic acid sequence of SEQ ID NO:1.

E66. The rAAV particle of embodiments E63-E65, wherein the transcription termination sequence comprises the nucleic acid sequence of SEQ ID NO:17.

E67. The rAAV particle of any one of E44-E48, E51, and E53-E66, wherein the vector genome comprises the nucleic acid sequence of SEQ ID NO:18 or the reverse-complement thereof.

E68. The rAAV particle of any one of E44-E48, E51, and E53-E66, wherein the vector genome consists essentially of the nucleic acid sequence of SEQ ID NO:18 or the reverse-complement thereof.

E69. The rAAV particle of any one of E44-E48, E51, and E53-E66, wherein the vector genome consists of the nucleic acid sequence of SEQ ID NO:18 or the reverse-complement thereof.

E70. A recombinant AAV particle, comprising an AAV9 capsid and a vector genome comprising the nucleic acid sequence of SEQ ID NO:18 or the reverse complement thereof.

E71. A recombinant AAV particle, comprising an AAV9 capsid and a vector genome consisting essentially of the nucleic acid sequence of SEQ ID NO:18 or the reverse complement thereof.

E72. A recombinant AAV particle, comprising an AAV9 capsid and a vector genome consisting of the nucleic acid sequence of SEQ ID NO:18 or the reverse complement thereof.

E73. A pharmaceutical composition comprising the rAAV particle of any one of E42-E72 and a pharmaceutically acceptable carrier.

E74. A method for treating a dystrophinopathy comprising administering to a subject in need of treatment for a dystrophinopathy a therapeutically effective amount of the composition of E73.

E75. Use of the recombinant AAV (rAAV) particle of any one of E42-E72 or use of the composition of E73 in the preparation of a medicament for treating a subject with a dystrophinopathy.

E76. The rAAV particle of any one of E42-E72 or the composition of E73 for use in the treatment of a subject having a dystrophinopathy.

E77. The method, use, rAAV particle, or composition for use of any one of E74-E76, wherein the dystrophinopathy is Duchenne muscular dystrophy (DMD), Becker muscular dystrophy (BMD), or DMD-associated dilated cardiomyopathy.

E78. The method, use, rAAV particle, or composition for use of any one of E74-E77, wherein the subject is a male or female human subject.

E79. The method, use, rAAV particle, or composition for use of any one of E74-E78, wherein the subject is ambulatory when first treated with or administered the composition.

E80. The method, use, rAAV particle, or composition for use of any one of E74-E79, wherein the subject is about or at least 4, 5, 6, 7, 8, 9, 10, 11, 12, 13, 14, 15, or 16 years of age when first treated with or administered the composition.

E81. The method, use, rAAV particle, or composition for use of any one of E74-E79, wherein the method, use, rAAV particle, or composition for use is effective to restore dystrophin associated protein complex at the sarcolemma of muscle cells compared to untreated controls.

E82. The method, use, rAAV particle, or composition for use of any one of E74-E79, wherein the method, use, rAAV particle, or composition for use is effective to improve the dystrophic histopathology in the heart compared to untreated controls.

E83. The method, use, rAAV particle, or composition for use of any one of E74-E79, wherein the method, use, rAAV particle, or composition for use is effective to inhibit fibrosis in limb muscle and diaphragm compared to untreated controls.

E84. The method, use, rAAV particle, or composition for use of any one of E74-E79, wherein the method, use, rAAV particle, or composition for use is effective to reduce muscle lesion score compared to untreated controls.

E85. The method, use, rAAV particle, or composition for use of any one of E74-E79, wherein the method, use, rAAV particle, or composition for use is effective to reduce muscle fatigue compared to untreated controls.

E86. The method, use, rAAV particle, or composition for use of any one of E74-E79, wherein the method, use, rAAV particle, or composition for use is effective to increase the maximum absolute or relative forelimb grip strength of $Dmd^{mdx}$ rats compared to untreated controls.

E87. The method, use, rAAV particle, or composition for use of any one of E74-E79, wherein the method, use, rAAV particle, or composition for use is effective to increase the detectable level of mini-dystrophin mRNA or protein in skeletal muscle, heart muscle or diaphragm.

E88. The method, use, rAAV particle, or composition for use of any one of E74-E79, wherein the method, use, rAAV particle, or composition for use is effective to reduce average MMP-9 levels in blood of subjects to within about 15-, 14-, 13-, 12-, 11-, 10-, 9-, 8-, 7-, 6-, 5-, 4-, 3-, or 2-fold greater than that in healthy controls.

E89. The method, use, rAAV particle, or composition for use of any one of E74-E79, wherein the method, use, rAAV particle, or composition for use is effective to reduce average ALT, AST, or LDH levels in blood of subjects to within about 7-, 6-, 5-, 4-, 3-, or 2-fold greater than that in healthy controls.

E90. The method, use, rAAV particle, or composition for use of any one of E74-E79, wherein the method, use, rAAV particle, or composition for use is effective to reduce average total CK levels in blood of subjects to within about 50-, 48-, 46-, 44-, 42-, 40-, 38-, 36-, 34-, 32-, 30-, 28-, 26-, 24-, 22-, 20-, 18-, 16-, 14-, 12-, 10-, 9-, 8-, 7-, 6-, 5-, 4-, 3-, or 2-fold greater than that in healthy controls.

E91. The method, use, rAAV particle, or composition for use of any one of E74-E79, wherein the method, use, rAAV particle, or composition for use is effective to increase the average 6 minute walk distance (6MWD) of subjects by at least 5, 10, 15, 20, 25, 30, 35, 40, 45, 50, 55, 60, 65, 70, 75, 80, 85, 90, 95, or 100 meters compared to the average 6MWD of untreated controls 3, 6, 9, 12, 15, 18, 21, 24, 27, 30, 33, or 36 months after administration of the vector.

E92. The method, use, rAAV particle, or composition for use of any one of E74-E79, wherein the method, use, rAAV particle, or composition for use is effective to reduce the average time required to perform the 4 stair climb test by at least 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 seconds compared to the average time of untreated controls 3, 6, 9, 12, 15, 18, 21, 24, 27, 30, 33, or 36 months after administration of the vector.

E93. The method, use, rAAV particle, or composition for use of any one of E74-E79, wherein the method, use, rAAV particle, or composition for use is effective to reduce the average proportion of subjects that have lost ambulation by at least 5%, 10%, 15%, 20%, 25%, 30%, 35%, 40%, 45%, 50%, 55%, 60% or 65% compared to the average proportion of untreated controls that have lost ambulation 3, 6, 9, 12, 15, 18, 21, 24, 27, 30, 33, or 36 months after administration of the vector.

E94. The method, use, rAAV particle, or composition for use of any one of E74-E79, wherein the method, use, rAAV particle, or composition for use is effective to reduce the average fat fraction in the lower extremities of subjects by at least 5%, 10%, 15%, 20%, 25%, 30%, 35%, 40%, 45%, 50%, 55%, 60%, 65%, 70% or 75% compared to the average fat fraction in the lower extremities of untreated controls 3, 6, 9, 12, 15, 18, 21, 24, 27, 30, 33, or 36 months after administration of the vector.

E95. The method, use, rAAV particle, or composition for use of any one of E88-E94, wherein the controls are age and sex matched to the subjects.

E96. The method, use, rAAV particle, or composition for use of any one of E91-E94, wherein the subjects and untreated controls are stratified according to age, prior corticosteroid treatment, and/or baseline performance on the 6MWT.

E97. The method, use, rAAV particle, or composition for use of any one of E74-E79, wherein the method, use, rAAV particle, or composition for use is effective to cause at least 5%, 10%, 15%, 20%, 25%, 30%, 35%, 40%, 45%, 50%, 55%, 60%, 65%, 70%, 75%, 80%, 85% or 90% of skeletal muscle fibers of a subject to express the mini-dystrophin protein 3, 6, 9, 12, 15, 18, 21, 24, 27, 30, 33, or 36 months after administration of the vector.

E98. The method, use, rAAV particle, or composition for use of any one of E97, wherein the skeletal muscle fibers are present in a biopsy obtained from the bicep, deltoid or quadriceps muscle of the subject.

E99. The method, use, rAAV particle, or composition for use of any one of E74-E98, wherein the method, use, rAAV particle, or composition for use causes a cellular immune response against the mini-dystrophin protein or muscle inflammation in less than or equal to about 0%, 1%, 2%, 3%, 4%, 5%, 6%, 7%, 8%, 9%, 10%, 11%, 12%, 13%, 14%, 15%, 16%, 17%, 18%, 19% or 20% of subjects 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 months after administration of the vector.

E100. The method, use, rAAV particle, or composition for use of any one of E74-E99, wherein the method, use, rAAV particle, or composition for use is effective without need for concomitant immune suppression in treated subjects.

E101. The method, use, rAAV particle, or composition for use of any one of E74-E76, wherein the subject is a $Dmd^{mdx}$ rat and the method, use, rAAV particle, or composition for use is effective to result in a reduction in serum AST, ALT, LDH, or total creatine kinase levels at 3 months or 6 months post-injection compared to age matched controls administered only vehicle.

E102. The method, use, rAAV particle, or composition for use of any one of E74-E76, wherein the subject is a $Dmd^{mdx}$ rat and the method, use, rAAV particle, or composition for use is effective to result in a reduction in fibrosis in biceps femoris, diaphragm, or heart muscle at 3 months or 6 months post-injection compared to age matched controls administered only vehicle.

E103. The method, use, rAAV particle, or composition for use of any one of E74-E76, wherein the subject is a $Dmd^{mdx}$ rat and the method, use, rAAV particle, or composition for use is effective to result in an increase in forelimb grip force at 3 months or 6 months post-injection compared to age matched controls administered only vehicle.

E104. The method, use, rAAV particle, or composition for use of any one of E74-E76, wherein the subject is a $Dmd^{mdx}$ rat and the method, use, rAAV particle, or composition for use is effective to result in a reduction in muscle fatigue as measured over 5 closely spaced trials testing forelimb grip force at 3 months or 6 months post-injection compared to age matched controls administered only vehicle.

E105. The method, use, rAAV particle, or composition for use of any one of E74-E76, wherein the subject is a $Dmd^{mdx}$ rat and the method, use, rAAV particle, or composition for use is effective to result in an increase in left ventricular ejection fraction as measured using echocardiography at 6 months post-injection compared to age matched controls administered only vehicle.

E106. The method, use, rAAV particle, or composition for use of any one of E74-E76, wherein the subject is a $Dmd^{mdx}$ rat and the method, use, rAAV particle, or composition for use is effective to result in an increase in the ratio of the velocity of early to late left ventricular filling (i.e., E/A ratio) as measured using echocardiography at 3 months or 6 months post-injection compared to age matched controls administered only vehicle.

E107. The method, use, rAAV particle, or composition for use of any one of E74-E76, wherein the subject is a $Dmd^{mdx}$ rat and the method, use, rAAV particle, or composition for use is effective to result in a decrease in the isovolumetric relaxation time (IVRT) or the time in milliseconds between peak E velocity and its return to baseline, wherein the E wave deceleration time (DT) is measured using echocardiography at 3 months or 6 months post-injection compared to age matched controls administered only vehicle.

E108. The method, use, rAAV particle, or composition for use of E74-E76, wherein the subject is a $Dmd^{mdx}$ rat and the method, use, rAAV particle, or composition for use is effective to transduce biceps femoris, diaphragm, heart muscle, or other striated muscles, and express the mini-dystrophin protein encoded by the opti-Dys3978 gene without inducing a cellular immune response against the mini-dystrophin protein by 3 months or 6 months post-injection.

E109. The method, use, rAAV particle, or composition for use of any one of E74-E76, wherein the subject is a $Dmd^{mdx}$ rat and the method, use, rAAV particle, or composition for use is effective to partially or completely reverse the increase in left ventricular end-diastolic diameter at 6 months post-injection compared to age matched controls administered only vehicle.

E110. The method, use, rAAV particle, or composition for use of any one of E74-E100, wherein the subject is also treated with, or the composition also comprises, at least a second agent effective for treating dystrophinopathy, examples of which include an antisense oligonucleotide that causes exon skipping of the DMD gene, an anti-myostatin antibody, an agent that promotes ribosomal read-through of nonsense mutations, an agent that suppresses premature stop codons, an anabolic steroid, or a corticosteroid (such as, without limitation, prednisone, deflazacort, or prednisolone).

E111. The method, use, rAAV particle, or composition for use of any one of E74-E110, wherein the composition is administered systemically, such as by intravenous injection, or locally, such as directly into a muscle.

E112. The method, use, rAAV particle, or composition for use of any one of E74-E111, wherein the dose of rAAV particles used in the method, use, rAAV particle, or composition for use is selected from the group of doses consisting of: $1\times10^{12}$ vg/kg, $2\times10^{12}$ vg/kg, $3\times10^{12}$ vg/kg, $4\times10^{12}$ vg/kg, $5\times10^{12}$ vg/kg, $6\times10^{12}$ vg/kg, $7\times10^{12}$ vg/kg, $8\times10^{12}$ vg/kg, $9\times10^{12}$ vg/kg, $1\times10^{13}$ vg/kg, $2\times10^{13}$ vg/kg, $3\times10^{13}$ vg/kg, $4\times10^{13}$ vg/kg, $5\times10^{13}$ vg/kg, $6\times10^{13}$ vg/kg, $7\times10^{13}$ vg/kg, $8\times10^{13}$ vg/kg, $9\times10^{13}$ vg/kg, $1\times10^{14}$ vg/kg, $1.5\times10^{14}$ vg/kg, $2\times10^{14}$ vg/kg, $2.5\times10^{14}$ vg/kg, $3\times10^{14}$ vg/kg, $3.5\times10^{14}$ vg/kg, $4\times10^{14}$ vg/kg, $5\times10^{14}$ vg/kg, $6\times10^{14}$ vg/kg, $7\times10^{14}$ vg/kg, $8\times10^{14}$ vg/kg, and $9\times10^{14}$ vg/kg, where vg/kg stands for vector genomes per kilogram of subject body weight.

E113. The composition of E73, further comprising empty capsids of the same AAV serotype as the rAAV particle, wherein the concentration ratio of empty capsids to rAAV particles is about or at least 0.5:1, 1:1, 2:1, 3:1, 4:1, 5:1, 6:1, 7:1, 8:1, 9:1, 10:1, or more. E114. A method of expressing a mini-dystrophin protein in a cell, comprising contacting the cell with the rAAV particle of any one of E42-E72.

E115. The method of E114, wherein the cell is a muscle cell.

E116. The method of E115, wherein the muscle cell is from skeletal muscle, diaphragm, or heart.

E117. A method of making the rAAV particle of any one of E42-E72, comprising introducing into a producer cell the vector of any one of E39-E41, an AAV rep gene, an AAV cap gene, and genes for helper functions, incubating the cells, and purifying the rAAV particles produced by the cells.

E118. The method of E117, wherein the producer cells are adherent.

E119. The method of E117, wherein the producer cells are non-adherent.

E120. The method of any one of E117-E119, wherein the vector is contained in one plasmid, the AAV rep and cap genes are contained in a second plasmid, and the helper function genes are contained in a third plasmid, where all three plasmids are introduced into the packaging cells.

E121. The method of any one of E117-E120, wherein the step of introducing is effected by transfection.

E122. The method of any one of E117-E121, wherein the producer cells are HEK 293 cells.

E123. The method of any one of E117-E122, wherein the producer cells are grown in serum free medium.

E124. The method of any one of E117-E123, wherein the AAV cap gene encodes the AAV9 VP1, VP2 and VP3 proteins.

E125. The method of any one of E117-E124, wherein the rAAV particles are purified using density gradient ultracentrifugation, or column chromatography.

E126. An rAAV particle produced by the method of any one of E117-E125.

BRIEF DESCRIPTION OF THE DRAWINGS

(FIG. 6A) Cryosections (8 μm) of tibialis anterior muscles from wild-type control C57BL/10 mice, untreated dKO mice, and vector-treated dKO (T-dKO) mice were subjected to hematoxylin and eosin (H&E) staining for histopathology (10× magnification). (FIG. 6B) Quantitative analyses of muscle mass, heart mass, percentage of centrally localized nuclei and serum creatine kinase activities.

(FIG. 9A) The PR interval of the ECG was improved in vector-treated dKO mice. (FIG. 9B) Quantitative data of the analysis. The experiment was done to carefully monitor the heart rate of the three groups so that the ECG was not affected by the variation in heart rate. *$p<0.05$.

FIGS. 55A-55C provide an alignment between the amino acid sequences of the mini-dystrophin protein Δ3990 (SEQ ID NO:27) and the mini-dystrophin protein Dys3978 (SEQ ID NO:7).

FIGS. 56A-56I provide an alignment between the nucleic acid sequence encoding mini-dystrophin Δ3990 (SEQ ID NO:28), which is derived from the wildtype nucleic acid sequence encoding human dystrophin protein, and the human codon-optimized nucleic acid sequence encoding mini-dystrophin Dys3978 (called Hopti-Dys3978; SEQ ID NO:1).

DETAILED DESCRIPTION OF THE INVENTION

Figure 1:
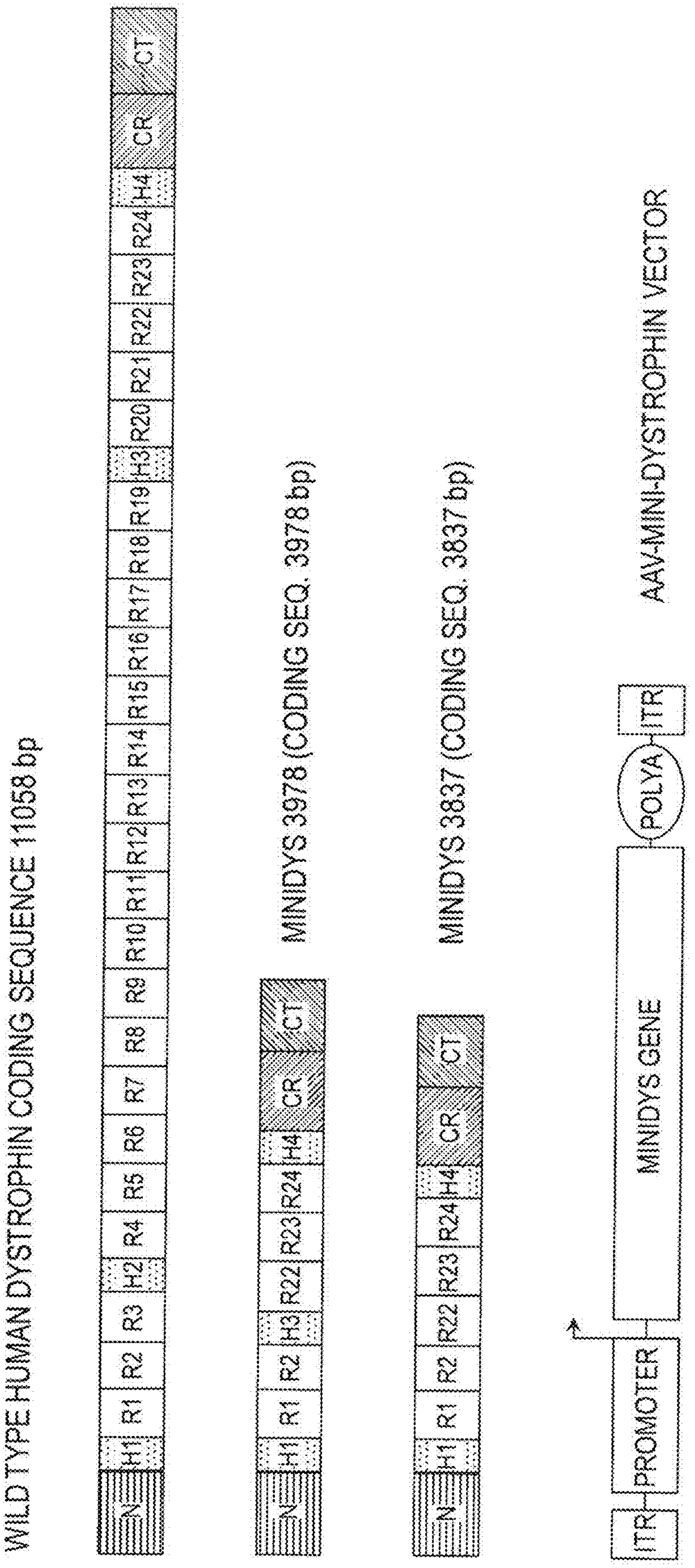
FIG. 1 shows construction of highly truncated mini-dystrophin genes. Wild-type muscle dystrophin has four major domains: the N-terminal domain (N); the central rod domain, which contains 24 rod repeats (R) and four hinges (H); a cysteine-rich (CR) domain, and the carboxy-terminal (CT) domain. The mini-dystrophin genes were constructed by deleting a large portion of the central rods and hinges and most of the CT domain. The mini-dystrophin genes were codon-optimized, fully synthesized and subsequently cloned between a CMV promoter or a muscle-specific synthetic hybrid promoter at the 5' end of the gene, and a small poly(A) sequence at the 3' end of the gene. This gene segment, containing promoter, codon-optimized mini-dystrophin gene, and polyA signal, was then cloned into a plasmid containing left and right AAV inverted terminal repeats (ITRs) so that the gene segment was flanked by the ITRs.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *Patent In User Manual,* 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); AUSUBEL et al., CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the term "adeno-associated virus" (AAV), includes but is not limited to, AAV type 1 (AAV1), AAV type 2 (AAV2), AAV type 3 (AAV3, including types 3A and 3B), AAV type 4 (AAV4), AAV type 5 (AAV5), AAV type 6 (AAV6), AAV type 7 (AAV7), AAV type 8 (AAV8), AAV type 9 (AAV9), AAV type 10 (AAV10), AAV type 11 (AAV11), AAV type 12 (AAV12), AAV type 13 (AAV13), Avian AAV ATCC VR-865, Avian AAV strain DA-1, Bb1, Bb2, Ch5, Cy2, Cy3, Cy4, Cy5, Cy6, Hut, Hu10, Hu11, Hu13, Hu15, Hu16, Hu17, Hu18, Hu19, Hu2, Hu20, Hu21, Hu22, Hu23, Hu24, Hu25, Hu26, Hu27, Hu28, Hu29, Hu3, Hu31, Hu32, Hu34, Hu35, Hu37, Hu39, Hu4, Hu40, Hu41, Hu42, Hu43, Hu44, Hu45, Hu46, Hu47, Hu48, Hu49, Hu51, Hu52, Hu53, Hu54, Hu55, Hu56, Hu57, Hu58, Hub, Hu60, Hu61, Hu63, Hu64, Hu66, Hu67, Hu7, Hu9, HuLG15, HuS17, HuT17, HuT32, HuT40, HuT41, HuT70, HuT71, HuT88, Pi1, Pi2, Pi3, Rh1, Rh10, Rh13, Rh2, Rh25, Rh32, Rh33, Rh34, Rh35, Rh36, Rh37, Rh38, Rh40, Rh43, Rh48, Rh49, Rh50, Rh51, Rh52, Rh53, Rh54, Rh55, Rh57, Rh58, Rh61, Rh62, Rh64, Rh74, Rh8, snake AAV, avian AAV, bovine AAV, canine AAV, equine AAV, ovine AAV, goat AAV, shrimp AAV, AAV1.1, AAV2.5, AAV6.1, AAV6.3.1, AAV9.45, RHM4-1 (SEQ ID NO:5 of WO 2015/013313), AAV2-TT, AAV2-TT-S312N, AAV3B-S312N, AAV-LK03, and any other AAV now known or later discovered. see, e.g., Fields et al., VIROLOGY, volume 2, chapter 69 (4th ed., Lippincott-Raven Publishers). Capsids may be derived from a number of AAV serotypes disclosed in U.S. Pat. No. 7,906,111; Gao et al., 2004, J. Virol. 78:6381; Moris et al., 2004, Virol. 33:375; WO 2013/063379; WO 2014/194132; and include true type AAV (AAV-TT) variants disclosed in WO 2015/121501, and RHM4-1, RHM15-1 through RHM15-6, and variants thereof, disclosed in WO 2015/013313, and one skilled in the art would know there are likely other variants not yet identified that perform the same or similar function, or may include components from two or more AAV capsids. A full complement of AAV cap proteins includes VP1, VP2, and VP3. The open reading frame comprising nucleotide sequences encoding AAV capsid proteins may comprise less than a full complement AAV cap proteins or the full complement of AAV cap proteins may be provided.

and any other AAV now known or later discovered. See, e.g., FIELDS et al., VIROLOGY, volume 2, chapter 69 (4th ed., Lippincott-Raven Publishers). A number of relatively new AAV serotypes and clades have been identified (See, e.g., Gao et al., (2004) J. Virol. 78:6381; Moris et al., (2004) Virol. 33-375).

AAV is a small non-enveloped virus with an icosahedral capsid about 20-30 nm in diameter. AAV are not able to replicate without the contribution of so-called helper proteins from other viruses (e.g., adenovirus, herpes simplex virus, vaccinia virus and human papillomavirus), and so were placed into a special genus, called dependovirus (because they depend on other viruses for replication) within the family of parvoviridae. Although many different serotypes of AAV have been discovered, and many humans produce antibodies against one or more AAV serotypes (suggesting widespread history of AAV infection), no diseases are known to be caused by AAV suggesting AAV is non-pathogenic in humans.

Although many different AAV serotypes have been discovered, one of the best characterized is AAV2, and the following discussion of AAV biology focuses on some of what has been learned regarding AAV2. The life cycle of other AAV serotypes is believed to be similar, although the details may differ. The particular details by which AAV2 or any other AAV serotype infect and replicate inside cells are provided merely to aid in the understanding of the inventions disclosed herein, and are not intended to limit their scope in any way. Even if some of this information is later found to be incorrect or incomplete, it should not be construed as detracting from the utility or enablement of the inventions disclosed and claimed herein. Further information about AAV lifecycle can be found in M. Goncalves, Virol J 2:43 (2005), MD Weitzman and R M Linden, Adeno-Associated Virus Biology, Ch. 1, pp. 1-23, Adeno-Associated Virus Methods and Protocols, Ed. RO Snyder and P Moullier, Humana Press (2011), GE Berry and A Asokan, Curr Opin Virol 21:54-60 (2016), and references cited therein.

The wild type genome of AAV2 is linear DNA approximately 4.7 kilobases in length. Although mostly single-stranded, the 5' and 3' ends of the genome consist of so-called inverted terminal repeats (ITR), each 145 base-pairs long and containing palindromic sequences that self-anneal through classic Watson-Crick base-pairing to form T-shaped hairpin structures. One of these structures contains a free 3' hydroxyl group that, relying on cellular DNA polymerases, permits initiation of viral DNA replication through a self-priming strand-displacement mechanism.

See, for example, M. Goncalves, Adeno-associated virus: from defective virus to effective vector, Virology J 2:43 (2005). Due to the mechanism by which the single-stranded viral genomes are replicated and then packaged into capsids in infected cells, plus (sense or coding) and minus (antisense or non-coding) strands are packaged with equal efficiency into separate particles.

In addition to the flanking ITRs, the wild type AAV2 genome contains two genes, rep and cap, that code respectively for four replication proteins (Rep 78, Rep 68, Rep 52, and Rep 40) and three capsid proteins (VP1, VP2, and VP3) through efficient use of alternative promoters and splicing. The large replication proteins, Rep 78 and 68, are multifunctional and play a role in AAV transcription, viral DNA replication, and site-specific integration of the viral genome into human chromosome 19. The smaller Rep proteins have been implicated in packing the viral genome into the viral capsids in infected cell nuclei. The three capsid proteins are produced through a combination of alternative splicing and use of alternative translational start sites, so that all three proteins share sequence towards their carboxy-termini, but VP2 includes additional amino-terminal sequence absent from VP3, and VP1 includes additional amino-terminal sequence absent from both VP2 and VP3. It is estimated that capsids contain a total of 60 capsid proteins in an approximate VP1:VP2:VP3 stoichiometry of 1:1:10, although these ratios can apparently vary.

Despite its relatively small size, and therefore capacity to carry heterologous genes, AAV has been identified as a leading viral vector for gene therapy. Advantages of using AAV compared to other viruses that have been proposed as gene therapy vectors include the ability of AAV to support long term gene expression in transduced cells, to transduce both dividing and nondividing cells, to transduce a wide variety of different types of cells depending on serotype, the inability to replicate without a helper virus, and an apparent lack of pathogenicity associated with wild type infections.

Because of their small size, AAV capsids can physically accommodate a single stranded DNA genome that is at most about 4.7-5.0 kilobases in length. Without modifying the genome, there would not be enough room to include a heterologous gene, such as coding sequence for a therapeutic protein, and gene regulatory elements, such as a promoter and optionally an enhancer. To create more room, the rep and cap genes can be removed and replaced with desired heterologous sequences, as long as the flanking ITRs are retained. The functions of the rep and cap genes can be provided in trans on a different piece of DNA. By contrast, the ITRs are the only AAV viral elements that must remain in cis with the heterologous sequence. Combining the ITRs with a heterologous gene and removing the rep and cap genes to a different plasmid lacking ITRs also prevents production of infectious wild type AAV at the same time that AAV vector for gene therapy is being produced. Removing rep and cap also means that AAV vectors for gene therapy cannot replicate in the cells they transduce.

In some embodiments, the genome of AAV vectors is linear single-stranded DNA flanked by AAV ITRs. Before it can support transcription and translation of the heterologous gene, the single stranded DNA genome must be converted to double-stranded form by cellular DNA polymerases that utilize the free 3'-OH of one of the self-priming ITRs to initiate second-strand synthesis. In alternative embodiments, full length-single stranded genomes of opposite polarity can anneal to generate a full length double-stranded genome, and can result when a plurality of AAV vectors carrying genomes of opposite polarity simultaneously transduce the same cell. After double-stranded vector genomes form, by whatever mechanism, the cellular gene transcription machinery can act on the double-stranded DNA to express the heterologous gene.

In other embodiments, the vector genome can be designed to be self-complementary (scAAV), having a wild type ITR at each end and a mutated ITR in the middle. See, for example, McCarty, D M, et al., Adeno-associated virus terminal repeat (TR) mutant generates self-complementary vectors to overcome the rate-limiting step to transduction in vivo. Gene Ther. 10:2112-18 (2003). It has been proposed that after entering a cell, self-complementary AAV genomes can self-anneal starting with the ITR in the middle to form a double-stranded genome without need for de novo DNA replication. This approach was shown to result in more efficient transduction and faster expression of heterologous gene, but reduces the size of the heterologous gene that may be used by about half.

Different strategies for producing AAV vectors for gene therapy have been developed, but one of the most common is the triple transfection technique, in which three different plasmids are transfected into producer cells. See, for example, N. Clement and J. Grieger, Mol Ther Methds Clin Dev, 3:16002 (2016), Grieger, J C, et al., Mol Ther 24(2): 287-97 (2016), and the references cited therein. In this technique, a plasmid is created that includes the sequence of the vector genome including, for example a heterologous promoter and optionally an enhancer, and a heterologous gene to express a desired RNA or protein, flanked by the left and right ITRs. The vector plasmid would be co-transfected into producer cells, such as HEK293 cells, with a second plasmid containing the rep and cap genes, and a third plasmid containing adenovirus (or other virus) helper genes required to replicate and package the vector genome into AAV capsids. In alternative embodiments of the technique, rep, cap and adenovirus helper genes all reside on the same plasmid, and two plasmids are co-transfected into producer cells. Examples of adenovirus helper genes include Ela, E1b, E2a, E4orf6, and VA RNA genes. For many AAV serotypes, the AAV2 ITRs can be substituted for native ITRs without significantly impairing the ability of the vector genome to be replicated and packaged into non-AAV2 capsids. This approach, known as pseudo-typing, merely requires using a rep/cap plasmid that contains the rep and cap genes from the other serotype. Thus, for example, an AAV gene therapy vector could use an AAV9 capsid and a vector genome containing AAV2 ITRs flanking a heterologous gene (which can be designated "AAV2/9"), such as a mini-dystrophin. After the AAV particles are produced by the cell, they can be collected and purified using standard techniques known in the art, such as ultracentrifugation in a CsCl gradient, or using chromatography columns of various types.

The parvovirus particles and genomes of the present invention can be from, but are not limited to AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J. Virol.* 73: 939; Chiorini et al., (1997) *J. Virol.* 71:6823; Chiorini et al., (1999) *J. Virol.* 73:1309; Gao et al., (2002) *Proc. Nat. Acad. Sci. USA* 99:11854; Moris et al., (2004) Virol. 33-375-383; Mori et al., (2004) *Virol.* 330:375; Muramatsu et al., (1996) *Virol.* 221:208; Ruffing et al., (1994) *J. Gen. Virol.* 75:3385; Rutledge et al., (1998) *J. Virol.* 72:309; Schmidt et al., (2008) *J. Virol.* 82:8911; Shade et al., (1986) *J. Virol.* 58:921; Srivastava et al., (1983) *J. Virol.* 45:555; Xiao et al., (1999) *J. Virol.* 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. ITR sequences from AAV1, AAV2 and AAV3 are provided by Xiao, X., (1996), "Characterization of Adeno-associated virus (AAV) DNA replication and integration," Ph.D. Dissertation, University of Pittsburgh, Pittsburgh, Pa. (incorporated herein it its entirety).

As used herein, "transduction" of a cell by AAV refers to AAV-mediated transfer of genetic material into the cell. See, e.g., FIELDS et al., VIROLOGY, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a linear sequence of nucleotides in which the 3'-position of each monomeric unit is linked to the 5'-position of the neighboring monomeric unit via a phosphate group. Polynucleotides may be RNA (containing RNA nucleotides only), DNA (containing DNA nucleotides only), RNA and DNA hybrids (containing RNA and DNA nucleotides), as well as other hybrids containing naturally occurring and/or non-naturally occurring nucleotides. The linear order of bases of the nucleotides in a polynucleotide is called the "nucleotide sequence," "nucleic acid sequence," "nucleobase sequence," or sometimes, just "sequence" of the polynucleotide. Typically, the order of bases is provided starting from the 5' end of the polynucleotide and ending at the 3' end of the polynucleotide. As known in the art, polynucleotides can adopt secondary structures, such as regions of self-complementarity. Polynucleotides can also hybridize with fully or partially complementary polynucleotides through classic Watson-Crick base pairing, or other mechanisms familiar to those of ordinary skill.

As used herein, a "gene" is a section of a polynucleotide, typically but not necessarily of DNA, that encodes a polypeptide or protein. In some embodiments, genes can be interrupted by introns. In some embodiments a polynucleotide can encode more than one polypeptide or protein due to mechanisms such as alternative splicing, use of alternate start codons, or other biological mechanisms familiar to those of ordinary skill in the art. The term "open reading frame," abbreviated "ORF," refers to a portion of a polynucleotide that encodes a polypeptide or protein.

The term "codon-optimized," as used herein, refers to a gene coding sequence that has been optimized to increase expression by substituting one or more codons normally present in a coding sequence (for example, in a wildtype sequence, including, e.g., a coding sequence for dystrophin or a mini-dystrophin) with a codon for the same (synonymous) amino acid. In this manner, the protein encoded by the gene is identical, but the underlying nucleobase sequence of the gene or corresponding mRNA is different. In some embodiments, the optimization substitutes one or more rare codons (that is, codons for tRNA that occur relatively infrequently in cells from a particular species) with synonymous codons that occur more frequently to improve the efficiency of translation. For example, in human codon-optimization one or more codons in a coding sequence are replaced by codons that occur more frequently in human cells for the same amino acid. Codon optimization can also increase gene expression through other mechanisms that can improve efficiency of transcription and/or translation. Strategies include, without limitation, increasing total GC content (that is, the percent of guanines and cytosines in the entire coding sequence), decreasing CpG content (that is, the number of CG or GC dinucleotides in the coding sequence), removing cryptic splice donor or acceptor sites, and/or adding or removing ribosomal entry sites, such as Kozak sequences. Desirably, a codon-optimized gene exhibits improved protein expression, for example, the protein encoded thereby is expressed at a detectably greater level in a cell compared with the level of expression of the protein provided by the wildtype gene in an otherwise similar cell.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.,* 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

"Substantial homology" or "substantial similarity," means, when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the sequence.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous" or "exogenous" nucleotide or nucleic acid sequence are used interchangeably herein and refer to a nucleic acid sequence that is not naturally occurring in the virus or a cell. In some embodiments, the heterologous nucleic acid comprises an open reading frame that encodes a polypeptide or nontranslated RNA of interest (e.g., for delivery to a cell or subject).

As used herein, the terms "virus vector," "viral vector," "gene delivery vector," or sometimes just "vector," refer to a virion or virus particle that functions as a nucleic acid delivery vehicle and which comprises a vector genome packaged within the virion or virus particle. Vectors can be infectious or non-infectious. Non-infectious vectors cannot replicate themselves without exogenously added factors. Vectors may be AAV particles or virions comprising an AAV capsid within which is packaged an AAV vector genome. These vectors may also be referred to herein as "recombinant AAV" (abbreviated "rAAV") vectors, particles or virions.

A vector genome is a polynucleotide for packaging within a vector particle or virion for delivery into a cell (which cell may be referred to as a "target cell"). Typically, a vector genome is engineered to contain a heterologous nucleic acid sequence, such as a gene, for delivery into the target cell. A vector genome may also contain one or more nucleic acid sequences that function as regulatory elements to control expression of the heterologous gene in the target cell. A vector genome may also contain wildtype or modified viral nucleic acid sequence(s) required for the production and/or function of the vector, such as, without limitation, replication of the vector genome in a host and packaging into vector particles. In some embodiments, the vector genome is an "AAV vector genome," which is capable of being packaged into an AAV capsid. In some embodiments, an AAV vector genome includes one or two inverted terminal repeats (ITRs) in cis with the heterologous gene to support replication and packaging. All other structural and non-structural protein coding sequences required for AAV vector production may be provided in trans (e.g., from a plasmid, or by stably integrating the sequences into a host cell). In certain embodiments, an AAV vector genome comprises at least one ITR (e.g., an AAV ITR), optionally two ITRs (e.g., two AAV ITRs), which typically will be at the 5' and 3' ends of the vector genome and flank the heterologous nucleic acid sequence, but need not be contiguous thereto. The ITRs can be the same or different from each other, and from the same or different AAV serotypes.

The terms "host cell," "host cell line," and "host cell culture" are used interchangeably and refer to cells into which exogenous nucleic acid has been introduced, including the progeny of such cells. Host cells include "transformants," "transformed cells," and "transduced cells," which include the primary transformed cell and progeny derived therefrom without regard to the number of passages. For purposes of producing AAV vectors, certain host cells may be used as "producer" or "packaging" cells that contain all the genes required to assemble functional virus particles including a capsid and vector genome. As understood by those of ordinary skill in the art, different host cells can usefully serve as producer cells, such as HEK293 cells, or the Pro10 cell line, but others are possible. The required genes for virion assembly include the vector genome as described elsewhere herein, AAV rep and cap genes, and certain helper genes from other viruses, including without limitation adenovirus. As appreciated by those ordinarily skilled, the requisite genes for AAV production can be introduced into producer cells in various ways, including without limitation transfection of one or more plasmids, however, certain of the genes can already be present in the producer cells, either integrated into the genome or carried on an episome.

The term "inverted terminal repeat" or "ITR" includes any palindromic viral terminal repeat or synthetic sequence that forms a hairpin structure and functions as an inverted terminal repeat (i.e., mediates certain viral functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, such as the "double-D sequence" as described in U.S. Pat. No. 5,478,745 to Samulski et al. See also FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered. An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like. The sequence of the AAV2 ITRs are 145 basepairs long, and are provided herein as SEQ ID NO:14 and SEQ ID NO:15.

"Cis-motifs" includes conserved sequences such as found at or close to the termini of the genomic sequence and recognized for initiation of replication; cryptic promoters or sequences at internal positions likely used for transcription initiation, splicing or termination.

"Flanked," with respect to a sequence that is flanked by other elements, indicates the presence of one or more the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence (e.g., a transgene) that is "flanked" by two other elements (e.g., TRs), indicates that one element is located 5' to the sequence and the other is located 3' to the sequence; however, there may be intervening sequences there between.

"Transfection" of a cell means that genetic material is introduced into a cell for the purpose of genetically modifying the cell. Transfection can be accomplished by a variety of means known in the art, such as calcium phosphate, polyethyleneimine, electroporation, and the like.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g. episomes), or integration of transferred genetic material into the genomic DNA of host cells.

"Transgene" is used to mean any heterologous nucleotide sequence incorporated in a vector, including a viral vector, for delivery to and including expression in a target cell (also referred to herein as a "host cell"), and associated expression control sequences, such as promoters. It is appreciated by those of skill in the art that expression control sequences will be selected based on ability to promote expression of the transgene in the target cell. An example of a transgene is a nucleic acid encoding a therapeutic polypeptide.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) *Mol. Therapy* 2:619.

Further, the viral capsid or genomic elements can contain other modifications, including insertions, deletions and/or substitutions.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral or vector genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered. A synthetic large Rep protein may be altered by insertion, deletion, truncation and/or missense mutations.

In the native AAV genome, the different Rep proteins are encoded by a single gene through use of two different promoters and alternative splicing. For purposes of AAV vector production, however, Rep proteins can be expressed in producer cells from a single gene, or from distinct polynucleotides, one sequence for each Rep protein to be expressed. Thus, for example, a Rep encoding gene can be engineered to inactivate the p5 or p19 promoter so that only small or only large Rep proteins are expressed the respective modified genes. Expression of the large and small Rep proteins from different genes can be advantageous when one of the viral promoters is inactive in a host cell, in which case a constitutively active promoter can be used instead, or where it is desired to express the Rep proteins at different levels under the control of separate transcriptional and/or translational control elements. For example, in some embodiments, it may be advantageous to down-regulate expression of the large Rep protein relative to small Rep protein (e.g., Rep78/68) to avoid toxicity to the host cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

A "micro-dystrophin" or a "mini-dystrophin" is an engineered protein comprising certain subdomains or portions of subdomains present in full length muscle dystrophin or isoforms thereof that possess at least some of the functionality of dystrophin when expressed in a muscle cell. Micro-dystrophins and mini-dystrophins are smaller than full length muscle dystrophin (Dp427m). Relative to full length muscle dystrophin, micro-dystrophins and mini-dystrophins may contain deletions at the N-terminus, the C-terminus, internally, or any combination thereof.

As used herein, a "dystrophinopathy" is a muscle disease caused by pathogenic variants in DMD, the gene encoding the protein dystrophin. Dystrophinopathies manifest as a spectrum of phenotypes depending on the nature of the underlying genetic lesion. The mild end of the spectrum includes without limitation the phenotypes of asymptomatic increase in serum concentration of creatine phosphokinase (CK) and muscle cramps with myoglobinuria. The severe end of the spectrum includes without limitation the progressive muscle diseases Duchenne muscular dystrophy (DMD) and Becker muscular dystrophy (BMD), in which skeletal muscle is primarily affected and heart to a lesser degree, and DMD-associated dilated cardiomyopathy (DCM), in which the heart is primarily affected.

Mini-Dystrophin Polynucleotides, Expression Cassettes and Vectors

The present disclosure provides codon-optimized mini-dystrophin gene sequences and expression cassettes containing the same. Such genes and expression cassettes are useful for, among other applications, gene therapy to prevent or treat dystrophinopathies, such as DMD, in subjects in need thereof. Expression of mini-dystrophin proteins in transduced muscle cells is able to replicate and replace at least some of the function normally attributable to full-length dystrophin, such as supporting a mechanically strong link between the extra-cellular matrix and the cytoskeleton.

The codon-optimized sequences are designed to fit within the size limitations of parvovirus vectors, e.g., AAV vectors, as well as provide enhanced expression of mini-dystrophin compared to non-optimized sequences. In some embodiments, the optimized mini-dystrophin sequences provide increased expression of mini-dystrophin protein in muscle cells or in muscle in animals that is at least about 5% greater than the expression of non-codon-optimized dystrophin sequences, e.g., at least about 5, 10, 20, 30, 40, 50, 75, 100, 200, 300, 400, or 500% or more, where the non-codon-optimized sequence is based on the mRNA encoding wild-type human full-length muscle dystrophin, as exemplified by *NCBI Reference Sequence* NM_004006.2, which is incorporated by reference.

Thus, one aspect of the invention relates to a polynucleotide encoding a mini-dystrophin protein, the polynucleotide comprising, consisting essentially of, or consisting of: (a) the nucleotide sequence of SEQ ID NO:1 or a sequence at least about 90% identical thereto; (b) the nucleotide sequence of SEQ ID NO:2 or a sequence at least about 90% identical thereto; or (c) the nucleotide sequence of SEQ ID NO:3 or a sequence at least about 90% identical thereto. In some embodiments, the polynucleotide is at least about 90%, 91%, 92%, 93%, 94%, 95%, 96%, 97%, 98%, or 99% identical to the nucleotide sequence of one of SEQ ID NOS: 1-3. In certain embodiments, the polynucleotide has a length that is within the capacity of a viral vector, e.g., a parvovirus vector, e.g., an AAV vector. In some embodiments, the polynucleotide is about 5000, 4900, 4800, 4700, 4600, 4500, 4400, 4300, 4200, 4100, or about 4000 nucleotides, or fewer.

In some embodiments, the mini-dystrophin protein encoded by the polynucleotide comprises, consists essentially of, or consists of the N-terminus, hinge H1, rods R1 and R2, hinge H3, rods R22, R23, and R24, hinge H4, the cysteine-rich domain (CR domain), and in some embodiments, all or a portion of the carboxy-terminal domain (CT domain) of wild-type dystrophin protein. In other embodiments, the mini-dystrophin protein encoded by the polynucleotide comprises, consists essentially of, or consists of the N-terminus, Actin-Binding Domain (ABD), hinge H1, rods R1 and R2, rods R22, R23, and R24, hinge H4, the CR domain, and in some embodiments, all or a portion of the CT domain of wild-type dystrophin protein. In further embodiments, the mini-dystrophin protein does not comprise the last three amino acids at the C-terminus of the wild-type dystrophin protein (SEQ ID NO:25). In certain embodiments, the polynucleotide encodes a mini-dystrophin protein comprising, consisting essentially of, or consisting of the amino acid sequence of SEQ ID NO:7 or SEQ ID NO:8 or a sequence at least about 90%, 91%, 92%, 93%, 94%, 95%, 96%, 97%, 98%, or 99% identical to the nucleotide sequence of SEQ ID NO:7 or SEQ ID NO:8.

The nucleotide sequence of dystrophin is well known in the art and may be found in sequence databases such as GenBank. For example, the human dystrophin mRNA sequence may be found at GenBank Accession No. M18533 or NCBI Reference Sequence NM_004006.2, which are incorporated by reference herein in their entirety.

In some embodiments, the polynucleotide is part of an expression cassette for production of dystrophin protein. The expression cassette may further comprise expression elements useful for increasing expression of dystrophin.

In some embodiments, the polynucleotide of the invention is operably linked to a promoter. The promoter may be a constitutive promoter or a tissue-specific or tissue-preferred promoter such as a muscle-specific or muscle-preferred promoter. In some embodiments, the promoter is a creatinine kinase promoter, e.g., a promoter comprising, consisting essentially of, or consisting of the nucleotide sequence of SEQ ID NO: 4 or SEQ ID NO: 5.

In some embodiments, the polynucleotide of the invention is operably linked to a polyadenylation element. In some embodiments, the polyadenylation element comprises the nucleotide sequence of SEQ ID NO: 6.

In some embodiments, the polynucleotide is part of an expression cassette comprising, consisting essentially of, or consisting or the polynucleotide operably linked to a promoter and a polyadenylation element. In certain embodiments, the gene expression cassette comprises, consists essentially or, or consists of the nucleotide sequence of any one of SEQ ID NOS: 9-12 or a sequence at least about 90% identical thereto, e.g., at least about 90%, 91%, 92%, 93%, 94%, 95%, 96%, 97%, 98%, or 99% identical.

Another aspect of the invention relates to a vector comprising the polynucleotides of the invention. Suitable vectors include, but are not limited to, a plasmid, phage, phagemid, viral vector (e.g., AAV vector, an adenovirus vector, a herpesvirus vector, an alphavirus, or a baculovirus vector), bacterial artificial chromosome (BAC), or yeast artificial chromosome (YAC). For example, the nucleic acid can comprise, consist of, or consist essentially of an AAV vector comprising a 5' and/or 3' terminal repeat (e.g., 5' and/or 3' AAV terminal repeat). In some embodiments, the vector is a viral vector, e.g., a parvovirus vector, e.g., an AAV vector, e.g., an AAV9 vector. The viral vector may further comprise a nucleic acid comprising a recombinant viral template, wherein the nucleic acid is encapsidated by the parvovirus capsid. The invention further provides a recombinant parvovirus particle (e.g., a recombinant AAV particle) comprising the polynucleotides of the invention. Viral vectors and viral particles are discussed further below.

In certain embodiments, the viral vector exhibits modified tissue tropism compared to vectors from which the modified vector is derived. In one embodiment, the parvovirus vector exhibits systemic tropism for skeletal, cardiac, and/or diaphragm muscle. In other embodiments, the parvovirus vector has reduced tropism for liver compared to a virus vector comprising a wild-type capsid protein. Tissue tropism can be modified by altering certain viral capsid amino acids, for example, those present in AAV capsid VP1, VP2, and/or VP3 proteins, according to the knowledge of those ordinarily skilled in the art.

In some embodiments, the vector genome is self-complementary or duplexed, and AAV virions containing such vector genomes are known as scAAV vectors. scAAV vectors are described in international patent publication WO 01/92551 (the disclosure of which is incorporated herein by reference in its entirety). Use of scAAV to express a mini-dystrophin may provide an increase in the number of cells transduced, the copy number per transduced cell, or both.

An additional aspect of the invention relates to a transformed cell comprising the polynucleotide and/or vector of the invention. The cell may be an in vitro, ex vivo, or in vivo cell.

A further aspect of the invention relates to a non-human transgenic animal comprising the polynucleotide and/or vector and/or transformed cell of the invention. In some embodiments, the transgenic animal is a laboratory animal, e.g., an animal model of a disease, e.g., an animal model of muscular dystrophy.

Another aspect of the invention relates to a mini-dystrophin protein encoded by the polynucleotides of the invention. The mini-dystrophin protein contains all of the sequences necessary for a functional dystrophin protein. The domains of dystrophin are well known in the art and sequences may be found in sequence databases such as GenBank. For example, the human dystrophin amino acid sequence may be found at NCBI Reference Sequence: NP_003997.1 and GenBank Accession No. AAA53189, which are incorporated by reference herein in their entirety.

In some embodiments, the mini-dystrophin protein comprises, consists essentially of, or consists of the N-terminus, hinge H1, rods R1 and R2, hinge H3, rods R22, R23, and R24, hinge H4, the CR domain, and in some embodiments, all or a portion of the CT domain, wherein the mini-dystrophin protein does not comprise the last three amino acids at the C-terminus of wild-type dystrophin protein (SEQ ID NO:25). According to some of these embodiments, the N-terminal actin binding domain comprises, consists essentially of, or consists of amino acid numbers 1-240 from SEQ ID NO:25, the amino acid sequence of full length human dystrophin protein; H1 comprises, consists essentially of, or consists of amino acid numbers 253-327 from SEQ ID NO:25; R1 comprises, consists essentially of, or consists of amino acid numbers 337-447 from SEQ ID NO:25; R2 comprises, consists essentially of, or consists of amino acid numbers 448-556 from SEQ ID NO:25; H3 comprises, consists essentially of, or consists of amino acid numbers 2424-2470 from SEQ ID NO:25; R22 comprises, consists essentially of, or consists of amino acid numbers 2687-2802 from SEQ ID NO:25; R23 comprises, consists essentially of, or consists of amino acid numbers 2803-2931 from SEQ ID NO:25; R24 comprises, consists essentially of, or consists of amino acid numbers 2932-3040 from SEQ ID NO:25; H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the CT domain comprises, consists essentially of, or consists of amino acid numbers 3300-3408 from SEQ ID NO:25. In certain embodiments, the mini-dystrophin protein comprises, consists essentially of, or consists of the amino acid sequence of SEQ ID NO: 7. Further description of this and related constructs is included in Example 1 herein.

In some embodiments, the mini-dystrophin protein comprises, consists essentially of, or consists of the N-terminus, hinge H1, rods R1 and R2, rods R22, R23, and R24, hinge H4, the CR domain, and in some embodiments, all or a portion of the CT domain. In certain embodiments, the mini-dystrophin protein does not comprise the last three amino acids at the C-terminus of wild-type dystrophin protein. According to some of these embodiments, the N-terminal actin binding domain comprises, consists essentially of, or consists of amino acid numbers 1-240 from SEQ ID NO:25, the amino acid sequence of full length human dystrophin protein; H1 comprises, consists essentially of, or consists of amino acid numbers 253-327 from SEQ ID NO:25; R1 comprises, consists essentially of, or consists of amino acid numbers 337-447 from SEQ ID NO:25; R2 comprises, consists essentially of, or consists of amino acid numbers 448-556 from SEQ ID NO:25; R22 comprises, consists essentially of, or consists of amino acid numbers 2687-2802 from SEQ ID NO:25; R23 comprises, consists essentially of, or consists of amino acid numbers 2803-2931 from SEQ ID NO:25; R24 comprises, consists essentially of, or consists of amino acid numbers 2932-3040 from SEQ ID NO:25; H4 comprises, consists essentially of, or consists of amino acid numbers 3041-3112 from SEQ ID NO:25; cysteine rich domain comprises, consists essentially of, or consists of amino acid numbers 3113-3299 from SEQ ID NO:25; and carboxy-terminal domain comprises, consists essentially of, or consists of amino acid numbers 3300-3408 from SEQ ID NO:25. In certain embodiments, the mini-dystrophin protein comprises, consists essentially of, or consists of the amino acid sequence of SEQ ID NO: 8.

A further aspect of the invention relates to a method of producing a mini-dystrophin protein in a cell, comprising contacting the cell with the polynucleotide or vector of the invention, thereby producing the mini-dystrophin in the cell. The cell may be an in vitro, ex vivo, or in vivo cell, e.g., a cell line or a primary cell. Methods of producing a protein in a cell by introduction of a polynucleotide encoding the protein are well known in the art.

Another aspect of the invention relates to a method of producing a mini-dystrophin protein in a subject, comprising delivering to the subject the polynucleotide, vector and/or transformed cell of the invention, thereby producing the mini-dystrophin protein in the subject.

An additional aspect of the invention relates to a method of treating muscular dystrophy in a subject in need thereof, comprising delivering to the subject a therapeutically effective amount of the polynucleotide, vector, and/or transformed cell of the invention, thereby treating muscular dystrophy in the subject. The muscular dystrophy may be any form of muscular dystrophy, e.g., Duchenne muscular dystrophy or Becker muscular dystrophy.

Recombinant Virus Vectors

The virus vectors of the present invention are useful for the delivery of polynucleotides encoding mini-dystrophin to cells in vitro, ex vivo, and in vivo. In particular, the virus vectors can be advantageously employed to deliver or transfer polynucleotides encoding mini-dystrophin to animal, including mammalian, cells.

The virus vector may also comprise a heterologous nucleic acid that shares homology with and recombines with a locus on a host chromosome. This approach can be utilized, for example, to correct a genetic defect in the host cell.

As a further alternative, the polynucleotides encoding mini-dystrophin can be used to produce mini-dystrophin protein in a cell in vitro, ex vivo, or in vivo. For example, the virus vectors may be introduced into cultured cells and the expressed mini-dystrophin protein isolated therefrom.

It will be understood by those skilled in the art that the polynucleotide encoding mini-dystrophin can be operably associated with appropriate control sequences. For example, the polynucleotide can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter and optionally enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced. An enhancer, if employed, can be chosen from the same gene and species as the promoter, from the orthologous gene in a different species as the promoter, from a different gene in the same species as the promoter, or from a different gene in a different species as the promoter.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred) promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the polynucleotide encoding mini-dystrophin is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering polynucleotide encoding mini-dystrophin into a broad range of cells, including dividing and non-dividing cells. The virus vectors can be employed to deliver the polynucleotide to a cell in vitro, e.g., to produce mini-dystrophin in vitro or for ex vivo gene therapy. The virus vectors are additionally useful in a method of delivering the polynucleotide to a subject in need thereof, e.g., to express mini-dystrophin. In this manner, the protein can be produced in vivo in the subject. The subject can be in need of mini-dystrophin because the subject has a deficiency of functional dystrophin. Further, the method can be practiced because the production of mini-dystrophin in the subject may impart some beneficial effect.

The virus vectors can also be used to produce mini-dystrophin in cultured cells or in a subject (e.g., using the subject as a bioreactor to produce the protein or to observe the effects of the protein on the subject, for example, in connection with screening methods).

In general, the virus vectors of the present invention can be employed to deliver the polynucleotide encoding mini-dystrophin to treat and/or prevent any disease state for which it is beneficial to deliver mini-dystrophin. Illustrative disease states include, but are not limited to muscular dystrophies including Duchenne and Becker.

Virus vectors according to the instant invention find use in diagnostic and screening methods, whereby a polynucleotide encoding mini-dystrophin is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

According to certain embodiments of the disclosure of AAV vectors or particles for treating dystrophinopathy, such as DMD, the disclosure provides AAV vectors or particles including AAV capsids from an AAV serotype that has tropism for striated muscle, including without limitation, skeletal muscle, including the diaphragm, and cardiac muscle. Non-limiting examples of naturally occurring AAV capsids having tropism for striated muscle are AAV1, AAV6, AAV7, AAV8, and AAV9. However, other embodiments include AAV capsids that are not known to occur naturally, but rather have been engineered for the express purpose of creating novel AAV capsids that preferentially transduce striated muscle compared to other tissues. Such engineered capsids are known in the art, but the disclosure encompasses new muscle-specific AAV capsids yet to be developed. Non-limiting examples of muscle-specific engineered AAV capsids were reported in Yu, C Y, et al., Gene Ther 16(8): 953-62 (2009), Asokan, A, et al., Nat Biotech 28(1):79-82 (2010 (describing AAV2i8), Bowles, D E, et al., Mol Therapy 20(2):443-455 (2012) (describing AAV 2.5), and Asokan, A, et al., Mol Ther 20(4):699-708 (2012). The amino acid sequences of the capsid proteins, including VP1, VP2, and VP3 proteins, for many naturally and non-naturally occurring AAV serotypes are known in the art. In one non-limiting example, the amino acid sequence for the AAV9 serotype is provided as the amino acid sequence of SEQ ID NO:13.

The AAV particles of the disclosure for treating dystrophinopathy, such as DMD, include a vector genome for expressing a mini-dystrophin protein with dystrophin subdomains selected to at least partially restore in transduced muscle cells the function supplied by the missing full length dystrophin protein. According to some embodiments, the mini-dystrophin protein is constructed from subdomains from the full length wild type human dystrophin protein. In some embodiments, the mini-dystrophin protein includes the following subdomains from the human dystrophin protein in the following order from N-terminus to C-terminus: N-terminal actin binding domain (ABD); H1 hinge domain; R1 and R2 spectrin-like repeat domains; H3 hinge domain; R22, R23 and R24 spectrin-like repeat domains; H4 hinge domain; cysteine rich (CR) domain; and carboxy-terminal (CT) domain. According to some of these embodiments, the N-terminal actin binding domain comprises, consists essentially of, or consists of amino acid numbers 1-240 from SEQ ID NO:25, the amino acid sequence of full length human dystrophin protein; H1 comprises, consists essentially of, or consists of amino acid numbers 253-327 from SEQ ID NO:25; R1 comprises, consists essentially of, or consists of amino acid numbers 337-447 from SEQ ID NO:25; R2 comprises, consists essentially of, or consists of amino acid numbers 448-556 from SEQ ID NO:25; H3 comprises, consists essentially of, or consists of amino acid numbers 2424-2470 from SEQ ID NO:25; R22 comprises, consists essentially of, or consists of amino acid numbers 2687-2802 from SEQ ID NO:25; R23 comprises, consists essentially of, or consists of amino acid numbers 2803-2931 from SEQ ID NO:25; R24 comprises, consists essentially of, or consists of amino acid numbers 2932-3040 from SEQ ID NO:25; H4 comprises, consists essentially of, or consists of amino acid numbers 3041-3112 from SEQ ID NO:25; the CR domain comprises, consists essentially of, or consists of amino acid numbers 3113-3299 from SEQ ID NO:25; and the CT domain comprises, consists essentially of, or consists of amino acid numbers 3300-3408 from SEQ ID NO:25. According to certain embodiments, the mini-dystrophin protein has the amino acid sequence of SEQ ID NO:7.

The vector genome of the AAV particles of the disclosure for treating dystrophinopathy, such as DMD, includes a gene for expressing a mini-dystrophin. Typically, the vector genome will lack the rep and cap genes normally present in wild type AAV to provide room for the gene expressing the mini-dystrophin. In some embodiments, the gene encodes a mini-dystrophin protein with the following subdomains from full length human dystrophin protein: ABD-H1-R1-R2-H3-R22-R23-R24-H4-CRD-CTD. In some embodiments, the CTD is only a portion of the CTD found in wildtype muscle dystrophin, and in some embodiments does not include the last three amino acids present in wildtype muscle dystrophin (SEQ ID NO:25). In certain embodiments, the gene encodes for a human mini-dystrophin protein having the amino acid sequence of SEQ ID NO:7.

According to some embodiments, the gene encoding the human mini-dystrophin protein is codon-optimized with respect to the species of the subject to which the AAV particles of the disclosure will be administered to effect gene therapy. Without wishing to be bound by theory, it is believed that codon-optimization improves the efficiency with which transduced cells are able to transcribe the gene into mRNA and/or translate the mRNA into protein, thereby increasing the amount of mini-dystrophin protein produced compared to expression of a mini-dystrophin encoding gene that is non-codon-optimized. In some non-limiting embodiments, the codon-optimization is human codon-optimization, but codon-optimization can be performed with respect to other species, including canine.

In some embodiments, codon-optimization substitutes one or more codons that pair with relatively rare tRNAs present in a species, such as human, with synonymous codons that pair with more prevalent tRNAs for the same amino acid. This approach can increase the efficiency of translation. In other embodiments, codon-optimization eliminates certain cis-acting motifs that can influence the efficiency of transcription or translation. Non-limiting examples of codon-optimization include adding a strong Kozak sequence at the intended start of the coding sequence, or eliminating internal ribosome entry sites downstream of the intended start codon. Other cis-acting motifs that may be eliminated through codon-optimization include internal TATA-boxes; chi-sites; ARE, INS, and/or CRS sequence elements; repeat sequences and/or RNA secondary structures; cryptic splice donor and/or acceptor sites, branch points; and SalI sites.

In certain embodiments, codon-optimization increases the GC content (that is, the number of G and C nucleobases present in a nucleic acid sequence, usually expressed as a percentage) relative to the wildtype sequence from which the mini-dystrophin gene was assembled. In some embodiments, the GC content is at least 5%, 10%, 15%, 20%, 25%, 30%, 35%, 40%, 45%, 50%, 55%, 60%, 65%, 70%, 75%, 80%, 85%, 90%, 95%, 100%, or greater than the GC content of the corresponding wildtype gene. In related embodiments, the GC content of a codon-optimized gene is about or at least 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, or greater.

In some embodiments, codon-optimization increases the codon adaptation index (CAI) of the gene encoding the mini-dystrophin protein. The CAI is a measure of synonymous codon usage bias in a particular species. The CAI value (which ranges from 0 to 1) in a particular species is positively correlated with gene expression levels. See, for example, Sharp, P M and W-H Lie, Nuc Acids Res 15(3): 1281-95 (1987). According to certain embodiments, codon-optimization increases the CAI of the mini-dystrophin gene in reference to highly expressed human genes to a value that is at least 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, or 0.99.

In other embodiments, codon-optimization reduces the number of CpG dinucleotides in the coding sequence of a mini-dystrophin. Without wishing to be bound by any particular theory of operation, it is believed that methylation at CpG dinucleotides can silence gene transcription, such that reducing the number of CpG dinucleotides in a gene sequence can reduce the level of methylation, thereby resulting in enhanced transcription efficiency. Thus, in some embodiments of the codon-optimized mini-dystrophin genes, the number of CpG dinucleotides is reduced by about or at least 5%, 10%, 15%, 20%, 25%, 30%, 35%, 40%, 45%, 50%, 55%, 60%, or more compared to the wildtype sequence from which the mini-dystrophin gene was assembled.

A non-limiting example of a human codon-optimized human mini-dystrophin gene is provided by the DNA sequence of SEQ ID NO:1. This DNA sequence, which is 3978 nucleobases long (including a stop codon) is referred to herein as Hopti-Dys3978, although the particular terminology is merely used for convenience and is not intended to be limiting. The mini-dystrophin protein sequence encoded by SEQ ID NO:1, which is called Dys3978, is provided by SEQ ID NO:7. An example of a canine codon-optimized human mini-dystrophin gene is provided by SEQ ID NO:3, which also encodes Dys3978. As described in additional detail herein, the coding sequence for the mini-dystrophin of SEQ ID NO:7 was assembled from subsequences of the wildtype full-length human muscle dystrophin gene (as exemplified by NCBI Reference Sequence NM_004006.2, which is incorporated by reference) corresponding to certain subdomains present in the dystrophin protein (SEQ ID NO:25). The resulting gene sequence is provided herein as SEQ ID NO:26, which was then human codon-optimized, resulting in the DNA sequence of SEQ ID NO:1. Without limitation, the codon-optimization increased the GC content, decreased the use of infrequent codons (that is, increased the codon-adaptation index (CAI)), and included a strong translation initiation site (Kozak consensus sequence or similar), compared to the gene sequence before codon-optimization.

The vector genome of the AAV particles of the disclosure for treating dystrophinopathy, such as DMD, further include AAV inverted terminal repeats (ITR) flanking the codon-optimized gene encoding mini-dystrophin protein. In some embodiments, the ITRs are from the same AAV serotype as the capsid (for example, without limitation AAV9 ITRs used with AAV9 capsid), but in other embodiments, AAV ITRs from a different serotype may be used. For example, ITRs from the AAV2 serotype may be used in a vector genome in combination with an AAV capsid from a different, non-AAV2 serotype. Non-limiting examples include use of AAV2 ITRs with a capsid from the AAV1, AAV6, AAV7, AAV8, or AAV9 serotypes, or a different naturally or non-naturally occurring AAV serotype. In a particular non-limiting example, AAV2 ITRs may be used in combination with the capsid from the AAV9 serotype. From the perspective of the plus or sense DNA strand of the vector genome, the sequence of the left, 5', or upstream AAV2 ITR is provided as the DNA sequence of SEQ ID NO:14, and the sequence of the right, 3', or downstream AAV2 ITR is provided as the DNA sequence of SEQ ID NO:15.

The vector genome of the AAV vectors of the disclosure for treating dystrophinopathy, such as DMD, further includes a transcriptional regulatory element operably linked with the gene encoding the mini-dystrophin protein so that the vector genome, once converted into its double stranded form can express the mini-dystrophin gene in transduced cells. Transcriptional regulatory elements typically include a promoter, but optionally one or more enhancer elements that can act to augment the rate of transcription initiation from the promoter.

Operable linkage of a transcriptional regulatory element with respect to the mini-dystrophin coding sequence means that the transcriptional regulatory element can function to control transcription and expression of the gene, but does not necessarily require any particular structural or spatial relationship. Because vector genomes of the disclosure are typically packaged into AAV capsids as single-stranded DNA molecules, it should be understood that the operable linkage may not be functional until the vector genome is converted into double-stranded form. Usually, a promoter will be positioned 5' or upstream of a gene sequence encoding the mini-dystrophin protein, but other transcriptional regulatory elements, such as enhancers, may be positioned 5' or elsewhere, such as 3', of the gene.

In some embodiments, the transcriptional regulatory element can be a strong constitutively active promoter, such those found in certain viruses that infect eukaryotic cells. A well-known example from the art include the promoter from the cytomegalovirus (CMV), but others are known as well such at the promoter from the Rous sarcoma virus (RSV). Strong viral promoters such as CMV or RSV are typically not tissue specific, so that if used the mini-dystrophin protein would be expressed not only in muscle cells, but any other cell type, such as liver, transduced by the AAV particles of the disclosure. Hence, in other embodiments, a muscle-specific transcriptional regulatory element can be used to reduce the amount of mini-dystrophin protein expressed in non-muscle cells, such as liver cells, that may also be transduced by the AAV particles of the disclosure.

Muscle-specific transcriptional regulatory elements can be derived from muscle-specific genes from any species, including mammalian species, such as without limitation, human or mouse muscle genes. Muscle-specific transcriptional regulatory elements will typically include at minimum a promoter from a muscle-specific gene as well as one or more enhancers from the same or a different muscle specific gene. Such enhancers can originate from many parts of the native gene, such as enhancers positioned 5' or 3' of the gene, or even reside in introns. Muscle-specific transcriptional regulatory elements can be removed en bloc from a muscle-specific gene and inserted into a plasmid for producing the AAV vector genomes of the disclosure, or can be engineered to tailor their activity and reduce their size as much as possible.

Non-limiting examples of muscle-specific genes from which muscle-specific transcriptional regulatory elements can be derived include the muscle creatine kinase gene, myosin heavy chain gene, or myosin light chain gene, or the alpha 1 actin gene from skeletal muscle, though others are possible as well. These genes can be from human, mouse, or other species.

Muscle-specific transcriptional regulatory elements that have been created for use in gene therapy applications are described in the art, and may be used in the AAV vectors of the disclosure for treating muscular dystrophy. In non-limiting examples, Hauser described muscle-specific transcriptional regulatory elements known as CK4, CK5, and CK6 derived from the mouse creatine kinase (MCK) gene (Hauser, M A, et al., Mol Therapy 2(1):16-25 (2000)), Salva described muscle-specific transcriptional regulatory elements known as CK1 and CK7, derived from the MCK gene, and MHCK1 and MHCK7, which additionally include enhancers from the mouse α-MHC gene (Salva, M Z, et al., Mol Therapy 15(2):320-9 (2007)), and Wang described muscle-specific transcriptional regulatory elements known as enh358MCK, dMCK and tMCK (Wang, B, et al., Gene Therapy 15:1489-9 (2008)). Use of other muscle-specific transcriptional regulatory elements in the AAV vectors of the disclosure for treating muscular dystrophy are also possible.

Non-limiting examples of muscle-specific transcriptional regulatory elements that may be used in the AAV vectors of the disclosure for treating muscular dystrophy include CK4, CK5, CK6, CK1, CK7, MHCK1, MHCK7, enh358MCK, dMCK and tMCK, each as described in the art, or those disclosed herein as having the DNA sequences of SEQ ID NO:4, SEQ ID NO:5, and SEQ ID NO:16. Other muscle-specific transcriptional regulatory elements may be used as well.

The vector genome of the AAV vectors of the disclosure for treating dystrophinopathy, such as DMD, further includes a transcription termination sequence positioned 3' of the coding sequence for the mini-dystrophin gene. Inclusion of transcription termination sequence ensures that the mRNA transcript encoding the mini-dystrophin protein will be appropriately polyadenylated by the transduced cell thereby ensuring efficient translation of the message into protein. Without intending to be limited by any particular theory of operation, research into mammalian transcription termination sequences identified a consensus sequence in the 3' UTR of genes that serves to terminate transcription and signal polyadenylation of the growing transcript. Specifically, these sequences typically include the motif AATAAA, followed by 15-30 nucleotides, and then CA. See, for example, N. Proudfoot, Genes Dev 25:1770-82 (2011). Other motifs, such as an upstream element (USE) and downstream element (DSE) may contribute to transcription termination in some genes. Many transcription termination sequences are known in the art and can be used in the AAV vectors of the disclosure. Non-limiting examples include the polyadenylation signal from the SV40 virus early or late genes (SV40 early or late polyA) or the polyadenylation signal from the bovine growth hormone gene (bGH polyA). Transcription termination sequences from other genes of any species may be used in the AAV vectors of the disclosure. Alternatively, synthetic transcription termination sequences may be designed and used to signal transcription termination and polyadenylation. Additional non-limiting examples of transcription termination sequences that may be used in the AAV vectors of the disclosure include those disclosed herein as having the DNA sequences of SEQ ID NO:6 and SEQ ID NO:17.

According to certain non-limiting embodiments, the disclosure provides an AAV viral particle or vector for treating dystrophinopathy, such as DMD, comprising an AAV capsid and a vector genome encoding a mini-dystrophin protein. In some embodiments, the mini-dystrophin protein includes the following subdomains from full length human dystrophin protein: ABD-H1-R1-R2-H3-R22-R23-R24-H4-CRD-CTD. In some embodiments, the CTD is only a portion of the CTD found in wildtype muscle dystrophin, and in some embodiments does not include the last three amino acids present in wildtype muscle dystrophin (SEQ ID NO:25). According to certain embodiments, the gene encoding the mini-dystrophin protein of SEQ ID NO:7 is human codon-optimized and has the DNA sequence of SEQ ID NO:1. In some embodiments, the AAV capsid is from the AAV9 serotype.

As noted elsewhere herein, single-stranded AAV vector genomes are packaged into capsids as the plus strand or minus strand in about equal proportions. Consequently, embodiments of the vector or particle include AAV particles in which the vector genome is in the plus strand polarity (that is, has the nucleobase sequence of the sense or coding DNA strand), as well as AAV particles in which the vector genome is in the minus strand polarity (that is, has the nucleobase sequence of the antisense or template DNA strand). Given the nucleobase sequence of the plus strand in its regular 5' to 3' order, the nucleobase sequence of the minus strand in its 5' to 3' order can be determined as the reverse-complement of the nucleobase sequence of the plus strand.

In some embodiments of the vector, the vector genome, when in plus polarity, comprises a muscle-specific transcriptional regulatory element derived from the creatine kinase gene having the DNA sequence of SEQ ID NO:16 positioned 5' of and operably linked with SEQ ID NO:1, the DNA sequence of the human codon-optimized gene encoding mini-dystrophin protein. Particles comprising the corresponding minus strand are also possible, where the sequence of nucleobases from its 5' end would be the reverse complement of the sequence of the aforementioned plus strand. In other embodiments, the vector genome, when in plus polarity comprises a first AAV2 ITR followed by the DNA sequence of SEQ ID NO:16 positioned 5' of and operably linked with the DNA sequence of SEQ ID NO:1, and a transcription termination sequence comprising the DNA sequence of SEQ ID NO:17 positioned 3' of the mini-dystrophin gene, followed by a second AAV2 ITR. Particles comprising the corresponding minus strand are also possible, where the sequence of nucleobases from its 5' end would be the reverse complement of the sequence of the aforementioned plus strand.

In certain other embodiments of the vector, the vector genome, when in plus polarity, comprises in 5' to 3' order a first AAV2 ITR, a transcriptional regulatory element sequence defined by the DNA sequence of SEQ ID NO:16, a human codon optimized gene sequence for expressing a mini-dystrophin, the gene sequence defined by the DNA sequence of SEQ ID NO:1 in operable linkage with the transcriptional regulatory element, a transcription termination sequence defined by the DNA sequence of SEQ ID NO:17, and a second AAV2 ITR. Particles comprising the corresponding minus strand are also possible, where the sequence of nucleobases from its 5' end would be the reverse complement of the sequence of the aforementioned plus strand.

According to a particular non-limiting embodiment, an AAV vector for treating dystrophinopathy, such as DMD, which may be referred to herein as AAV9.hCK.Hopti-Dys3978.spA, comprises a capsid from the AAV9 serotype and a vector genome, which vector genome may be referred to herein as hCK.Hopti-Dys3978.spA, comprising, consisting essentially of, or consisting of, when the genome is in plus polarity, the DNA sequence of SEQ ID NO:18 or, when the genome is in the minus polarity, the reverse-complement of the DNA sequence of SEQ ID NO:18 (that is, when the vector genome sequence is read 5' to 3').

Methods of Producing Virus Vectors

The present disclosure further provides methods of producing AAV vectors. In one particular embodiment, the present disclosure provides a method of producing a recombinant parvovirus particle, comprising providing to a cell permissive for AAV replication and packaging a recombinant AAV vector genome, comprising a mini-dystrophin gene, associated genetic control elements and flanking AAV ITRs, and AAV replication and packaging functions, such as those provided by the AAV rep and cap genes, under conditions sufficient for the replication and packaging of the recombinant AAV particles, whereby rAAV particles are produced by the cell. Conditions sufficient for the replication and packaging of the rAAV particles include without limitation helper functions, such as those from adenovirus and/or herpesvirus. Cells permissive for AAV replication and packaging are known herein as packaging cells or producer cells, terms encompassed by the broader term host cells. The rAAV particle vector genome, replication and packaging functions and, where required, helper functions can be provided via viral or non-viral vectors, such as plasmids, and can exist within the packaging cells stably or transiently, either integrated into the cell's genome or in an episome.

Recombinant AAV vectors of the disclosure can be made by several methods known to skilled artisans (see, e.g., WO 2013/063379). An exemplary method is described in Grieger, et al. 2015, Molecular Therapy 24(2):287-297, the contents of which are incorporated by reference. Briefly, efficient transfection of HEK293 cells is used as a starting point, wherein an adherent HEK293 cell line from a qualified clinical master cell bank is used to grow in animal component-free suspension conditions in shaker flasks and WAVE bioreactors that allow for rapid and scalable rAAV particle production. Using the triple transfection method (e.g., WO 96/40240), the suspension HEK293 cell line is capable of generating, in some embodiments, greater than $1\times10^5$ vector genome (vg) containing particles per cell, or greater than $1\times10^{14}$ vg/L of cell culture when harvested 48 hours post-transfection. Triple transfection refers to the fact that the packaging cell is transfected with three plasmids: one plasmid encodes the AAV rep and cap genes, another plasmid encodes various helper functions (e.g., adenovirus or HSV proteins such as E1a, E1b, E2a, E4, and VA RNA, and another plasmid encodes the vector genome, i.e., the mini-dystrophin gene and its various control elements flanked by AAV ITRs. To achieve the desired yields, a number of variables can be optimized such as selection of a compatible serum-free suspension media that supports both growth and transfection, selection of a transfection reagent, transfection conditions and cell density. Vectors can be collected from the medium and/or by lysing the cells, and then purified using the classic density gradient ultracentrifugation technique, or using column chromatographic or other techniques.

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon, a Baculovirus, or HSV helper construct. The packaging functions may exist extrachromosomally within the packaging cell, but may also be integrated into the cell's chromosomal DNA. Examples include genes encoding AAV Rep and Cap proteins. Rep and cap genes can be provided to packaging cell together as part of the same viral or non-viral vector. For example, the rep and cap sequences may be provided by a hybrid adenovirus vector (e.g., inserted into the Ela or E3 regions of a deleted adenovirus vector) or herpesvirus vector, such as an EBV vector. Alternatively, AAV rep and cap genes can be provided separately. Rep and cap genes can also be stably integrated into the genome of a packaging cell, or exist on an episome. Typically, rep and cap genes will not be flanked by ITRs to avoid packaging of these sequences into rAAV vector particles.

The helper functions include helper virus elements needed for establishing active infection of the packaging cell which is required to initiate packaging of the viral vector. Examples include functions derived from adenovirus, baculovirus and/or herpes virus sufficient to result in packaging of the viral vector. For example, adenovirus helper functions will typically include adenovirus components Ela, E1b, E2a, E4, and VA RNA. The packaging functions may be supplied by infection of the packaging cell with the required virus. Alternatively, use of infectious virus can be avoided, whereby the packaging functions may be supplied together or separately to the packaging cell using a non-viral vector such as a plasmid or an amplicon. See, e.g., pXR helper plasmids as described in Rabinowitz et al., 2002, J. Virol. 76:791, and pDG plasmids described in Grimm et al., 1998, Human Gene Therapy 9:2745-2760. The packaging functions may exist extrachromosomally within the packaging cell, but may also be integrated into the cell's chromosomal DNA (e.g., E1 or E3 in HEK 293 cells).

Any method of introducing the nucleotide sequence carrying the helper functions into a cellular host for replication and packaging may be employed, including but not limited to electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRCS, A549, HEK 293 cells (which express functional adenoviral E1 under the control of a constitutive promoter), B-50 or any other HeLa cells, HepG2, Saos-2, HuH7, and HT1080 cell lines. In one aspect, the packaging cell is capable of growing in suspension culture, especially in serum-free growth media. In one embodiment, the packaging cell is a HEK293 that grows in suspension in serum free medium. In another embodiment, the packaging cell is the HEK293 cell described in U.S. Pat. No. 9,441,206 and deposited as ATCC No. PTA 13274. Numerous rAAV particle packaging cell lines are known in the art, including, but not limited to, those disclosed in WO 2002/46359.

Cell lines for use as packaging cells include insect cell lines, particularly when baculoviral vectors are used to introduce the genes required for rAAV particle production as described herein. Any insect cell that allows for replication of AAV and that can be maintained in culture can be used in accordance with the present disclosure. Examples include *Spodoptera frugiperda*, such as the Sf9 or Sf21 cell lines, *Drosophila* spp. cell lines, or mosquito cell lines, e.g., *Aedes albopictus*-derived cell lines.

After AAV vector particles of the disclosure have been produced and purified, they can be titered to prepare compositions for administration to subjects, such as human subjects with muscular dystrophy. AAV vector titering can be accomplished using methods known in the art. In certain embodiments, AAV vector particles can be titered using quantitative PCR (qPCR) using primers against sequences in the vector genome, for example, AAV2 ITR sequences if present, or other sequences in the vector genome. By performing qPCR in parallel on dilutions of a standard of known concentration, such as a plasmid containing the sequence of the vector genome, a standard curve can be generated permitting the concentration of the AAV vector to be calculated as the number of vector genomes (vg) per unit volume, such as microliters or milliliters. Alternatively, the number of AAV vector particles containing genomes can be determined using dot blot using a suitable probe for the vector genome. These techniques are described further in Gray, S J, et al., Production of recombinant adeno-associated viral vectors and use in in vitro and in vivo administration, Curr Protoc Neurosci (2011) and Werling N J, et al., Gene Ther Meth 26:82-92 (2015). Once the concentration of AAV vector genomes in the stock is determined, it can be diluted into or dialyzed against suitable buffers for use in preparing a composition for administration to subjects.

Methods of Treatment

The disclosure provides methods for treating a dystrophinopathy by administering to a subject in need of treatment for dystrophinopathy a therapeutically effective dose or amount of an AAV vector of the disclosure, such as, without limitation, the vector known as AAV9.hCK.Hopti-Dys3978.spA. In some embodiments, the dystrophinopathy is a muscular dystrophy, including without limitation Duchenne muscular dystrophy (DMD), Becker muscular dystrophy (BMD), DMD-associated dilated cardiomyopathy (DCM), and symptomatic carrier states in females. Thus, in some embodiments, the disclosure provides methods for treating muscular dystrophy by administering to a subject in need of treatment for muscular dystrophy a therapeutically effective dose or amount of an AAV vector of the disclosure, such as, without limitation, the vector known as AAV9.hCK.Hopti-Dys3978.spA. In related embodiments, the disclosure provides methods for treating Duchenne muscular dystrophy (DMD), Becker muscular dystrophy (BMD), DMD-associated dilated cardiomyopathy (DCM), and symptomatic carrier states in females, in subjects in need of treatment therefore.

Also provided is the use of an AAV vector or pharmaceutical composition of the disclosure in the manufacture of a medicament for use in the methods of treatment disclosed herein. In addition, there is provided an AAV vector or pharmaceutical composition of the disclosure for use in a method of treatment disclosed herein.

Treatment of subjects with a dystrophinopathy, such as DMD, need not result in a cure to be considered effective, where cure is defined as either halting disease progression, or partially or completely restoring the subject's muscle function. Rather a therapeutically effective dose or amount of an AAV vector of the disclosure is one that serves to reduce or ameliorate the symptoms of, slow the progression of, or improve the quality of life of a subject with the dystrophinopathy, such as DMD. According to certain non-limiting embodiments, treatment of subjects with a dystrophinopathy can improve their mobility, delay the time to their loss of ambulation or other mobility, and in the cases of severe dystrophinopathy, such as DMD, extend the life of subjects with the disorder.

The methods of treatment of the disclosure can be used to treat male or female subjects with a dystrophinopathy, such as DMD. In the case of females, treatment can be provided to symptomatic carriers, or to the rare female subject with full blown disease. The methods of the disclosure can also be used to treat subjects of any age with a dystrophinopathy, including subjects less than 1 year old, or about or at least 1 year old, or about or at least 2, 3, 4, 5, 6, 7, 8, 9, 10, 11, 12, 13, 14, 15, 16, 17, 18, 19, 20, 21, 22, 23, 24, 25, 26, 27, 28, 29, 30 years old or older. Subjects, when treated, may be ambulatory, or non-ambulatory.

The methods of treatment of the disclosure can be used to treat subjects with a dystrophinopathy regardless of the underlying genetic lesion (for example, deletions, duplications, splice site variants, or nonsense mutations in the dystrophin gene), so long as the lesion results in a reduction or loss in the function of the native human dystrophin gene.

In certain embodiments of the disclosure, treating a subject with a therapeutically effective dose or amount of an AAV mini-dystrophin vector will reduce tissue concentrations of one or more biomarkers that are associated with the existence or progression of muscular dystrophy.

According to certain embodiments, the biomarkers are certain enzymes released from damaged skeletal muscle or cardiac muscle cells into the blood (including serum or plasma). Non-limiting examples include creatinine kinase (CK), the transaminases alanine aminotransferase (ALT) and aspartate aminotransferase (AST), and lactic acid dehydrogenase (LDH), the average levels of which are all known to be elevated in subjects with DMD.

In some embodiments, a therapeutically effective dose or amount of an AAV mini-dystrophin vector of the disclosure is effective to reduce elevated ALT levels in blood of DMD patients to within about 7-, 6-, 5-, 4-, 3-, or 2-fold greater than that typically found in healthy subjects of similar age and sex. In other embodiments, a therapeutically effective dose or amount of an AAV mini-dystrophin vector of the disclosure is effective to reduce elevated AST levels in blood of DMD patients to within about 7-, 6-, 5-, 4-, 3-, or 2-fold greater than that typically found in healthy subjects of similar age and sex. In some embodiments, a therapeutically effective dose or amount of an AAV mini-dystrophin vector of the disclosure is effective to reduce elevated LDH levels in blood of DMD patients to within about 7-, 6-, 5-, 4-, 3-, or 2-fold greater than that typically found in healthy subjects of similar age and sex. And in some other embodiments, a therapeutically effective dose or amount of an AAV mini-dystrophin vector of the disclosure is effective to reduce elevated total CK levels in blood of DMD patients to within about 50-, 48-, 46-, 44-, 42-, 40-, 38-, 36-, 34-, 32-, 30-, 28-, 26-, 24-, 22-, 20-, 18-, 16-, 14-, 12-, 10-, 9-, 8-, 7-, 6-, 5-, 4-, 3-, or 2-fold greater than that typically found in healthy subjects of similar age and sex. It has also been found that matrix metalloproteinase-9 (MMP-9), an enzyme associated with degradation or remodeling of the extracellular matrix, is elevated in the blood of DMD patients. See, for example, Nadaraja, V D, et al., Neuromusc. Disorders 21:569-578 (2011). Thus, in some embodiments, a therapeutically effective dose or amount of an AAV mini-dystrophin vector of the disclosure is effective to reduce elevated MMP-9 levels in blood of DMD patients to within about 15-, 14-, 13-, 12-, 11-, 10-, 9-, 8-, 7-, 6-, 5-, 4-, 3-, or 2-fold greater than that typically found in healthy subjects of similar age and sex.

In other embodiments, a therapeutically effective dose or amount of an AAV mini-dystrophin vector of the disclosure is effective to alter the levels of ALT, AST, LDH, CK and MMP-9 as indicated above alone or in combination with one or more of these same or other biomarkers. Thus, in an exemplary non-limiting embodiment, a therapeutically effective dose or amount of an AAV mini-dystrophin vector of the disclosure is effective to reduce ALT and AST, ALT and LDH, AST and CK, or AST and MMP-9, etc.

In some methods of treatment of the disclosure, an effective dose or amount of an AAV vector is one that improves average subject performance in the 6 minute walk-test (6MWT). The 6MWT has been established as a reproducible and valid measure of muscle function and mobility of human subjects with muscular dystrophy, in particular, DMD. See, for example, McDonald, C M, et al., Muscle Nerve 41(4):500-10 (2010); Henricson, E, et al., PLOS Currents Musc Dys, 8 Jul. 2013; McDonald, C M, et al., Muscle Nerve 48:343-56 (2013). In the test, the distance in meters that a subject can, starting from rest, walk continually and unaided during a 6 minute period is recorded. This distance is also known as the 6 minute walk distance (6MWD). In some applications of the test, an individual subject may be tested more than once over a period of days, and the results averaged. Due to its advantages, the 6MWT has been adopted as a primary clinical endpoint in drug trials involving ambulatory DMD patients. See, for example, Bushby, K, et al., Muscle Nerve 50:477-87 (2014); Mendell, J R, et al., Ann Neurol 79:257-71 (2016); Campbell, C, et al., Muscle Nerve 55(4):458-64 (2017). Usually, in these trials, each subject in the treatment group has his ambulation tested using the 6MWT over a period of months or years to determine if a treatment effect exists.

According to some embodiments of the methods of treatment of the disclosure, therapeutic efficacy is determined statistically by comparing the treatment effect of AAV vectors of the disclosure on the average 6MWT performance of treated subjects, such as those with DMD, in comparison with the average 6MWT performance of untreated control subjects with the same type of dystrophinopathy, such as DMD. Such controls can have been included in the same studies used to evaluate the therapeutic efficacy of AAV vectors of the disclosure, or can be similar subjects drawn from natural history studies of the progression of DMD or other dystrophinopathies. Controls can be age matched (or stratified, for example and without limitation, into those subjects younger than or older than some threshold age, such as 6, 7, 8, 9, or 10 years), matched for status of prior corticosteroid treatment (that is, yes or no, or length of time of previous treatment), matched for baseline performance in the 6MWT before any treatment (except perhaps with corticosteroids) (or stratified, for example and without limitation, into those subjects whose baseline performance is below and above some threshold, such as 200 m, 250 m, 300 m, 350 m, 400 m, 450 m, or 500 m), or some other attribute determined to be clinically relevant.

According to certain embodiments of the methods of treatment of the disclosure, a therapeutically effective dose or amount of an AAV vector of the disclosure is effective to increase the average 6MWD of subjects with dystrophinopathy, such as DMD, by about or at least 5, 10, 15, 20, 25, 30, 35, 40, 45, 50, 55, 60, 65, 70, 75, 80, 85, 90, 95, or 100 meters or more compared to similar matched or stratified controls 3, 6, 9, 12, 15, 18, 21, 24, 27, 30, 33, or 36 months after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

According to certain embodiments of the methods of treatment of the disclosure, a therapeutically effective dose or amount of an AAV vector of the disclosure is effective to increase the average 6MWD of subjects with dystrophinopathy, such as DMD, by about or at least 5, 10, 15, 20, 25, 30, 35, 40, 45, 50, 55, 60, 65, 70, 75, 80, 85, 90, 95, or 100 meters or more compared to similar matched or stratified controls 30, 60, 90, 120, 150, 180, 210, 240, 270, 300, 330, 360, 390, 420, 450, 480, 510, 540, 570, 600, 630, 660, 690 or 720 days after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

As an alternative to the 6MWT, therapeutic efficacy can be expressed as reduction in the time it takes a subject to ascend 4 standard sized stairs, a test known as the 4 stair climb test. This test has been used to assess the effectiveness of corticosteroid treatment in DMD patients. Griggs, R C, et al., Arch Neurol 48(4):383-8 (1991). Thus, according to certain embodiments of the methods of treatment of the disclosure, a therapeutically effective dose or amount of an AAV vector of the disclosure is effective to reduce the average time it takes for subjects with dystrophinopathy, such as DMD, to perform the 4 stair climb test by about or at least 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 seconds or more compared to similar matched or stratified controls 3, 6, 9, 12, 15, 18, 21, 24, 27, 30, 33, or 36 months after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In related embodiments of the methods of treatment of the disclosure, a therapeutically effective dose or amount of an AAV vector of the disclosure is effective to reduce the average time it takes for subjects with dystrophinopathy, such as DMD, to perform the 4 stair climb test by about or at least 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, or 4.0 seconds or more compared to similar matched or stratified controls 30, 60, 90, 120, 150, 180, 210, 240, 270, 300, 330, 360, 390, 420, 450, 480, 510, 540, 570, 600, 630, 660, 690 or 720 days after administration of the vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

Therapeutic efficacy can also be expressed as a reduction over time in the percentage of subjects that experience loss of ambulation a specified time after treatment compared to controls. Loss of ambulation is defined as start of continuous reliance on wheelchair use. Thus, according to yet other embodiments of the methods of treatment of the disclosure, a therapeutically effective dose or amount of an AAV vector of the disclosure reduces, 3, 6, 9, 12, 15, 18, 21, 24, 27, 30, 33, or 36 months after administration to subjects with dystrophinopathy, such as DMD, the average number of subjects that have lost ambulation by at least 5%, 10%, 15%, 20%, 25%, 30%, 35%, 40%, 45%, 50%, 55%, 60%, 65% or more compared to similar matched or stratified controls. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In some embodiments of the methods of treatment of the disclosure, a therapeutically effective dose or amount of an AAV vector of the disclosure is effective to delay the onset of one or more symptoms in a subject having a dystrophinopathy, such as DMD. Diagnosis before onset of symptoms can be accomplished through prenatal, perinatal or postnatal genetic testing for mutations in the DMD gene. According to certain embodiments, treatment with an AAV vector of the disclosure is effective to delay onset of one or more symptoms of DMD by at least or about 3, 4, 5, 6, 7, 8, 9, 10, 12, 14, 15, 16, 18, 20, 22, 24, 25, 26, 28, 30, 32, 34, 35, 36, 38, 40, 42, 44, 45, 46, 48, 50, 52, 54, 55, 56, 28, 60, 62, 64, 65, 66, 68, 70, 72, 74, 75, 76, 78, or 80 months, or more compared to similar matched or stratified controls. As appreciated by those of ordinary skill, early symptoms of DMD include without limitation delay in walking ability (to an average age of about 18 months, compared to an average of 12-15 months in babies without DMD); difficulty jumping, running or climbing stairs; proneness to falling; proximal muscle weakness, evidenced, for example, by exhibiting the Gowers' maneuver when rising from the floor; enlarged calves, due to pseudohypertrophy; waddling gait due to subjects' walking on toes and/or balls of feet; tendency to maintain balance by sticking out bellies and pulling back shoulders; and cognitive impairments, such as diminished receptive language, expressive language, visuospatial ability, fine motor skills, attention, and memory skills. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

Therapeutic efficacy can also be expressed as a reduction over time in the percentage of vector treated subjects that experience an increase in the amount of adipose tissue that replaces lean muscle tissue compared to untreated controls. In some embodiments, this progression toward increased adiposity can be determined using MM analysis of the leg muscles of DMD patients and expressed as the fat fraction (FF), as explained further in Willcocks, R J, et al., Multicenter prospective longitudinal study of magnetic resonance biomarkers in a large Duchenne muscular dystrophy cohort, *Ann Neurol* 79:535-47 (2016). In related embodiments, treatment of DMD subjects with an AAV vector of the disclosure is effective to reduce the average FF in their lower extremities as determined by MRI by about or at least 5%, 10%, 15%, 20%, 25%, 30%, 35%, 40%, 45%, 50%, 55%, 60%, 65%, 70%, 75%, or more 3, 6, 9, 12, 15, 18, 21, 24, 27, 30, 33, or 36 months after treatment compared to matched controls. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In some embodiments, a therapeutically effective dose or amount of an AAV vector of the disclosure is one that results in at least 5%, 10%, 15%, 20%, 25%, 30%, 35%, 40%, 45%, 50%, 55%, 60%, 65%, 70%, 75%, 80%, 85%, 90%, or more of skeletal muscle fibers expressing the mini-dystrophin protein 3, 6, 9, 12, 15, 18, 21, 24, 27, 30, 33, or 36 months after treatment. The percentage of muscle fibers that are positive for mini-dystrophin protein expression may be determined by immunolabeling sections of biopsied muscle from treated subjects with an anti-dystrophin antibody capable of specifically binding the mini-dystrophin protein. Suitable immunolabeling techniques are described in the Examples, and are familiar to those of ordinary skill in the art. Exemplary muscles of treated subjects from which biopsies may be taken include bicep, deltoid, and quadriceps, although other muscles may be biopsied as well. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In some embodiments, a dose or amount of an AAV vector of the disclosure for treating dystrophinopathy, such as muscular dystrophy, such as DMD, is determined to be therapeutically effective and at the same time causes either no cellular (T cell) immune response specific for the mini-dystrophin protein in treated subjects, or in only a low percentage of such subjects. Existence or extent of a T cell response against the mini-dystrophin protein can be determined using the ELISPOT assay to detect peripheral blood mononuclear cells (PBMCs) isolated from subject blood that produce gamma interferon (IFNγ) in response to exposure to an overlapping peptide library covering the mini-dystrophin protein amino acid sequence. In certain embodiments, the threshold for a positive IFNγ response can be set as greater than 50 spot-forming cells per million PBMCs tested. Use of other assays to detect a T cell response against the mini-dystrophin protein are also possible including without limitation detection of T cell infiltrates in biopsies of muscle or other tissues expressing mini-dystrophin protein obtained from vector treated subjects. Subjects can be human subjects or animal subjects, such as animal models of DMD, such as the mdx mouse, mdx rat, or GRMD dog models. In other embodiments, a dose or amount of an AAV vector of the disclosure for treating dystrophinopathy, such as muscular dystrophy, such as DMD, is determined to be therapeutically effective and at the same time causes either no inflammatory response against the capsid, vector genome (or any component thereof), or mini-dystrophin protein expressed by transduced cells, or in only a low percentage of such subjects. Without wishing to be bound by any particular theory of operation, inflammation in response to an AAV vector may be caused by an innate immune response. Inflammation, if any exists, in the muscles of vector treated subjects can be detected using magnetic resonance imaging. See, for example, J Garcia, Skeletal Radiol 29:425-38 (2000) and Schulze, M, et al., Am J Radiol 192:1708-16 (2009). Subjects can be human subjects or animal subjects, such as animal models of DMD, such as the mdx mouse, mdx rat, or GRMD dog models. In some of the embodiments described above, existence or absence of cellular immune response or inflammation is determined 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months after treatment, or some other time after treatment. In related embodiments, a low percentage of subjects exhibiting a cellular immune response to the mini-dystrophin protein would be less than or equal to about 0%, 1%, 2%, 3%, 4%, 5%, 6%, 7%, 8%, 9%, 10%, 11%, 12%, 13%, 14%, 15%, 16%, 17%, 18%, 19% or 20% of subjects administered vector. In some of these embodiments, the AAV vector comprises the AAV9 capsid and a genome including a human codon-optimized gene encoding a mini-dystrophin protein, such as, without limitation, the vector designated as AAV9.hCK.Hopti-Dys3978.spA.

In related embodiments, a dose or amount of an AAV vector of the disclosure for treating dystrophinopathy, such as muscular dystrophy, such as DMD, is therapeutically effective without need for concomitant immune suppression in treated subjects. Thus, in certain embodiments, treatment of a subject with dystrophinopathy, such as DMD, is effective without need to administer to the subject before, during or after treatment with AAV vector one or more immune-suppressing drugs (apart from steroid treatment, which is the current standard of care). Exemplary immune-suppressing drugs include but are not limited to calcineurin inhibitors, such as tacrolimus and cyclosporin, antiproliferative agents, such as mycophenolate, leflunomide, and azathioprine, or mTOR inhibitors, such as sirolimus and everolimus.

As explored in greater detail in the Examples, efficacy of the AAV vectors of the disclosure, including without limitation the vector designated as AAV9.hCK.Hopti-Dys3978.spA, can be tested in animal models of Duchenne muscular dystrophy, and results used to predict efficacious doses of such vectors in human DMD patients. Various animal models are known in the art, including the mdx mouse model, the Golden Retriever muscular dystrophy model, and more recently, the $Dmd^{mdx}$ rat model, which is described in greater detail in the Examples.

Based on the $Dmd^{mdx}$ rat model, effective doses of AAV vectors of the disclosure, including the vector designated as AAV9.hCK.Hopti-Dys3978.spA, can be established with respect to various biological parameters and aspects of the disease course in the rats.

Thus, according to certain embodiments of the disclosure, treatment of $Dmd^{mdx}$ rats with a dose of AAV9.hCK.Hopti-Dys3978.spA of at least $1\times10^{14}$ vg/kg or $3\times10^{14}$ vg/kg is effective to reduce serum AST, ALT, LDH, or total creatine kinase levels at 3 months or 6 months post-injection compared to controls.

In other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to reduce fibrosis in biceps femoris, diaphragm, or heart muscle at 3 months or 6 months post-injection compared to controls.

In yet other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to increase forelimb grip force at 3 months or 6 months post-injection compared to controls.

According to other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to reduce muscle fatigue as measured over 5 closely spaced trials testing forelimb grip force at 3 months or 6 months post-injection compared to controls.

In some other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to increase the left ventricular ejection fraction as measured using echocardiography at 6 months post-injection compared to controls.

In other embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to increase the ratio of the velocity of early to late left ventricular filling (i.e., E/A ratio) as measured using echocardiography at 3 months or 6 months post-injection compared to controls.

According to some embodiments, treatment of $Dmd^{mdx}$ rats with a dose of AAV9.hCK.Hopti-Dys3978.spA of at least $1\times10^{14}$ vg/kg or $3\times10^{14}$ vg/kg is effective to decrease the isovolumetric relaxation time (IVRT) or the time in milliseconds between peak E velocity and its return to baseline (i.e., the E wave deceleration time (DT)) as measured using echocardiography at 3 months or 6 months post-injection compared to controls.

In each of the foregoing embodiments, the increase or decrease of the physiologic measurement in vector-treated animals compared to control animals can, in some embodiments, be tested for statistical significance. The choice of which statistical test to apply is within the knowledge of those ordinarily skilled in the art. Where a p-value is adopted as the way in which to assess statistical significance, such p-values, once calculated, can be compared to a predefined significance level, and if the p-value is smaller than the significance level, the treatment effect can be determined to be statistically significant. In some embodiments, the significance level can be predefined as 0.25, 0.20, 0.15, 0.10, 0.05, 0.04, 0.03, 0.02, 0.01, 0.005, or some other significance level. Thus, in an exemplary non-limiting embodiment, where the significance level is predefined as 0.05, then calculation of a p-value $<0.05$ would be interpreted to represent a statistically significant difference between vector-treated and control groups.

In each of the foregoing embodiments, the controls can be age matched animals of the same sex and genetic background that are untreated, or treated only with vehicle and not vector. Other controls are also possible, however.

In some other embodiments, treatment of $Dmd^{mdx}$ rats with a dose of AAV9.hCK.Hopti-Dys3978.spA of at least $3\times10^{14}$ vg/kg is effective to transduce biceps femoris, diaphragm, heart muscle, or other striated muscles, and express the mini-dystrophin protein encoded by the opti-Dys3978 gene without inducing a cellular immune response against the mini-dystrophin protein by 3 months or 6 months post-injection. Cellular immune response against the mini-dystrophin protein can be assessed by isolating splenocytes, or blood lymphocytes, such as peripheral blood mononuclear cells (PBMCs), from test animals, incubating the cells with peptides from an overlapping peptide library covering the mini-dystrophin protein amino acid sequence (for example, peptides 15 amino acids long overlapping by 10 amino acids each) in pools (for example, 5 pools), and determining whether the cells produce gamma interferon (IFNγ) in response to being exposed to the peptides. Production of IFNγ can be determined using the ELISPOT assay according to the knowledge of those ordinarily skilled in the art. See, for example, Smith, J G, et al., Clin Vaccine Immunol 8(5):871-9 (2001), Schmittel A, et al., J Immunol Methods 247:17-24 (2001), and Marino, A T, et al., Measuring immune responses to recombinant AAV gene transfer, Ch. 11, pp. 259-72, Adeno-Associated Virus Methods and Protocols, Ed. RO Snyder and P Moullier, Humana Press (2011). In certain embodiments, the threshold for a positive IFNγ response can be set as greater than 50 spot-forming cells per million cells tested, or in other embodiments, as at least 3-times the number of spot-forming cells detected using a negative control (for example, medium only without added peptides), so that a negative response would be considered below these thresholds.

In some embodiments of the methods of treatment of the present disclosure, an AAV vector for treating dystrophinopathy, such as DMD, is administered to a subject in need of treatment for dystrophinopathy, such as DMD, jointly with at least a second agent established or believed to be effective for treating dystrophinopathy, such as DMD. Joint administration of the AAV vector means treating a subject before, contemporaneously with, or after treatment of the second agent. According to certain embodiments, the AAV vector is jointly administered with an antisense oligonucleotide that causes exon skipping of the DMD gene, for example of exon 51 of the dystrophin gene, or some other exon of the dystrophin gene. Agents that cause skipping of exon 51 of the dystrophin gene include drisapersen and eteplirsen, but others are possible. In other embodiments, the AAV vector is jointly administered with an agent that inhibits myostatin function in the subject, such as an anti-myostatin antibody, examples of which are provided in U.S. Pat. Nos. 7,888,486, 8,992,913, and 8,415,459. In other embodiments, where the dystrophinopathy of the subject can be attributed to a nonsense mutation in the dystrophin gene, the AAV vector is jointly administered with an agent that promote ribosomal read-through of nonsense mutations, such as ataluren, or with an agent that suppresses premature stop codons, such as an aminoglycoside, such as gentamicin. In other embodiments, the AAV vector is jointly administered with an anabolic steroid, such as oxandrolone. And in yet other embodiments, the AAV vector is jointly administered with a corticosteroid, such as without limitation prednisone, deflazacort, or prednisolone. In some embodiments of these methods, the AAV vector is an AAV9 vector comprising a genome including a human codon-optimized gene encoding a mini-dystrophin protein, such as, without limitation, the vector designated as AAV9.hCK.Hopti-Dys3978.spA.

Pharmaceutical Formulations and Modes of Administration

Virus vectors and capsids according to the present invention find use in both veterinary and human medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults. Optionally, the subject is "in need of" the methods of the present invention, e.g., because the subject has or is believed at risk for a disorder including those described herein or that would benefit from the delivery of a polynucleotide including those described herein. As a further option, the subject can be a laboratory animal and/or an animal model of disease.

In particular embodiments, the present invention provides a pharmaceutical composition comprising a virus vector (such as an rAAV particle) and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a polynucleotide encoding mini-dystrophin to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to muscle cells (e.g., skeletal muscle cells, cardiac muscle cells, smooth muscle cells and/or diaphragm muscle cells), stem cells, germ cells, and the like. In representative embodiments, the cell can be any progenitor cell. As a further possibility, the cell can be a stem cell (e.g., muscle stem cell). Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g. U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

A further aspect of the invention is a method of administering the virus vector to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$-$10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

In certain embodiments, an AAV vector or particle of the disclosure can be administered to a subject in compositions comprising empty AAV capsids of the same or a different serotype. Empty capsids are AAV capsids comprising the typical arrangement and ratios of VP1, VP2 and VP3 capsid proteins, but do not contain a vector genome. Without wishing to be bound by any particular theory of operation, it is hypothesized that the presence of empty capsids can reduce the immune response against the capsid of the AAV vector, and thereby increase transduction efficiency. Empty capsids can occur naturally in a preparation of AAV vector, or be added in known quantities to achieve known ratios of empty capsids to AAV vector (that is, capsids containing vector genomes). Preparation, purification and quantitation of empty capsids is within the knowledge of those ordinarily skilled in the art. Compositions comprising AAV vectors of the disclosure and empty capsids can be formulated with an excess of empty capsids relative to AAV vectors, or an excess of genome containing AAV vectors relative to empty capsids. Thus, in some embodiments, compositions of the disclosure comprise AAV vectors of the disclosure and empty capsids of the same or a different serotype, wherein the ratio of empty capsids to AAV vectors is about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10 to 1, or some other ratio.

In other embodiments, the disclosure provides exemplary efficacious doses of AAV vector particles for treating dystrophinopathy, such as muscular dystrophy, such as DMD, quantified as vector genomes (vg) per kilogram of subject body weight (kg), abbreviated vg/kg. According to certain embodiments, an efficacious dose of an AAV vector of the disclosure, including those comprising an AAV9 capsid and a genome including a human codon-optimized gene encoding a mini-dystrophin protein, such as, without limitation, the vector designated as AAV9.hCK.Hopti-Dys3978.spA, is about $1\times10^{12}$ vg/kg, $2\times10^{12}$ vg/kg, $3\times10^{12}$ vg/kg, $4\times10^{12}$ vg/kg, $5\times10^{12}$ vg/kg, $6\times10^{12}$ vg/kg, $7\times10^{12}$ vg/kg, $8\times10^{12}$ vg/kg, $9\times10^{12}$ vg/kg, $1\times10^{13}$ vg/kg, $2\times10^{13}$ vg/kg, $3\times10^{13}$ vg/kg, $4\times10^{13}$ vg/kg, $5\times10^{13}$ vg/kg, $6\times10^{13}$ vg/kg, $7\times10^{13}$ vg/kg, $8\times10^{13}$ vg/kg, $9\times10^{13}$ vg/kg, $1\times10^{14}$ vg/kg, $1.5\times10^{14}$ vg/kg, $2\times10^{14}$ vg/kg, $2.5\times10^{14}$ vg/kg, $3\times10^{14}$ vg/kg, $3.5\times10^{14}$ vg/kg, $4\times10^{14}$ vg/kg, $5\times10^{14}$ vg/kg, $6\times10^{14}$ vg/kg, $7\times10^{14}$ vg/kg, $8\times10^{14}$ vg/kg, or $9\times10^{14}$ vg/kg, or some other dose. In any of these embodiments, the AAV vector may be administered to a subject in a pharmaceutically acceptable composition alone, or with empty capsids of the same capsid serotype at an empty capsid to vector ratio of about 0.5:1, 1:1, 2:1, 3:1, 4:1, 5:1, 6:1, 7:1, 8:1, 9:1, 10:1, or some other ratio.

Exemplary modes of administration include oral, rectal, transmucosal, intranasal, inhalation (e.g., via an aerosol), buccal (e.g., sublingual), vaginal, intrathecal, intraocular, transdermal, intraendothelial, in utero (or in ovo), parenteral (e.g., intravenous, subcutaneous, intradermal, intracranial, intramuscular (including administration to skeletal, diaphragm and/or cardiac muscle), intrapleural, intracerebral, and intra-articular), topical (e.g., to both skin and mucosal surfaces, including airway surfaces, and transdermal administration), intra-lymphatic, and the like, as well as direct tissue or organ injection (e.g., to skeletal muscle, cardiac muscle, or diaphragm muscle).

Administration can be to any site in a subject, including, without limitation, a site selected from the group consisting of a skeletal muscle, a smooth muscle, the heart, and the diaphragm.

Administration to skeletal muscle according to the present invention includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis *brevis*, abductor pollicis longus, adductor *brevis*, adductor hallucis, adductor longus, adductor magnus, adductor pollicis, anconeus, anterior scalene, articularis genus, biceps brachii, biceps femoris, *brachialis*, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis *brevis*, extensor carpi radialis longus, extensor carpi ulnaris, extensor digiti minimi, extensor digitorum, extensor digitorum *brevis*, extensor digitorum longus, extensor hallucis *brevis*, extensor hallucis longus, extensor indicis, extensor pollicis *brevis*, extensor pollicis longus, flexor carpi radialis, flexor carpi ulnaris, flexor digiti minimi *brevis* (in the hand), flexor digiti minimi *brevis* (in the foot), flexor digitorum *brevis*, flexor digitorum longus, flexor digitorum *profundus*, flexor digitorum superficialis, flexor hallucis *brevis*, flexor hallucis longus, flexor pollicis *brevis*, flexor pollicis longus, *frontalis*, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris *brevis*, palmaris longus, pectineus, pectoralis major, pectoralis minor, peroneus *brevis*, peroneus longus, peroneus tertius, *piriformis*, plantar interossei, plantaris, platysma, popliteus, posterior scalene, pronator quadratus, pronator *teres*, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus *intermedius*, vastus lateralis, vastus *medialis*, zygomaticus major, and zygomaticus minor, and any other suitable skeletal muscle as known in the art.

The virus vector can be delivered to skeletal muscle by intravenous administration, intra-arterial administration, intraperitoneal administration, limb perfusion, (optionally, isolated limb perfusion of a leg and/or arm; see, e.g. Arruda et al., (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration. In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

Administration to cardiac muscle includes administration to the left atrium, right atrium, left ventricle, right ventricle and/or septum. The virus vector and/or capsid can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Administration to smooth muscle can be by any suitable method including intravenous administration, intra-arterial administration, and/or intra-peritoneal administration. In one embodiment, administration can be to endothelial cells present in, near, and/or on smooth muscle.

Delivery to a target tissue can also be achieved by delivering a depot comprising the virus vector and/or capsid. In representative embodiments, a depot comprising the virus vector and/or capsid is implanted into skeletal, smooth, cardiac and/or diaphragm muscle tissue or the tissue can be contacted with a film or other matrix comprising the virus vector and/or capsid. Such implantable matrices or substrates are described in U.S. Pat. No. 7,201,898.

In particular embodiments, a virus vector according to the present invention is administered to skeletal muscle, diaphragm muscle and/or cardiac muscle (e.g., to treat and/or prevent muscular dystrophy).

In representative embodiments, the invention is used to treat and/or prevent disorders of skeletal, cardiac and/or diaphragm muscle.

In a representative embodiment, the invention provides a method of treating and/or preventing muscular dystrophy in a subject in need thereof, the method comprising: administering a treatment or prevention effective amount of a virus vector of the invention to a mammalian subject, wherein the virus vector comprises a heterologous nucleic acid encoding dystrophin, a mini-dystrophin, or a micro-dystrophin. In particular embodiments, the virus vector can be administered to skeletal, diaphragm and/or cardiac muscle as described elsewhere herein.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

EXAMPLE 1

Synthesis of Codon-Optimized Human Mini-Dystrophin Genes

Previously we generated a number of miniature versions of human dystrophin gene by PCR cloning of human muscle dystrophin cDNA, generating mini-dystrophin genes that have large deletions in the central rod domain and nearly complete deletion of the C-terminal region of the dystrophin coding sequence (Wang et al., *Proc. Natl. Acad. Sci., USA* 97:13714 (2000); U.S. Pat. Nos. 7,001,761 and 7,510,867). These mini-dystrophin genes were tested to be highly functional in vivo in DMD mdx mouse models (Watchko et al., *Human Gene Therapy* 13:1451 (2002)). One of these mini-dystrophin proteins, named Δ3990, was described in U.S. Pat. No. 7,510,867 under SEQ ID NO:6. The protein sequence of Δ3990 and the DNA encoding it are provided herein by SEQ ID NO:27 and SEQ ID NO:28, respectively.

A modification of the Δ3990 mini-dystrophin was also designed, codon-optimized, and tested for activity. This new human mini-dystrophin, called Dys3978, is 1325 amino acids in length, and includes the following portions or subdomains from wildtype full-length human muscle dystrophin (SEQ ID NO:25): the N-terminus and actin-binding domain (ABD), hinge H1, rods R1 and R2, hinge H3, rods R22, R23 and R24, hinge H4, the cysteine-rich domain (CR domain) and part of the carboxy-terminal domain (CT domain). The amino acid sequence of this protein is provided by SEQ ID NO:7 and is illustrated schematically in FIG. 1. To reduce potential immunogenicity, the last four amino acids at the C-terminus of the Δ3990 protein were deleted. In creating Δ3990, this sequence had been formed by joining part of the amino-terminal end of the dystrophin carboxy-terminal domain (ending at P3409) with the last three amino acids of dystrophin (3683-3685, or DTM). This stretch of four amino acids has no known function and could function as a new epitope because the sequence does not occur in wildtype dystrophin. In addition, a valine at amino acid position 2 in Δ3990, not present in wildtype dystrophin, but which resulted from creation of a consensus Kozak initiation sequence around the start codon of Δ3990 was changed to the leucine ordinarily present in dystrophin. Thus there are 5 amino acid differences between Δ3990 and Dys3978. An amino acid sequence alignment between Δ3990 and Dys3978 is provided in FIGS. 55A-55C.

The gene encoding Dys3978 was constructed by combining subsequences from the wildtype dystrophin coding sequence corresponding to the protein subdomains described above. The resulting gene is provided by SEQ ID NO:26. To increase the expression of Dys3978, the gene sequence was codon-optimized using human codon algorithms. The resulting human codon-optimized gene, called Hopti-Dys3978, is provided as SEQ ID NO:1. A canine codon-optimized gene encoding Dys3978, called Copti-Dys3978, was also generated, the sequence of which is provided as SEQ ID NO:3. An alignment comparing the DNA sequences of Hopti-Dys3978 and the non-codon-optimized gene encoding Δ3990 is provided in FIGS. 56A-56I.

Among other changes, codon-optimization of the gene encoding Dys3978 increased total GC content from about 46% in the non-codon-optimized gene to about 61% in the human codon-optimized gene (i.e., Hopti-Dys3978). Increasing GC content can result in increased mRNA levels in mammalian cells. See, for example, Grzegorz, K, et al., PLoS Biol, 4(6):e180 (2006); and Newman, Z R, et al., PNAS, E1362-71 (2016). Codon-optimization also increased the codon adaptation index (CAI) and included addition of a Kozak consensus transcription initiation recognition site at the beginning of the coding sequence.

Figure 2:
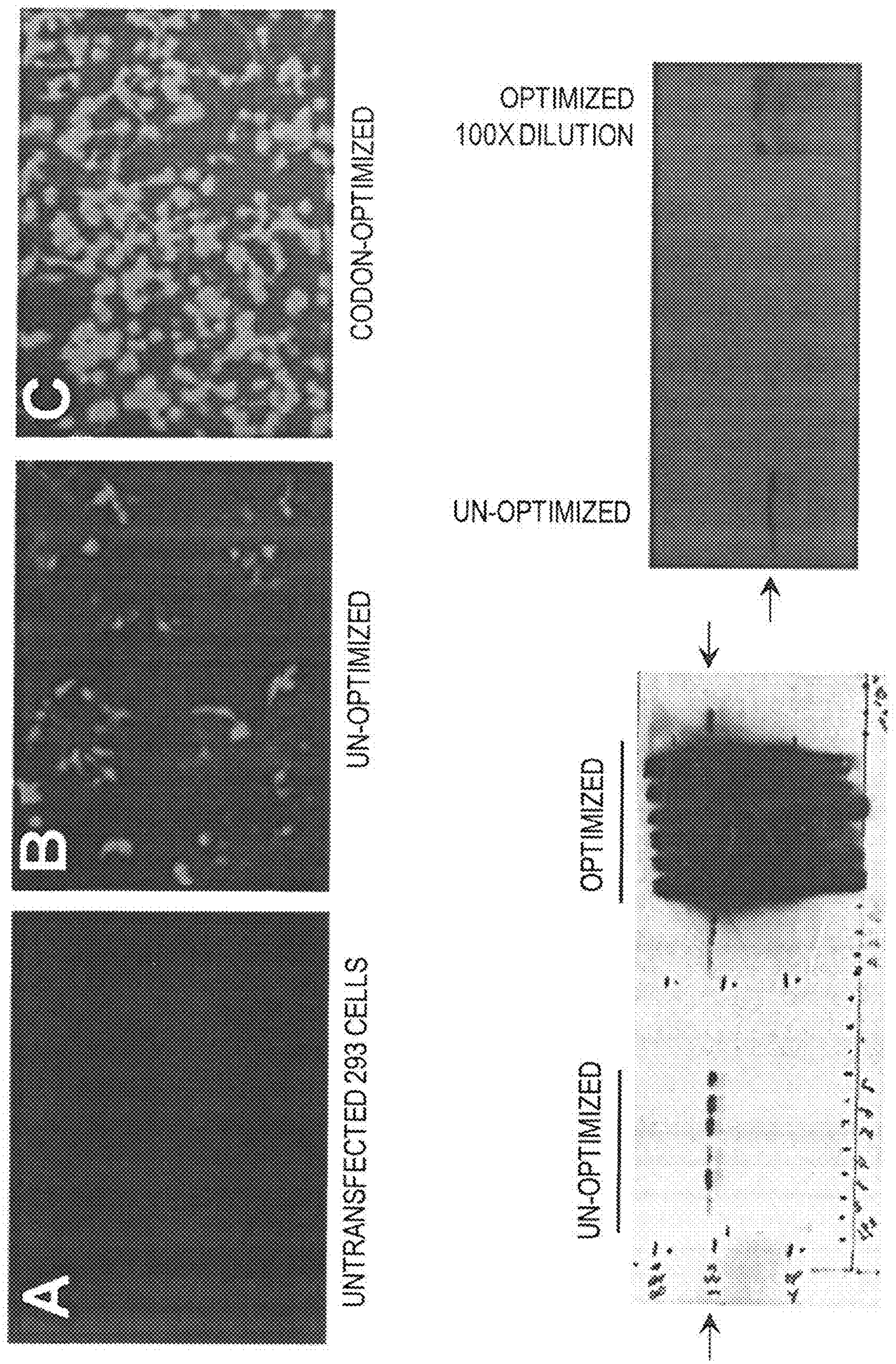
FIG. 2 shows codon-optimization effectively enhances mini-dystrophin gene expression. The top panels show immunofluorescence (IF) staining of mini-dystrophin protein in (A) untransfected 293 cells or after transfection of original un-optimized (B), or optimized (C) mini-dystrophin Dys3978 vector plasmids. The bottom panels show Western blots of the mini-dystrophin in the transfected 293 cells. Blot on the left used an equal amount of cell lysates and shows overwhelming expression by the optimized cDNA. Blot on the right used a 100× dilution of the cell lysate from 293 cells transfected with optimized mini-dystrophin cDNA, while the non-optimized sample was not diluted. Note that the signal of the optimized one is still stronger after 100× dilution.

To examine if human codon optimization could enhance gene expression, the Hopti-Dys3978 gene was cloned into an AAV vector expression cassette containing the constitutively active CMV promoter and a small synthetic polyadenylation (polyA) signal sequence (SEQ ID NO: 6). After transfection into human HEK 293 cells, the vector plasmid containing the Hopti-Dys3978 gene showed surprisingly greater protein expression than the non-optimized gene encoding Dys3978, as determined qualitatively using immunofluorescent staining and Western blot against dystrophin protein (FIG. 2).

A gene encoding a human mini-dystrophin similar in structure to Dys3978, except that hinge H3 is absent, was also generated and codon-optimized. This gene, called Hopti-Dys3837 (SEQ ID NO: 2) encodes a human mini-dystrophin protein of 1278 amino acids called Dys3837 (SEQ ID NO: 8), which is also illustrated schematically in FIG. 1.

For other experiments described herein, the human and canine codon-optimized Dys3978 genes were placed under the control of one of two different synthetic muscle-specific promoter and enhancer combinations derived from the muscle creatine kinase gene identified below:

1) Synthetic hybrid muscle-specific promoter (hCK) (SEQ ID NO: 4); and

2) Synthetic hybrid muscle-specific promoter plus (hCK-plus) (SEQ ID NO: 5);

For use in the experiments, the following vectors were constructed using standard molecular cloning techniques. The gene expression cassettes of the specified promoter, mini-dystrophin gene and polyA sequence were cloned into an AAV vector plasmid backbone containing AAV2 inverted terminal repeats (ITRs) flanking the expression cassette.

1) AAV-CMV-Hopti-Dys3978
2) AAV-hCK-Hopti-Dys3978 (SEQ ID NO: 9)
3) AAV-hCK-Hopti-Dys3837 (SEQ ID NO: 10)
4) AAV-hCKplus-Hopti-Dys3837 (SEQ ID NO: 11)
5) AAV-hCK-Copti-Dys3978 (SEQ ID NO: 12)

EXAMPLE 2

CMV-Hopti-Dys3978 in Dystrophin/Utrophin Double Knockout Mice

Figure 3:
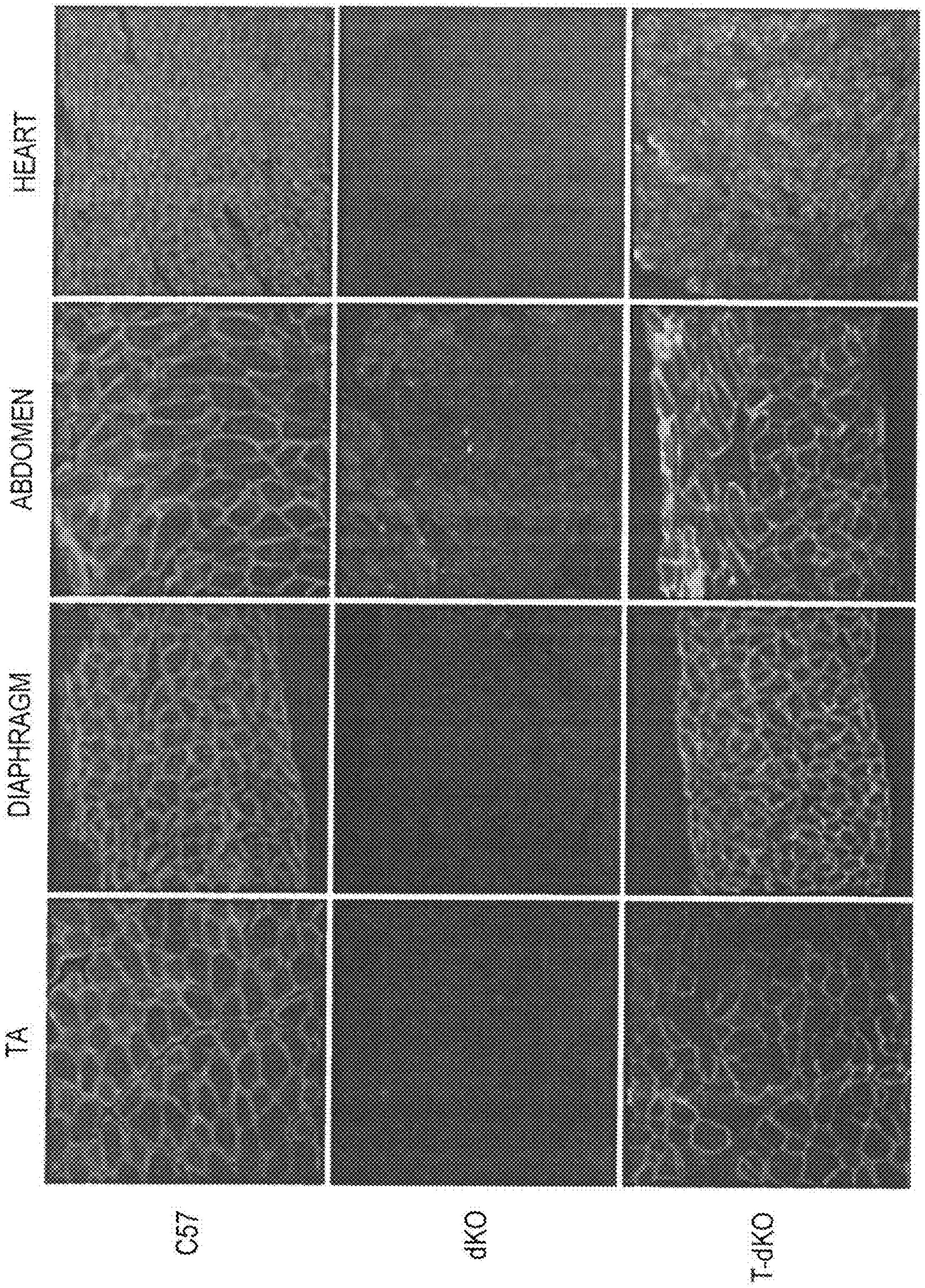
FIG. 3 shows IF staining of human mini-dystrophin expression in dystrophin/utrophin double knockout (dKO) mice treated with AAV9 vector. Muscle and heart samples from wild-type control mice C57BL/10 (C57), untreated dKO mice, and AAV9-CMV-Hopti-Dys3978 treated dKO mice (T-dKO) were thin-sectioned and stained with an antibody that also recognizes both the mouse wild-type dystrophin and human mini-dystrophin protein. Highly efficient expression was achieved in all samples examined.
Figure 4:
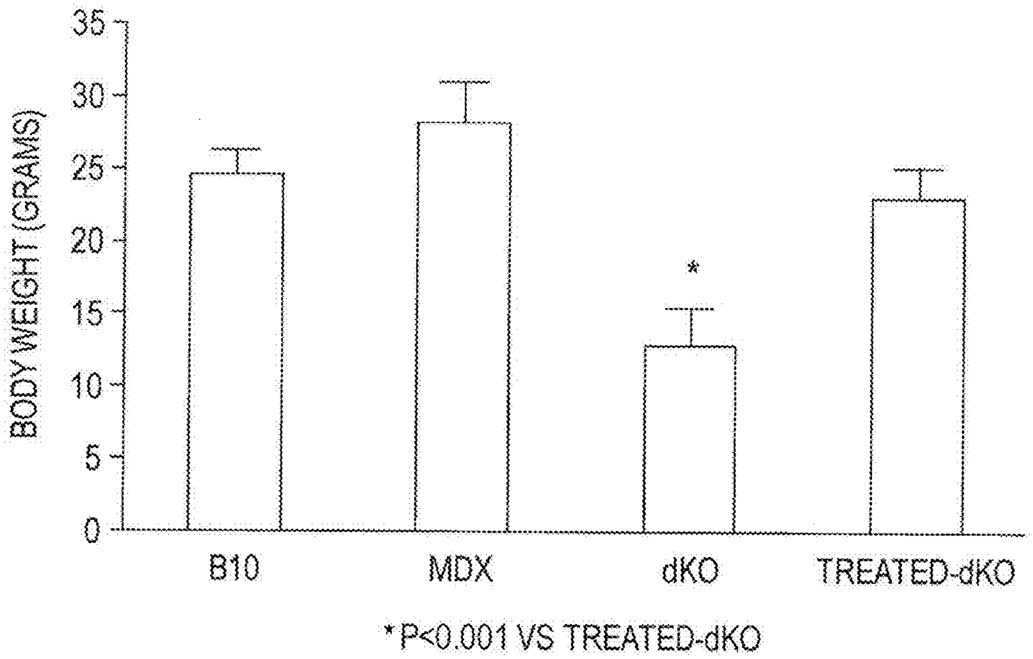
FIG. 4 shows normalization of body weight of dKO mice as a result of AAV9-CMV-Hopti-Dys3978 treatment. Data were obtained at 4 months of age from wild-type control B10 mice (C57BL/10), untreated mdx mice, untreated dKO mice, and vector-treated dKO mice.
Figure 6A:
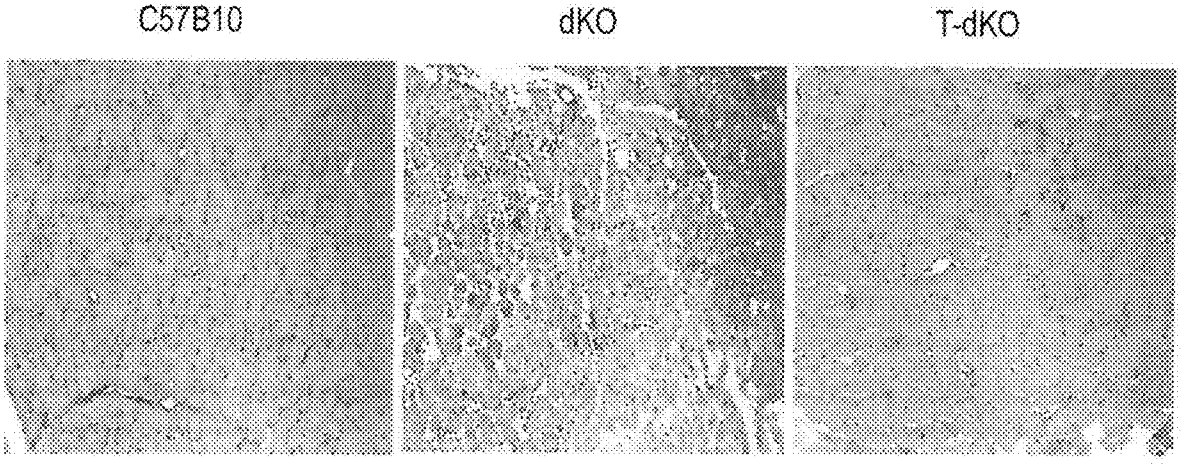
FIGS. 6A-6B show amelioration of dystrophic pathology of dKO mice as a result of AAV9-CMV-Hopti-Dys3978 treatment.
Figure 5:
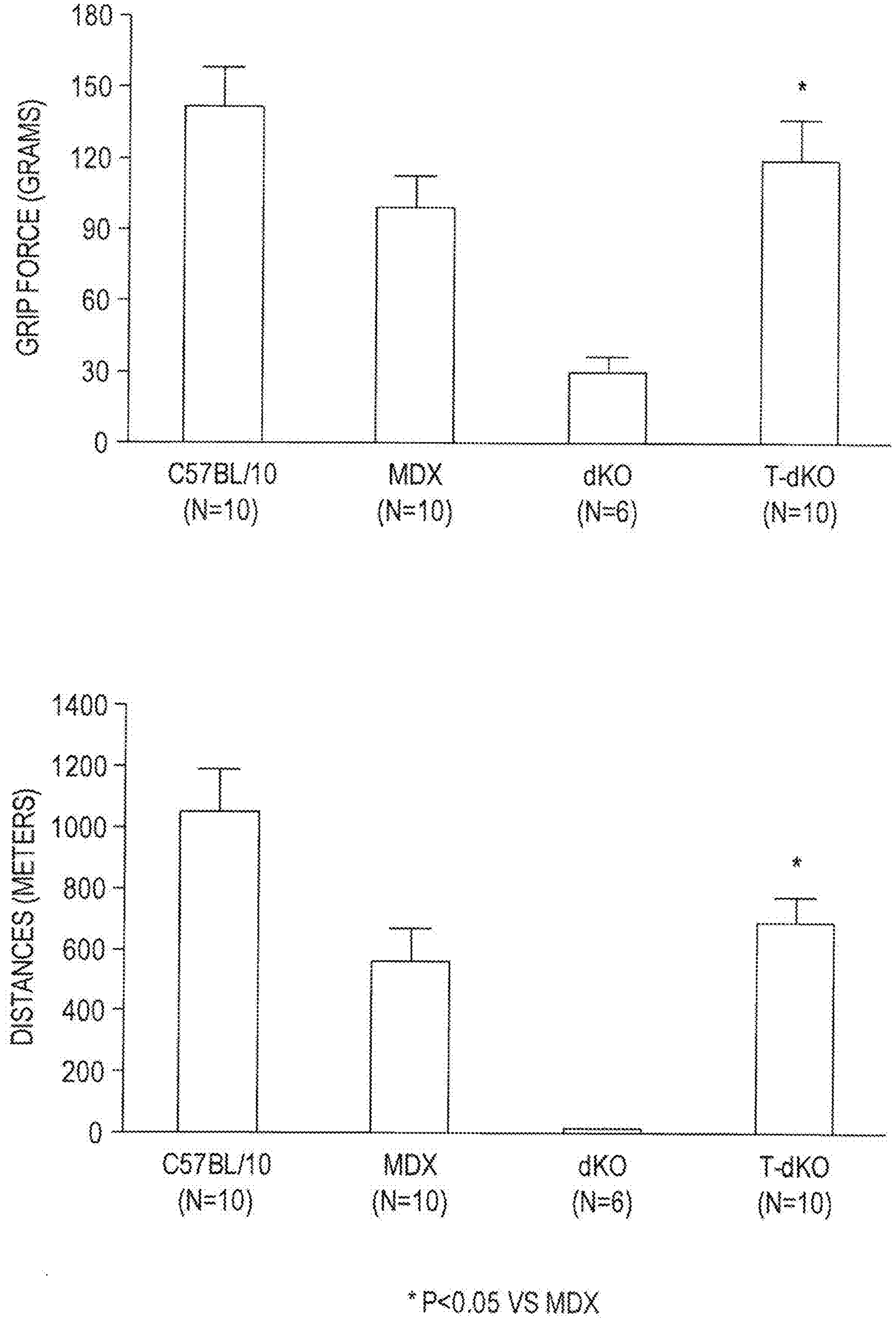
FIG. 5 shows improvement of grip force and treadmill running of dKO mice as a result of AAV9-CMV-Hopti-Dys3978 treatment. Data were obtained at 3 months of age from wild-type control B10 mice (C57BL/10), untreated mdx mice, untreated dKO mice, and vector-treated dKO mice (T-dKO).
Figure 6B:
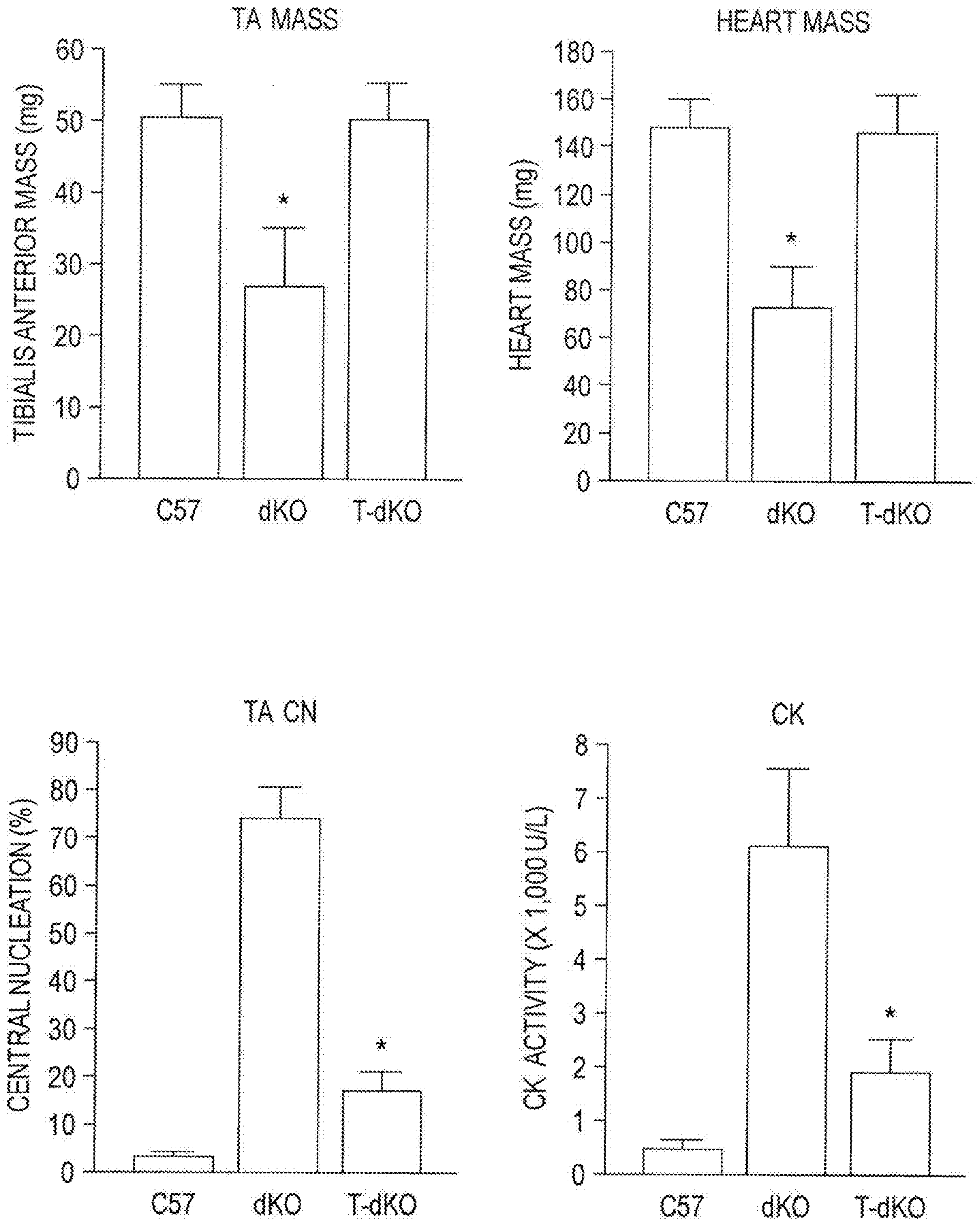
Figure 7:
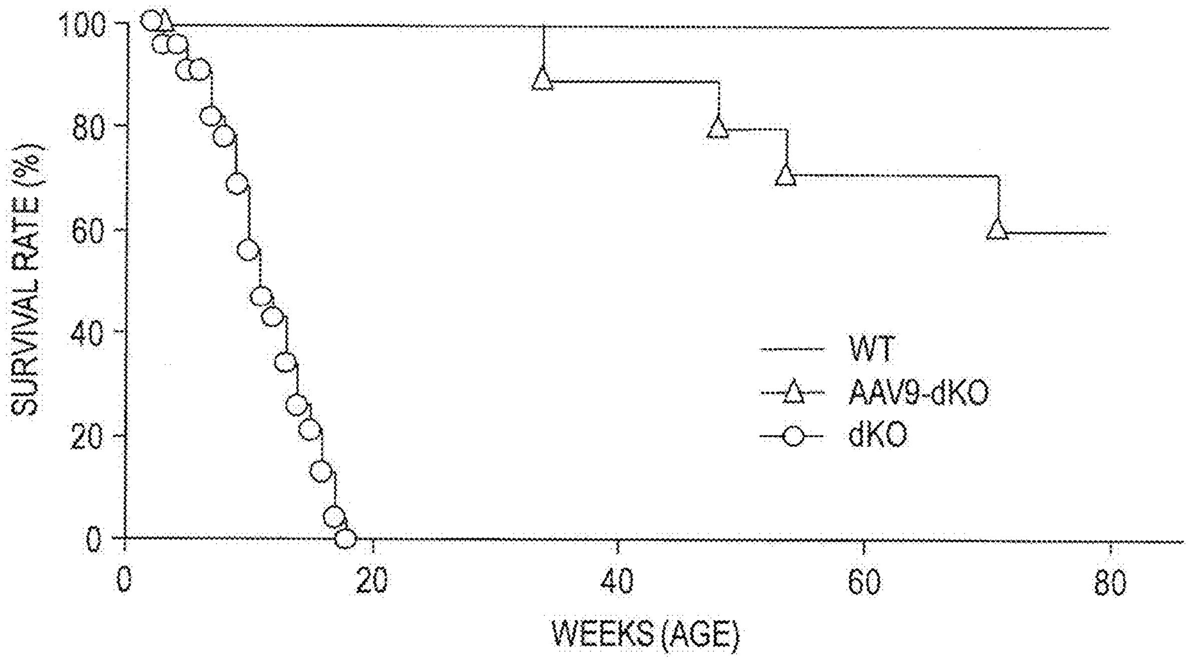
FIG. 7 shows survival curves of dKO mice treated with human codon-optimized mini-dystrophin Dys3978 vector (AAV9-CMV-Hopti-Dys3978) compared to untreated dKO mice and wildtype mice. Greater than 50% of the treated dKO mice survived longer than 80 weeks (duration of the experiment).

The loss of dystrophin in the patients of Duchenne muscular dystrophy (DMD) results in devastating skeletal muscle degeneration and cardiomyopathy. Mdx mice lacking only dystrophin have a much milder phenotype, whereas double knockout (dKO) mice lacking both dystrophin and its homolog utrophin exhibit the similarly severe dystrophic clinical signs seen in DMD patients. It was previously demonstrated that intraperitoneal injection in neonatal homozygous dKO mice with $3\times10^{11}$ vg/mouse of AAV1-CMV-Δ3990 (not codon-optimized) was able to partially restore growth, functions and prolong life-span for a few months (50% survival rate at 22 weeks) (see FIG. 6B from Wang et al., *J. Orthop. Res,* 27:421 (2009)). Here, the therapeutic effects of systemic delivery of human codon-optimized Hopti-Dys3978 gene were evaluated using AAV9 as the capsid. The results demonstrate that a single systemic administration (IP) of AAV9-CMV-Hopti-Dys3978 at about $2\times10^{13}$ vg/kg into 1-week-old neonatal dKO mice led to widespread expression of the mini-dystrophin gene in skeletal muscles and in the entire heart muscle (FIG. 3). The AAV9-treated dKO mice showed near normal growth curve and body weight (FIG. 4) and significantly improved muscle function as evaluated by the grip force and treadmill running tests (FIG. 5). The treated dKO mice also showed amelioration of dystrophic pathology (FIGS. 6A-6B) and great improvement of overall health. When compared to the dKO mice treated with an AAV1 vector expressing non-codon-optimized Δ3990, the dKO mice treated with Hopti-Dys3978 gene showed a much prolonged life-span (50% survival rate: 22 weeks vs. more than 80 weeks) (FIG. 7). Unexpectedly, the fertility of both male and female dKO mice were restored (Table 1), suggesting overall function improvement and possibly improvement in smooth muscle function as well.

TABLE 1

Mini-dystrophin restores fertility of dKO mice

| Breeding pairs: | | |
|---|---|---|
| Pair #1: | T-dKO male × T-dKO female | 5 pups |
| Pair #2: | T-dKO male × T-dKO female | 4 pups |
| Pair #3: | T-dKO male × T-dKO female | 0 pups |
| Pair #4: | mdx male × T-dKO female | 5 pups |
| Pair #5: | mdx male × T-dKO female | 6 pups |

The untreated dKO mice are completely infertile. However fertility was restored by AAV-CMV-Hopti-Dys3978 in both males and females of treated dKO (T-dKO) mice.

The results described above demonstrate that systemic delivery of codon-optimized Hopti-Dys3978 gene was more efficacious than the non-codon optimized Δ3990 gene.

Figure 8:
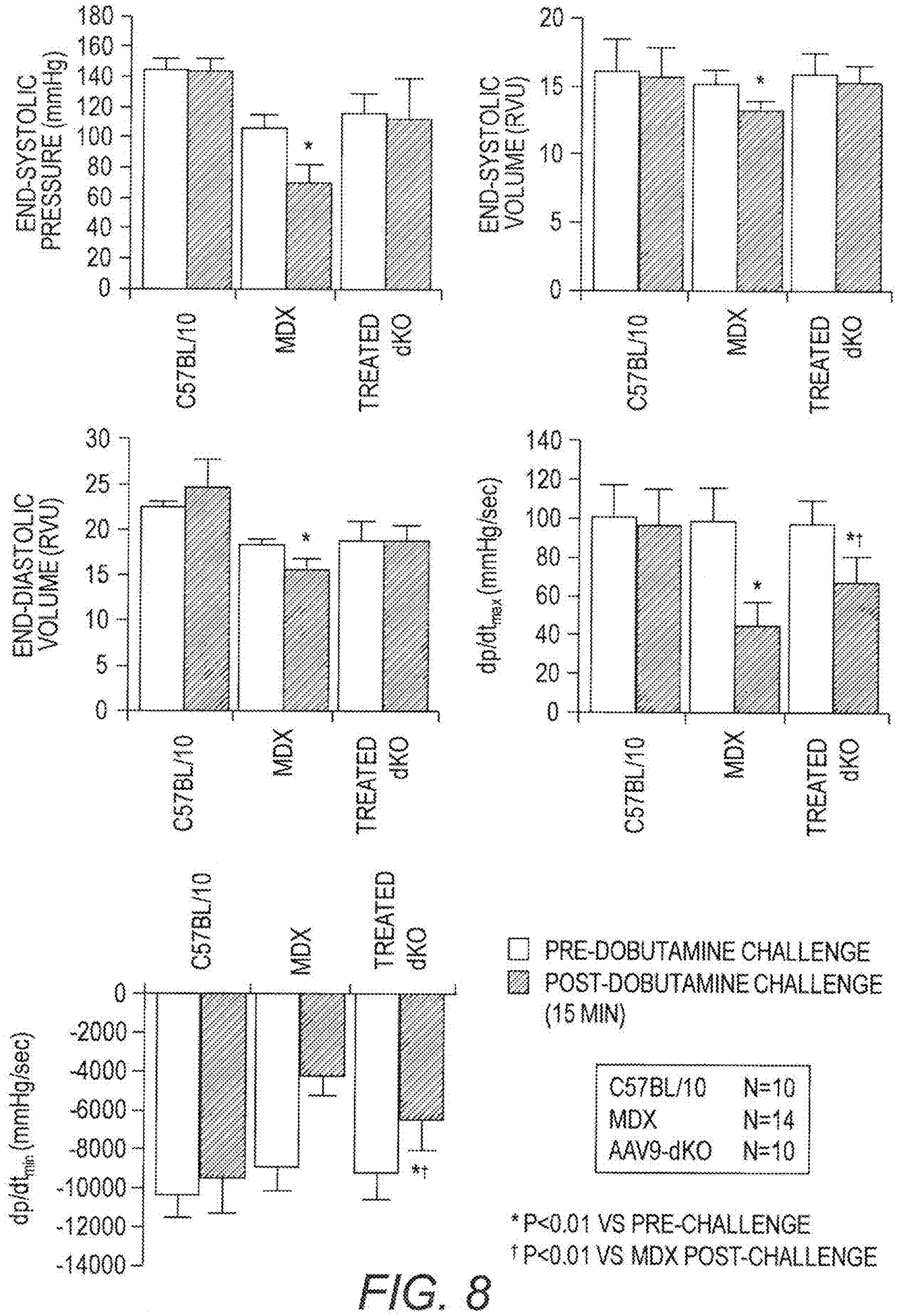
FIG. 8 shows improvement in cardiac functions of dKO mice as a result of AAV9-CMV-Hopti-Dys3978 treatment. Hemodynamic analysis was performed on wild-type control C57BL/10 mice, untreated mdx mice, and AAV9 vector-treated dKO mice. The untreated dKO mice were too sick to sustain the procedure. Data were collected from the three groups of mice without or with dobutamine challenge.
Figure 9A:
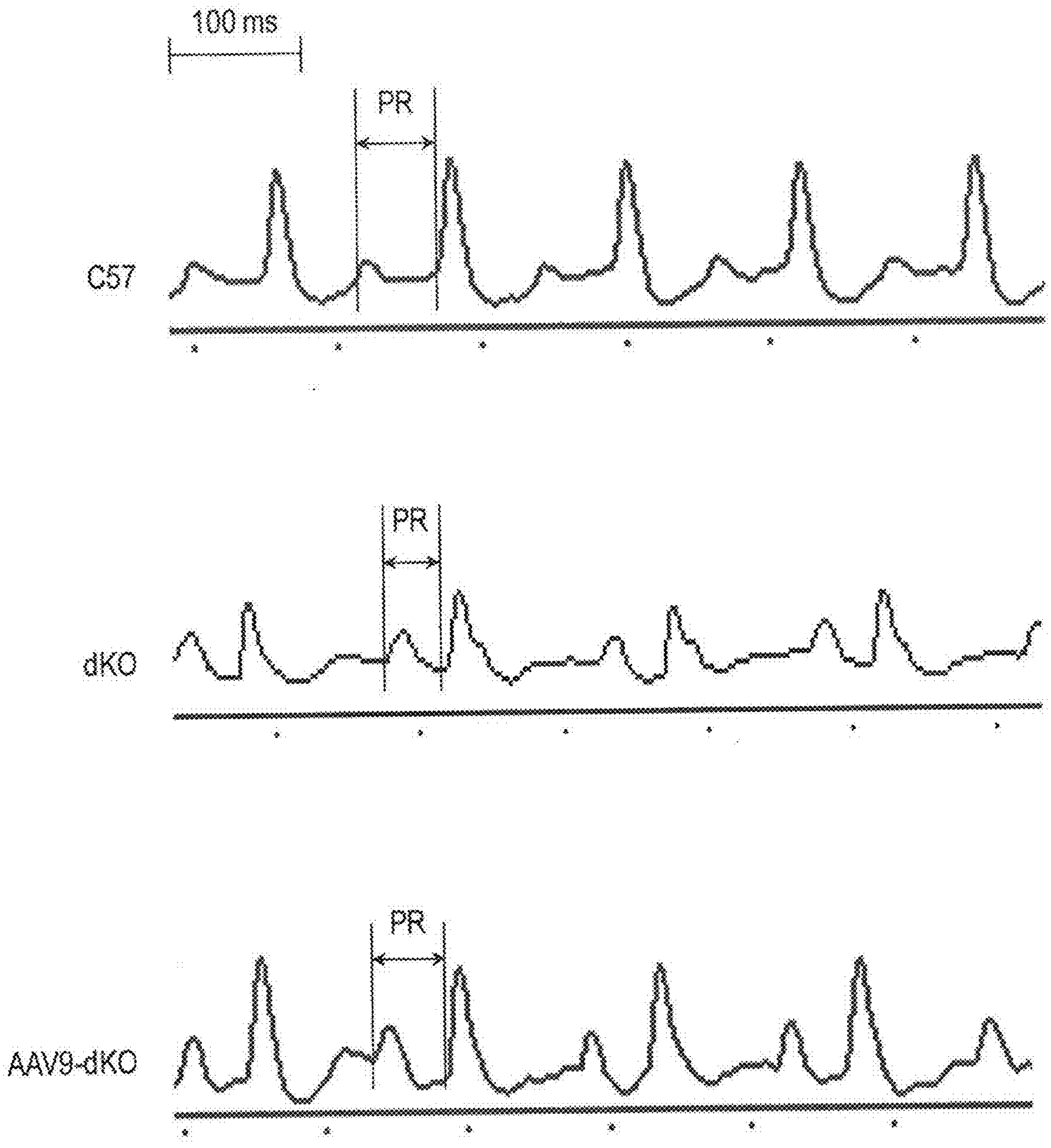
FIGS. 9A-9B show improvement in electrocardiography (ECG) of dKO mice as a result of AAV9-CMV-Hopti-Dys3978 treatment.
Figure 9B:
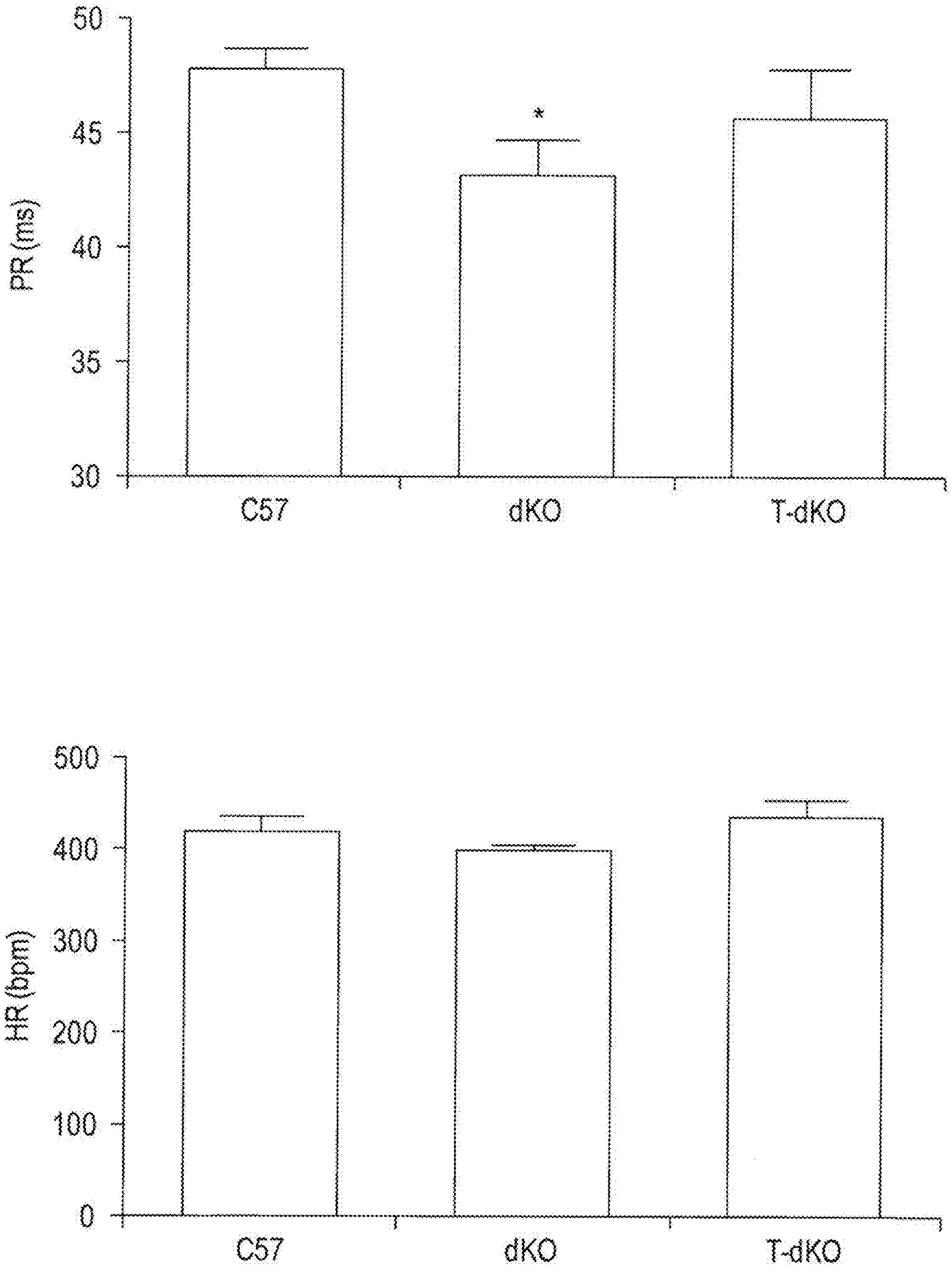

Importantly, great improvement in cardiac functions was also observed. Therapeutic effects in the heart were evaluated at 4 months of age by hemodynamic analysis using the Millar Pressure-volume system. Untreated dKO mice barely survived over 4 months. The very small body size, kyphosis and severe muscle and cardiac dysfunctions made dKO mice too sick to tolerate the hemodynamic analysis procedure. Therefore, the AAV9-treated dKO mice were compared with untreated, age-matched mdx mice which had much milder phenotypes due to an intact utrophin gene, which is known to compensate for lack of dystrophin in this model. While measurement by echocardiography showed mdx mice had no apparent cardiac deficit under baseline condition when compared with C57/B10 wildtype mice, they did show apparent deficits as measured by hemodynamics at the baseline (FIG. 8, open bars). The results herein show that the AAV9-treated dKO mice displayed similar baseline cardiac hemodynamics to that of the mdx mice, including end-systolic pressure, end-diastolic volume, maximal rate of isovolumic contraction ($dp/dt_{max}$) and maximal rate of isovolumic relaxation ($dp/dt_{min}$). However, after challenge with dobutamine, treated dKO mice displayed similar baseline cardiac hemodynamics to that of the mdx mice, including end-systolic pressure, end-diastolic volume, maximal rate of isovolumic contraction ($dp/dt_{max}$ and $dp/dt_{min}$), whereas the AAV9-treated dKO mice performed significantly better than mdx mice in every parameter examined (FIG. 8, filled bars). Furthermore, greater than 50% of the mdx mice died within the 30-min dobutamine challenge window, consistent with our previous report (Wu et al., *Proc. Natl. Acad. Sci. USA* 105:14814 (2008)). In striking contrast, due to cardiac expression of the mini-dystrophin transgene in the AAV9-treated dKO mice, dobutamine-induced heart failure was largely prevented. Greater than 90% of the AAV9-treated dKO mice survived the dobutamine stress test in the 30 min window. Finally, the commonly seen PR interval deficit shown in electrocardiograms (ECG) was also improved (FIGS. 9A-9B). The PR interval is time from the onset of the P wave to the start of the QRS complex. Taken together, these results demonstrate the effectiveness of AAV9-CMV-Hopti-Dys3978 gene therapy for cardiomyopathy in a severe DMD mouse model.

EXAMPLE 3 hCK-Hopti-Dys3978 in Mdx Mice

Figure 10:
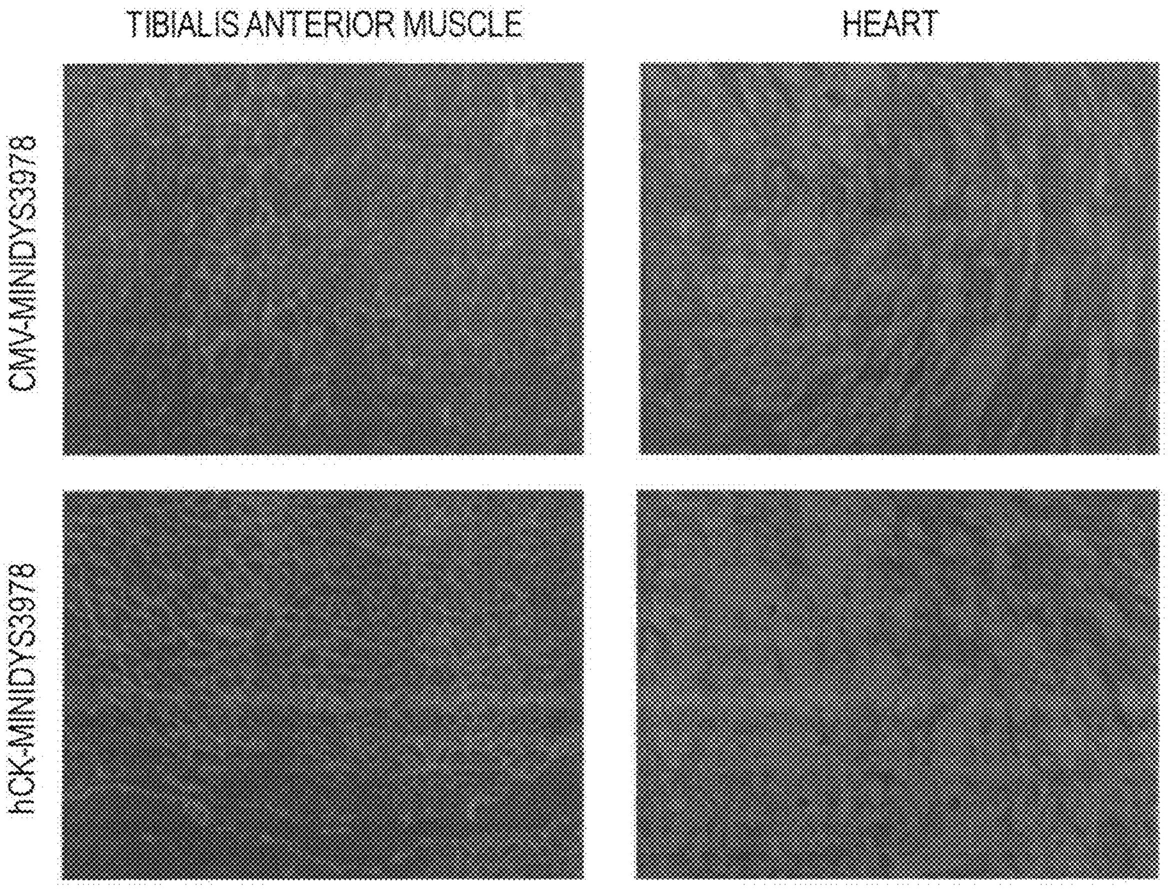
FIG. 10 shows a comparison of the non-tissue specific CMV promoter and the muscle-specific hCK promoter in driving human codon-optimized mini-dystrophin Dys3978 in mdx mice after tail vein injection of AAV9-Hopti-Dys3978 vectors containing CMV or hCK promoter. Using IF staining, the human mini-dystrophin Dys3978 showed robust expression in limb muscle and heart muscle as well. It appeared that the hCK promoter was more effective over the CMV promoter.

To examine if the hybrid synthetic muscle-specific promoter hCK was able to effectively drive Dys3978 gene expression, it was compared with the same construct driven by the strong non-specific CMV promoter. Immunofluorescent staining of mini-dystrophin expression in mdx mice following tail vein injection of the respective vectors showed that the two promoters, i.e., hCK and CMV, delivered equivalent expression levels in muscle and heart (FIG. 10).

EXAMPLE 4

CMV-Hopti-Dys3978 in DMD Canine Model Gold Retriever Muscular Dystrophy (GRMD) Dogs Based on studies in the mdx mice and dystrophin/utrophin double KO (dKO) mice, the same vector, AAV9-CMV-Hopti-Dys3978 was tested in the golden retriever muscular dystrophy (GRMD) dog, a large animal DMD model. Specifically, the vector was administered to a 2.5-month-old GRMD dog, "Jelly," and then followed for more than 8 years post injection.

Figure 11:
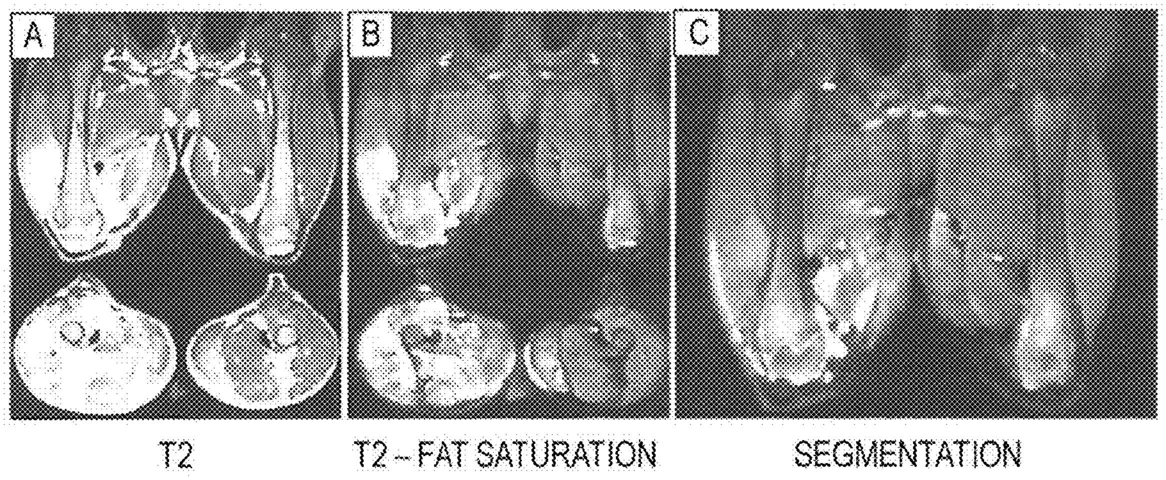
FIG. 11 shows magnetic resonance imaging (MM) images of the hind limb of GRMD dog "Jelly" after isolated limb vein perfusion of the AAV9-CMV-Hopti-Dys3978 vector. The vector was infused with pressure in the right hind leg which had a tight tourniquet placed at the groin area. The whitish signals indicated vector solution retention in the perfused limb.

Experimental Procedures:

GRMD dog "Jelly" (2.5 months old female; 6.3 kg; serum CK: 20262 units/L before treatment) was injected with AAV9-CMV-Hopti-Dys3978 vector at a dose of $1\times10^{13}$ vg/kg via the right hind limb. Under general anesthesia, a rubber tourniquet was positioned at the proximal pelvic extremity (the groin area) to cover a majority of muscles in the right hind limb. The AAV9 vector was injected via the great saphenous vein using a Harvard pump set at injection speed lml/sec. The vector volume was 20 ml/kg body weight (130 ml total). The tourniquet was released after 10 minutes accounting from the start of injection. Muscles in the injected limb became harder as revealed by palpation. MM images on the hind limbs were collected at about 1 hour post injection and confirmed vector fluid in the injected limb (FIG. 11). No immuno-suppressant such as steroid was used at any time point throughout the more than 8 years of observation. Muscle biopsy procedures were performed at 5 time points up to 4 years post vector injection. Final necropsy was done at the age of 8 years, 4 months, at which time "Jelly" was still ambulant but much less active than before.

Figure 12:
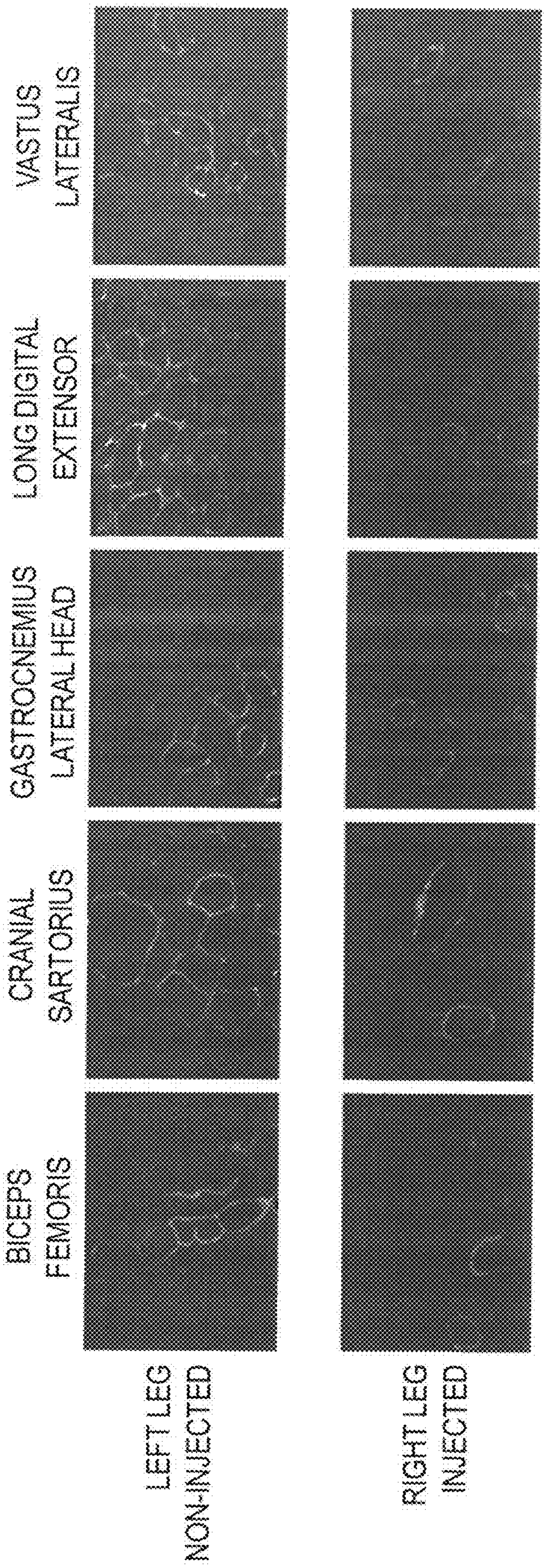
FIG. 12 shows IF staining of human mini-dystrophin Dys3978 expression at 2 months post vector injection in GRMD dog "Jelly." Biopsy samples of 5 different muscle groups in both right and left hind legs were examined. The non-injected left leg also had detectable dys3978, suggesting that the AAV9 vector had traveled from the site of injection to the contralateral leg.
Figure 13:
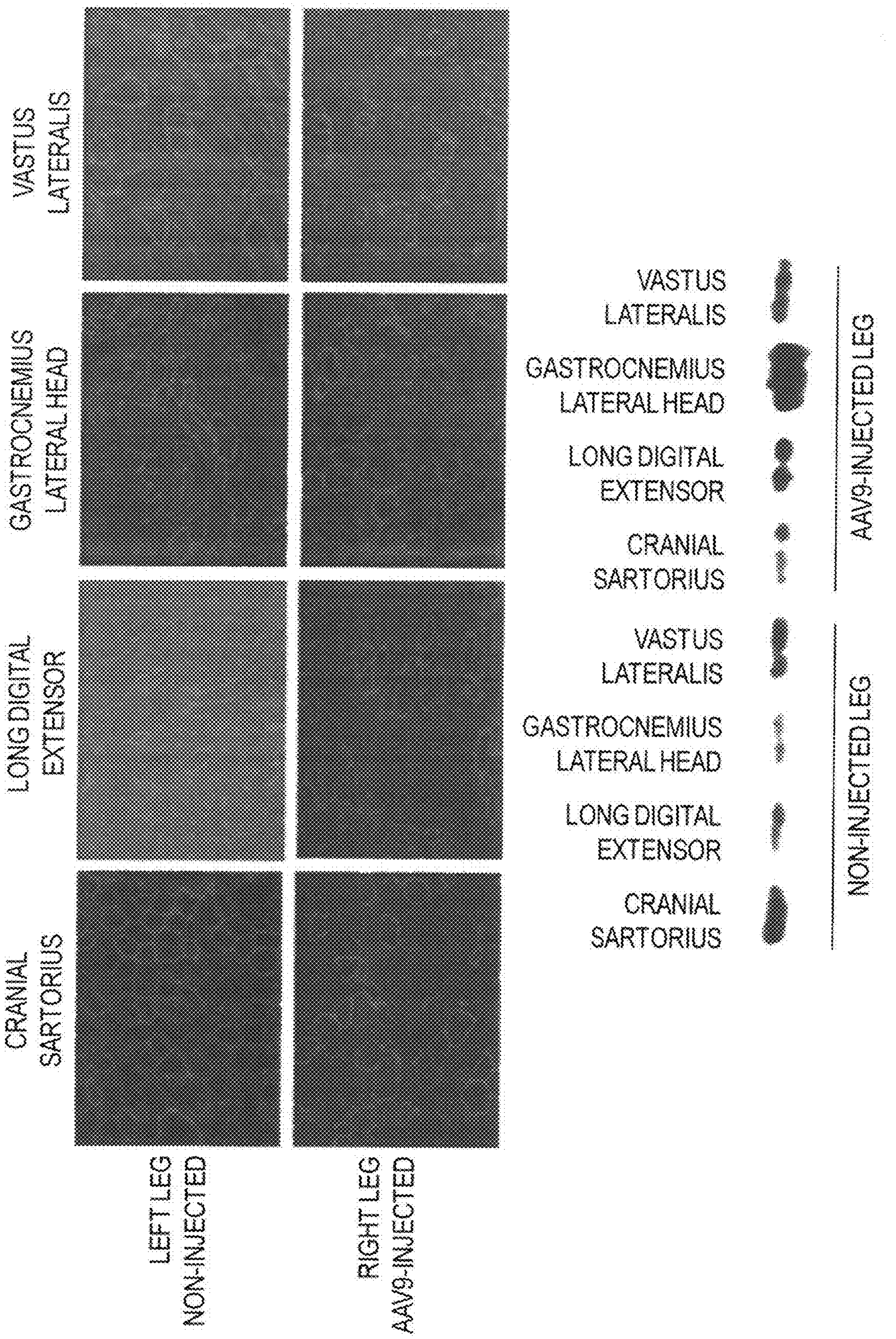
FIG. 13 shows IF staining of human mini-dystrophin Dys3978 expression at 7 months post vector injection in GRMD dog "Jelly." Biopsy samples of 4 different muscle groups in both right and left hind legs were examined. The non-injected left leg also had detectable Dys3978, suggesting that the AAV9 vector had traveled from the site of injection to the contralateral leg. Western blot analysis of Dys3978 was done on the same samples.
Figure 14:
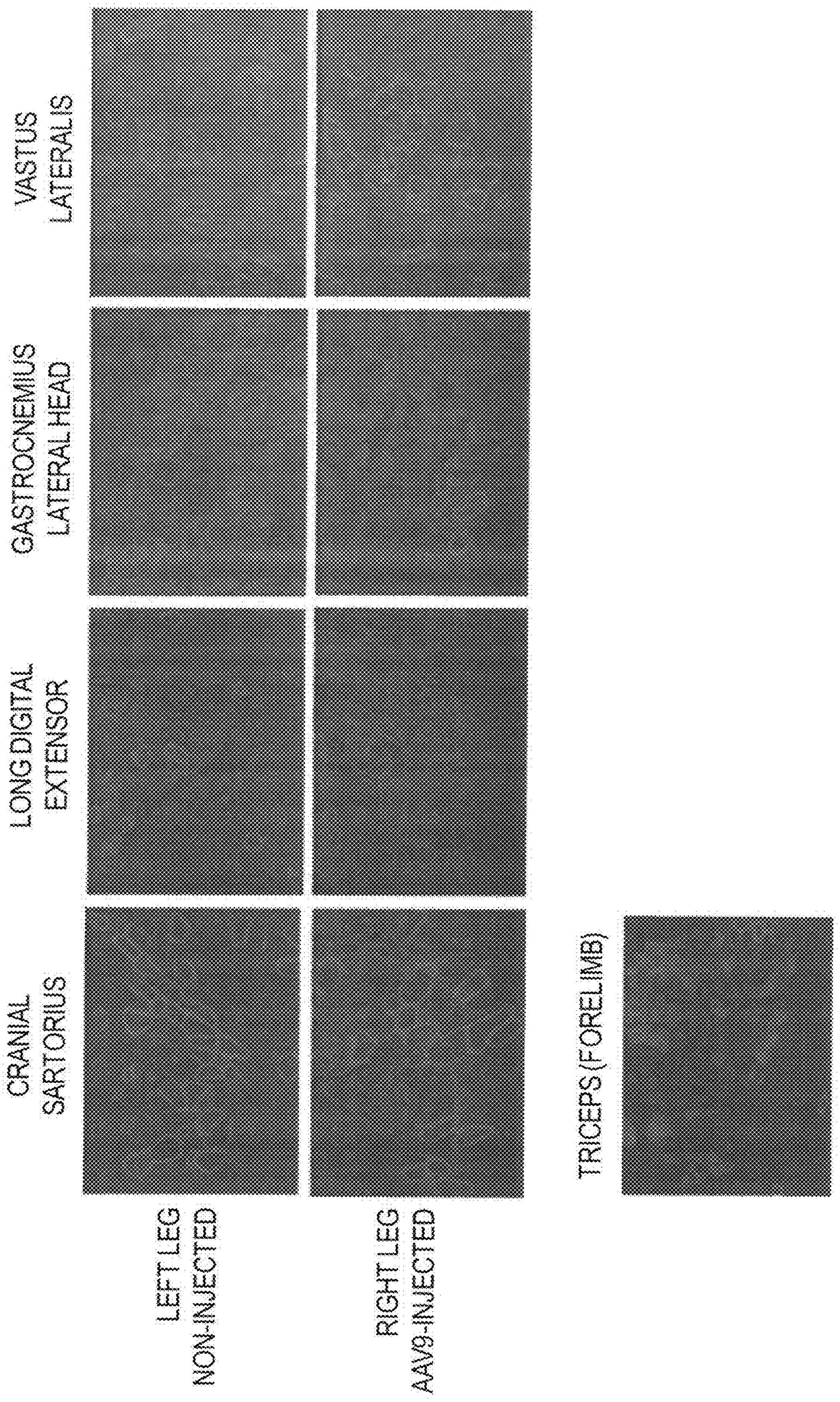
FIG. 14 shows IF staining of human mini-dystrophin Dys3978 expression at 12 months post vector injection in GRMD dog "Jelly." Biopsy samples of 4 different muscle groups in both right and left hind legs and 1 sample in the forelimb were examined. The non-injected left leg also had detectable Dys3978, suggesting that the AAV9 vector had traveled from the site of injection to the contralateral leg.
Figure 15:
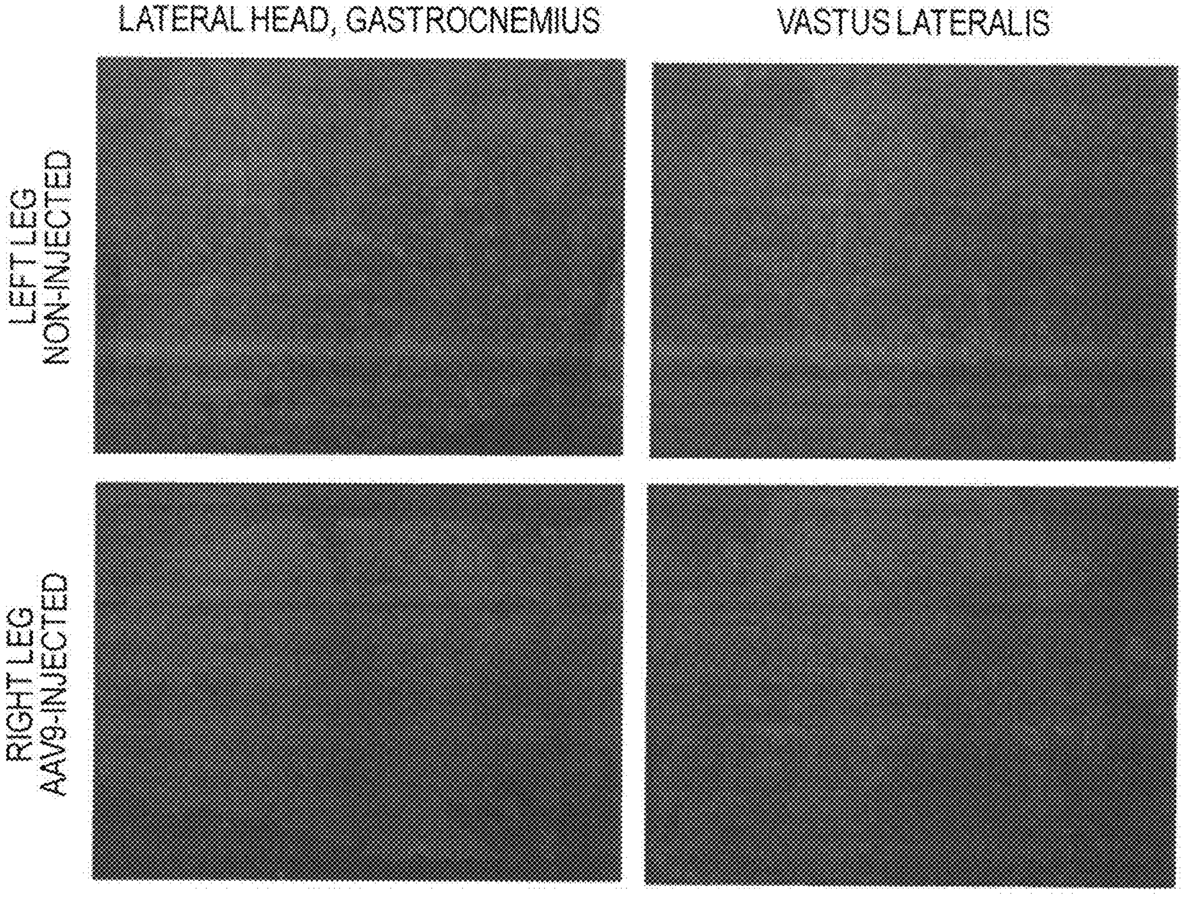
FIG. 15 shows IF staining of human mini-dystrophin Dys3978 expression at 2 years post vector injection in GRMD dog "Jelly." Biopsy samples of 2 different muscle groups in both right and left hind legs were examined. Note the non-injected left leg appeared to have more detectable Dys3978 than the injected leg.
Figure 16:
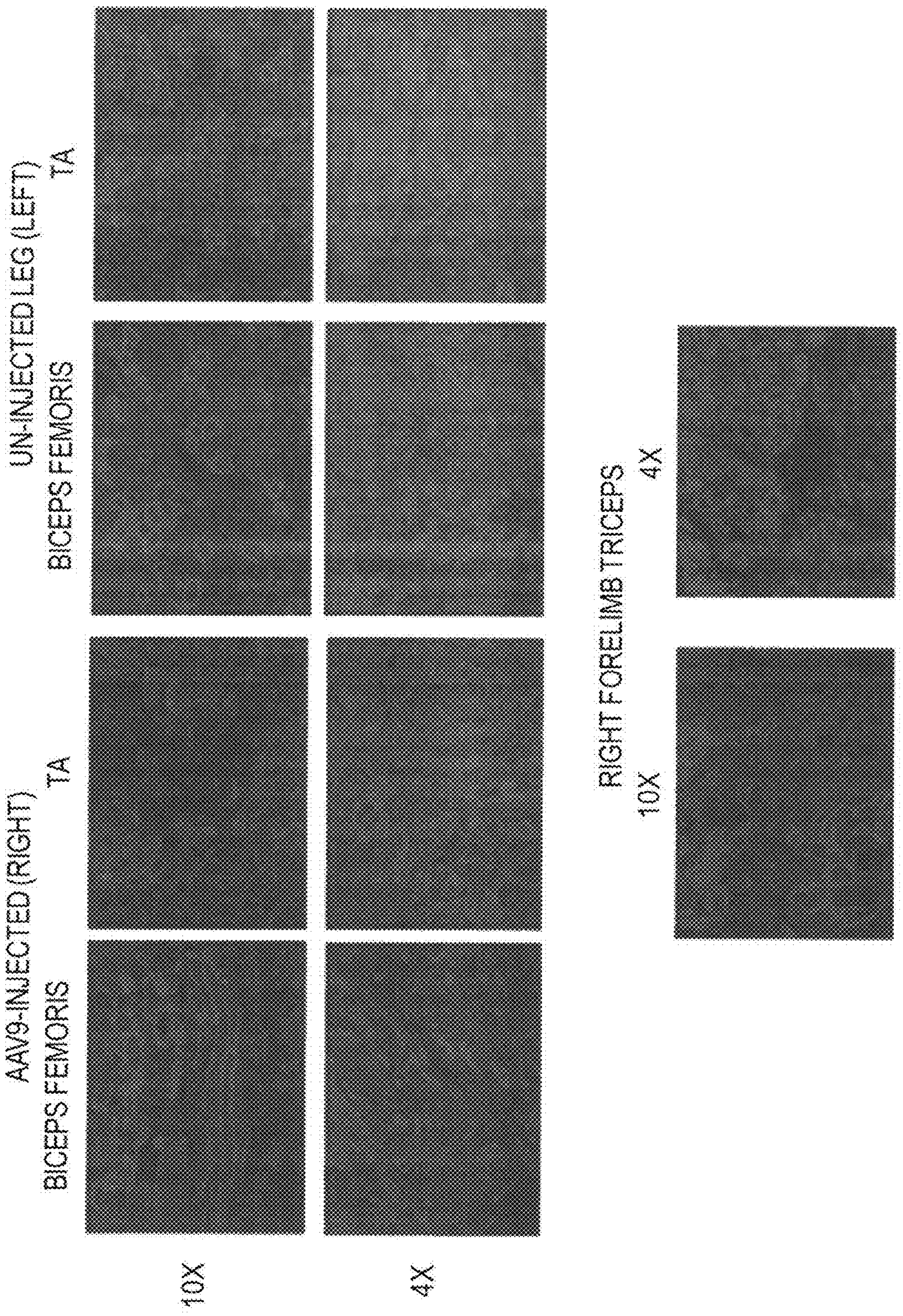
FIG. 16 shows IF staining of human mini-dystrophin Dys3978. Biopsy samples of two additional (compared with FIG. 15) muscle groups in both right and left hind legs and one sample in the forelimb were examined from GRMD dog "Jelly." Samples were also collected at 2 years post vector injection.
Figure 17:
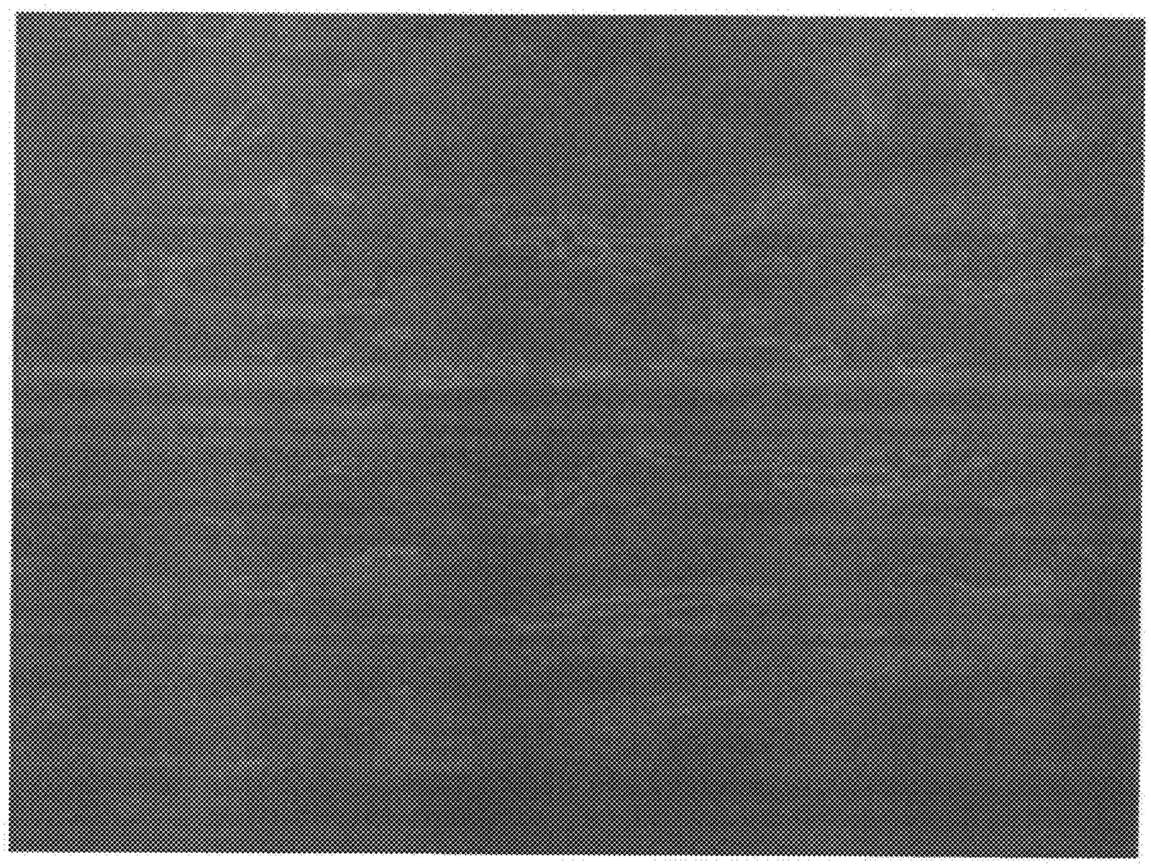
FIG. 17 shows IF staining of human mini-dystrophin Dys3978 at 4 years post vector injection in the non-injected left hind leg from GRMD dog "Jelly."
Figure 18:
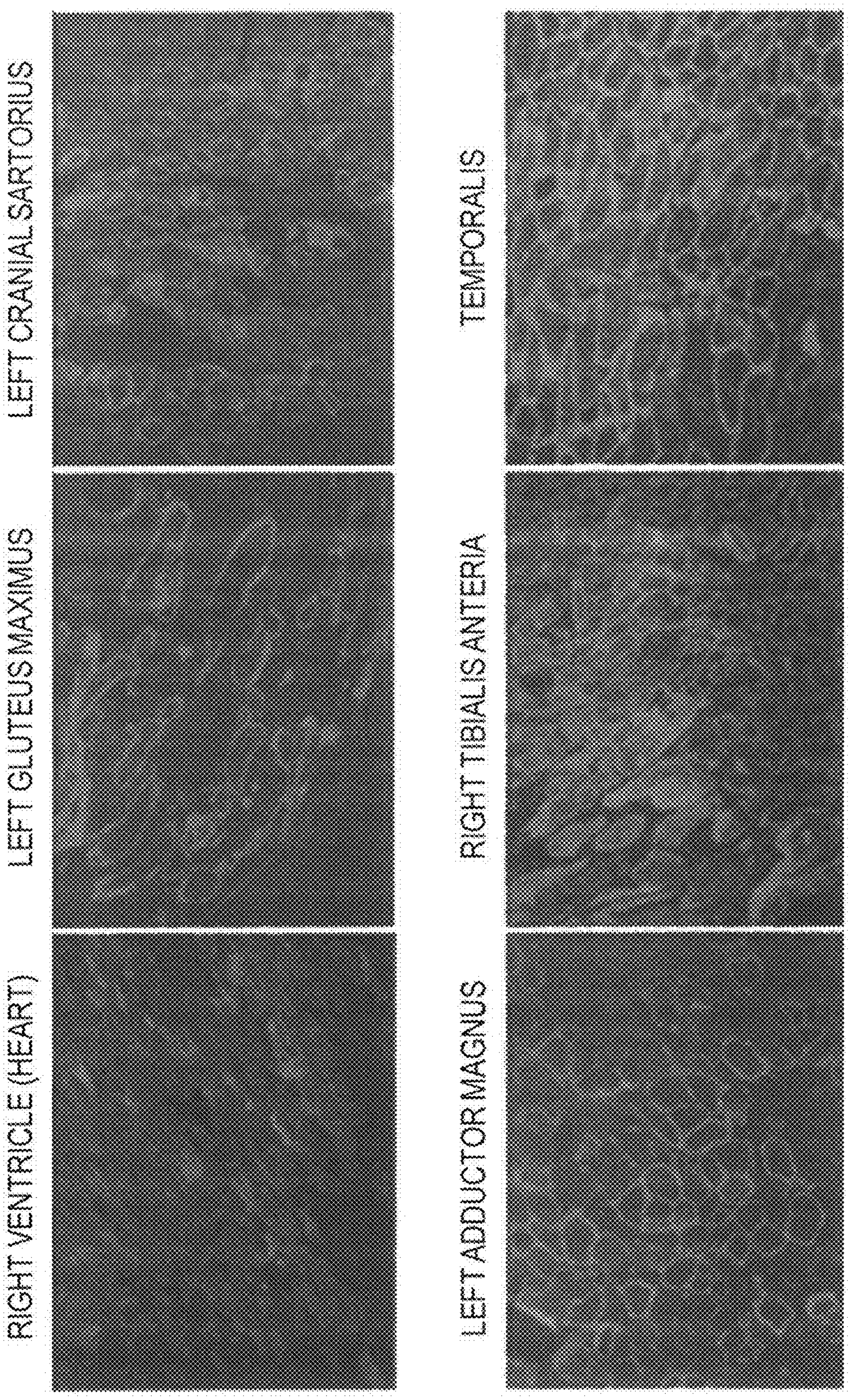
FIG. 18 shows IF staining of human mini-dystrophin Dys3978 at greater than 8 years post vector injection in GRMD dog "Jelly." Necropsy muscle samples of 5 different muscle groups and heart were examined.
Figure 19:
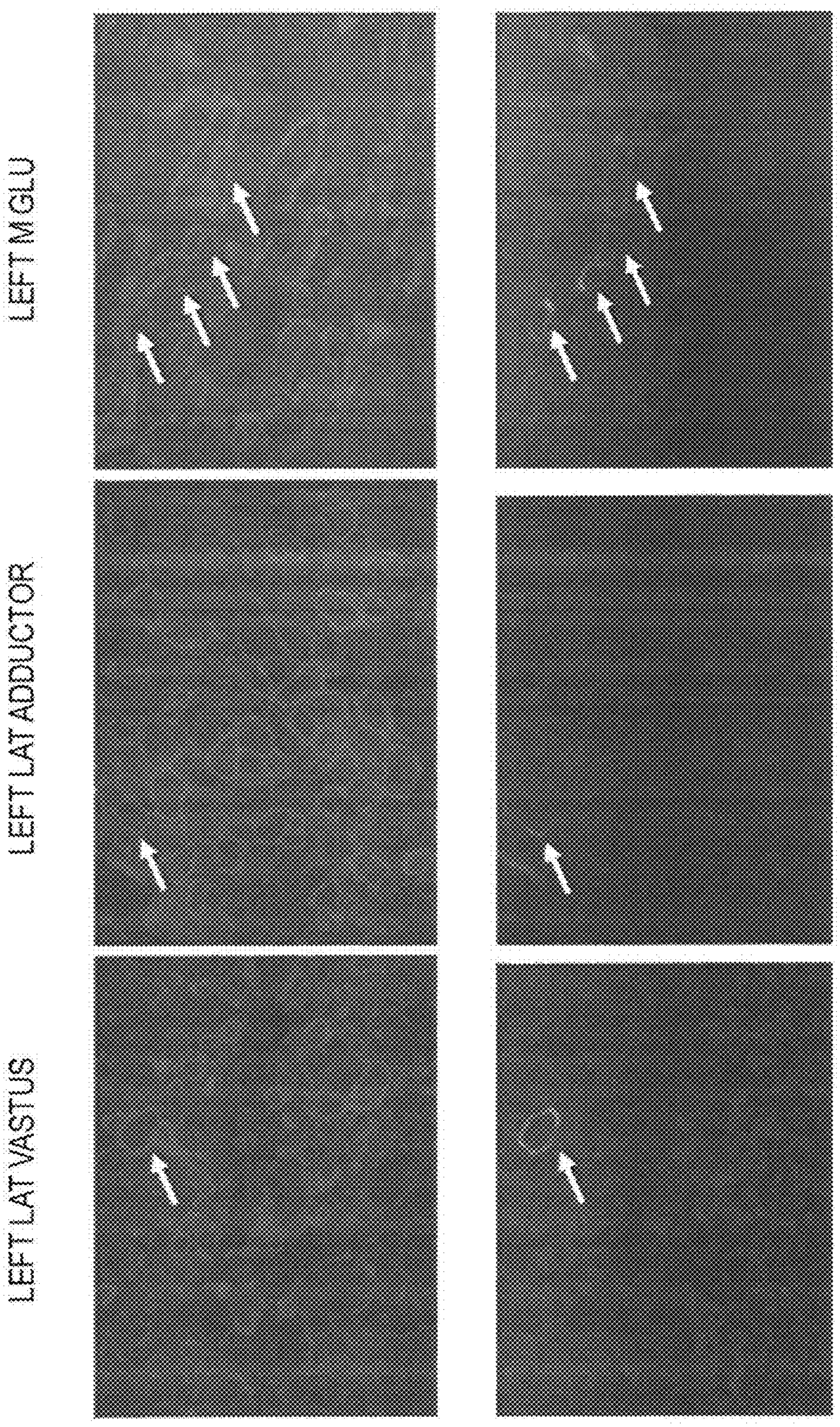
FIG. 19 shows IF staining of human mini-dystrophin Dys3978 and endogenous revertant dystrophin at greater than 8 years post vector injection in GRMD dog "Jelly." Necropsy muscle samples of three different muscle groups were stained with an antibody that recognized both human and dog dystrophin (upper panel) or an antibody that only recognized dog revertant dystrophin (lower panel). The revertant dystrophin positive myofibers were highlighted by arrows. Revertant fibers are rare muscle fibers that stain positively for dystrophin protein that occur in human DMD patients, as well as the mdx mouse and GRMD dogs. The precise mechanism by which revertant fibers occur is not completely understood, but may involve exon skipping in rare muscle cells that produces a shortened dystrophin with the epitopes recognized by antibody probes. See, for example, Lu, Q L, et al., J Cell Biol 148:985-96 (2000).
Figure 20:
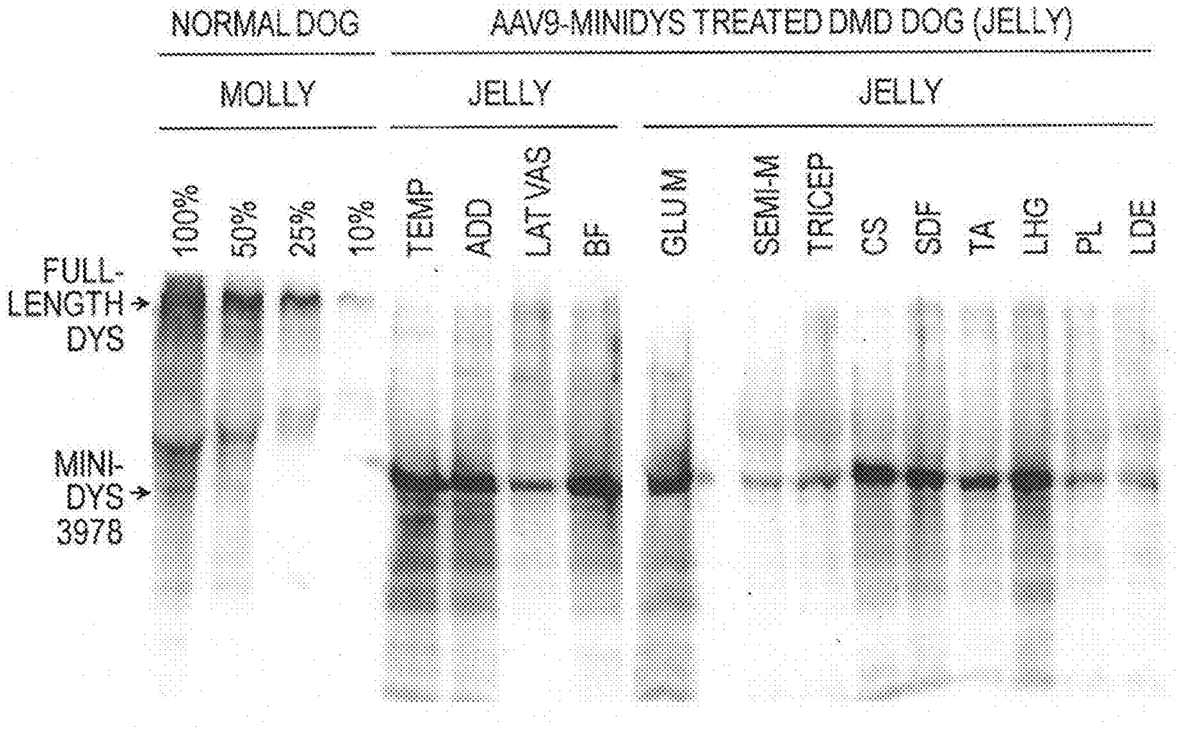
FIG. 20 shows Western blot analyses of human mini-dystrophin Dys3978 present in muscle samples of GRMD dog "Jelly" at necropsy more than 8 years after AAV9 vector injection. Western blot showed human mini-dystrophin Dys3978 was present in all skeletal muscles examined. Muscle from an age and sex matched normal dog named "Molly" was used as a positive control with serial 2-fold dilutions to indicate the quantitation of dystrophin protein. The molecular weight of wildtype full length dystrophin is about 400 kDa while the mini-dystrophin Dys3978 protein is about 150 kDa.

Results:

Immunofluorescent (IF) staining showed long-term mini-dystrophin expression in a majority of muscle samples examined up to final necropsy. Interestingly, the injected limb initially (at 2 months post-injection biopsy) had lower expression than the non-injected limb, suggesting procedure-related inflammation and partial inactivation of the CMV promoter (FIG. 12). Nonetheless, the human mini-dystrophin expression persisted for 8 years in "Jelly" despite initial inflammation in the injected limb. Muscle biopsies and immunofluorescent staining and Western blot of the human mini-dystrophin at subsequent time points (7 months, 1 year, 2 years, and 4 years post vector injection) showed persistent gene expression (FIGS. 13-17). While the percentages of mini-dystrophin-positive myofibers varied among different muscles, certain muscles had greater than 90% of myofibers positive upon necropsy (FIG. 18). Co-staining of mini-dystrophin and revertant myofibers (anti-C-terminus antibody) showed co-existence of both (FIG. 19). Mini-dystrophin was also observed in approximately 20% of the cardiomyocytes (FIG. 18). Overall gene expression was largely stable. For example, positive myofibers in the cranial sartorius muscle remained comparable throughout the 6 time points, from 2 and 7 months to 1, 4 and 8 years (compare FIGS. 12, 13, 14, 17 and 18). Western blot confirmed the IF staining results (FIG. 20).

Figure 21:
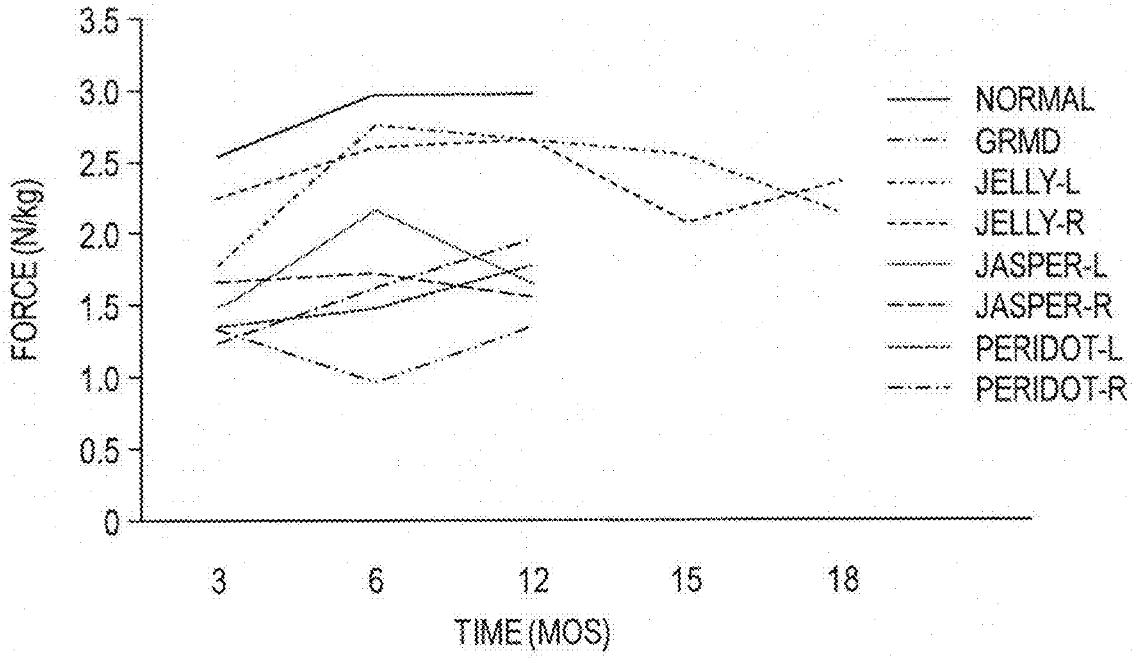
FIG. 21 shows muscle contractile force improvement in GRMD dog "Jelly" after injection of the AAV9-CMV-Hopti-Dys3978 vector and body wide gene expression. The top curve represents the muscle force of a normal dog, while the bottom curve represents the muscle force of the untreated GRMD dog. The two curves extended into more time points represents the muscle force of dog "Jelly." Two more GRMD dogs treated with AAV9-CMV-canine-mini-dystrophin Dys3849 vector (Wang, et al., PNAS 97(25):13714-9 (2000)) were also examined for muscle force, and showed improvement ("Jasper" and "Peridot").

Contractile force measurement showed partial improvement when compared to the untreated dogs (FIG. 21). "Jelly" remained ambulant throughout the greater than 8 year post treatment period of observation and was euthanized due to cardiomyopathy in the final year. No tumors were found in any of the tissues upon necropsy and examination by a pathologist. DNA sequencing showed that "Jelly" did not carry the disease-modifying Jagged 1 mutation found in two phenotypically mild GRMD dogs as recently reported (Vieira et al., Ce11163:1204 (2015)).

EXAMPLE 5 hCK-Copti-Dys3978 in GRMD Dog

In this study, AAV9-hCK-Copti-Dys3978 vector (a modified creatine kinase promoter driving a canine codon-optimized human mini-dystrophin 3978) was used in a GRMD dog named "Dunkin." The gene encodes the same human mini-dystrophin Dys3978 protein used in other studies, but was canine codon-optimized. The DNA sequence is 94% identical to the human codon-optimized gene. Transfection experiments in human HEK 293 cells comparing CK-Copti-Dys3978 (canine codon-optimized) and CK-Hopti-Dys3978 (human codon-optimized) revealed essentially the same level of expression. Multiple experiments comparing both constructs in mdx mice also showed essentially the same expression levels.

Experimental Procedure:

GRMD dog "Dunkin" (female, 2.5 m old, 6.5 kg) was intravenously injected with AAV9-hCK-Copti-Dys3978 vector at the dose of $4\times10^{13}$ vg/kg via the great saphenous vein. The dog was not sedated during injection. There was no noticeable adverse reaction or behavior change. A muscle biopsy was done 4 months post vector injection and necropsy was done at 14 months post injection.

Figure 22:
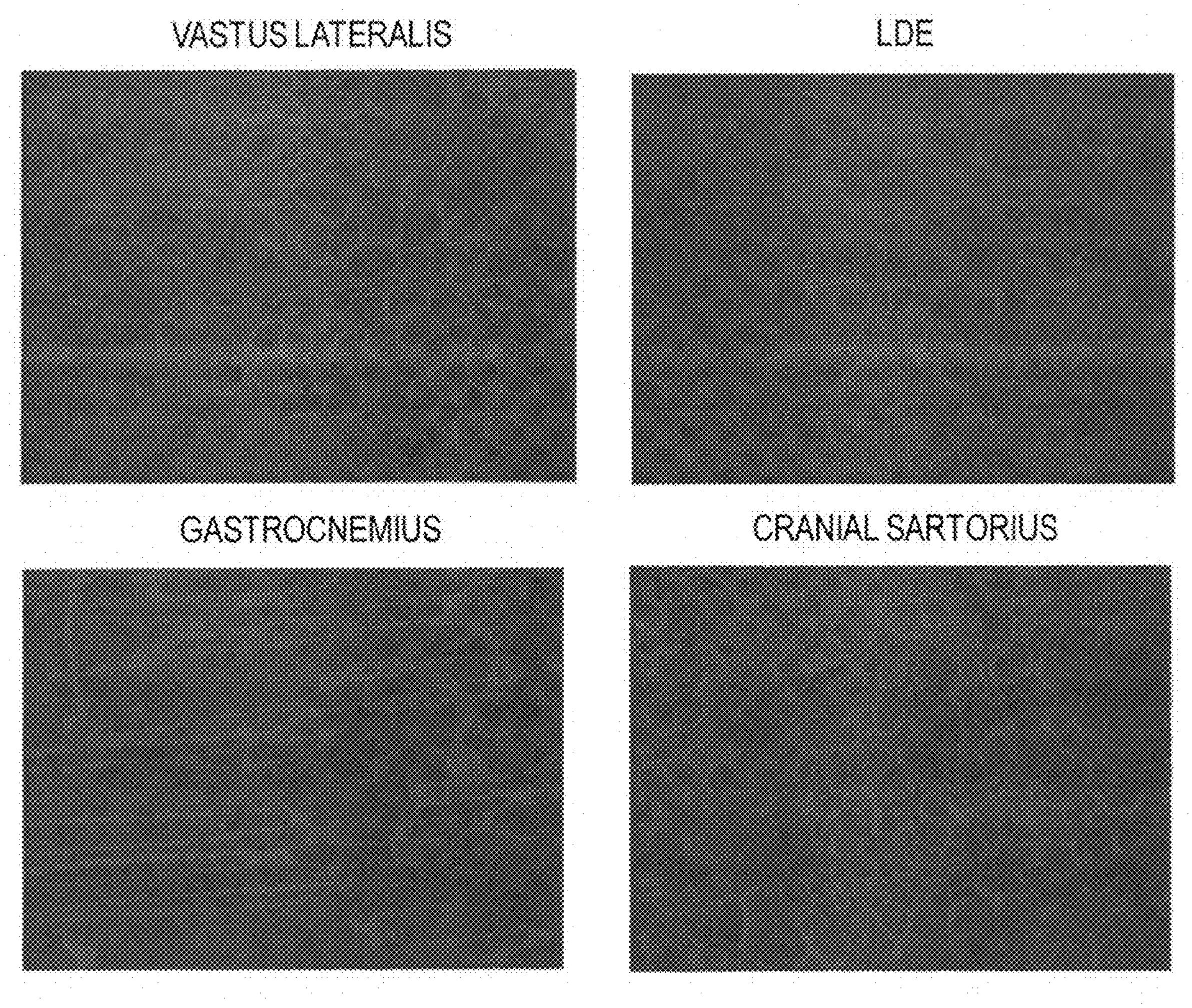
FIG. 22 shows muscle biopsy IF staining of human mini-dystrophin expression at 4 months post AAV9-hCK-Copti-Dys3978 vector injection in GRMD dog "Dunkin." The vector was delivered by intravenous injection to achieve body wide gene expression. Biopsy samples of 4 different muscle groups in the hind limbs were examined. Note nearly uniform mini-dystrophin Dys3978 detected in all muscle groups.
Figure 23:
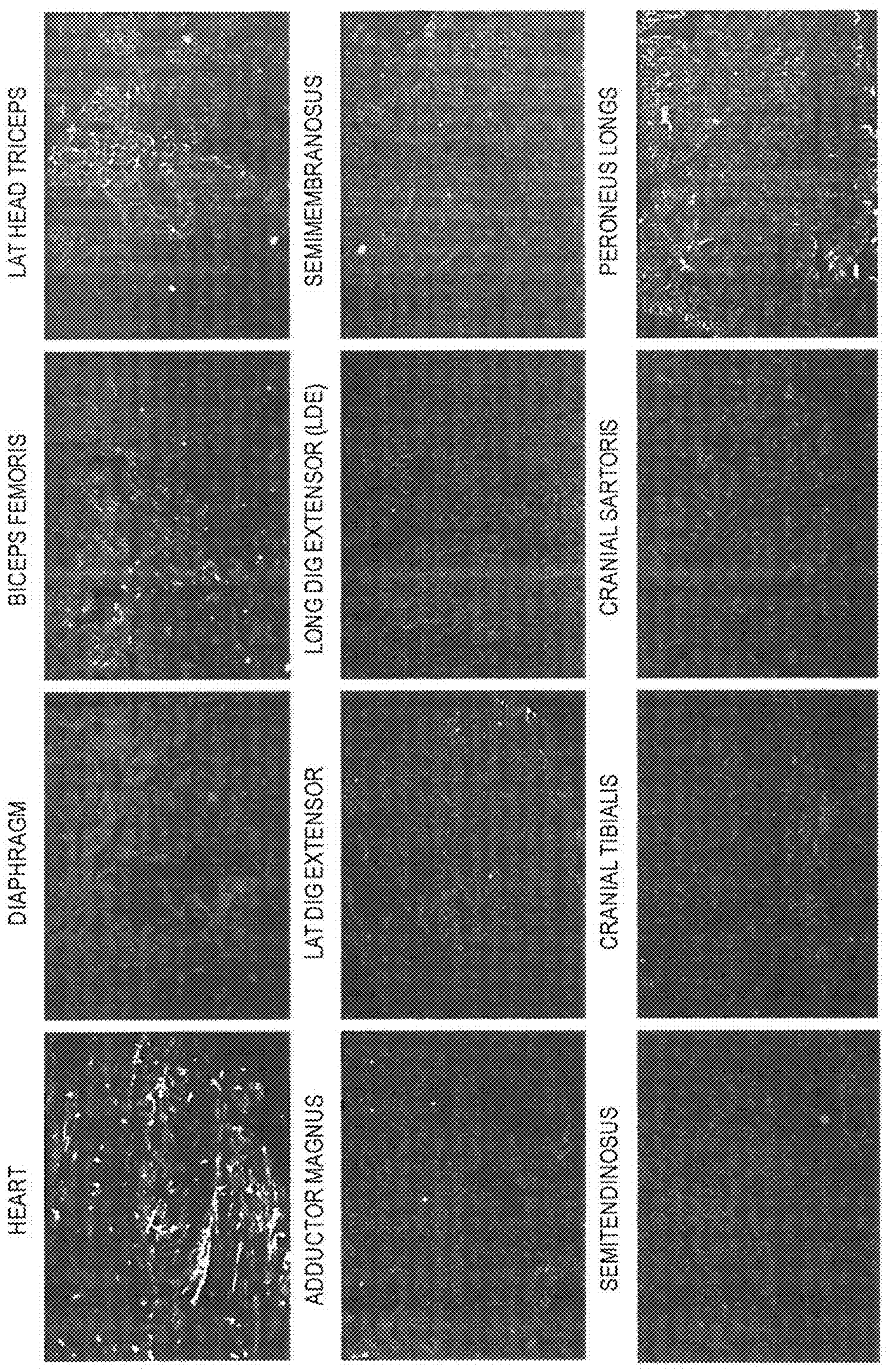
FIG. 23 shows IF staining of human mini-dystrophin expression at 14 months post AAV9-hCK-Copti-Dys3978 vector injection in GRMD dog "Dunkin." Necropsy samples were taken and examined. Note widespread and robust levels of mini-dystrophin Dys3978 detected in heart and all muscle groups. Magnification 4×.
Figure 24:
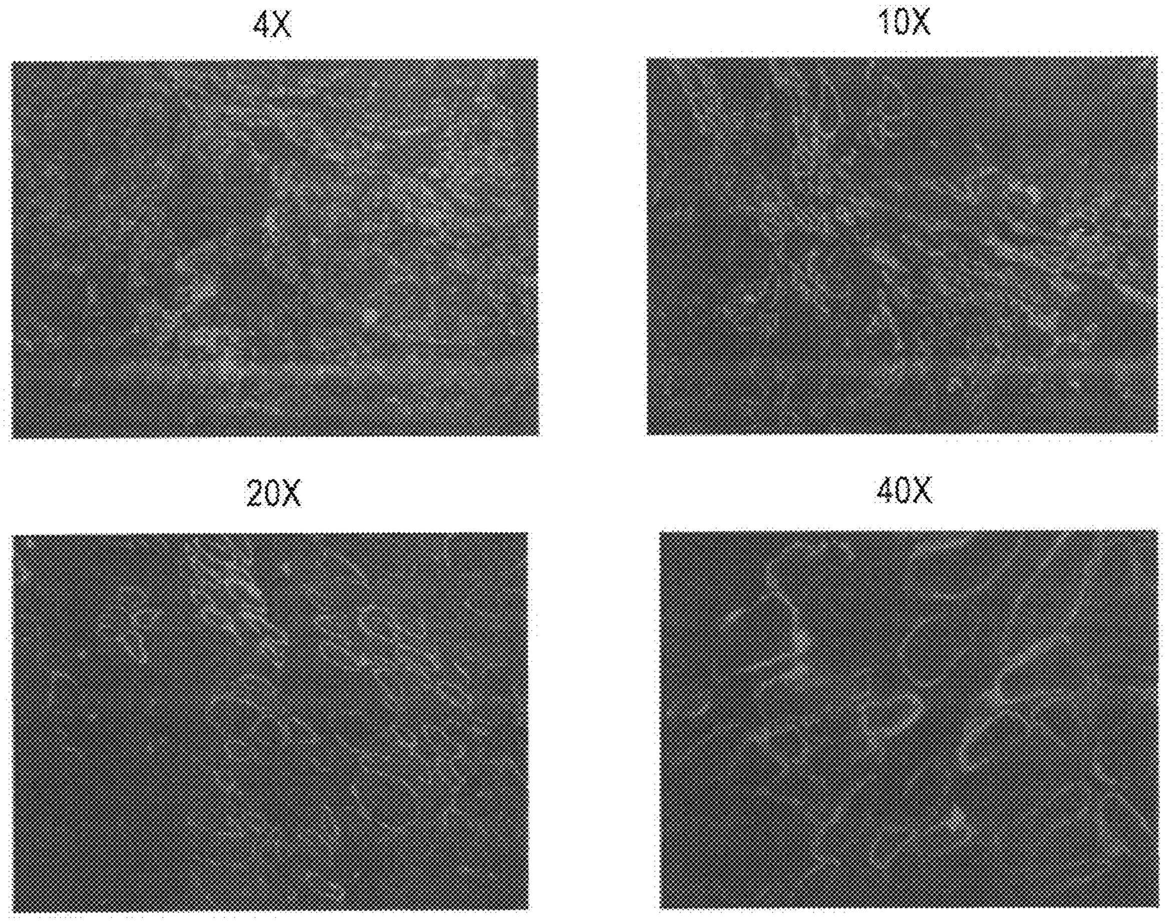
FIG. 24 shows IF staining of diaphragm muscle with robust levels of human mini-dystrophin detected at 14 months post AAV9-hCK-Copti-Dys3978 vector injection in GRMD dog "Dunkin."
Figure 25:
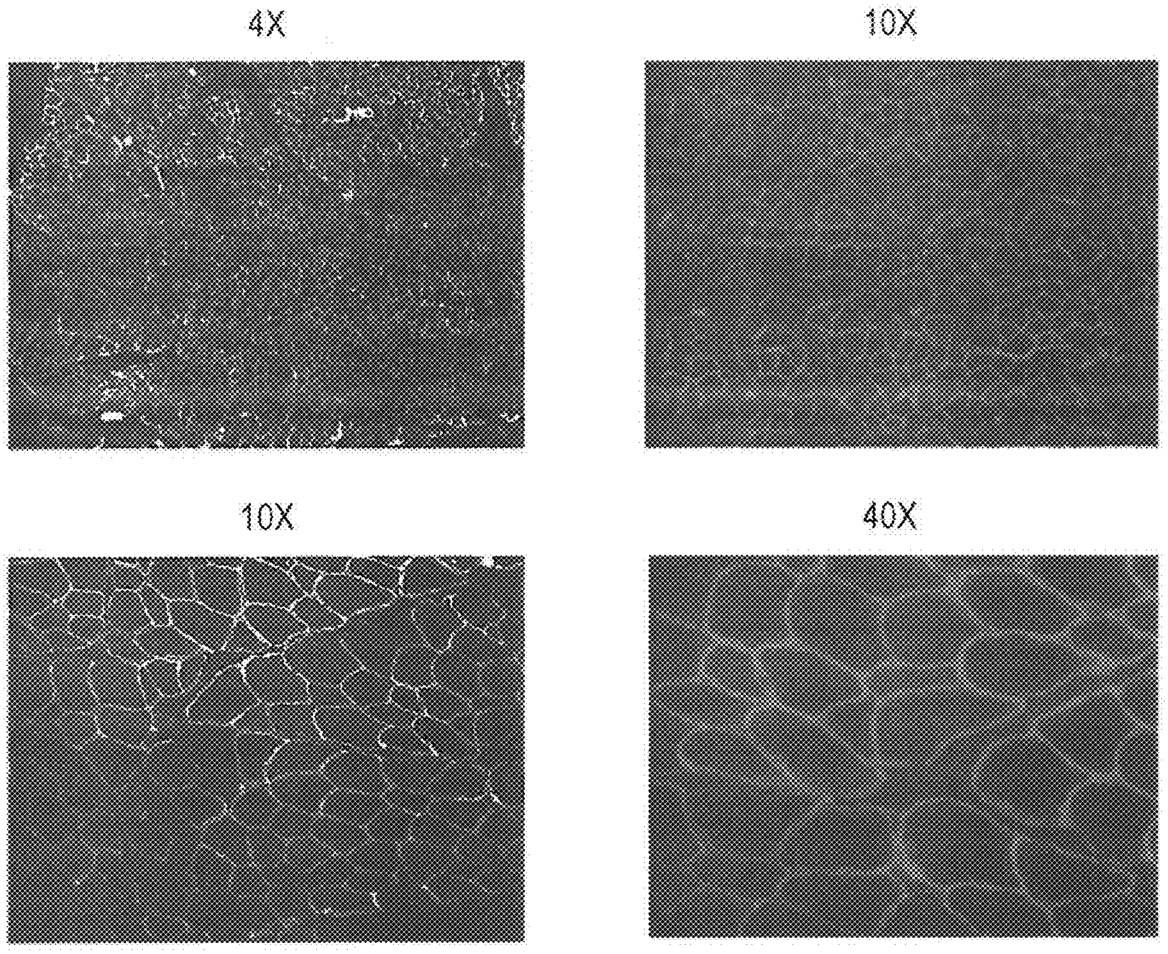
FIG. 25 shows IF staining of peroneus longus muscle with robust levels of human mini-dystrophin detected at 14 months post AAV9-hCK-Copti-Dys3978 vector injection in GRMD dog "Dunkin."
Figure 26:
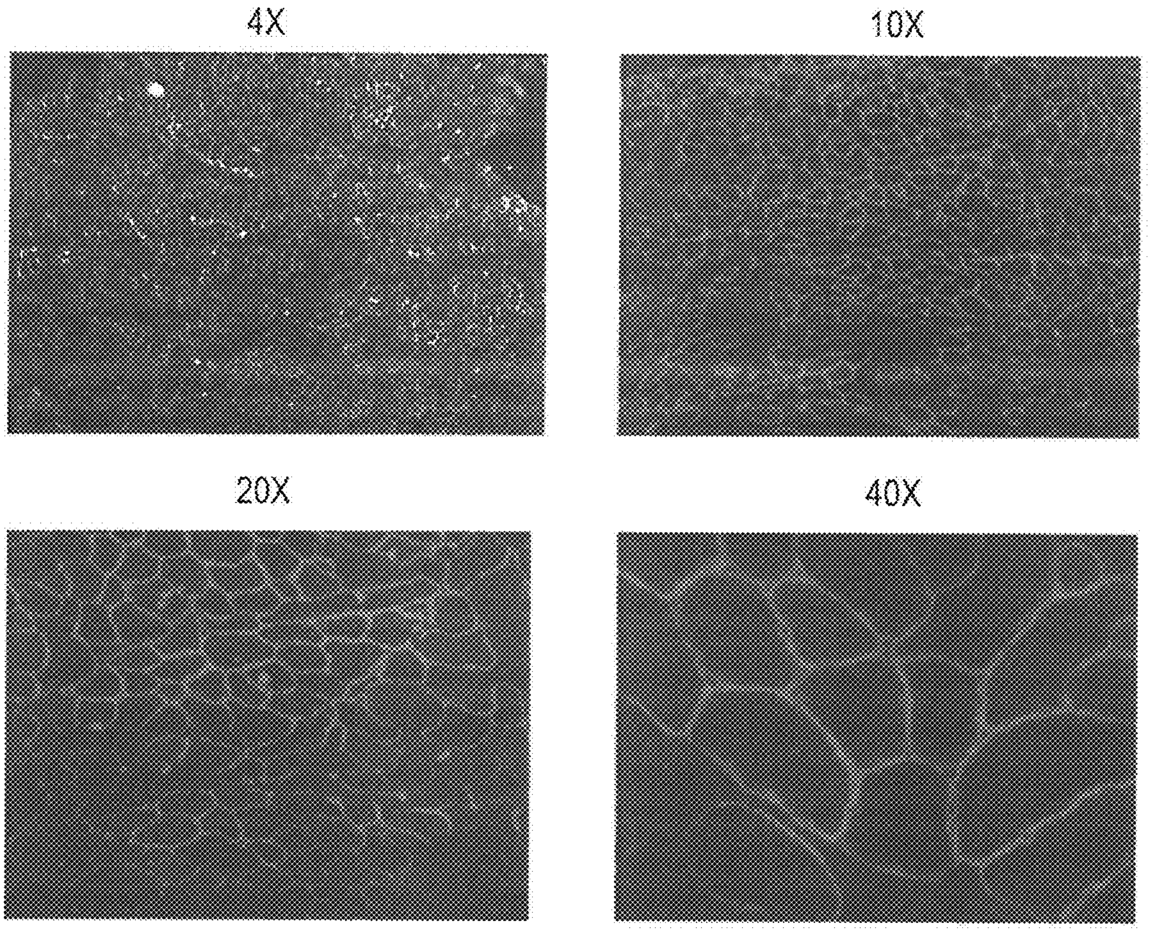
FIG. 26 shows IF staining of semi-membranosus muscle with robust levels of human mini-dystrophin detected at 14 months post AAV9-hCK-Copti-Dys3978 vector injection in GRMD dog "Dunkin."

Results:

Very high level and nearly uniform mini-dystrophin expression was observed by immunofluorescent staining of mini-dystrophin 3978 on skeletal muscle samples from 4-month post injection biopsy (FIG. 22) to 14-month post injection necropsy (FIGS. 23-26 for necropsy).

Figure 27:
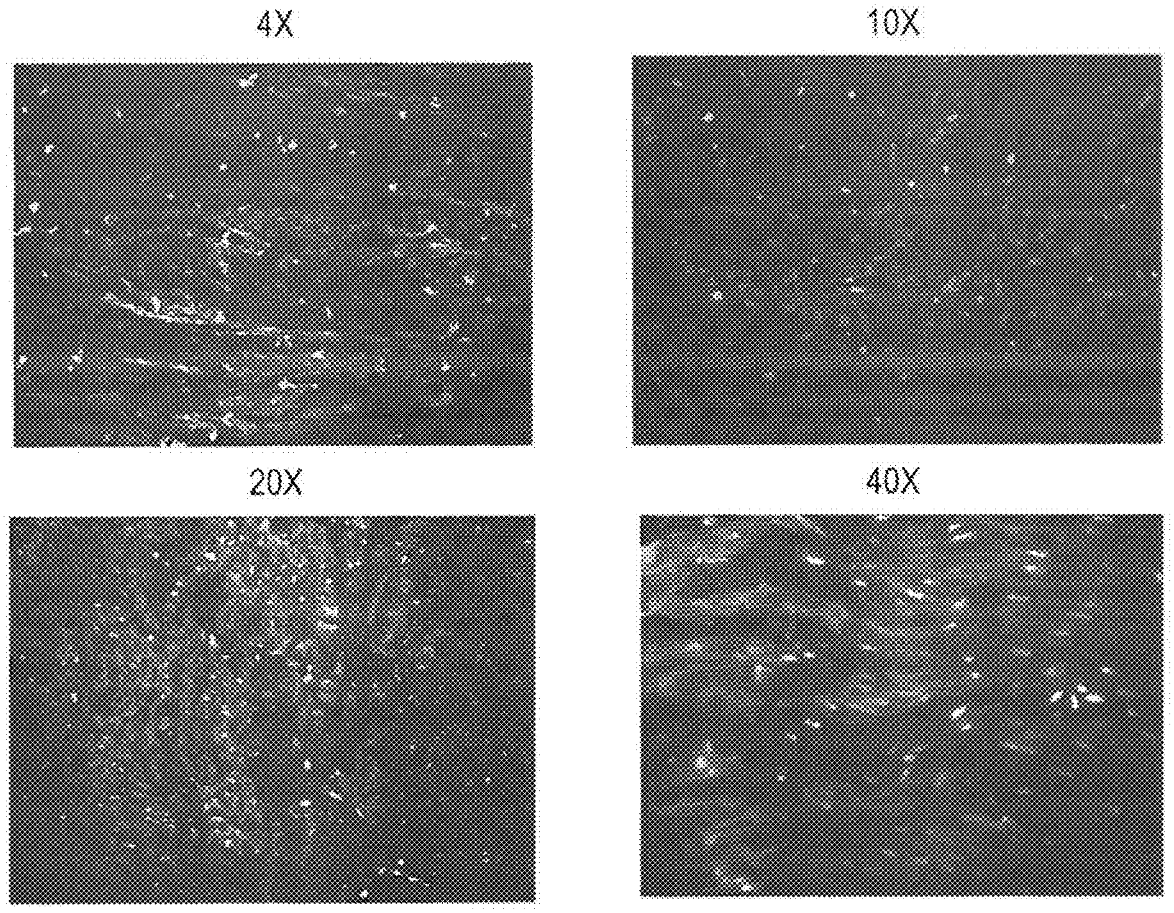
FIG. 27 shows IF staining of heart left ventricle (LV) muscle with robust levels of human mini-dystrophin detected at 14 months post AAV9-hCK-Copti-Dys3978 vector injection in GRMD dog "Dunkin."

Significantly high levels of mini-dystrophin in cardiac muscles was also observed by IF staining (FIG. 27). The expression from the CK promoter appeared stronger and more uniform than from the CMV promoter.

Figure 28:
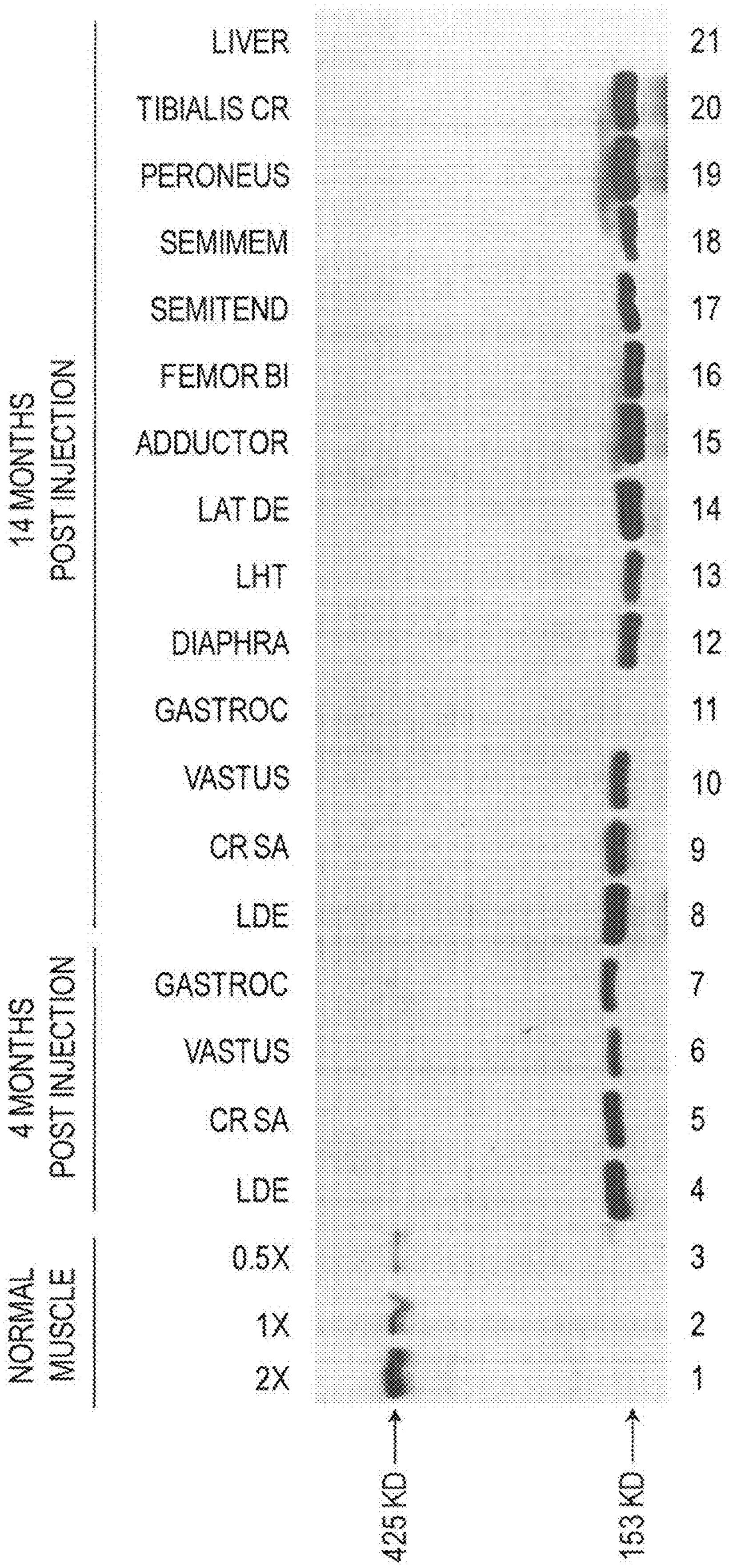
FIG. 28 shows detection by Western blot of human mini-dystrophin Dys3978 in muscle samples of GRMD dog "Dunkin" at 4 months and 14 months post vector injection. Muscle from an age matched normal dog was used as a positive control with serial 2-fold dilutions to indicate the quantitation of dystrophin protein. The molecular weight of wildtype full length dystrophin is about 400 kDa while the mini-dystrophin Dys3978 is about 150 kDa. Note that no mini-dystrophin Dys3978 was detected in the liver.
Figure 29:
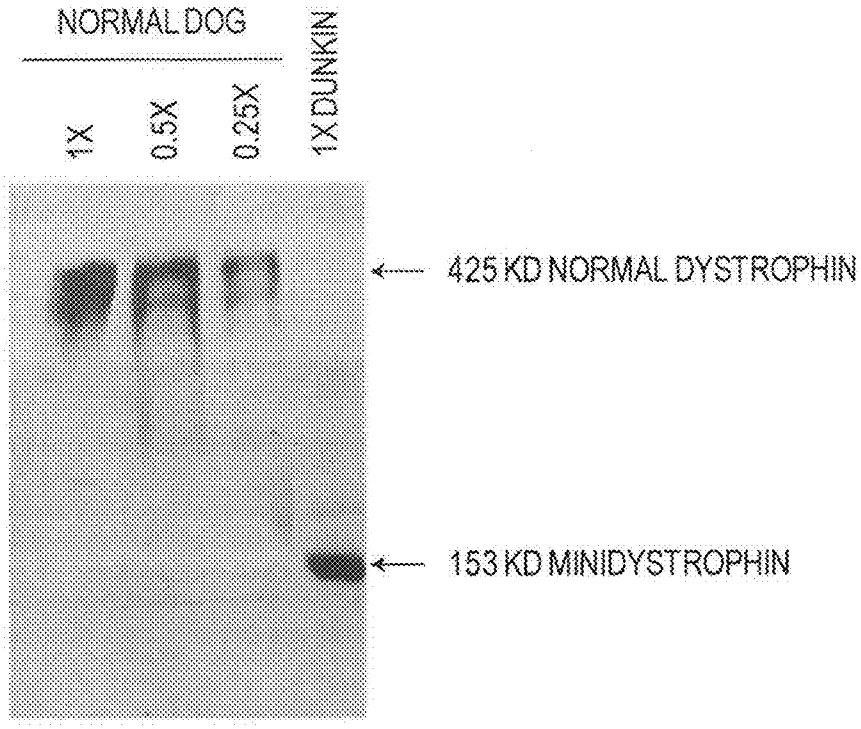
FIG. 29 shows detection by Western blot of human mini-dystrophin Dys3978 expression in heart (LV) sample of GRMD dog "Dunkin" at 14 months post vector injection. Heart sample from an age-matched normal dog was used as a positive control with serial 2-fold dilutions to indicate the quantitation of dystrophin protein.

Western blot analysis confirmed the IF staining results. In the skeletal muscles, the mini-dystrophin levels were mostly higher than the normal level of wildtype dystrophin from the normal dog control (FIG. 28). The level of Dys3978 in the heart was roughly half that of the wildtype dystrophin level (FIG. 29).

Figure 30:
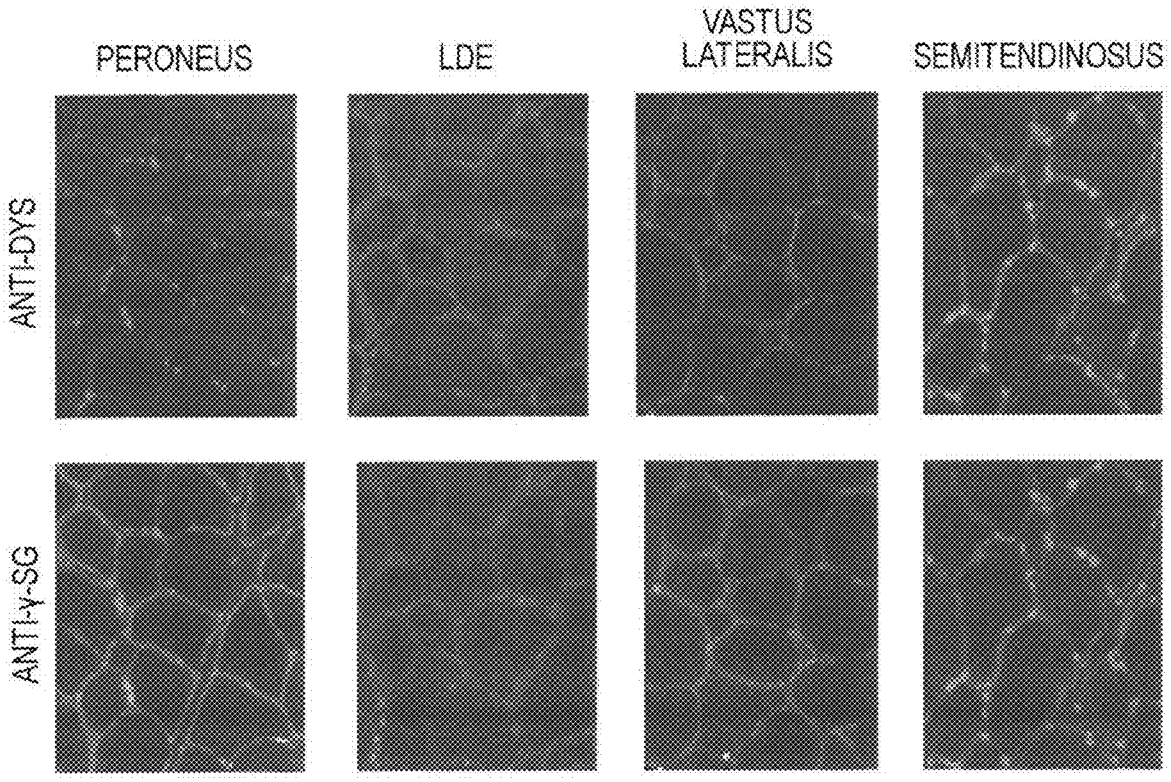
FIG. 30 shows restoration of dystrophin associated protein complex as shown by IF staining of human mini-dystrophin Dys 3978 as well as gamma-sarcoglycan (r-SG) of various muscle groups.

Expression of Dys3978 from the canine codon-optimized gene Copti-Dys3978 effectively restored dystrophin associated protein complex including gamma-sarcoglycan (FIG. 30).

Figure 31:
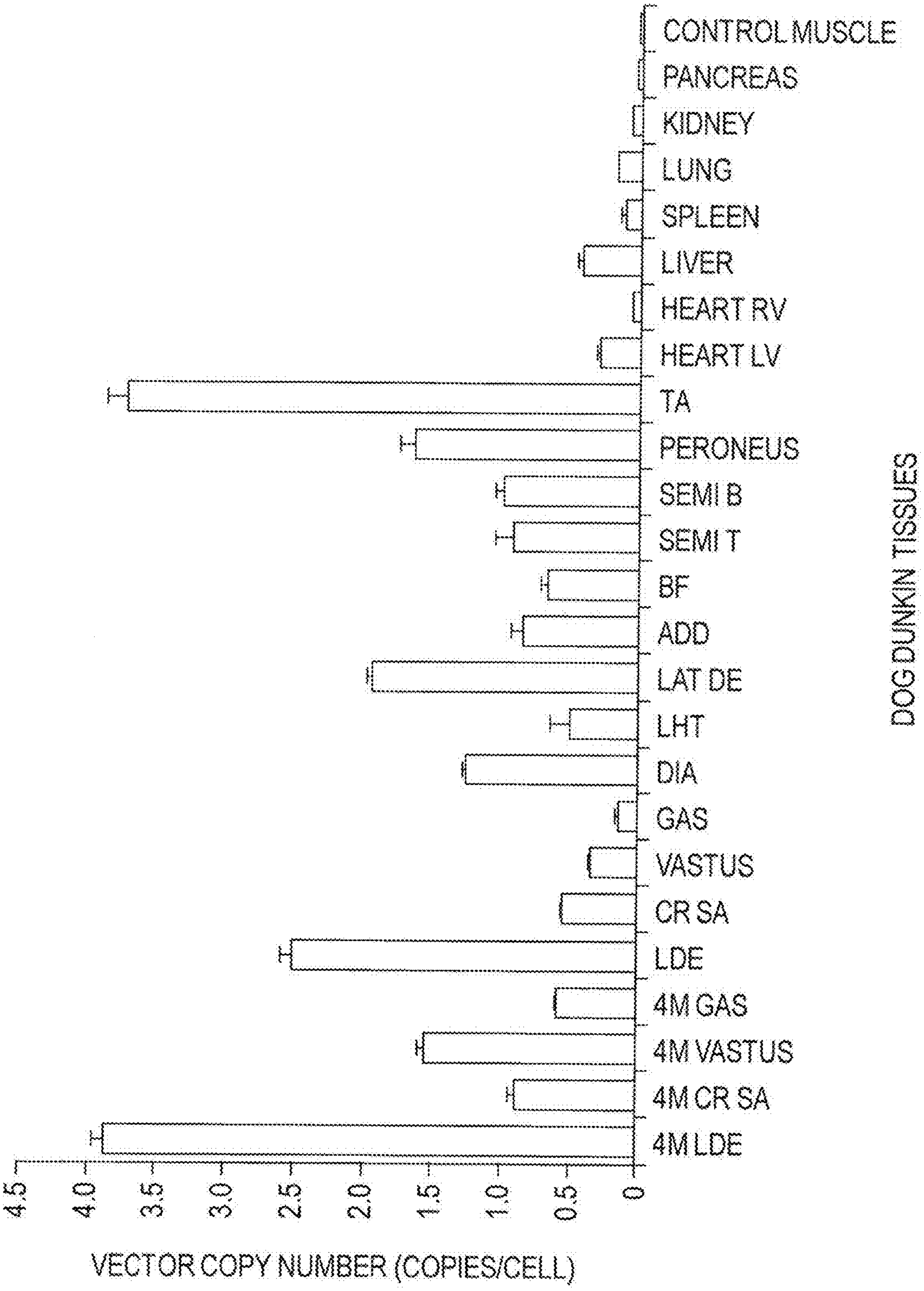
FIG. 31 shows analysis of AAV9-CMV-Copti-Dys3978 vector DNA copy in various muscle and tissues. Quantitative PCR (qPCR) was performed to determine the AAV vector DNA genome copy numbers, which were normalized on a per diploid cell basis.

Quantitative PCR of vector DNA copy numbers showed a consistent trend to the mini-dystrophin protein expression levels (FIG. 31).

There was no innate or cellular immune responses found in all the samples examined. This is very different from the results of AAV9-CMV-opH-dys3978, suggesting the muscle-specific hCK promoter was not only strong but also safer than the CMV promoter.

Figure 32:
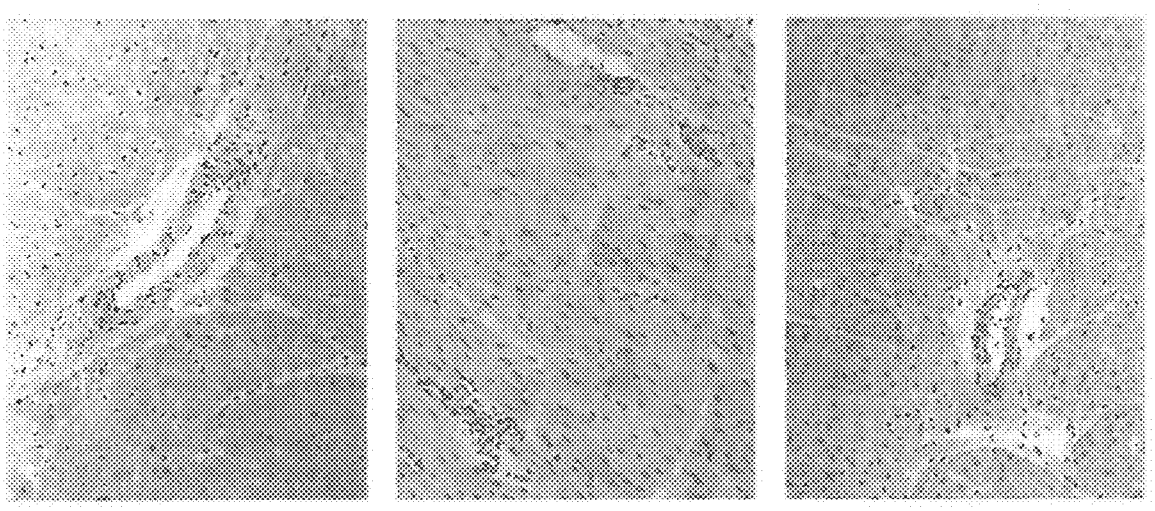
FIG. 32 shows improvement of dystrophic histopathology in the heart of AAV9-CMV-Copti-Dys3978 vector GRMD dog "Dunkin" compared to age-matched normal and untreated GRMD dog. HE staining.
Figure 33:
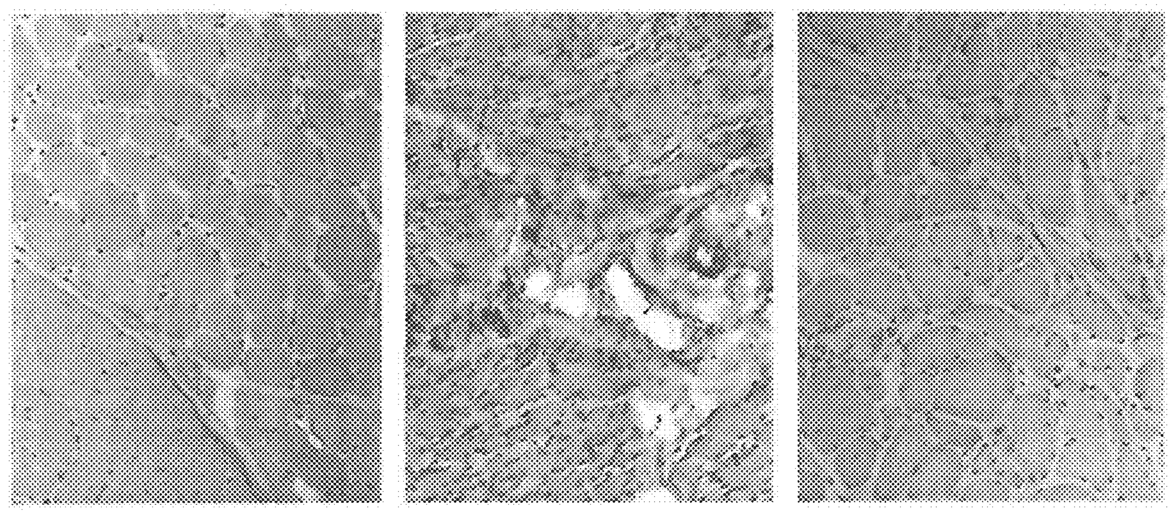
FIG. 33 shows improvement of dystrophic histopathology in the diaphragm muscle of AAV9-CMV-Copti-Dys3978 vector GRMD dog "Dunkin." Compared to age-matched normal and untreated GRMD dog. HE staining.
Figure 34:
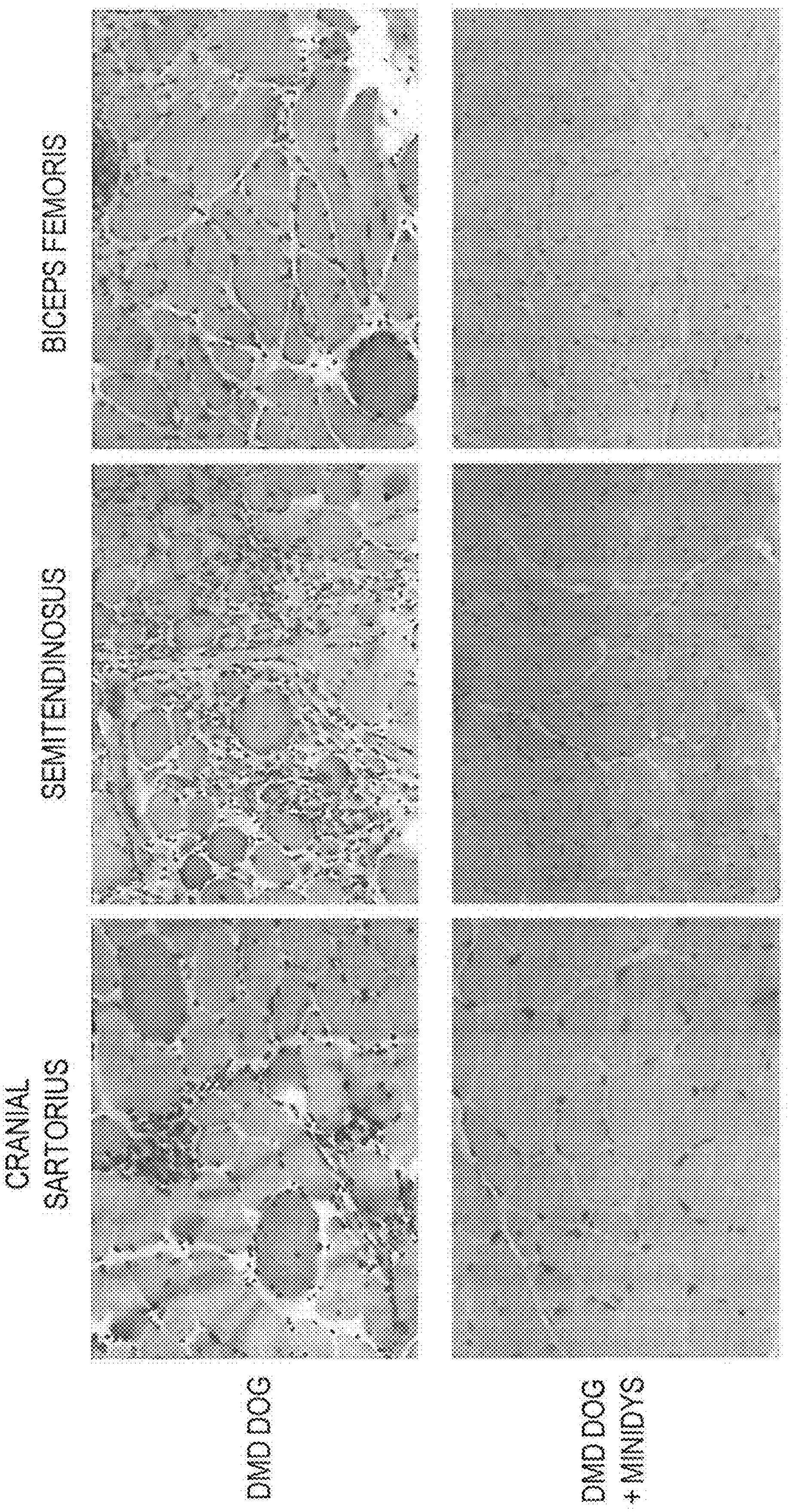
FIG. 34 shows improvement of dystrophic histopathology in the limb muscles of AAV9-CMV-Copti-Dys3978 vector GRMD dog "Dunkin" compared to age-matched untreated GRMD dog. HE staining.
Figure 35:
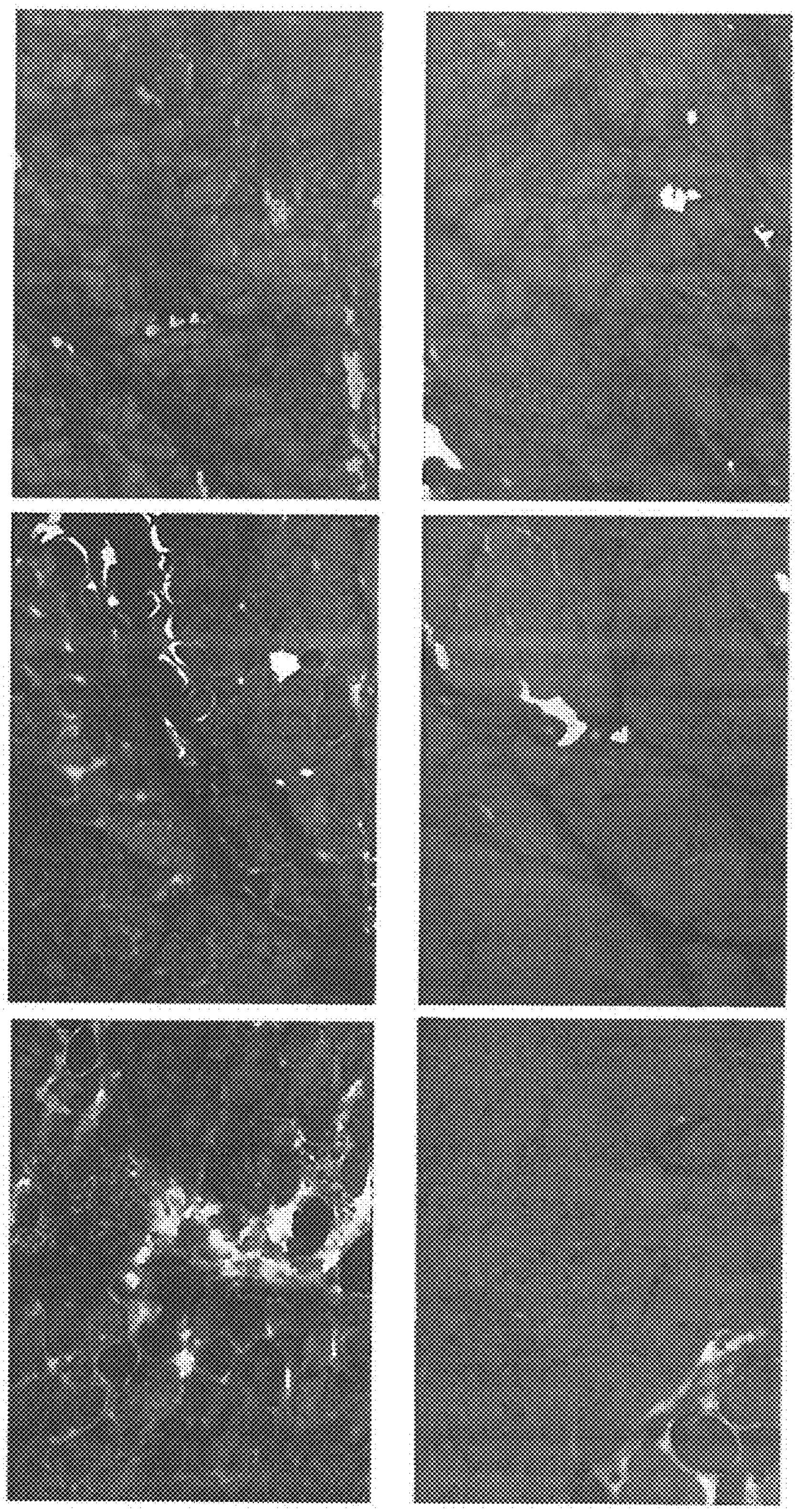
FIG. 35 shows inhibition of fibrosis in limb muscle and diaphragm of GRMD dog "Dunkin" compared to age-matched untreated GRMD dog. Mason Trichrome blue staining.
Figure 36A:
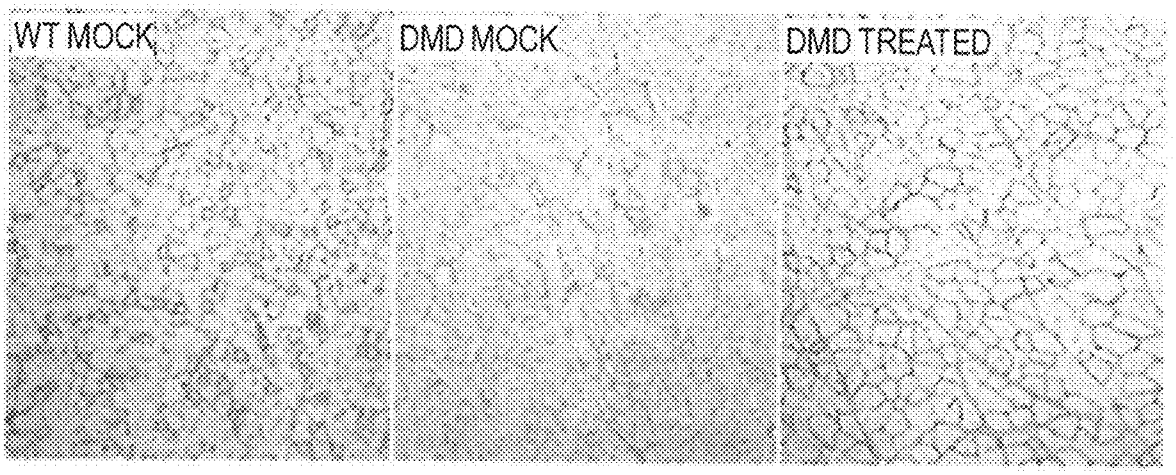
FIG. 36A provides photomicrographs showing immunolabeling with anti-dystrophin DYSB antibody of biceps femoris muscle obtained from a WT rat mock treated with PBS (left panel), a mock treated DMD rat (central panel), and a $Dmd^{mdx}$ rat treated with AAV9.hCK.Hopti-Dys3978.spA vector (right panel). The dark outline around the fibers shows the subsarcolemmal localization of the dystrophin in WT rat and mini-dystrophin in vector treated $Dmd^{mdx}$ rat.
Figure 36B:
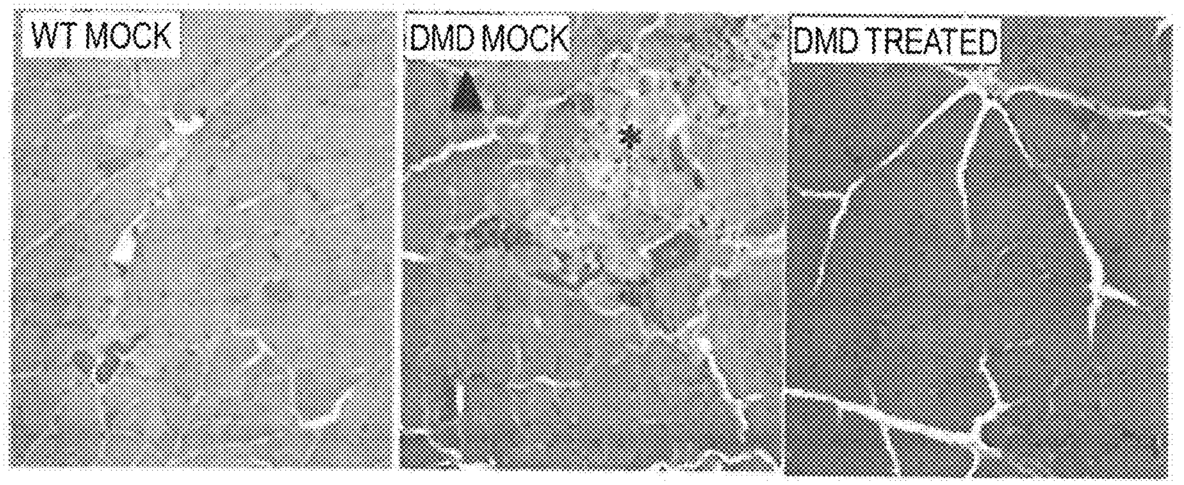
FIG. 36B provides photomicrographs showing haematoxylin and eosin (HES) stained biceps femoris muscle obtained from a mock treated WT rat (left panel), a mock treated $Dmd^{mdx}$ rat (central panel) and a DMD rat treated with AAV9.hCK.Hopti-Dys3978.spA vector (right panel). Cluster of necrotic fibers (*) and endomysial mild fibrosis (black arrowhead) are shown.
Figure 36C:
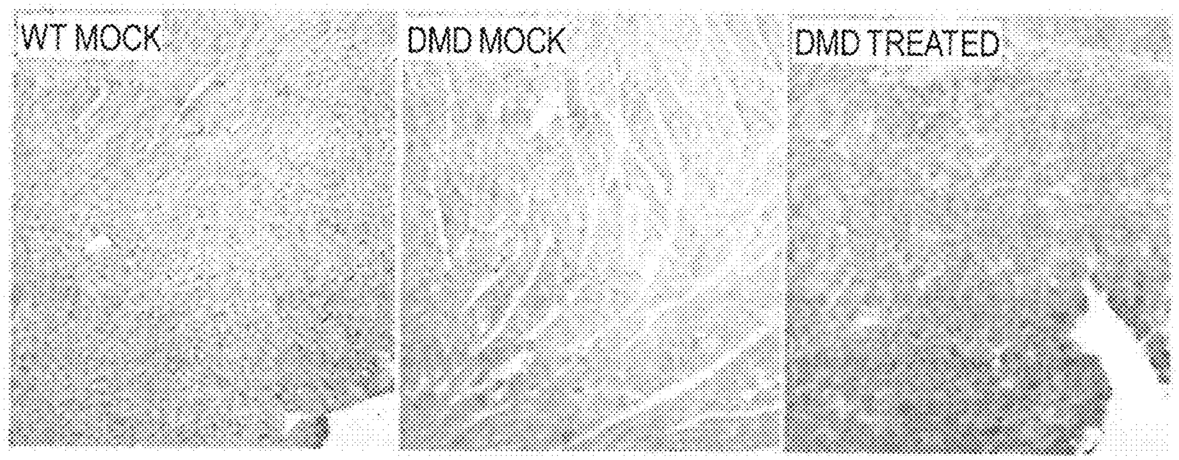
FIG. 36C provides photomicrographs showing immunolabeling with anti-dystrophin DYSB antibody of cardiac muscle obtained from a mock treated WT rat (left panel), a mock treated $Dmd^{mdx}$ rat (central panel) and a $Dmd^{mdx}$ rat treated with AAV9.hCK.Hopti-Dys3978.spA vector (right panel). The dark outline around the fibers shows the subsarcolemmal localization of the dystrophin in WT rat and mini-dystrophin in vector treated $Dmd^{mdx}$ rat.
Figure 36D:
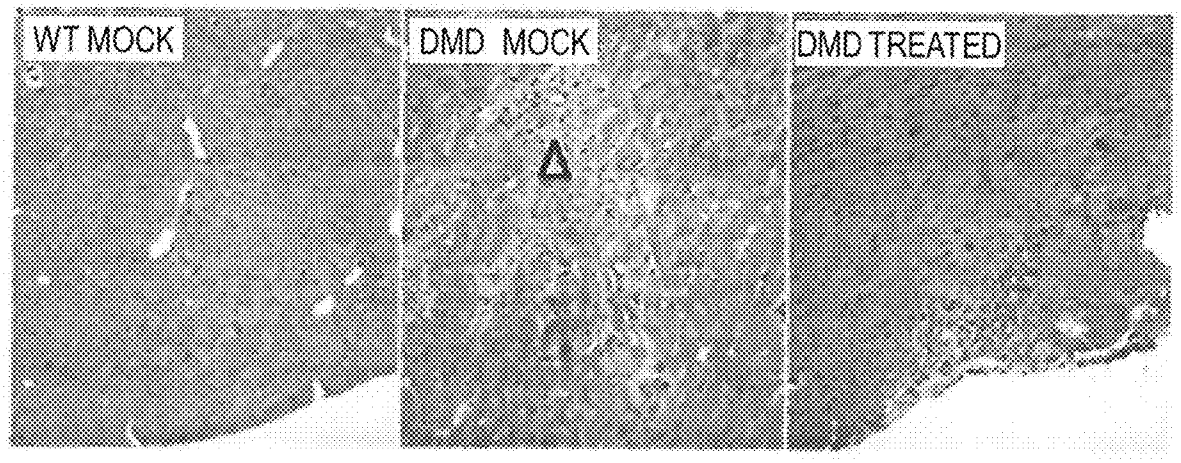
FIG. 36D provides photomicrographs showing HES stained cardiac muscle obtained from a mock treated WT rat (left panel), a mock treated $Dmd^{mdx}$ rat (central panel) and a $Dmd^{mdx}$ rat treated with AAV9.hCK.Hopti-Dys3978.spA vector (right panel). A focus of fibrosis (open arrowhead) is shown in the center panel, and a focus of mononuclear cell infiltration is illustrated in the right panel.

Dystrophic pathology was largely ameliorated as shown by H&E staining for histology of the heart (FIG. 32), diaphragm (FIG. 33) and limb muscles (FIG. 34). Trichrome Mason blue staining also showed significant reduction of fibrosis in limb muscle and diaphragm (FIG. 35).

EXAMPLE 6

Preparation of AAV9.hCK.Hopti-Dys3978.spA Vector for In Vivo Experiments

The AAV9.hCK.Hopti-Dys3978.spA vector used in Dmd$^{mdx}$ rat studies described further in Examples 7, 8 and 9 includes an AAV9 capsid and an expression cassette designed to express a miniaturized version of human dystrophin protein including the N-terminus region, hinge 1 (H1), rod 1 (R1), rod 2 (R2), hinge 3 (H3), rod 22 (R22), rod 23 (R23), rod 24 (R24), hinge 4 (H4), cysteine-rich (CR) domain, and portion of the carboxy-terminal (CT) domain from full length human Dp427m dystrophin protein (SEQ ID NO:25), which are domains minimally required for function. The protein sequence of the mini-dystrophin protein is provided as the amino acid sequence of SEQ ID NO:7, which is encoded by the human codon-optimized DNA sequence provided as the nucleic acid sequence of SEQ ID NO:1. The vector genome of the AAV9.hCK.Hopti-Dys3978.spA vector is provided as the nucleic acid sequence of SEQ ID NO:18, or its reverse complement when the single-stranded genome is packaged in its minus polarity.

The vector genome comprises 5' and 3' flanking AAV2 inverted terminal repeats (ITRs) (having the DNA sequence of SEQ ID NO:14 or SEQ ID NO:15, respectively), a synthetic hybrid enhancer and promoter derived from the creatine kinase (CK) gene to serve as a muscle specific transcription regulatory element (hCK; having the DNA sequence of SEQ ID NO:16), a 3978 base pair long human codon-optimized gene encoding the human mini-dystrophin protein described above (i.e., the Hopti-Dys3978 gene), and a small synthetic transcription termination sequence including a polyadenylation (polyA) signal (spA; having the DNA sequence of SEQ ID NO:17).

Vector was manufactured using the triple transfection technique and a serum free non-adherent cell line derived from HEK 293 cells. The plasmids used included a helper plasmid to express adenovirus helper proteins required for efficient replication and packaging of the vector, a packaging plasmid expressing the AAV2 rep gene and the AAV9 capsid proteins, and a third plasmid containing the sequence of the expression cassette described above.

Cells were grown and expanded from a working cell bank sample, and once sufficient volume and cell density had been reached, the cells were transfected using a transfection reagent. After incubation to permit vector production from the transfected cells, the cells were lysed to release vector, the lysate clarified, and vector purified using a nuclease treatment step to remove contaminating nucleic acids, followed by iodixanol step gradient centrifugation, anion exchange chromatography, dialysis against the formulation buffer, sterile filtration, and then storage at 2-8° C.

EXAMPLE 7

Effects of Single Dose of AAV9.hCK.Hopti-Dys3978.spA in a Rat Model of DMD

This example describes testing AAV9.hCK.Hopti-Dys3978.spA in a recently developed Dmd$^{mdx}$ rat model, which has certain advantages compared to the classic mdx mouse and GRMD dog models. Larcher, T., et al., Characterization of dystrophin deficient rats: a new model for Duchenne muscular dystrophy. *PLoS One.* 2014; 9(10): e110371. In particular, in the Dmd$^{mdx}$ rat model, the skeletal and cardiac disease are both present at an early stage and develop in a sequential manner similar to the disease progression seen in humans.

In these studies, male Dmd$^{mdx}$ rats 5-6 weeks of age were systemically administered by IV injection into tail veins a single dose ($1\times10^{14}$ vector genomes per kilogram body weight, or vg/kg) of Dys3978 vector suspended in PBS. As a control, wild-type ("WT") rats from the same genetic background (Sprague Dawley) were also treated in this way. All procedures were conducted blinded to the rat genotype or treatment cohort to avoid bias. Three Dmd$^{mdx}$ rats and 4 WT rats were treated with vector, whereas 3 Dmd$^{mdx}$ rats and 2 WT rats were administered PBS only as a negative control (mock treatment). Three months post-injection, animals were euthanized and underwent necropsy for tissue analysis by histology and immunocytochemistry for dystrophin protein expression.

For histopathological evaluation, tissue samples were fixed in 10% neutral buffered formalin, embedded in paraffin wax, and 5-μm-thick sectioned before staining with hematoxylin eosin saffron (HES). For dystrophin immunolabelling, additional samples (liver, heart, biceps femoris, pectoralis and diaphragm muscles) were frozen and 8-μm-thick sectioned. Mouse monoclonal antibody NCL-DYSB for dystrophin (Novocastra Laboratories, Newcastle on Tyne, UK) was used for both dystrophin and mini-dystrophin protein detection (1:50), since this antibody does not distinguish between full length wild type dystrophin and the engineered mini-dystrophin. All necropsies and histological observations were performed in blinded fashion.

By histological examination, no lesions were observed in skeletal or cardiac muscle of PBS and vector treated WT rats. In all $Dmd^{mdx}$ rats, skeletal muscle fiber lesions showing individual necrosis, clusters of regenerative small fibers, scattered giant hyaline fibers, anisocytosis, centronucleation, endomysial fibrosis and sporadic adiposis were present and characteristic of DMD skeletal muscle. The incidence and intensity of these lesions was globally decreased in $Dmd^{mdx}$ rats treated with vector compared to those treated only PBS. In the heart, lesions of multifocal necrosis, mononuclear cell focal infiltration and mild focal extensive fibrosis were present in one of the $Dmd^{mdx}$ rats (rat 49) treated with PBS, which is characteristic of DMD cardiac muscle. In all the $Dmd^{mdx}$ rats treated with vector, cardiac muscle presentation was similar and showed mild mononuclear cell focal infiltration as seen in the $Dmd^{mdx}$ rat receiving PBS, but in contrast, no fibrotic foci were observed in the hearts of the vector treated $Dmd^{mdx}$ rats.

Using immunocytochemistry, WT rats displayed subsarcolemmal dystrophin detected in skeletal, diaphragm and cardiac muscle fibers, and localization of dystrophin detected did not differ between rats treated with vector compared to only PBS. However, mini-dystrophin detection in the vector treated WT rats could not be confirmed using this assay because the anti-dystrophin antibody used could not distinguish between wild type dystrophin and the mini-dystrophin protein. By contrast, one of the $Dmd^{mdx}$ rats (rat 49) displayed rare skeletal muscle fibers (from about 5% to 10%) with subsarcolemmal dystrophin detectable, which is in accordance with the previous description of the presence of scattered revertant fibers in this model with a frequency of about 5% (Larcher et al., PlosOne, 2014). However no dystrophin was detected in diaphragm or cardiac muscle fibers from this rat. In all Dys3978 vector treated $Dmd^{mdx}$ rats, subsarcolemmal dystrophin was also detected in about 80% to 95% of skeletal muscle fibers, about 30% to 50% in diaphragm muscle fibers, and about 70% to 80% in heart muscle fibers, although no systematic counting performed. In these rats, very rare skeletal muscle fibers (1 or 2 per muscle section) displayed some cytoplasmic interfibrillar dystrophin. In both vector treated WT and $Dmd^{mdx}$ rats, there was no evidence of inflammatory cell infiltrates or increased necrosis that might indicate that a cellular immune response had been stimulated by vector transduction, or production of the mini-dystrophin.

In sum, 3 months after systemic administration of $1\times10^{14}$ vg/kg of AAV9.hCK.opti-Dys3978.spA vector, no histological alteration of the muscle tissues was observed in WT rats treated with vector compared to PBS, suggesting that expression of the mini-dystrophin protein was well tolerated in healthy animals. Furthermore, vector treatment of the $Dmd^{mdx}$ rats resulted in a significant and generalized detection of mini-dystrophin in fibers of all muscles studied (biceps femoris, pectoralis, diaphragm and heart) with a pattern of subsarcolemmal localization similar to that in WT rat muscles. The expression of mini-dystrophin Dys3978 from the vector was associated with reduction in fibrosis and necrosis (FIGS. 36A-36D).

EXAMPLE 8

Effects of Increasing Doses of AAV9.hCK.Hopti-Dys3978.spA in $Dmd^{dx}$ Rats Determined at 3 Months and 6 Months Post-Injection This example describes the results of treating $Dmd^{mdx}$ rats, an animal model for Duchenne muscular dystrophy, with increasing doses of AAV9.hCK.Hopti-Dys3978.spA, and measuring the effects at 3 months and 6 months after administration.

Rats were dosed at 7-8 weeks of age by IV injection into the dorsal penile vein, which resulted in systemic administration of the test articles. Four different vector doses were tested in 10-12 $Dmd^{mdx}$ rats: $1\times10^{13}$ vg/kg (5 rats at the 3 month time point and 6 rats at the 6 month time point), $3\times10^{13}$ vg/kg (6 rats at the 3 month time point and 5 rats at the 6 month time point), $1\times10^{14}$ vg/kg (7 rats at the 3 month time point and 6 rats at the 6 month time point), and $3\times10^{14}$ vg/kg (5 rats at the 3 month time point and 5 rats at the 6 month time point). In addition, $Dmd^{mdx}$ rats and WT rats each received vehicle only (1×PBS, 215 mM NaCl, 1.25% human serum albumin, 5% (w/v) sorbitol) as a negative control (6 $Dmd^{mdx}$ rats at the 3 month time point, 4 $Dmd^{mdx}$ rats at the 6 month time point, 5 WT rats at the 3 month time point, and 7 WT rats at the 6 month time point). Five untreated (that is, no vector and no vehicle either) $Dmd^{mdx}$ rats were also included as further negative controls. At 3 months and 6 months post-injection, rats from each test arm were euthanized and necropsied to take tissue samples for further analysis. Prior to sacrifice, cardiac function and grip strength tests were carried out in the test animals to assess the effect of vector treatment on DMD disease progression.

Note that vector doses may be represented in two different numerically equivalent ways in the text and figures. Thus, "$1\times10^{13}$" is equivalent to "1E13," "$3\times10^{13}$" is equivalent to "3E13," "$1\times10^{14}$" is equivalent to "1E14," and "$3\times10^{14}$" is equivalent to "3E14."

Body Weight

Figure 37:
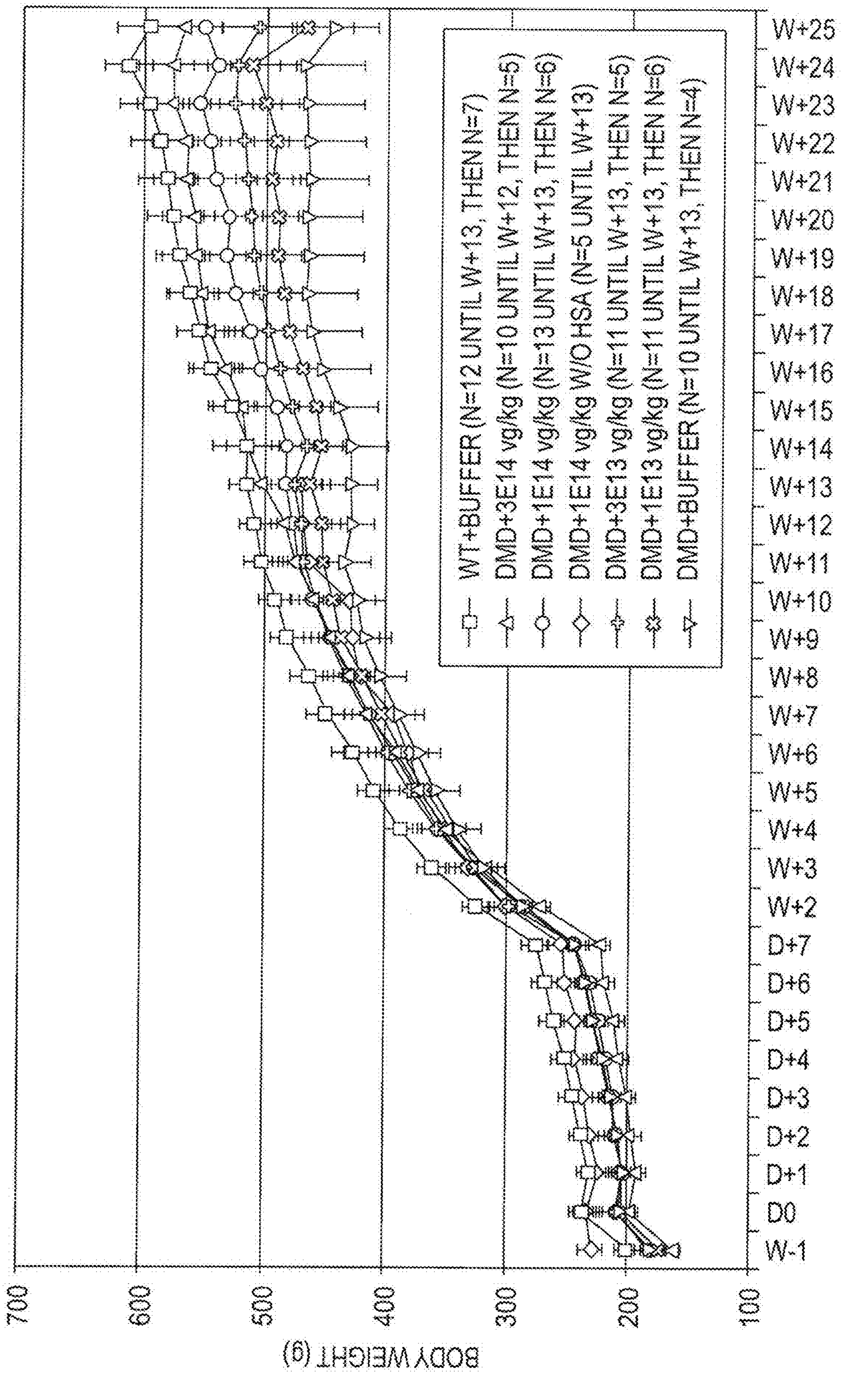
FIG. 37 shows average body weight in grams of WT rats treated with vehicle (buffer) and $Dmd^{mdx}$ rats treated with vehicle and increasing doses of AAV9.hCK.Hopti-Dys3978.spA vector over time to 25 weeks after dosing. "WT" refers to wild type rats; "DMD" refers to $Dmd^{mdx}$ rats; "n" refers to sample size; "D" refers to number days since dosing; "W" refers to number of weeks since dosing; "E" is notation for the specified coefficient times ten raised to the power of the specified exponent (thus, "1E13" stands for $1\times10^{13}$, "3E13" stands for $3\times10^{13}$, "1E14" stands for $1\times10^{14}$, and "3E14" stands for $3\times10^{14}$); "vg/kg" stands for vector genomes per kilogram body weight; and "w/o HAS" refers to a treatment arm where the vector was administered in PBS without human serum albumin. On the right side of the graph, at 25 weeks, the order of average body weight data from top to bottom is the same as the top to bottom order of the treatment arms listed in the legend (except for treatment of Dmd$^{mdx}$ rats with $1\times10^{14}$ vg/kg vector administered in vehicle without HSA, for which data collection ended at 13 weeks from the study start). These same abbreviations are used in other figures herein.

After treatment and prior to sacrifice, rats in each treatment arm were weighed daily for the first week, and weekly thereafter until sacrifice. The average weight of all rats in each treatment arm is listed in Table 2 (pre-injection until 9 weeks post-injection) and Table 3 (weeks 10-25 post-injection) and are graphed against time in FIG. 37. In the graph, error bars represent the standard error of the mean (SEM), which are also reported in the table. At all times, the average weight of WT rats exceeded that of $Dmd^{mdx}$ rats, including those that were treated with vector. Due to age differences and natural variability in body mass among the $Dmd^{mdx}$ rats there was no consistent correlation between dose and body weight until by 4 weeks post-injection when weights of all vector treated $Dmd^{mdx}$ rats except in the highest dose arm were higher than untreated $Dmd^{mdx}$ rats, but lower than WT rats. By 12 weeks post-injection, a dose effect in all treatment arms was evident, with body weight being proportional to vector dose at all doses tested through the end of the study.

TABLE 2

| MEAN WEIGHTS (g) | W − 1 | D0 | D + 1 | D + 2 | D + 3 | D + 4 | D + 5 | D + 6 | D + 7 | W + 2 | W + 3 | W + 4 | W + 5 | W + 6 | W + 7 | W + 8 | W + 9 |
|---|---|---|---|---|---|---|---|---|---|---|---|---|---|---|---|---|---|
| WT + Buffer (n = 12 until W + 13, then n = 7) | 200.0 | 237.9 | 231.7 | 237.9 | 247.1 | 253.1 | 262.1 | 268.7 | 276.6 | 325.0 | 361.8 | 388.8 | 410.2 | 428.8 | 449.6 | 463.4 | 482.1 |
| SEM | 10.9 | 10.5 | 10.1 | 10.5 | 10.1 | 9.8 | 10.0 | 10.4 | 10.7 | 10.8 | 11.7 | 11.9 | 13.6 | 14.8 | 15.4 | 15.5 | 14.1 |
| DMD + Buffer (n = 10 until W + 13, then n = 4) | 180.4 | 207.4 | 203.4 | 208.8 | 214.5 | 221.5 | 229.8 | 235.4 | 244.3 | 286.3 | 318.4 | 340.5 | 358.7 | 374.4 | 389.1 | 403.6 | 418.6 |
| SEM | 11.9 | 12.3 | 11.9 | 12.6 | 12.4 | 13.0 | 12.4 | 13.1 | 12.6 | 15.1 | 17.7 | 18.7 | 19.4 | 20.3 | 21.3 | 21.0 | 22.3 |
| DMD +1E13 vg/kg (n = 11 until W + 13, then n = 6) | 173.4 | 206.4 | 205.8 | 208.4 | 216.7 | 223.8 | 229.8 | 236.8 | 243.1 | 286.3 | 325.6 | 346.5 | 368.6 | 388.1 | 403.8 | 419.5 | 439.1 |
| SEM | 10.3 | 8.3 | 7.9 | 7.5 | 7.9 | 7.2 | 7.6 | 7.8 | 8.7 | 9.5 | 12.6 | 13.2 | 14.2 | 15.6 | 16.1 | 16.7 | 16.2 |
| DMD + 3E13 vg/kg (n = 11 until W + 13, then n = 5) | 180.2 | 210.8 | 206.3 | 209.1 | 217.6 | 224.9 | 230.9 | 237.2 | 245.2 | 297.7 | 329.5 | 357.3 | 380.8 | 398.4 | 416.7 | 432.9 | 448.2 |
| SEM | 11.9 | 10.9 | 10.3 | 10.9 | 11.3 | 10.5 | 10.6 | 10.7 | 11.0 | 13.4 | 13.5 | 15.3 | 16.5 | 17.1 | 18.0 | 19.4 | 19.3 |
| DMD + 1E14 vg/kg (n = 13 until W + 13, then n = 6) | 178.2 | 209.4 | 204.3 | 210.5 | 213.0 | 220.1 | 225.3 | 232.5 | 244.5 | 288.2 | 329.6 | 356.6 | 375.9 | 395.7 | 413.4 | 431.5 | 448.6 |
| SEM | 9.6 | 7.9 | 7.5 | 7.7 | 7.5 | 7.4 | 7.0 | 7.5 | 9.9 | 9.6 | 11.7 | 12.3 | 12.2 | 12.4 | 12.7 | 13.8 | 13.3 |
| DMD + 1E14 vg/kg w/o HSA (n = 5 until W + 13) | 230.1 | 234.9 | 224.5 | 233.7 | 238.7 | 245.3 | 243.0 | 252.7 | 254.9 | 300.6 | 331.7 | 352.7 | 370.3 | 382.2 | 392.3 | 421.3 | 428.5 |
| SEM | 10.2 | 9.9 | 9.3 | 9.3 | 9.5 | 9.5 | 9.3 | 9.8 | 10.4 | 13.0 | 15.4 | 15.8 | 17.1 | 18.1 | 16.3 | 17.2 | 22.7 |
| DMD + 3E14 vg/kg (n = 10 until W +12, then n = 5) | 161.8 | 198.4 | 193.2 | 197.1 | 202.3 | 208.6 | 212.3 | 220.6 | 223.7 | 272.6 | 316.2 | 350.7 | 373.0 | 393.3 | 414.9 | 429.2 | 445.8 |
| SEM | 6.1 | 7.5 | 8.8 | 9.9 | 9.3 | 8.9 | 8.7 | 8.7 | 8.5 | 8.2 | 8.7 | 10.5 | 11.4 | 13.9 | 13.6 | 14.4 | 14.7 |

TABLE 3

| MEAN WEIGHTS (g) | W + 10 | W + 11 | W + 12 | W + 13 | W + 14 | W + 15 | W + 16 | W + 17 | W + 18 | W + 19 | W + 20 | W + 21 | W + 22 | W + 23 | W + 24 | W + 25 |
|---|---|---|---|---|---|---|---|---|---|---|---|---|---|---|---|---|
| WT + Buffer (n = 12 until W + 13, then n = 7) | 490.7 | 505.2 | 509.1 | 516.8 | 514.0 | 527.8 | 545.0 | 553.8 | 562.2 | 572.0 | 577.2 | 581.9 | 586.9 | 597.3 | 613.8 | 596.4 |
| SEM | 14.0 | 12.4 | 13.2 | 13.3 | 18.8 | 19.6 | 19.2 | 18.5 | 19.4 | 18.8 | 21.6 | 22.9 | 24.1 | 23.1 | 19.5 | 26.6 |
| DMD + Buffer (n = 10 until W + 13, then n = 4) | 423.0 | 435.2 | 428.2 | 430.3 | 430.2 | 440.6 | 452.7 | 461.8 | 464.8 | 463.5 | 464.9 | 463.0 | 465.8 | 467.1 | 467.4 | 444.8 |
| SEM | 22.8 | 21.8 | 17.4 | 21.6 | 30.5 | 32.3 | 37.7 | 39.4 | 39.2 | 42.7 | 43.6 | 46.5 | 46.6 | 46.6 | 46.6 | 34.9 |
| DMD + 1E13 vg/kg (n = 11 until W + 13, then n = 6) | 444.8 | 452.5 | 453.5 | 464.5 | 453.2 | 457.7 | 469.9 | 481.3 | 484.8 | 491.7 | 490.1 | 496.3 | 491.6 | 513.3 | 513.3 | 467.2 |
| SEM | 16.6 | 17.3 | 15.4 | 17.7 | 17.4 | 17.2 | 18.7 | 17.6 | 18.3 | 21.2 | 23.7 | 24.2 | 27.0 | 35.8 | 35.8 | 36.4 |
| DMD + 3E13 vg/kg (n = 11 until W + 13, then n = 5) | 458.2 | 467.4 | 469.7 | 476.1 | 465.8 | 478.5 | 489.1 | 496.9 | 505.2 | 510.7 | 512.6 | 517.4 | 519.7 | 525.7 | 525.7 | 507.0 |
| SEM | 20.2 | 19.4 | 20.7 | 23.1 | 28.9 | 31.4 | 34.2 | 34.2 | 35.3 | 39.4 | 38.9 | 38.3 | 37.7 | 35.6 | 35.6 | 30.4 |
| DMD + 1E14 vg/kg (n = 13 until W + 13, then n = 6) | 459.3 | 472.7 | 478.0 | 483.2 | 482.1 | 492.5 | 504.5 | 513.6 | 525.0 | 532.7 | 530.6 | 541.9 | 545.9 | 539.7 | 539.7 | 551.3 |
| SEM | 12.7 | 12.3 | 11.8 | 12.2 | 13.7 | 14.1 | 14.3 | 13.0 | 14.8 | 15.4 | 13.8 | 14.8 | 15.4 | 9.2 | 9.2 | 15.1 |
| DMD + 1E14 vg/kg w/o HSA (n = 5 until W + 13) | 430.2 | 464.5 | 469.1 | 470.3 | N/A | N/A | N/A | N/A | N/A | N/A | N/A | N/A | N/A | N/A | N/A | N/A |

TABLE 3-continued

| MEAN WEIGHTS (g) | W + 10 | W + 11 | W + 12 | W + 13 | W + 14 | W + 15 | W + 16 | W + 17 | W + 18 | W + 19 | W + 20 | W + 21 | W + 22 | W + 23 | W + 24 | W + 25 |
|---|---|---|---|---|---|---|---|---|---|---|---|---|---|---|---|---|
| SEM | 20.4 | 18.0 | 18.7 | 18.1 | N/A | N/A | N/A | N/A | N/A | N/A | N/A | N/A | N/A | N/A | N/A | N/A |
| DMD + 3E14 vg/kg (n = 10 until W + 13, then n = 5) | 457.4 | 475.3 | 483.9 | 502.1 | 515.9 | 519.1 | 532.8 | 547.1 | 552.6 | 558.0 | 558.1 | 565.9 | 566.4 | 577.6 | 577.6 | 566.9 |
| SEM | 14.8 | 15.0 | 15.6 | 27.5 | 26.7 | 24.9 | 27.2 | 26.5 | 27.4 | 27.2 | 27.3 | 27.3 | 28.8 | 29.2 | 29.2 | 28.5 |

Quantification of Vector Transduction and RNA and Protein Expression in Dmd$^{mdx}$ Rats Treated with AAV9.hCK.Hopti-Dys3978.spA Vector Materials and Methods Standard molecular biology techniques were used to quantitate the transgene copy number by quantitative PCR (qPCR), relative expression levels of the mini-dystrophin mRNA transcripts by reverse transcriptase qPCR (RT-qPCR), and the amount of mini-dystrophin protein expression qualitatively by Western blot analysis.

For qPCR, genomic DNA (gDNA) was purified from tissues using the Gentra Puregene kit from Qiagen. Samples were then analyzed using a StepOne Plus™ Real Time PCR System (Applied Biosystems®, Thermo Fisher Scientific) using 50 ng gDNA in duplicate. All reactions were performed in duplex in a final volume of 20 µL containing template DNA, Premix Ex taq (Ozyme), 0.3 µL of ROX reference Dye (Ozyme), 0.2 µmol/L of each primer and 0.1 µmol/L of Taqman® probe.

Vector copy numbers were determined using primers and probe designed to amplify a region of the mini-dystrophin transgene:

```
Forward:
                                      SEQ ID NO: 19
5'-CCAACAAAGTGCCCTACTACATC-3'

Reverse:
                                      SEQ ID NO: 20
5'-GGTTGTGCTGGTCCAGGGCGT-3'

Probe:
                                      SEQ ID NO: 21
5'-FAM-CCGAGCTGTATCAGAGCCTGGCC-TAMRA-3'
```

Endogenous gDNA copy numbers were determined using primers and probe designed to amplify the rat HPRT1 gene:

```
Forward:
                                      SEQ ID NO: 22
5'-GCGAAAGTGGAAAAGCCAAGT-3'

Reverse:
                                      SEQ ID NO: 23
5'-GCCACATCAACAGGACTCTTGTAG-3'

Probe:
                                      SEQ ID NO: 24
5'-JOE-CAAAGCCTAAAAGACAGCGGCAAGTTGAAT-TAMRA-3'
```

For each sample, threshold cycle (Ct) values were compared with those obtained with different dilutions of linearized standard plasmids (containing either the mini-dystrophin expression cassette or the rat HPRT1 gene). The absence of qPCR inhibition in the presence of gDNA was checked by analyzing 50 ng of gDNA extracted from tissues samples from a control animal, spiked with different dilutions of standard plasmid. Duplex qPCR (amplification of the 2 sequences in the same reaction) was used and results were expressed in vector genome per diploid genome (vg/dg). The sensitivity of the test was 0.003 vg/dg.

For RT-qPCR, total RNA was extracted from tissue samples with TRIzol® reagent (Thermo Fisher Scientific), and then treated with RNAse-free DNAse I from the TURBO DNA-free kit (Thermo Fischer Scientific). Total RNA (500 ng) was reverse transcribed using random primers (Thermo Fischer Scientific) and M-MLV reverse transcriptase (Thermo Fischer Scientific) in a final volume of 25 µL. Duplex qPCR analysis was then performed 1/15-diluted cDNA using the same mini-dystrophin and rat HPRT1 specific primers and probes as for the quantification of transgene copy numbers by qPCR. The absence of qPCR inhibition in the presence of cDNA was checked by analyzing cDNA obtained from tissues samples from a control animal spiked with different dilutions of standard plasmid. For each RNA sample, Ct values were compared with those obtained with different dilutions of standard plasmids (containing either the mini-dystrophin expression cassette or the rat HPRT1 gene). Results were expressed in relative quantities (RQ):

$$RQ=2^{-\Delta Ct}=2^{-(Ct\ target-Ct\ endogenous\ control)}$$

For each RNA sample, the absence of DNA contamination was also confirmed by analysis of "cDNA-like samples" obtained without addition of reverse transcriptase in the reaction mix.

For Western blot analysis of expressed protein levels, total proteins were extracted from tissue samples using RIPA buffer containing a protease inhibitor cocktail (Sigma-Aldrich). Protein extracts, 50 µg for biceps femoris, heart and diaphragm, or 100 µg for liver, were loaded on a NuPAGE® Novex 3-8% Tris Acetate gel and analyzed using the NuPAGE® large protein blotting kit (Thermo Fischer Scientific). A final concentration of 200 mM DTT was used to reduce proteins before loading. Membranes were then blocked in 5% skim milk, 1% NP40 (Sigma-Aldrich) in TBST (tris-buffered saline, 0.1% Tween 20) and hybridized with an anti-dystrophin antibody specific for exons 10 and 11 of the dystrophin protein (1:100, MANEX 1011C monoclonal antibody) and with a secondary anti-mouse IgG HRP-conjugated antibody (1:2000, Dako). For protein loading control, the same membrane was also hybridized with an anti-rat alpha-tubulin antibody (1:10000, Sigma) and with a secondary anti-mouse IgG HRP-conjugated antibody (1:2000, Dako). Immunoblots were visualized by ECL Chemiluminescent analysis system (Thermo Fisher Scientific).

Human Mini-Dystrophin Transgene Copy Numbers at 3 and 6 Months Post-Injection

Results of testing for transgene copy numbers (as vector genomes per diploid genome (vg/dg)) in whole blood, spleen, heart, biceps femoris, pectoralis, diaphragm, and liver in Dmd$^{mdx}$ rats treated with vector and vehicle, and in WT rats administered vehicle only are described in the tables below. Data at 3 months post-injection is provided in Table 4, and at 6 months post-injection is provided in Table 5. Data are the mean of results from individual test animals.

TABLE 4

| 3 Months Post-Injection | | | | | | |
|---|---|---|---|---|---|---|
| | DMD + vehicle | WT + vehicle | DMD + $1 \times 10^{13}$ vg/kg | DMD + $3 \times 10^{13}$ vg/kg | DMD + $1 \times 10^{14}$ vg/kg | DMD + $3 \times 10^{14}$ vg/kg |
| Whole blood | <0.002 | <0.002 | <0.002 | <0.002 | <0.002 | <0.002 |
| Spleen | <0.002 | <0.002 | <0.002 | 0.010 | 0.005 | 0.013 |
| Heart (basal part) | <0.002 | <0.002 | 0.090 | 0.270 | 0.670 | 4.350 |
| Biceps femoris | <0.002 | <0.002 | <0.002 | 0.070 | 0.260 | 1.700 |
| Pectoralis | <0.002 | <0.002 | 0.010 | 0.030 | 0.400 | 0.760 |
| Diaphragm | <0.002 | <0.002 | 0.003 | 0.030 | 2.410 | 2.810 |
| Liver (central lobe) | <0.002 | <0.002 | 0.830 | 5.460 | 30.780 | 112.880 |

TABLE 5

| 6 Months Post-Injection | | | | | | |
|---|---|---|---|---|---|---|
| | DMD + vehicle | WT + vehicle | DMD + $1 \times 10^{13}$ vg/kg | DMD + $3 \times 10^{13}$ vg/kg | DMD + $1 \times 10^{14}$ vg/kg | DMD + $3 \times 10^{14}$ vg/kg |
| Whole blood | <0.002 | <0.002 | <0.002 | <0.002 | <0.002 | <0.002 |
| Spleen | <0.002 | <0.002 | <0.002 | <0.002 | <0.002 | 0.010 |
| Heart (basal part) | <0.002 | <0.002 | 0.160 | 0.140 | 1.460 | 5.380 |
| Biceps femoris | <0.002 | <0.002 | 0.009 | 0.020 | 0.390 | 1.400 |
| Pectoralis | <0.002 | <0.002 | 0.006 | 0.020 | 0.530 | 0.800 |
| Diaphragm | <0.002 | <0.002 | 0.010 | 0.010 | 4.850 | 1.270 |
| Liver (central lobe) | <0.002 | <0.002 | 1.080 | 8.130 | 30.490 | 82.230 |

No qPCR signal was detected in the $Dmd^{mdx}$ or WT rats injected with vehicle only, confirming that these animals had not received any vector, and no qPCR signal was detected in whole blood at 3 and 6 months post-injection.

Mini-dystrophin DNA was detected in $Dmd^{mdx}$ rats that had been injected with vector at both 3 and 6 months post-injection. Transgene copy numbers in the tissues under study followed a pattern of prevalence of liver>heart>biceps femoris diaphragm pectoralis>spleen. Of the tissues analyzed, liver was by far the most efficiently transduced, with vector copy numbers reaching up to an average of 80-110 vg/dg in rats administered with $3\times10^{14}$ vg/kg vector. Vector copy numbers in liver were 7-45 fold higher than in heart and 40-300 fold higher than in biceps femoris, diaphragm, or pectoralis muscles. In heart, vector copy numbers averaged about 1.0 vg/dg in rats dosed with $1\times10^{14}$ vg/kg vector and about 5.0 vg/dg in rats dosed with $3\times10^{14}$ vg/kg vector. At a dose of $1\times10^{14}$ vg/kg, transgene copy numbers in biceps femoris and pectoralis were similar and never exceeded about 0.5 vg/dg. When the vector dose increased to $3\times10^{14}$ vg/kg, the average transgene copy number increased to about 1.2 vg/dg. The data was particularly variable for diaphragm due to certain unusually high results among 4 animals that had received the two highest dose levels of vector, in which the transgene copy numbers ranged from about 9-15 vg/dg. If these outlying data points are excluded, then the transduction efficiency of diaphragm is relatively low at both the 3 and 6 month time points, with transgene copy numbers averaging about 0.2-0.4 vg/dg at the $1\times10^{14}$ vg/kg dose and about 1.05-1.3 vg/dg at the $3\times10^{14}$ vg/kg dose.

Human Mini-Dystrophin mRNA Expression at 3 and 6 Months Post-Injection

Two to four animals per treatment arm were randomly chosen for analysis by RT-qPCR to quantify levels of human mini-dystrophin mRNA transcripts in samples of biceps femoris, diaphragm, heart, spleen, and liver obtained at sacrifice. The results obtained from test animals sacrificed at 3 months and 6 months post-injection are provided in Table 6 and Table 7, respectively. Data is expressed in relative quantities (RQ) of mini-dystrophin mRNA relative to mRNA from the rat HPRT1 gene.

No transcripts were detected in any tissue from animals in the negative control arms (WT rats and $Dmd^{mdx}$ rats treated with vehicle), or in spleen of animals treated with vector, regardless of dose. In all other tissues examined, vector-derived transcripts were detected, the levels of which tended to increase in a dose-responsive manner, although with some variability in the data. Transcript levels in the tissues followed the pattern biceps femoris>heart diaphragm>liver. As discussed above, liver was the most transduced tissue among those sampled, with vector copy numbers varying about 60-130 fold higher than in biceps femoris muscle. Despite this, the level of mini-dystrophin mRNA in liver was about 5-15 fold lower than in biceps femoris, evidence of the highly muscle-specific activity of the promoter used in the vectors.

TABLE 6

| 3 Months Post-Injection | | | | | | | | | | | | | | |
|---|---|---|---|---|---|---|---|---|---|---|---|---|---|---|
| | Rat 1 RQ DMD + vehicle | Rat 2 RQ DMD + vehicle | Rat 3 RQ WT + vehicle | Rat 4 RQ WT + vehicle | Rat 5 RQ DMD + $1 \times 10^{13}$ vg/kg | Rat 6 RQ DMD + $1 \times 10^{13}$ vg/kg | Rat 7 RQ DMD + $3 \times 10^{13}$ vg/kg | Rat 8 RQ DMD + $3 \times 10^{13}$ vg/kg | Rat 9 RQ DMD + $1 \times 10^{14}$ vg/kg | Rat 10 RQ DMD + $1 \times 10^{14}$ vg/kg | Rat 11 RQ DMD + $1 \times 10^{14}$ vg/kg | Rat 12 RQ DMD + $1 \times 10^{14}$ vg/kg | Rat 13 RQ DMD + $3 \times 10^{14}$ vg/kg | Rat 14 RQ DMD + $3 \times 10^{14}$ vg/kg |
| Spleen | <0.03 | <0.03 | <0.03 | <0.03 | <0.03 | <0.03 | <0.03 | <0.03 | <0.03 | <0.03 | <0.03 | <0.03 | <0.03 | <0.03 |
| Biceps femoris | <0.03 | <0.03 | <0.03 | <0.03 | 2.6 | 0.9 | 7.8 | 7.2 | 23.8 | 18.4 | 40.9 | 79.6 | 33.1 | 33.3 |
| Heart (basal part) | <0.03 | <0.03 | <0.03 | <0.03 | 1.7 | 1.8 | 3.3 | 1.4 | 4.5 | 4.5 | 3.2 | 6.5 | 9.6 | 12.4 |
| Diaphragm | <0.03 | <0.03 | <0.03 | <0.03 | 0.2 | 0.3 | 1.6 | 2.7 | 13.6 | 5.1 | 4.2 | 23.2 | 9.7 | 18.8 |
| Liver (central lobe) | <0.03 | <0.03 | <0.03 | <0.03 | 0.1 | 0.2 | 0.7 | 0.8 | 2.2 | 4.7 | 3.8 | 0.8 | 7.4 | 3.3 |

TABLE 7

| 6 Months Post-Injection | | | | | | | | | | | | |
|---|---|---|---|---|---|---|---|---|---|---|---|---|
| | Rat 15 RQ DMD + vehicle | Rat 16 RQ DMD + vehicle | Rat 17 RQ WT + vehicle | Rat 18 RQ WT + vehicle | Rat 19 RQ DMD + $1 \times 10^{13}$ vg/kg | Rat 20 RQ DMD + $1 \times 10^{13}$ vg/kg | Rat 21 RQ DMD + $3 \times 10^{13}$ vg/kg | Rat 22 RQ DMD + $3 \times 10^{13}$ vg/kg | Rat 23 RQ DMD + $1 \times 10^{14}$ vg/kg | Rat 24 RQ DMD + $1 \times 10^{14}$ vg/kg | Rat 25 RQ DMD + $3 \times 10^{14}$ vg/kg | Rat 26 RQ DMD + $3 \times 10^{14}$ vg/kg |
| Spleen | <0.03 | <0.03 | <0.03 | <0.03 | <0.03 | <0.03 | <0.03 | <0.03 | <0.03 | <0.03 | <0.03 | <0.03 |
| Biceps femoris | <0.03 | <0.03 | <0.03 | <0.03 | 0.6 | 0.3 | 3.0 | 8.9 | 15.8 | 24.2 | 64.0 | 19.7 |
| Heart (basal part) | <0.03 | <0.03 | <0.03 | <0.03 | 1.2 | 1.6 | 1.3 | 1.4 | 3.7 | 4.3 | 9.2 | 6.1 |
| Diaphragm | <0.03 | <0.03 | <0.03 | <0.03 | 0.5 | 0.1 | 1.4 | 1.1 | 4.5 | 8.0 | 19.7 | 17.1 |
| Liver (central lobe) | <0.03 | <0.03 | <0.03 | <0.03 | 0.1 | 0.1 | 0.2 | 0.5 | 0.7 | 0.6 | 4.6 | 2.1 |

Human Mini-Dystrophin Protein Expression at 3 and 6 Months Post-Injection

The same animals randomly selected for analysis to determine human mini-dystrophin mRNA levels were also analyzed to determine mini-dystrophin protein levels using Western blot. No mini-dystrophin protein was detected in any tissue from animals in the negative control arms (WT rats and $Dmd^{mdx}$ rats treated with vehicle). At both the 3 and 6 month time points, mini-dystrophin protein was detected in biceps femoris, heart and diaphragm of $Dmd^{mdx}$ rats dosed with vector. At the lowest dose tested ($1 \times 10^{13}$ vg/kg), mini-dystrophin protein was detected less frequently in the tissue samples compared to rats dosed with vector at higher levels. These results are summarized qualitatively in Table 8.

TABLE 8

| Rat | Time | Dose | Biceps femoris | Heart (basal part) | Diaphragm |
|---|---|---|---|---|---|
| 5 | 3 mo | $1 \times 10^{13}$ vg/kg | + | + | + |
| 6 | 3 mo | $1 \times 10^{13}$ vg/kg | − | + | − |
| 7 | 3 mo | $3 \times 10^{13}$ vg/kg | + | + | + |
| 8 | 3 mo | $3 \times 10^{13}$ vg/kg | + | + | + |
| 9 | 3 mo | $1 \times 10^{14}$ vg/kg | + | + | + |
| 10 | 3 mo | $1 \times 10^{14}$ vg/kg | + | + | + |
| 11 | 3 mo | $1 \times 10^{14}$ vg/kg | + | + | + |
| 12 | 3 mo | $1 \times 10^{14}$ vg/kg | + | − | + |
| 13 | 3 mo | $3 \times 10^{14}$ vg/kg | + | + | + |
| 14 | 3 mo | $3 \times 10^{14}$ vg/kg | + | + | + |
| 19 | 6 mo | $1 \times 10^{13}$ vg/kg | + | + | − |
| 20 | 6 mo | $1 \times 10^{13}$ vg/kg | − | + | − |

TABLE 8-continued

| Rat | Time | Dose | Biceps femoris | Heart (basal part) | Diaphragm |
|---|---|---|---|---|---|
| 21 | 6 mo | $3 \times 10^{13}$ vg/kg | + | + | + |
| 22 | 6 mo | $3 \times 10^{13}$ vg/kg | + | + | − |
| 23 | 6 mo | $1 \times 10^{14}$ vg/kg | + | + | + |
| 24 | 6 mo | $1 \times 10^{14}$ vg/kg | + | + | + |
| 25 | 6 mo | $3 \times 10^{14}$ vg/kg | + | + | + |
| 26 | 6 mo | $3 \times 10^{14}$ vg/kg | + | + | + |

There was a positive correlation between the amount of protein detected by Western blot and the vector dose, as well as the amount of mini-dystrophin mRNA in the same tissue samples. A mini-dystrophin mRNA RQ of approximately 1.5 was required to permit detection of the protein. Consistent with the low levels of mini-dystrophin transcript measured in liver, no mini-dystrophin protein was detected in this tissue, even at the highest vector dose used.

Histopathological Assessment

Immediately after sacrifice of WT and $Dmd^{mdx}$ rats, tissue samples were obtained for histopathological and immunocytochemical analysis.

Materials and Methods

Tissue samples vehicle treated WT rats, vehicle and vector treated $Dmd^{mdx}$ rats were obtained during whole necropsy evaluation at 3 and 6 months post-injection. Samples were also obtained from untreated $Dmd^{mdx}$ rats sacrificed at 7-9 weeks of age to serve as a baseline comparison. Tissues were immediately fixed in formalin for histopathology or snap frozen for immunohistochemistry (immunolabeling) and stored until processing. For histopathology, tissue samples were fixed in 10% neutral buffered formalin, embedded in paraffin wax, and sectioned (5 μm) before staining with hematoxylin eosin saffron (HES) stain. An additional section of paraffin embedded heart tissue was stained to visualize collagen with picrosirius red F3B (Sigma-Aldrich Chimie SARL, Lyon, FR). To identify dystrophin and connective tissue by immunolabeling, samples were frozen and sectioned (8 μm). A mouse monoclonal antibody, NCL-DYSB (1:50, Novocastra Laboratories, Newcastle on Tyne, UK), that specifically binds to rat dystrophin as well as human mini-dystrophin opti-Dys3978 was used in immunolabeling studies to visualize dystrophin protein. Alexa Fluor 555 wheat germ agglutinin (WGA) conjugate (1:500, Molecular Probes, Eugene, Oreg.) was used to visualize connective tissue. Nuclei were stained with DRAQS (1:1000, BioStatus Ltd, Shepshed, UK). Necropsies and histological examination were performed blinded.

Quantification of the picrosirius positive areas in heart sections was performed using Nikon Imaging Software (Nikon, Champigny sur Marne, France). Quantification of DYSB positive fibers and WGA positive areas was performed using ImageJ open source image processing software (v 2.0.0-rc-49/1.51a).

Results

Figure 38A:
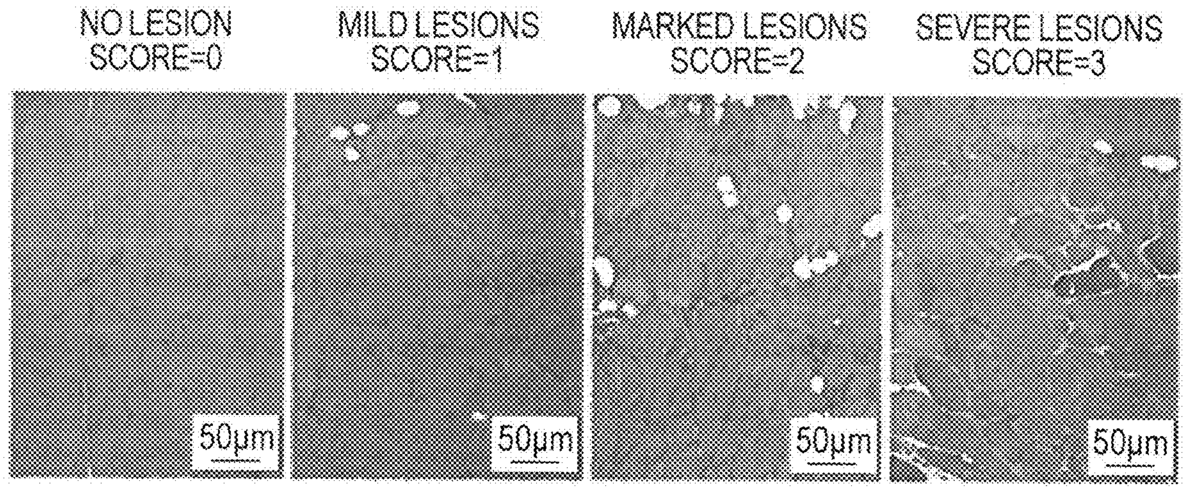
FIG. 38A provides exemplary photomicrographs of skeletal muscle from Dmd$^{mdx}$ rats stained for histological examination illustrating a semi-quantitative scoring scheme used to estimate the degree of severity of muscle lesions caused by the absence of dystrophin. In skeletal muscle, such as that illustrated, a score of 0 corresponded to the absence of lesions; 1 corresponded to the presence of some regenerative activity as evidenced by centronucleated fibers and small foci of regeneration; 2 corresponded to the presence of degenerated fibers, isolated or in small clusters; and 3 corresponded to tissue remodeling and fiber replacement by fibrotic or adipose tissue. Scoring for heart used different criteria as explained in the text.

Histopathological Analysis of DMD Lesions in Muscle at 3 and 6 Months Post-Injection Tissue samples stained for histology were examined microscopically and lesions related to the DMD phenotype systematically recorded. Lesions in skeletal and cardiac muscle were scored semi-quantitatively as illustrated in FIG. 38A. In skeletal muscle (biceps femoris, pectoralis and diaphragm), a score of 0 corresponded to absence of significant lesion; a score of 1 corresponded to the presence of some regeneration activity as evidenced by centro-nucleated fibers and regeneration foci; a score of 2 corresponded to degenerative fibers, isolated or in small clusters; and a score of 3 corresponded to tissue remodeling and fiber replacement by fibrotic or adipose tissue. In the heart, scoring was based on the intensity of fibrosis (score of 1 for lower, and score of 2 for higher) and the presence of degenerative fibers (score of 3). A total lesion score for each rat was calculated as the mean of the animal's scores for biceps femoris, pectoralis, diaphragm and cardiac muscles. Lesion scores for individual rats within each treatment arm were also averaged.

Figure 38B:
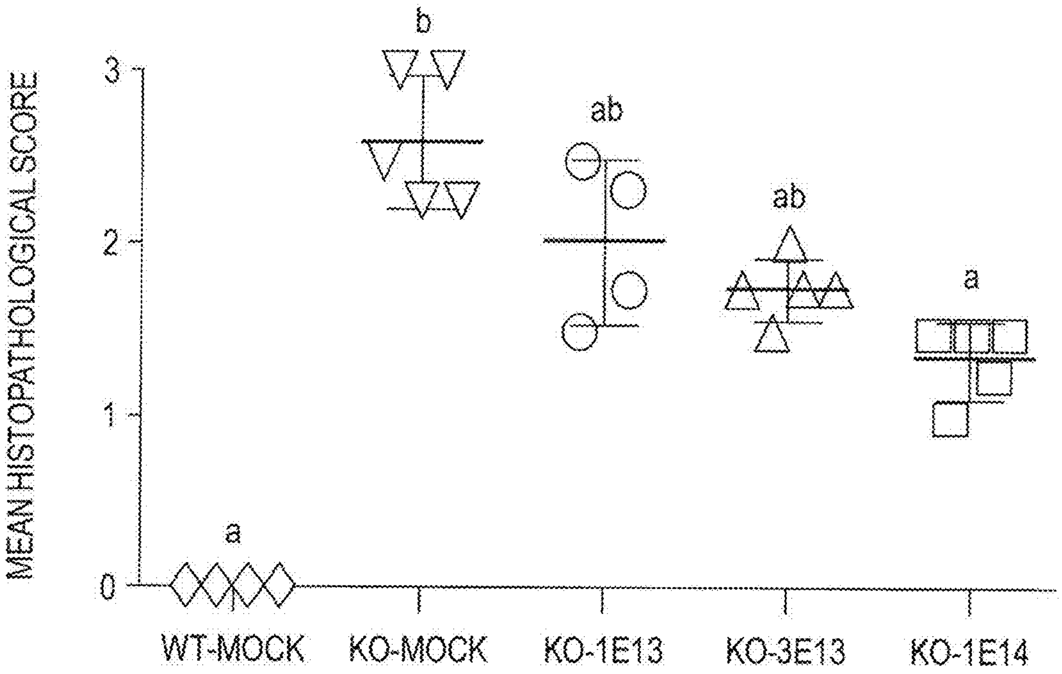
FIG. 38B shows total DMD lesion scores for rats (that is, average of lesion subscores for biceps femoris, pectoralis, diaphragm and cardiac muscles) at 3 months post-injection are shown, individually as well as the mean among all rats in each treatment arm, and compared to show a vector dose-responsive reduction in lesion score. "WT mock" refers to WT rats treated with vehicle, "KO mock" refers to Dmd$^{mdx}$ rats treated with vehicle, "KO 1E13", "3E13", and "1E14", refer to Dmd$^{mdx}$ rats treated with the indicated doses of AAV9.hCK.Hopti-Dys3978.spA vector in vg/kg. Letters above bars indicate that the underlying data is not statistically different from other bars over which the same letters appear. Conversely, bars over which different letters appear are statistically different from each other. Statistics were calculated using the Kruskal-Wallis and Dunn's tests.

Total lesion scores of individual rats and averages grouped by treatment arm at 3 months post-injection are shown in FIG. 38B, in which WT mock refers to WT rats treated with vehicle, for which lesion scores were 0. KO mock refers to $Dmd^{mdx}$ rats treated with vehicle, whereas KO 1E13, 3E13, and 1E14, refer to $Dmd^{mdx}$ rats treated with the indicated doses (i.e., $1\times10^{13}$, $3\times10^{13}$, and $1\times10^{14}$, respectively) of vector in vg/kg. As can be seen, the prevalence of muscular lesions associated with the dystrophic phenotype in $Dmd^{mdx}$ rats was reduced by vector treatment in a dose-responsive manner.

Statistical analysis of lesion scores (by multiple paired comparisons using Dunn's test) revealed the following differences among treatment arms. In samples of biceps femoris muscles at 3 months post-injection, there were no significant differences in lesion scores between WT rats treated with vehicle and $Dmd^{mdx}$ rats treated with vector at the two highest doses ($1\times10^{14}$ and $3\times10^{14}$ vg/kg) and at 6 months post-injection, there were no significant differences between WT treated with vehicle and $Dmd^{mdx}$ rats treated with vector at any of the four doses tested. In samples of pectoralis muscle and diaphragm at 3 months post-injection there were no significant differences in lesion scores between vehicle treated WT rats and $Dmd^{mdx}$ rats treated with the three highest vector doses tested ($3\times10^{13}$, $1\times10^{14}$ and $3\times10^{14}$ vg/kg) and at 6 months post-injection, there were no significant differences in scores between WT rats treated with vehicle and $Dmd^{mdx}$ rats treated with all four vector doses. Finally, in heart muscle, at both time points, there were no significant differences in lesion scores between vehicle treated WT rats and $Dmd^{mdx}$ rats treated with all four doses of vector.

Histomorphometry at 3 and 6 Months Post-Injection

After labeling tissue samples with the DYSB antibody, which specifically binds to both rat dystrophin and the human mini-dystrophin expressed from the vector, the percentage of positively stained muscle fibers in three randomly selected microscopic fields from each rat was calculated for biceps femoris, diaphragm, and cardiac muscles. In addition, the area in three randomly selected microscopic fields staining positively with WGA conjugate was calculated to determine the extent of connective tissue fibrosis in frozen tissue samples from biceps femoris and diaphragm. In a related analysis, the amount of connective tissue (collagen) in transverse sections of heart was determined by quantifying the area staining positive with picrosirius red in histological preparations. Results from these studies are provided in FIGS. 39A-39C, FIGS. 40A-40C, and FIGS. 41A-41C.

Figure 39A:
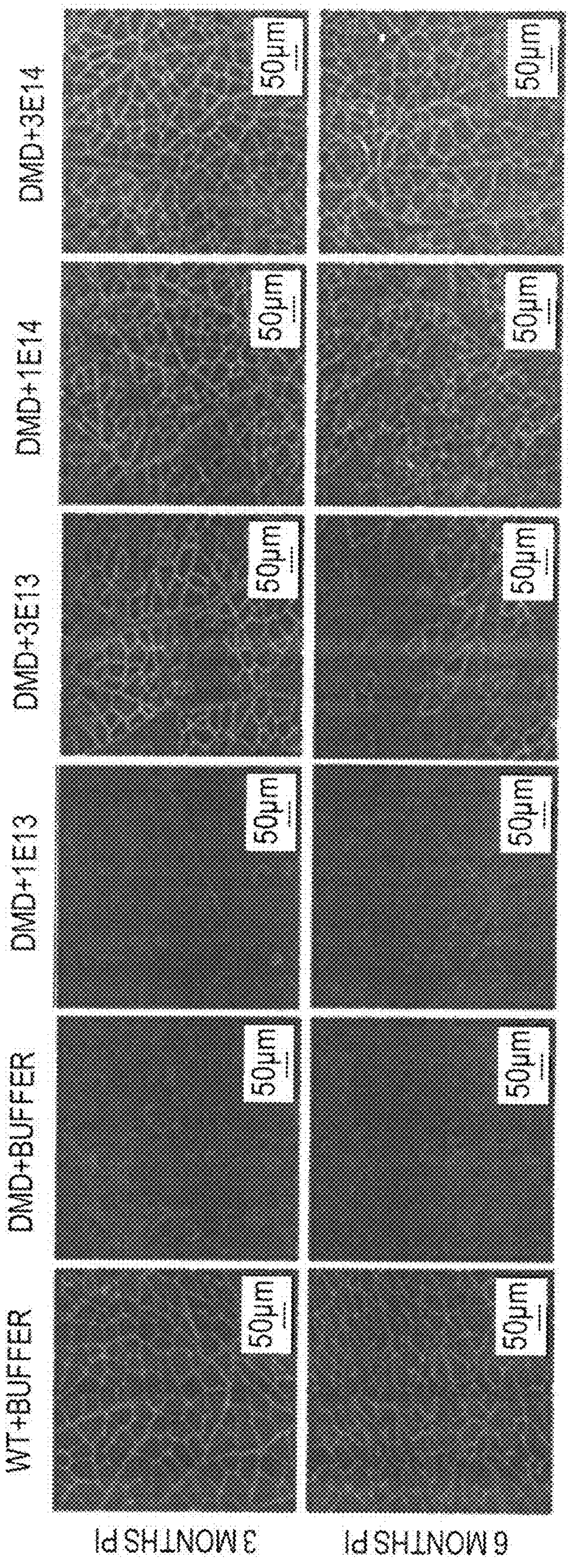
FIG. 39A provides representative sections from biceps femoris muscle samples from Dmd$^{mdx}$ rats treated with increasing doses of AAV9.hCK.Hopti-Dys3978.spA vector, and negative controls. Samples were dual labeled with an antibody that specifically binds to full length rat dystrophin and human mini-dystrophin, and wheat germ agglutinin conjugate which stains connective tissue. Top panel are micrographs from animals sacrificed at 3 months post-injection. Bottom panel are micrographs from animals sacrificed at 6 months post-injection.
Figure 39B:
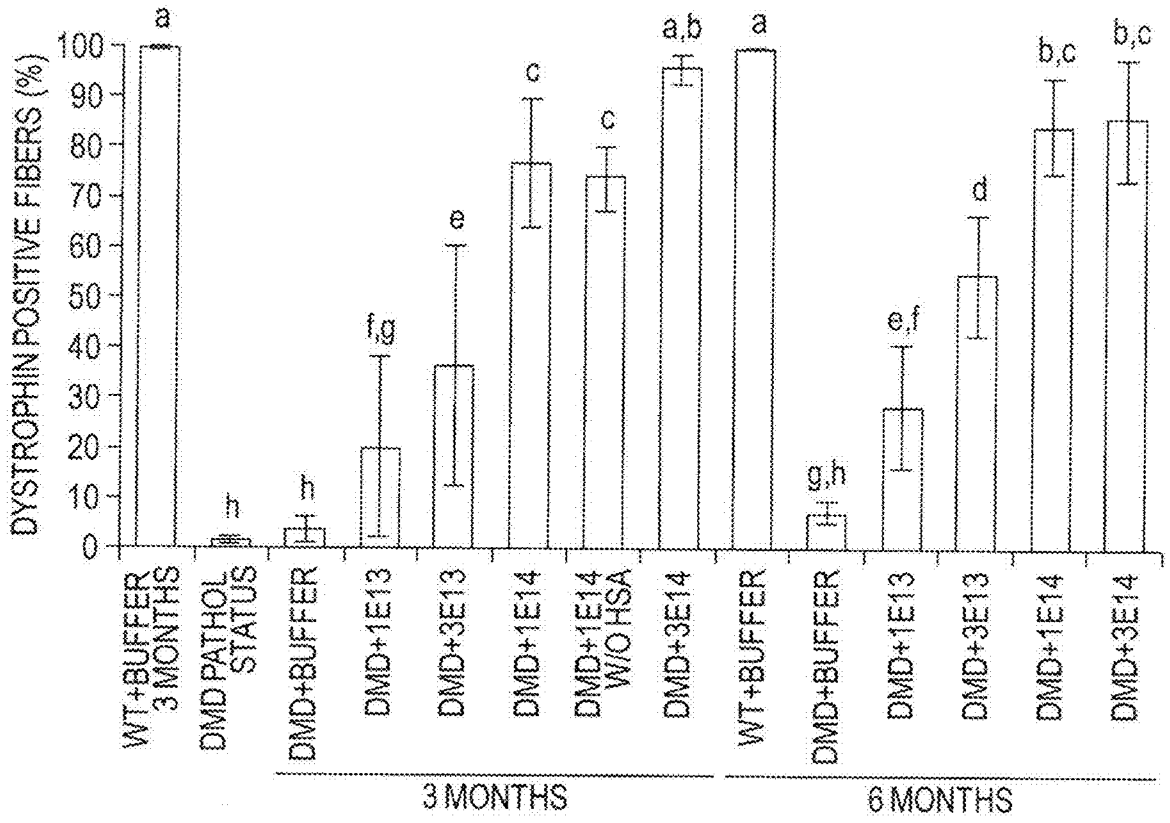
FIG. 39B provides percent fibers in random sections from biceps femoris muscle samples from Dmd$^{mdx}$ rats treated with increasing doses of AAV9.hCK.Hopti-Dys3978.spA vector, and negative controls, that stained positive for presence of dystrophin protein. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.
Figure 39C:
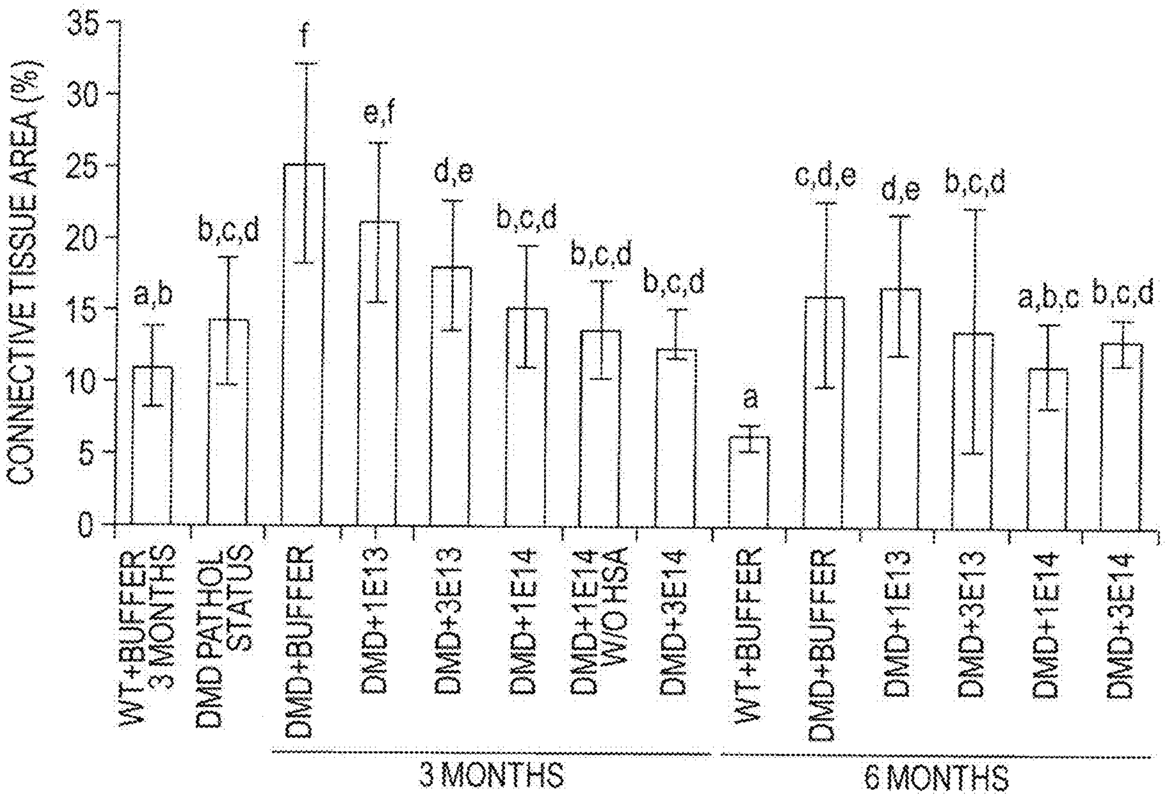
FIG. 39C provides percent area in random sections of biceps femoris muscle samples from Dmd$^{mdx}$ rats treated with increasing doses of AAV9.hCK.Hopti-Dys3978.spA vector, and negative controls, that stained positive for presence of connective tissue. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

FIG. 39A shows representative photomicrographs of stained tissue sections from biceps femoris muscle samples from WT rats treated with vehicle (WT+buffer), $Dmd^{mdx}$ rats treated with vehicle (DMD+buffer), and $Dmd^{mdx}$ rats treated with vector at increasing doses of $1\times10^{13}$, $3\times10^{13}$, $1\times10^{14}$ and $3\times10^{14}$ vg/kg (DMD+1E13, 3E13, 1E14, and 3E14, respectively). The top panel of photos are from samples taken at 3 months post-injection and the bottom panel are from samples taken at 6 months post-injection. FIG. 39B is a graph showing the percentage of dystrophin positive fibers in biceps femoris muscle samples from WT rats and $Dmd^{mdx}$ rats, each treated with vehicle, and $Dmd^{mdx}$ rats treated with increasing doses of vector, at 3 and 6 month time points. Also included are results from untreated $Dmd^{mdx}$ rats 7-9 weeks of age ("DMD pathol status"). FIG. 39C is a graph showing the percentage area occupied by connective tissue (as a measure of fibrosis) in biceps femoris muscle samples from similarly treated WT and $Dmd^{mdx}$ rats at 3 and 6 month time points, and untreated $Dmd^{mdx}$ rats 7-9 weeks of age. In the graphs, the same letter over error bars indicates no statistically significant difference between the data, whereas no common letter indicates there is a significant difference (for example, two bars both having an "a" above them would not be significantly different from each other).

Figure 40A:
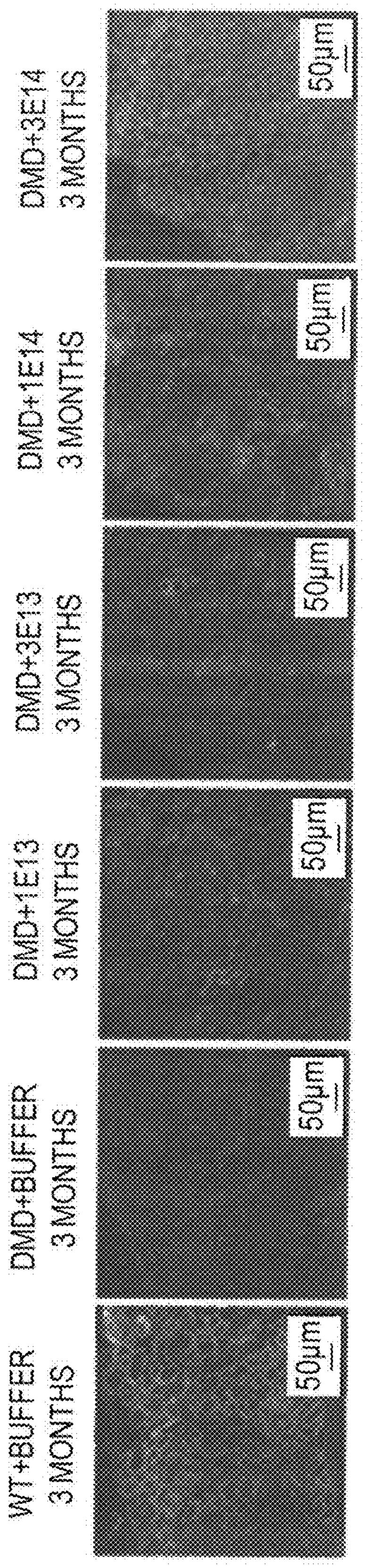
FIG. 40A provides representative sections from diaphragm muscle samples from Dmd$^{mdx}$ rats treated with increasing doses of AAV9.hCK.Hopti-Dys3978.spA vector, and negative controls, sacrificed at 3 months post-injection. Samples were dual labeled with an antibody that specifically binds to full length rat dystrophin and human mini-dystrophin, and wheat germ agglutinin conjugate which stains connective tissue.
Figure 40B:
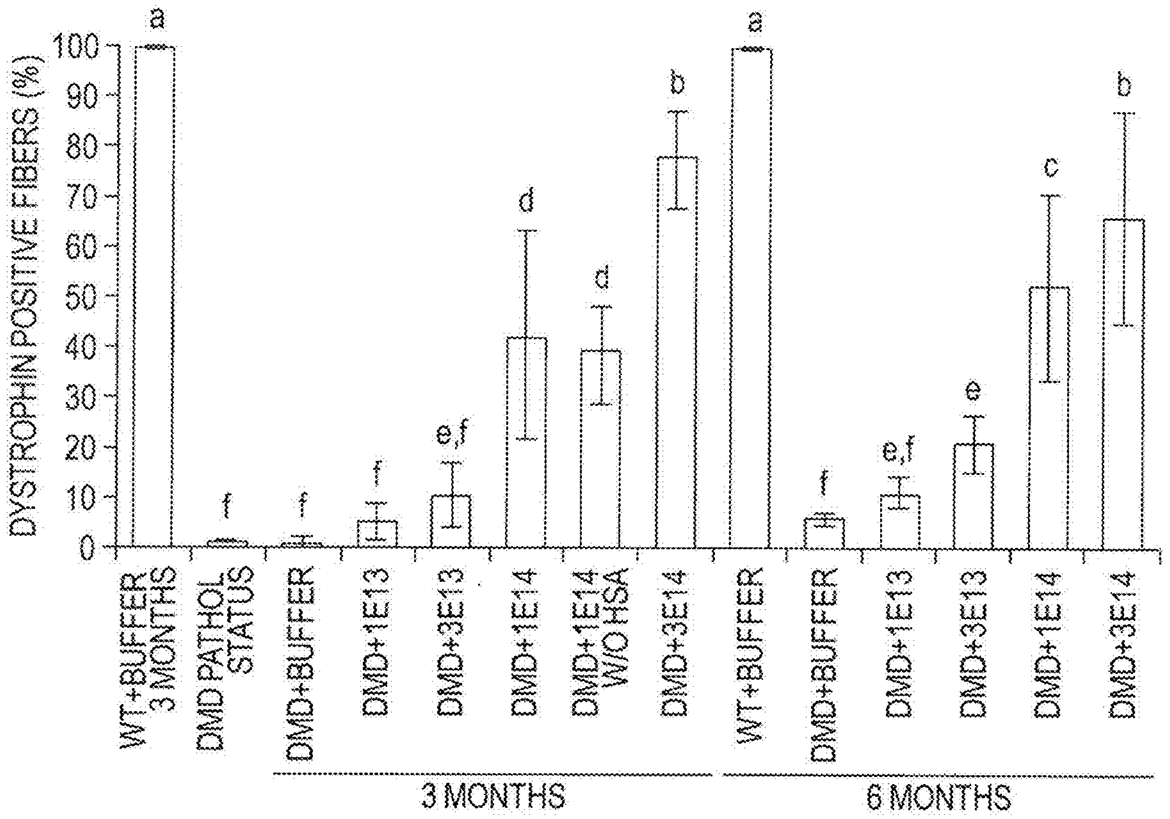
FIG. 40B provides percent fibers in random sections from diaphragm muscle samples from Dmd$^{mdx}$ rats treated with increasing doses of AAV9.hCK.Hopti-Dys3978.spA vector, and negative controls, that stained positive for presence of dystrophin. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.
Figure 40C:
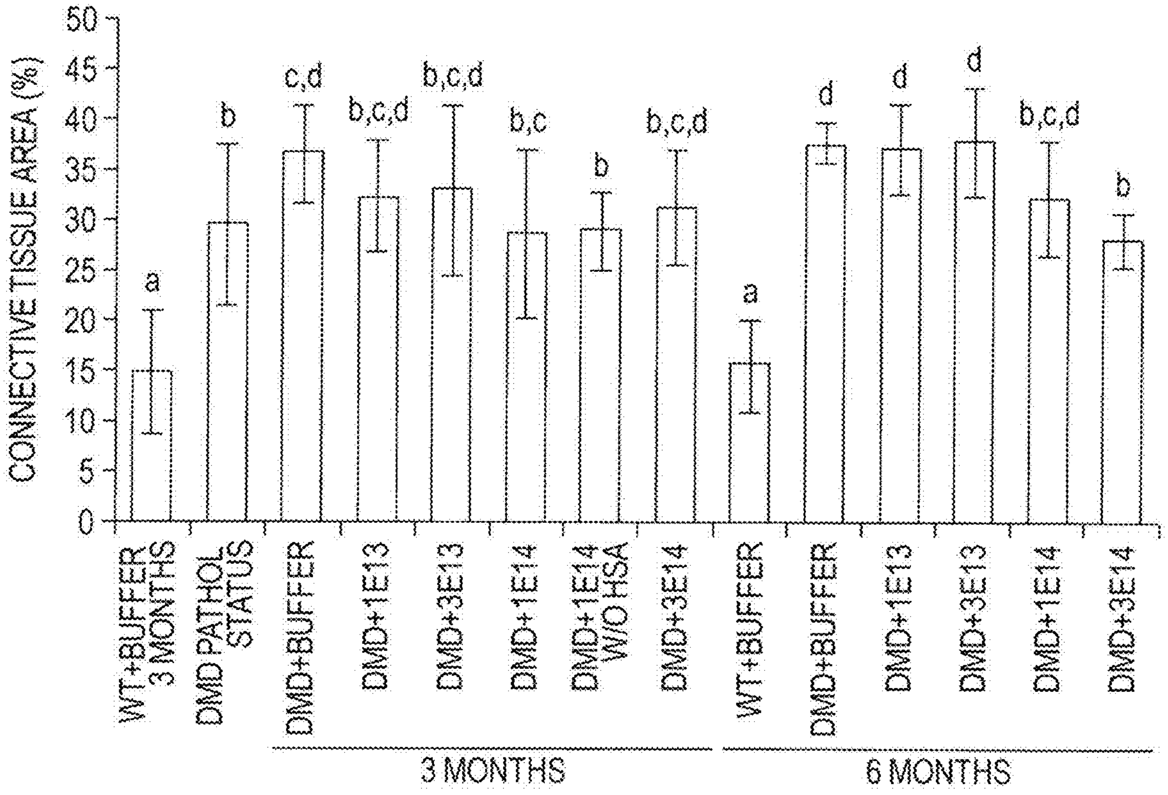
FIG. 40C provides percent area in random sections of diaphragm muscle samples from Dmd$^{mdx}$ rats treated with increasing doses of AAV9.hCK.Hopti-Dys3978.spA vector, and negative controls, that stained positive for presence of connective tissue. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

FIG. 40A shows representative photomicrographs of stained tissue sections from diaphragm samples from WT rats treated with vehicle (WT+buffer), $Dmd^{mdx}$ rats treated with vehicle (DMD+buffer), and $Dmd^{mdx}$ rats treated with vector at increasing doses of $1\times10^{13}$, $3\times10^{13}$, $1\times10^{14}$ and $3\times10^{14}$ vg/kg (DMD+1E13, 3E13, 1E14, and 3E14, respectively), all taken at 3 months post-injection. FIG. 40B is a graph showing the percentage of dystrophin positive fibers in diaphragm samples from WT rats and $Dmd^{mdx}$ rats, each treated with vehicle, and $Dmd^{mdx}$ rats treated with increasing doses of vector, at 3 and 6 month time points. Also included are results from untreated Dmd$^{mdx}$ rats 7-9 weeks of age ("DMD pathol status"). FIG. 40C is a graph showing the percentage area occupied by connective tissue (as a measure of fibrosis) in diaphragm samples from similarly treated WT and Dmd$^{mdx}$ rats at 3 and 6 month time points, and untreated Dmd$^{mdx}$ rats 7-9 weeks of age. In the graphs, the same letter over error bars indicates no statistically significant difference between the data, whereas no common letter indicates there is a significant difference (for example, two bars both having an "a" above them would not be significantly different from each other).

Figure 41A:
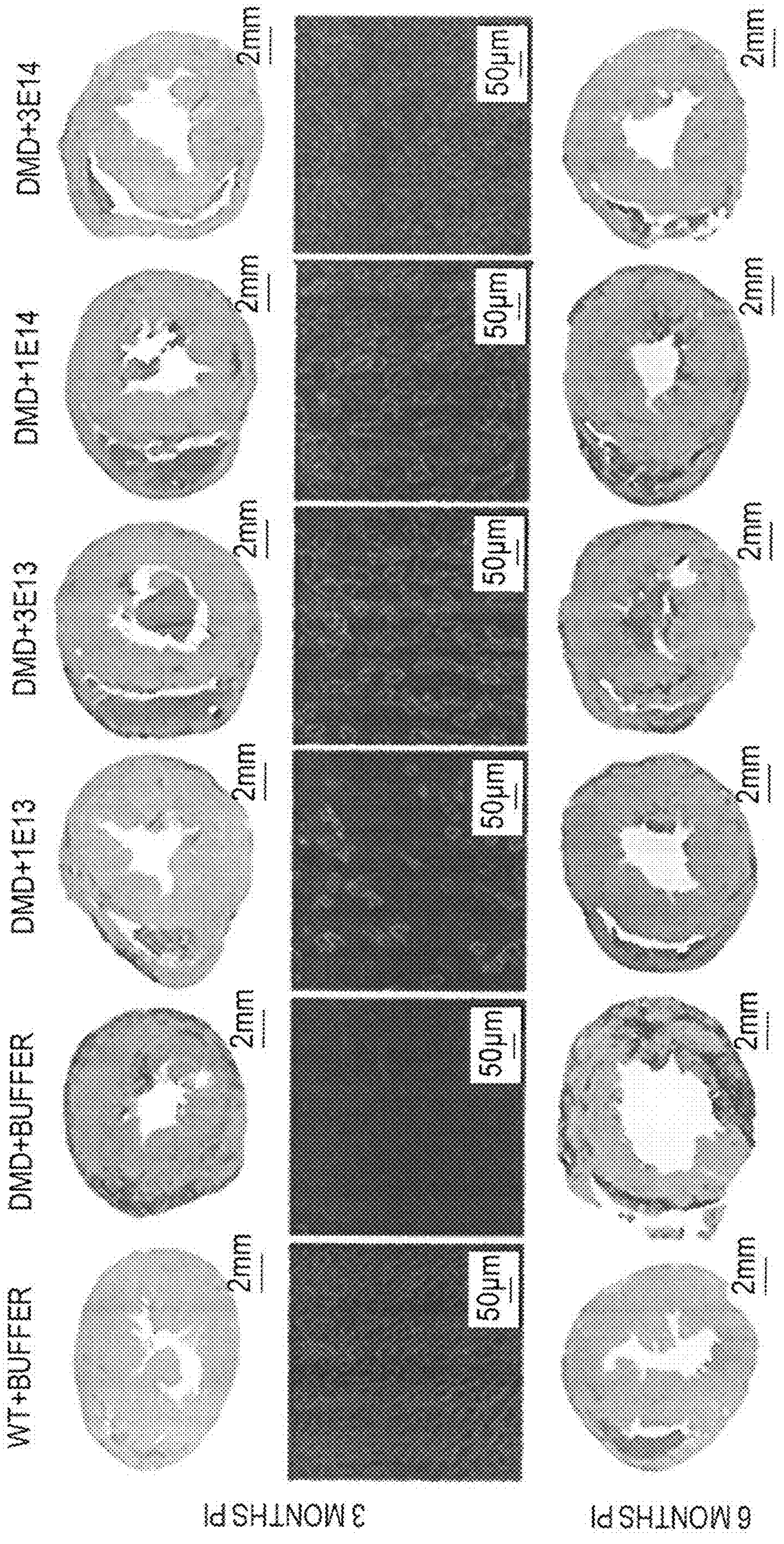
FIG. 41A shows representative transverse sections of heart at one-third from the apex taken from Dmd$^{mdx}$ rats treated with increasing doses of AAV9.hCK.Hopti-Dys3978.spA vector (top panel), and negative controls (bottom panel), sacrificed at 3 months and 6 months post-injection. Histology sections were stained with picrosirius red to permit visualization of connective tissue. The middle panel contains representative sections of heart muscle taken from vector and vehicle treated Dmd$^{mdx}$ rats dual labeled with an antibody that specifically binds to full length rat dystrophin and human mini-dystrophin, and wheat germ agglutinin conjugate which stains connective tissue.
Figure 41B:
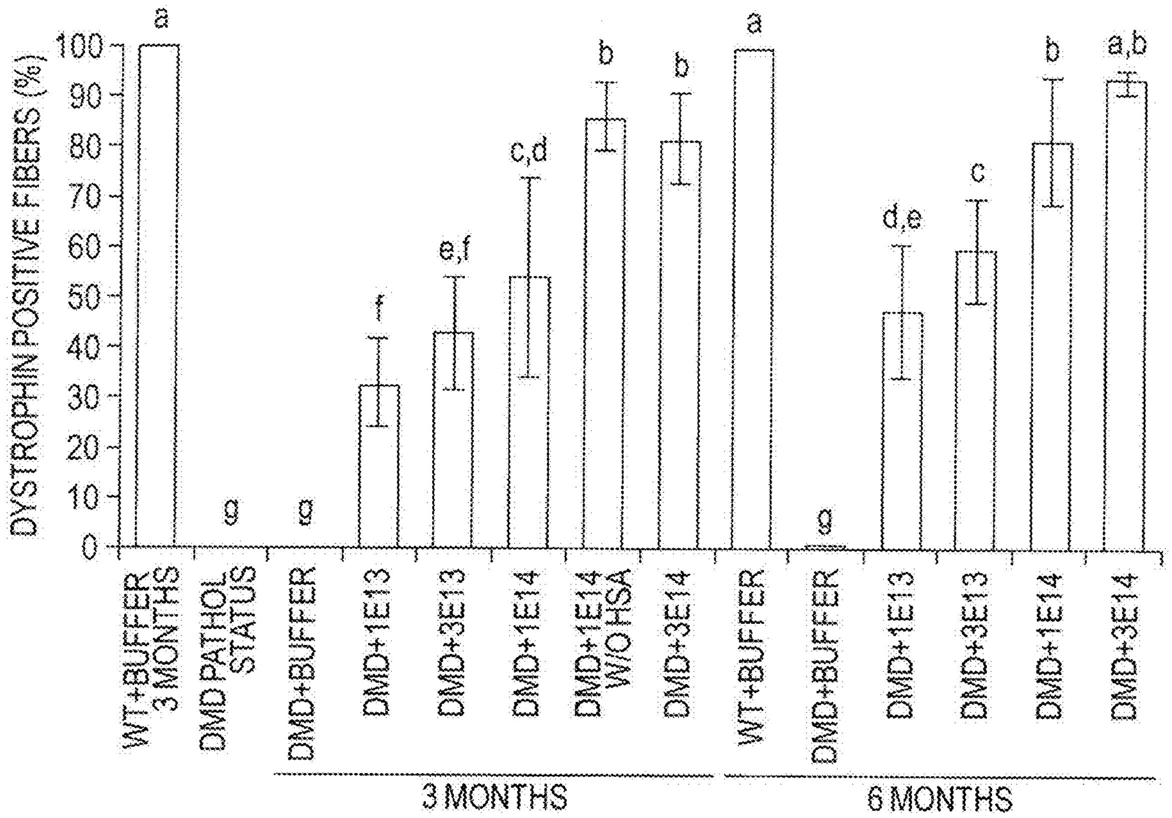
FIG. 41B provides percent fibers in random sections from heart muscle samples from Dmd$^{mdx}$ rats treated with increasing doses of AAV9.hCK.Hopti-Dys3978.spA vector, and negative controls, stained for presence of dystrophin protein. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.
Figure 41C:
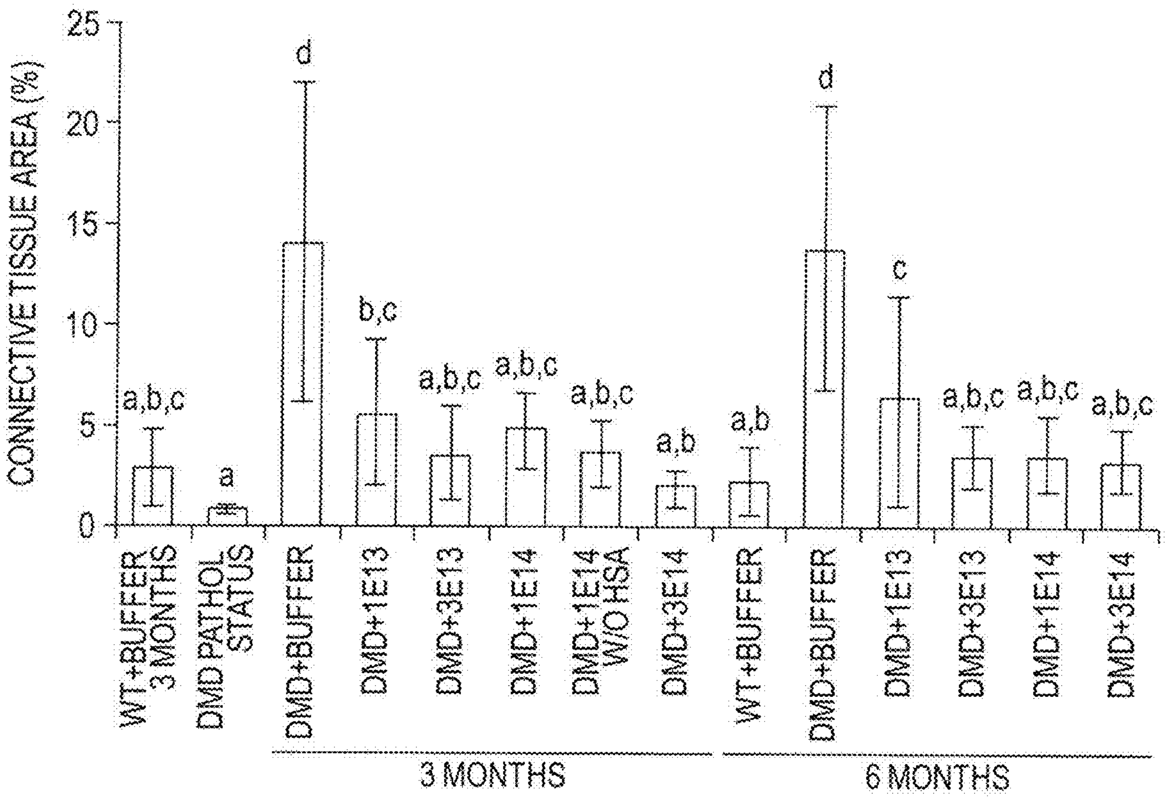
FIG. 41C provides percent area in random sections of heart muscle samples from Dmd$^{mdx}$ rats treated with increasing doses of AAV9.hCK.Hopti-Dys3978.spA vector, and negative controls, stained for presence of connective tissue. Data for 3 and 6 months post-injection are included. Letters above bars indicate that the underlying data is not statistically different from other bars over which the same letters appear. Conversely, bars over which different letters appear are statistically different from each other. Statistics were calculated using ANOVA analysis and Fisher's post-hoc bilateral test.

FIG. 41A shows representative photomicrographs of stained tissue sections from heart muscle samples from WT rats treated with vehicle (WT+buffer), Dmd$^{mdx}$ rats treated with vehicle (DMD+buffer), and Dmd$^{mdx}$ rats treated with vector at increasing doses of $1\times10^{13}$, $3\times10^{13}$, $1\times10^{14}$ and $3\times10^{14}$ vg/kg (DMD+1E13, 3E13, 1E14, and 3E14, respectively). The top and bottom panels show transverse sections of hearts from the third of the apex prepared histologically and stained with picrosirius red taken from test animals sacrificed at 3 and 6 months post-injection, respectively. The black bars indicate length of 2 mm. The middle panel shows immunolabeling with anti-dystrophin antibody and WGA conjugate in heart muscle samples taken at the 3 month time point. FIG. 41B is a graph showing the percentage of dystrophin positive fibers in heart muscle samples from WT rats and Dmd$^{mdx}$ rats, each treated with vehicle, and Dmd$^{mdx}$ rats treated with increasing doses of vector, at 3 and 6 month time points. Also included are results from untreated Dmd$^{mdx}$ rats 7-9 weeks of age ("DMD pathol status"). FIG. 41C is a graph showing the percentage area occupied by connective tissue (as a measure of fibrosis) in heart muscle samples from similarly treated WT and Dmd$^{mdx}$ rats at 3 and 6 month time points, and untreated Dmd$^{mdx}$ rats 7-9 weeks of age. In the graphs, the same letter over error bars indicates no statistically significant difference between the data, whereas no common letter indicates there is a significant difference (for example, two bars both having an "a" above them would not be significantly different from each other).

Statistical analysis (ANOVA analysis and Fisher's post-hoc bilateral test) of the data demonstrated that at both 3 and 6 months post-injection, there was a significant difference in dystrophin labeling in biceps femoris and heart between Dmd$^{mdx}$ rats treated with vehicle and Dmd$^{mdx}$ rats treated at all vector doses. In diaphragm, differences at 3 months post-injection were significant at the two highest doses tested, whereas at 6 months post-injection, the differences were significant at the three highest doses tested. Comparison between WT rats treated with vehicle and Dmd$^{mdx}$ rats treated with $3\times10^{14}$ vg/kg revealed no significant difference in biceps femoris muscle at 3 months post-injection or in cardiac muscle at 6 months post-injection.

In muscles from WT rats treated with vehicle, all muscle fibers displayed intense homogeneous subsarcolemmal labeling with the DYSB antibody. In muscles from Dmd$^{mdx}$ rats treated with vehicle, a small percentage of scattered revertant fibers displayed similar labeling (at 3 and 6 months post-injection, respectively: biceps femoris, 3.7±2.4% and 7.3±2.3%; diaphragm, 0.7±1.5% and 5.8±1.3%; cardiac muscle, 0.0±0.0% and 0.1±0.1%). In Dmd$^{mdx}$ rats administered vector, the percentage of fibers staining positive for dystrophin was increased in all observed muscles with fibers displaying weak to intense subsarcolemmal labeling. Labeling of two thirds of the fiber was required to be considered positive. At both 3 and 6 month time points, the percentage of dystrophin-positive fibers was similar between biceps femoris and cardiac muscle, which was higher than in diaphragm. In Dmd$^{mdx}$ rats treated with vector, the number and size of the fibrotic foci measured by the area occupied by connective tissue was reduced in skeletal muscle, and the intensity of fibrosis decreased in heart muscle.

In untreated Dmd$^{mdx}$ rats sacrificed at 7-9 weeks of age, no fibrosis was evident in biceps femoris or heart muscle, but there was already significant connective tissue expansion in diaphragm. Compared to WT rats, vehicle treated Dmd$^{mdx}$ rats displayed focal or generalized thickening of the endomysial and perimysial space in skeletal muscle, which is indicative of fibrosis. In the heart, these rats displayed scattered and extensive fibrotic foci in ventricular and septal subepicardial regions. In severe cases, transmural fibrosis was observed that altered the shape of the heart. Compared with Dmd$^{mdx}$ rats treated with vehicle, there was a significant reduction in the number and size of fibrotic foci at 3 months post-injection in the biceps femoris of Dmd$^{mdx}$ rats treated with $3\times10^{13}$ vg/kg vector and higher doses, and at 6 months post-injection in the diaphragm of Dmd$^{mdx}$ rats treated with $3\times10^{14}$ vg/kg vector. In heart, significant differences in fibrosis were found between Dmd$^{mdx}$ rats treated with vehicle and Dmd$^{mdx}$ rats treated at all vector doses at both time points. At 3 months post-injection, no significant difference in fibrosis was observed between WT rats treated with vehicle and Dmd$^{mdx}$ rats treated with vector at a dose of $3\times10^{13}$ vg/kg and higher. The amount of fibrosis observed and vector dose were negatively correlated ($p=0.019$ for biceps femoris; $p=0.004$ for diaphragm; and $p=0.003$ for cardiac muscle, all by linear regression).

In Dmd$^{mdx}$ rats treatment with vector induced mini-dystrophin expression in all muscles analyzed (biceps femoris, diaphragm, and heart), and the percentage of fibers expressing mini-dystrophin was positively correlated with vector dose ($p<0.001$ by linear regression). The number of mini-dystrophin-positive fibers in vector treated Dmd$^{mdx}$ rats was higher in biceps femoris and heart than in diaphragm, suggesting some heterogeneity in biodistribution or expression efficacy. Mini-dystrophin expression was similar in terms of its sub sarcolemmal localization, regardless dose, and no abnormal localization was detected even at the highest dose analyzed, $3\times10^{14}$ vg/kg. In some fibers, discontinuous dystrophin staining was detected along the sarcolemma, although the frequency of this observation decreased with increasing vector dose.

Comparison of the number of mini-dystrophin positive muscle fibers between 3 and 6 months post-injection revealed no significant differences among treatment arms for biceps femoris. In diaphragm, there was a significant increase between 3 and 6 months post-injection at the $1\times10^{14}$ vg/kg dose, whereas in heart muscle, there was a significant increase between the two time points at the doses $1\times10^{13}$, $3\times10^{13}$, and $1\times10^{14}$ vg/kg.

The incidence and degree of certain classic DMD related muscle lesions varied among the treatment groups. For example, there were fewer necrotic or degenerative fibers vector treated Dmd$^{mdx}$ rats compared to those that received only vehicle, and newly regenerated fibers were observed in all Dmd$^{mdx}$ rats, but their number tended to decrease as vector dose was increased.

Grip Force and Muscle Fatigue Measurements

Forelimb grip force of Dmd$^{mdx}$ rats injected with vehicle or increasing doses of vector were tested 3 and 6 months post-injection. WT rats injected with vehicle were included as negative controls. Rats were injected when they were 7-9 weeks old so that grip force testing was conducted when they were about 4.5 and 7.5 months old. Maximum grip force and grip force after repeated trials as an indication of fatigue were both measured.

Materials and Methods

A grip meter (Bio-GT3, BIOSEB, France) attached to a force transducer was used to measure the peak force generated when rats were placed with their forepaws on the T-bar and gently pulled backward until they released their grip. Five tests were performed in sequence with a short latency (20-40 seconds) between each test, and the reduction in strength between the first and the last determination taken as an index of fatigue. Results are expressed in grams (g) and are normalized to the body weight (g/g BW). Grip test measurements were performed by an experimenter blind to genotype and treatment arm. Data are presented as the mean±SEM, and evaluated statistically using the non-parametric Kruskal-Wallis test to analyze differences between groups. Where significant overall effects were detected, differences between groups were assessed using Dunn's post-hoc test. Evolution of grip force was analyzed using the Friedman test, followed by Dunn's post-hoc test. All data analyses were performed using GraphPad Prism 5 (GraphPad Software Inc., La Jolla, Calif.). In figures, significant differences at confidence levels of 95%, 99%, and 99.9% are represented by one, two and three symbols, respectively.

Results

Results of grip force tests for rats sacrificed at 3 months post-injection are provided in Table 9 and Table 10. As shown in Table 9, vehicle treated $Dmd^{mdx}$ rats exhibited a reduction in absolute grip strength (i.e., not corrected for body mass differences) compared to vehicle treated WT rats (decrease of 24±2%). By contrast, $Dmd^{mdx}$ rats that were treated with vector exhibited a dose-dependent increase in absolute grip strength compared to vehicle treated $Dmd^{mdx}$ rat controls. At the two lowest doses, $1\times10^{13}$ and $3\times10^{13}$ vg/kg, grip force increased by 13±7% and 24±8%, respectively, but did not reach statistical significance, while at the two highest doses, $1\times10^{14}$ and $3\times10^{14}$ vg/kg, grip force increased by 40±9% and 55±6%, respectively, which did reach statistical significance ($p<0.01$ and $p<0.001$, respectively). Also as shown in Table 9, when forelimb grip force was corrected for differences in body mass, there was no statistically significant difference between grip force of WT and $Dmd^{mdx}$ rats when both were treated with vehicle. However, there was a dose responsive increase in relative grip force of vector treated $Dmd^{mdx}$ rats compared with $Dmd^{mdx}$ rats treated with vehicle, which reached statistical significance at the two highest doses tested, $1\times10^{14}$ and $3\times10^{14}$ vg/kg (27±8% increase, $p<0.05$, and 39±6% increase, $p<0.001$, respectively).

Figure 42A:
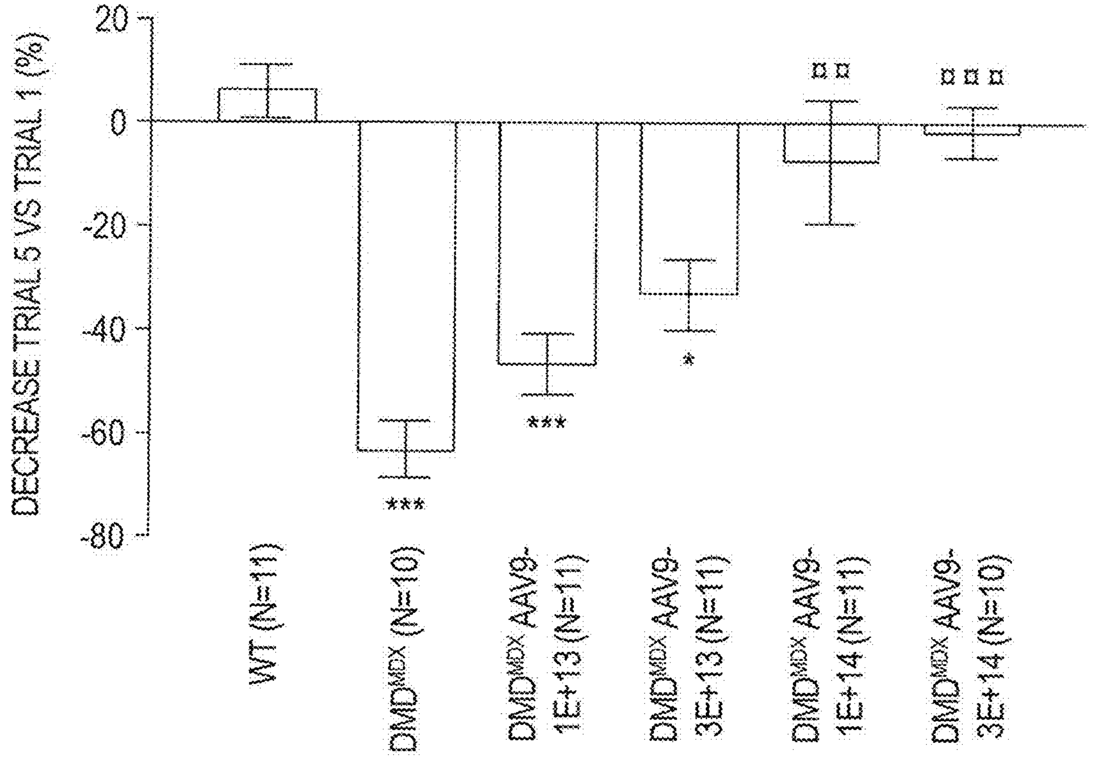
FIG. 42A provides data regarding muscle fatigue in Dmd$^{mdx}$ rats treated with increasing doses of AAV9.hCK.Hopti-Dys3978.spA vector compared to Dmd$^{mdx}$ and WT rats treated with vehicle measured by repeating five closely spaced grip strength tests. Tests were conducted 3 months post-injection in rats injected at 7-9 weeks of age, or when the rats were approximately 4.5 months old. Graph shows the decrease in forelimb grip force measured between trials 1 and 5 (expressed as percentage of trial 1 force). Results are represented as mean±SEM. Statistics compare Dmd$^{mdx}$ rats treated with vector against WT rats receiving vehicle (*p<0.05; ***p<0.001), and Dmd$^{mdx}$ rats receiving vehicle (¤¤p<0.01; ¤¤¤<0.001), both as negative controls.

Forelimb grip force was also measured during five closely spaced repeated trials to determine the extent to which vector treatment might affect the muscle fatigue known to occur in the $Dmd^{mdx}$ rat model. As shown in FIG. 42A, vehicle treated $Dmd^{mdx}$ rats exhibited a marked decrease of forelimb strength between the first and fifth trials (reduction of 63±5%), whereas WT rats treated with vehicle were just as strong after the fifth trial as after the first, an effect seen before in this model (Larcher, et al., 2014).

In contrast, a dose-dependent improvement was observed in vector treated $Dmd^{mdx}$ rats compared to similar rats treated only with vehicle. As indicated in Table 10, at the two lowest doses tested ($1\times10^{13}$ and $3\times10^{13}$ vg/kg) there was delay before a decrease in grip strength manifested, suggesting a reduction in fatigue, at least early in the trials. However, at the lower doses, by the fifth trial, there was still not a statistically significant difference between grip strength of the vector treated $Dmd^{mdx}$ rats and $Dmd^{mdx}$ rats treated only with vehicle. Nevertheless, a strong trend toward waning reduction in grip strength was apparent even at these lower doses. At the two highest doses, $1\times10^{14}$ and $3\times10^{14}$ vg/kg, the $Dmd^{mdx}$ rats showed no statistically significant difference in the extent of fatigue compared to WT rats treated with vehicle. In other words, after five trials, these vector treated $Dmd^{mdx}$ rats were indistinguishable from wild type. In fact, in all trials, the mean grip force of $Dmd^{mdx}$ rats treated with the highest vector dose was higher than that of WT controls, although the difference was not statistically significant.

Results of grip force tests for rats sacrificed at 6 months post-injection are provided in Table 11 and Table 12. As shown in Table 11, vehicle treated $Dmd^{mdx}$ rats exhibited a reduction in grip strength (i.e., not corrected for body mass differences) compared to vehicle treated WT rats (decrease of 38±3% in absolute grip force). This difference was statistically significant when measured in absolute terms, but not when measured in relative terms. By contrast, $Dmd^{mdx}$ rats that were treated with vector exhibited a dose-dependent increase in absolute grip strength compared to vehicle treated $Dmd^{mdx}$ rat controls. At the two lowest doses, $1\times10^{13}$ and $3\times10^{13}$ vg/kg, grip force increased by 20±5% and 21±6%, respectively, but did not reach statistical significance, while at the two highest doses, $1\times10^{14}$ and $3\times10^{14}$ vg/kg, grip force increased by 39±9% and 41±5%, respectively, which did reach statistical significance ($p<0.05$ and $p<0.01$, respectively).

Figure 42B:
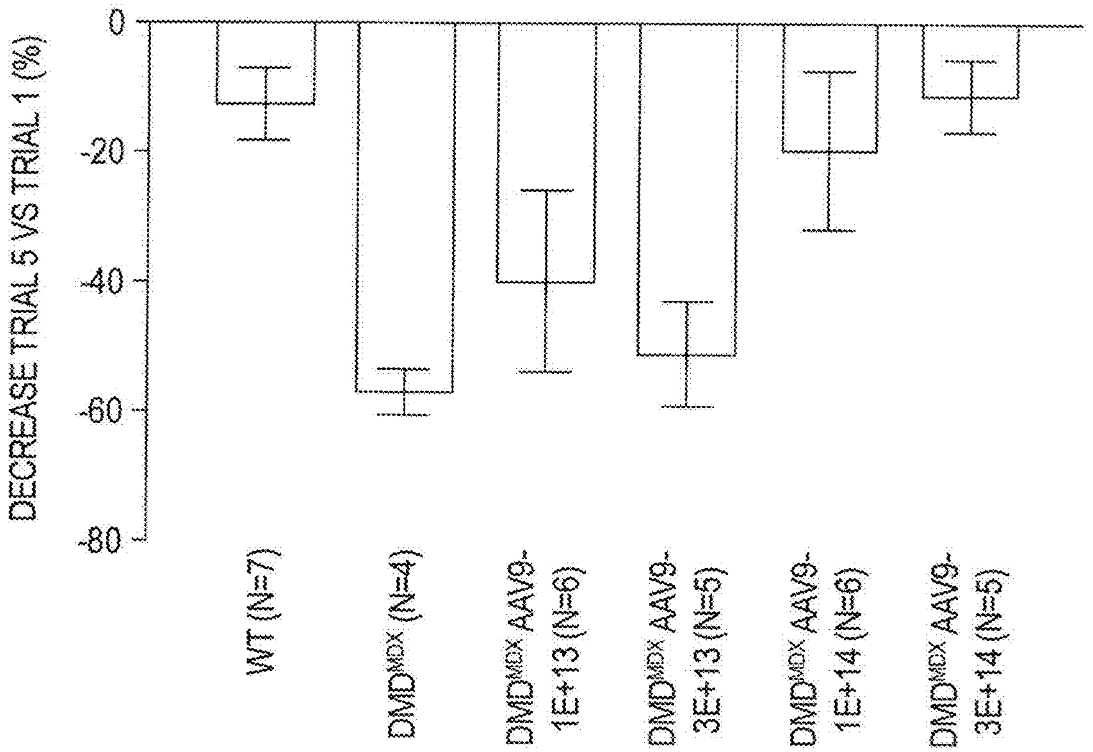
FIG. 42B provides data regarding muscle fatigue in Dmd$^{mdx}$ rats treated with increasing doses of AAV9.hCK.Hopti-Dys3978.spA vector compared to Dmd$^{mdx}$ and WT rats treated with vehicle measured by repeating five closely spaced grip strength tests. Tests were conducted 6 months post-injection in rats injected at 7-9 weeks of age, or when the rats were approximately 7.5 months old. Graph shows the decrease in forelimb grip force measured between trials 1 and 5 (expressed as percentage of trial 1 force). Results are represented as mean±SEM.

Similar to the $Dmd^{mdx}$ rats sacrificed 3 months after injection, vehicle treated $Dmd^{mdx}$ rats sacrificed at 6 months post-injection also exhibited a substantial decrease of forelimb strength between the first and fifth trials (reduction of 57±3%) (FIG. 42B), although this difference was not statistically significant compared to the slight reduction in grip force over five trials seen with WT rats treated with vehicle, most likely due to the small sample sizes involved in these studies.

In contrast, a dose-dependent improvement was observed in vector treated $Dmd^{mdx}$ rats compared to similar rats treated only with vehicle. As indicated in Table 12, while the two lowest doses ($1\times10^{13}$ and $3\times10^{13}$ vg/kg) did not significantly impact the decline in grip strength over multiple trials, at the two highest doses ($1\times10^{14}$ and $3\times10^{14}$ vg/kg), the $Dmd^{mdx}$ rats showed no statistically significant difference in the extent of fatigue compared to WT rats treated with vehicle. Further, at the highest dose, the grip force of vector treated $Dmd^{mdx}$ rats was statistically significantly higher than $Dmd^{mdx}$ rats treated with vehicle at every trial. In other words, after five trials, these vector treated $Dmd^{mdx}$ rats were indistinguishable from wild type. In fact, in all trials, the mean grip force of $Dmd^{mdx}$ rats treated with the highest vector dose was higher than that of WT controls, although the difference was not statistically significant.

Based on these studies, it is evident that at both 3 and 6 months post-injection, a vector dose of$1\times10^{14}$ vg/kg was sufficient to reverse the reduction in grip force exhibited by $Dmd^{mdx}$ rats and the muscle fatigue caused by multiple closely spaced grip force tests. Furthermore, a vector dose of $3\times10^{14}$ vg/kg actually improved grip force and fatigue resistance in the $Dmd^{mdx}$ rats to a level that exceeded WT rats of the same genetic background.

TABLE 9

Grip Force at 4.5 Months of Age (3 Months Post-Injection)

| | Genotype | | | | | |
|---|---|---|---|---|---|---|
| | WT | DMD$^{mdx}$ | DMD$^{mdx}$ | DMD$^{mdx}$ | DMD$^{mdx}$ | DMD$^{mdx}$ |
| | Treatment | | | | | |
| | — | — | AAV9-optidys3978 | AAV9-optidys3978 | AAV9-optidys3978 | AAV9-optidys3978 |
| | Dose (vg/kg) | | | | | |
| | — | — | 1E + 13 | 3E + 13 | 1E + 14 | 3E + 14 |
| Body weight (g) | 510.0 ± 12.2 | 438.1 ± 22.0* | 462.7 ± 16.2 | 469.1 ± 21.0 | 477.2 ± 11.3 | 482.9 ± 15.8 |
| Maximum forelimb grip force g | 1743.1 ± 77.2 | 1318.8 ± 41.8* | 1493.6 ± 87.3 | 1640.1 ± 102.7 | 1848.5 ± 124.8□□ | 2044.2 ± 83.1□□ |
| g/g BW | 3.43 ± 0.15 | 3.06 ± 0.14 | 3.25 ± 0.19 | 3.50 ± 0.19 | 3.87 ± 0.24□ | 4.24 ± 0.13*□ |
| n | 12 | 10 | 11 | 11 | 11 | 10 |

Animal body weight (g); maximum absolute forelimb grip force (g); and relative forelimb grip force (g/g of body weight)

Values are mean ± SEM n: number of animals tested

*$p<0.05$ vs WT

¤$p<0.05$, ¤¤$p<0.01$ vs Dmd$^{mdx}$ treated with vehicle

TABLE 10

Grip Force Fatigue at 4.5 Months of Age (3 Months Post-Injection)

| | Genotype | | | | | |
|---|---|---|---|---|---|---|
| | WT | DMD$^{mdx}$ | DMD$^{mdx}$ | DMD$^{mdx}$ | DMD$^{mdx}$ | DMD$^{mdx}$ |
| | Treatment | | | | | |
| | — | — | AAV9-Optidys3978 | AAV9-Optidys3978 | AAV9-Optidys3978 | AAV9-Optidys3978 |
| | Dose (vg/kg) | | | | | |
| | — | — | 1E + 13 | 3E +13 | 1E + 14 | 3E + 14 |
| Relative forelimb grip force g/g BW | | | | | | |
| Trial 1 | 2.98 ± 0.23 | 2.97 ± 0.14 | 3.14 ± 0.16 | 3.16 ± 0.18 | 3.35 ± 0.31 | 3.65 ± 0.13□ |
| Trial 2 | 2.92 ± 0.21 | 2.44 ± 0.31§ | 2.86 ± 0.23 | 2.98 ± 0.25 | 3.35 ± 0.29 | 3.70 ± 0.13□□ |
| Trial 3 | 2.89 ± 0.20 | 1.79 ±00.26§§§ | 2.52 ± 0.31§ | 3.02 ± 0.28□ | 3.07 ± 0.28□ | 3.66 ± 0.26□□□ |
| Trial 4 | 3.09 ± 0.16 | 1.45 ± 0.24*§§§ | 1.81 ± 0.27*§§§ | 2.32 ± 0.23§§§ | 3.14 ± 0.31□□ | 3.84 ± 0.24□□□ |
| Trial 5 | 3.08 ± 0.20 | 1.10 ± 0.17***§§§ | 1.66 ± 0.18**§§§ | 2.12 ± 0.25§§§ | 2.82 ± 0.26□□□ | 3.59 ± 0.22□□□ |
| Total decrease Trial 5 vs Trial 1 (% Trial 1) | 6.13 ± 5.21 | −63.53 ± 5.49*** | −46.65 ± 5.88*** | −33.23 ± 7.04* | −7.35 ± 11.83□□ | −1.70 ± 4.95□□□ |
| n | 11 | 10 | 11 | 11 | 11 | 10 |

Relative forelimb grip force (g/g of body weight) and decrease in grip force between 1st and 5th trials expressed as percent decrease from 1st trial Values are mean ± SEM n: number of animals tested

*$p<0.05$, $p<0.01$, *$p<0.001$ vs WT

¤$p<0.05$, ¤¤$p<0.01$, ¤¤¤$p<0.001$ vs Dmd$^{mdx}$ treated with vehicle

§$p<0.05$, §§§$p<0.001$ vs 1st trial

TABLE 11

Grip Force at 7.5 Months of Age (3 Months Post-Injection)

| | Genotype | | | | | |
|---|---|---|---|---|---|---|
| | WT | DMD$^{mdx}$ | DMD$^{mdx}$ | DMD$^{mdx}$ | DMD$^{mdx}$ | DMD$^{mdx}$ |
| | | | | Treatment | | |
| | — | — | AAV9-optidys3978 | AAV9-optidys3978 | AAV9-optidys3978 | AAV9-optidys3978 |
| | | | | Dose (vg/kg) | | |
| | — | — | $1^E + 13$ | $3^E + 13$ | $1^E + 14$ | $3^E + 14$ |
| Body weight (g) | 601.3 ± 24.3 | 464.7 ± 48.8* | 502.6 ± 29.1 | 527.6 ± 38.0 | 556.1 ± 14.4 | 577.6 ± 29.2 |
| Maximum forelimb grip force g | 2142.7 ± 98.0 | 132.0 ± 73.6* | 1760.0 ± 150.7 | 1825.4 ± 72.8 | 2223.8 ± 122.9$^{\square\square}$ | 2350.0 ± 134.1$^{\square}$ |
| g/g BW | 3.59 ± 0.21 | 2.90 ± 0.17 | 3.48 ± 0.16 | 3.50 ± 0.16 | 4.02 ± 0.26$^{\square}$ | 4.07 ± 0.15$^{\square\square}$ |
| n | 7 | 4 | 6 | 6 | 6 | 5 |

Animal body weight (g); maximum absolute forelimb grip force (g); and relative forelimb grip force (g/g of body weight)
Values are mean ± SEM
n: number of animals tested
*p<0.05 vs WT
□p<0.05, □□p<0.01 vs Dmd$^{mdx}$ treated with vehicle

TABLE 12

Grip Force Fatigue at 7.5 Months of Age (6 Months Post-Injection)

| | Genotype | | | | | |
|---|---|---|---|---|---|---|
| | WT | DMD$^{mdx}$ | DMD$^{mdx}$ | DMD$^{mdx}$ | DMD$^{mdx}$ | DMD$^{mdx}$ |
| | | | | Treatment | | |
| | — | — | AAV9-0ptidys3978 | AAV9-0ptidys3978 | AAV9-0ptidys3978 | AAV9-0ptidys3978 |
| | | | | Dose (vg/kg) | | |
| | — | — | 1E+3013 | 3E+3013 | 1E+3014 | 3E+3014 |
| Relative forelimb grip force g/g BW | | | | | | |
| Trial 1 | 3.48 ± 0.23 | 2.86 ± 0.18 | 3.27 ± 0.23 | 3.44 ± 0.20 | 3.60 ± 0.32 | 4.00 ± 0.14$^{\square\square}$ |
| Trial 2 | 3.22 ± 0.30 | 2.58 ± 0.27 | 3.07 ± 0.20 | 3.21 ± 0.12 | 3.31 ± 0.34 | 3.78 ± 0.12$^{\square}$ |
| Trial 3 | 3.45 ± 0.19 | 2.07 ± 0.26*$^{\S\S}$ | 2.46 ± 0.32$^{\S}$ | 2.40 ± 0.35$^{\S\S}$ | 3.72 ± 0.33$^{\square}$ | 3.66 ± 0.14$^{\square}$ |
| Trial 4 | 3.01 ± 0.16 | 1.52 ± 0.17*$^{\S\S\S}$ | 2.19 ± 0.27$^{\S\S}$ | 1.83 ± 0.14$^{\S\S\S}$ | 3.00 ± 0.38 | 3.76 ± 0.20$^{\square\square\square}$ |
| Trial 5 | 3.01 ± 0.16 | 1.24 ± 0.1*$^{\S\S\S}$ | 1.87 ± 0.33$^{\S\S\S}$ | 1.63 ± 0.16$^{\S\S\S}$ | 2.91 ± 0.51$^{\square}$ | 3.54 ± 0.20$^{\S\square\square}$ |
| Total decrease trial 5 vs Trial 1 (% Trial 1) | −12.27 ± 5.56 | −56.61 ± 3.52 | −39.55 ± 13.94 | −50.81 ± 8.11 | −19.48 ± 11.88 | −11.11 ± 5.69 |
| n | 7 | 4 | 6 | 5 | 6 | 5 |

Relative forelimb grip force (g/g of body weight) and decrease in grip force between 1st and 5th trials expressed as percent decrease from 1st trial
Values are mean ± SEM
n: number of animals tested
*p<0.05 vs WT
□p<0.05, □□p<0.01, □□□p<0.001 vs Dmd$^{mdx}$ treated with vehicle
$^{\S}$p<0.05, $^{\S\S}$p<0.01, $^{\S\S\S}$p<0.001 vs 1st trial Cardiac Function Cardiac function of Dmd$^{mdx}$ rats and WT controls were tested 3 and 6 months post-injection (about 5 and 8 months of age, respectively) to determine if vector treatment could improve the structural or functional effects on heart of the muscular dystrophy disease process in the rat DMD model. Using two-dimensional echocardiography, free wall diastolic thickness, LV end-diastolic diameter, LV ejection fraction, and E/A ratio were measured 3 and 6 months post-injection.

Materials and Methods

Echocardiographic measurements were conducted by an experimenter blind as to genotype and treatment arm. Two-dimensional (2D) echocardiography was performed on test animals using a Vivid 7 Dimension ultrasound (GE Healthcare) with a 14-MHz transducer. To observe possible structural remodeling, left ventricular end-diastolic diameter and free wall end-diastolic thickness were measured during diastole from long and short-axis images obtained with M-mode echocardiography. Systolic function was assessed by the ejection fraction, and diastolic function was determined by taking trans-mitral flow measurements of ventricular filling velocity using pulsed Doppler in an apical four-chamber orientation to determine the E/A ratio, isovolumetric relaxation time, and the E wave deceleration time, indicators of diastolic dysfunction explained further below.

The E/A ratio is the ratio of the peak velocity of blood movement from the left atrium to the left ventricle during two stages of atrial emptying and ventricular filling. Blood is transferred from the left atrium to the left ventricle in two steps. In the first, the blood in the left atrium moves passively into the ventricle below when the mitral valve opens due to negative pressure created by the relaxing ventricle. The speed at which the blood moves during this initial action is called the "E," for early, ventricular filling velocity. Later in time, the left atrium contracts to eject any remaining blood in the atrium, and the speed at which the blood moves at this stage is called the "A," for atrium, ventricular filling velocity. The E/A ratio is the ratio of the early (E) to late (A) ventricular filling velocities. In healthy heart, the E/A ratio is greater than 1. In Duchenne myopathy, however, the left ventricular wall becomes stiff, reducing ventricular relaxation and pull on atrial blood, thereby slowing the early (E) filling velocity and lowering the E/A ratio. The isovolumetric relaxation time (IVRT) is the interval between the closure of the aortic valve to onset of ventricular filling by opening of the mitral valve, or the time until ventricular filling starts after relaxation begins. Longer than normal IVRT indicates poor ventricular relaxation, which has been described in both human DMD patients (RC Bahler et al., J Am Soc Echocardiogr 18(6), 666-73 (2005); L W Markham et al., J Am Soc Echocardiogr 19(7), 865-71 (2006)) and the DMD dog model (V Chetboul et al., Eur Heart J 25(21), 1934-39 (2004); V Chetboul et al., Am J Vet Res 65(10), 1335-41 (2004)), and precede the dilated cardiomyopathy associated with DMD. Lastly, the E wave deceleration time (DT) corresponds to the time in milliseconds between peak E velocity and its return to baseline, an increase in which is indicative of a diastolic dysfunction.

Results

Figure 43:
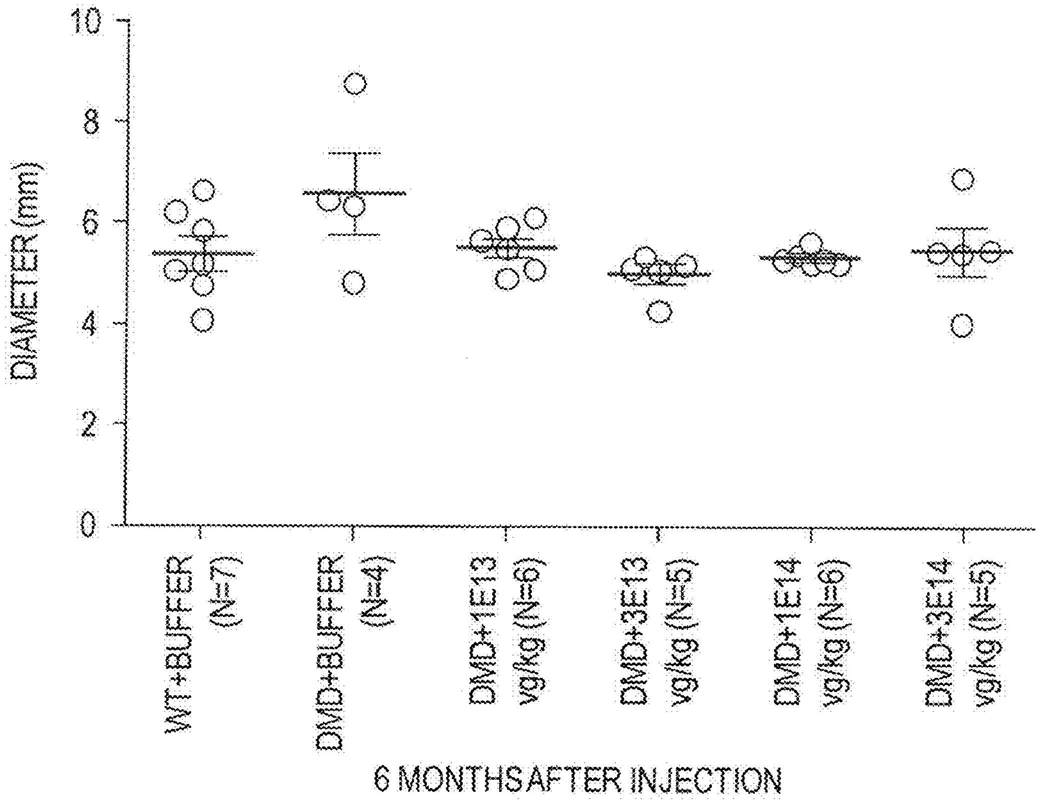
FIG. 43 provides left ventricular (LV) end-diastolic diameter measured during diastole from long-axis images obtained by M-mode echocardiography 6 months post-injection in WT and Dmd$^{mdx}$ rats administered vehicle or AAV9.hCK.Hopti-Dys3978.spA vector. Descriptive statistics shown are mean±SEM.

At both 3 and 6 months post-injection, no significant differences in free wall diastolic thickness between WT rats and Dmd$^{mdx}$ rats, both treated with vehicle, indicating that this measurement was not informative regarding disease course in this model at the ages examined. At 6 months, but not 3 months, post-injection, however, there was a trend toward increasing left ventricular end-diastolic diameter in Dmd$^{mdx}$ rats treated with vehicle compared to WT controls, which was reversed when the Dmd$^{mdx}$ rats were treated with vector, although statistical significance was not reached (FIG. 43).

Figure 44:
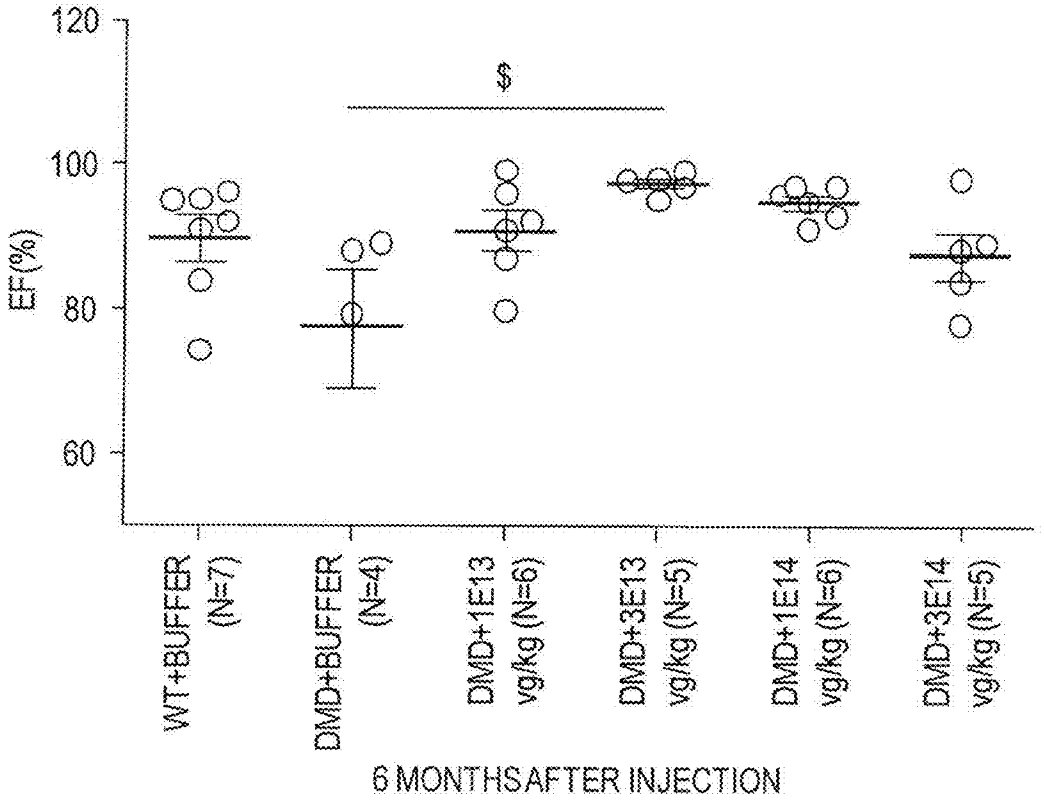
FIG. 44 provides ejection fractions measured during diastole from long-axis images obtained by M-mode echocardiography 6 months post-injection in WT and Dmd$^{mdx}$ rats administered vehicle or AAV9.hCK.Hopti-Dys3978.spA vector. Descriptive statistics shown are mean±SEM, and the "$" symbol indicates a statistically significant difference between the data over which it is placed and the data for Dmd$^{mdx}$ rats treated with vehicle (buffer) (p<0.05).

To assess systolic function, left ventricular (LV) ejection fraction was measured. No difference was found in Dmd$^{mdx}$ rats 3 months post-injection, but at 6 months post-injection, Dmd$^{mdx}$ rats administered vehicle only exhibited reduced LV ejection fraction that was prevented by treatment with vector, although the difference was statistically significant only at one of the lower doses, $3\times10^{13}$ vg/kg (FIG. 44).

Figure 45A:
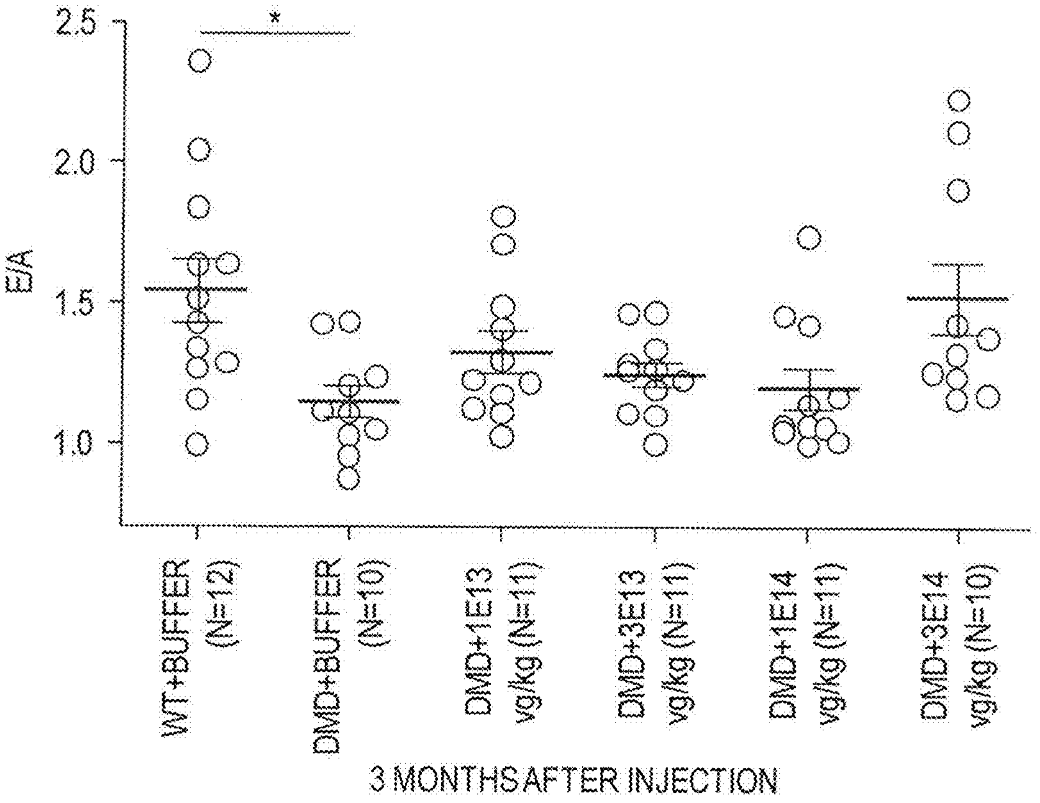
FIG. 45A provides E/A ratios measured using pulsed Doppler with an apical four-chamber orientation 3 months post-injection in WT and Dmd$^{mdx}$ rats administered vehicle or AAV9.hCK.Hopti-Dys3978.spA vector. Descriptive statistics shown are mean±SEM, and the "*" symbol indicates a statistically significant difference between the data over which it is placed and the data for WT rats treated with vehicle (buffer) (p<0.05).
Figure 45B:
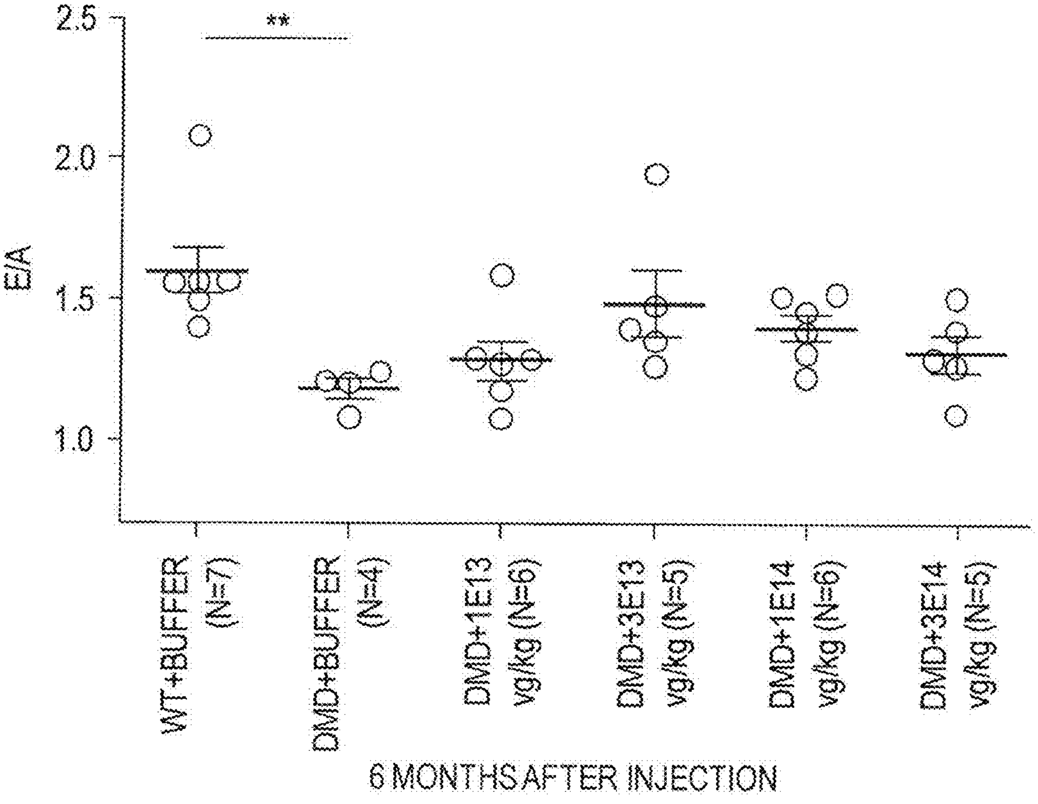
FIG. 45B provides E/A ratios measured using pulsed Doppler with an apical four-chamber orientation 6 months post-injection in WT and Dmd$^{mdx}$ rats administered vehicle or AAV9.hCK.Hopti-Dys3978.spA vector. Descriptive statistics shown are mean±SEM, and the "**" symbol indicates a statistically significant difference between the data over which it is placed and the data for WT rats treated with vehicle (buffer) (p<0.01).

To assess diastolic dysfunction, Doppler echocardiography was used to measure early (E) and late diastolic (A) velocities, the E/A ratio, isovolumetric relaxation time (IVRT), and deceleration time (DT). At 3 months post-injection there was a statistically significant reduction in the E/A ratio for Dmd$^{mdx}$ rats treated with vehicle compared to WT controls, and a trend suggesting return to a normal E/A ratio in Dmd$^{mdx}$ rats treated with the highest vector dose, $3\times10^{14}$ vg/kg, although the difference did not reach statistical significance (FIG. 45A). At 6 months post-injection, the E/A ratio of Dmd$^{mdx}$ rats treated with vehicle were also significantly reduced compared to WT controls, and as with the earlier time point, there was a trend suggesting some treatment effect of the vector, although the data was quite variable and did not reach statistical significance (FIG. 45B).

Figure 46A:
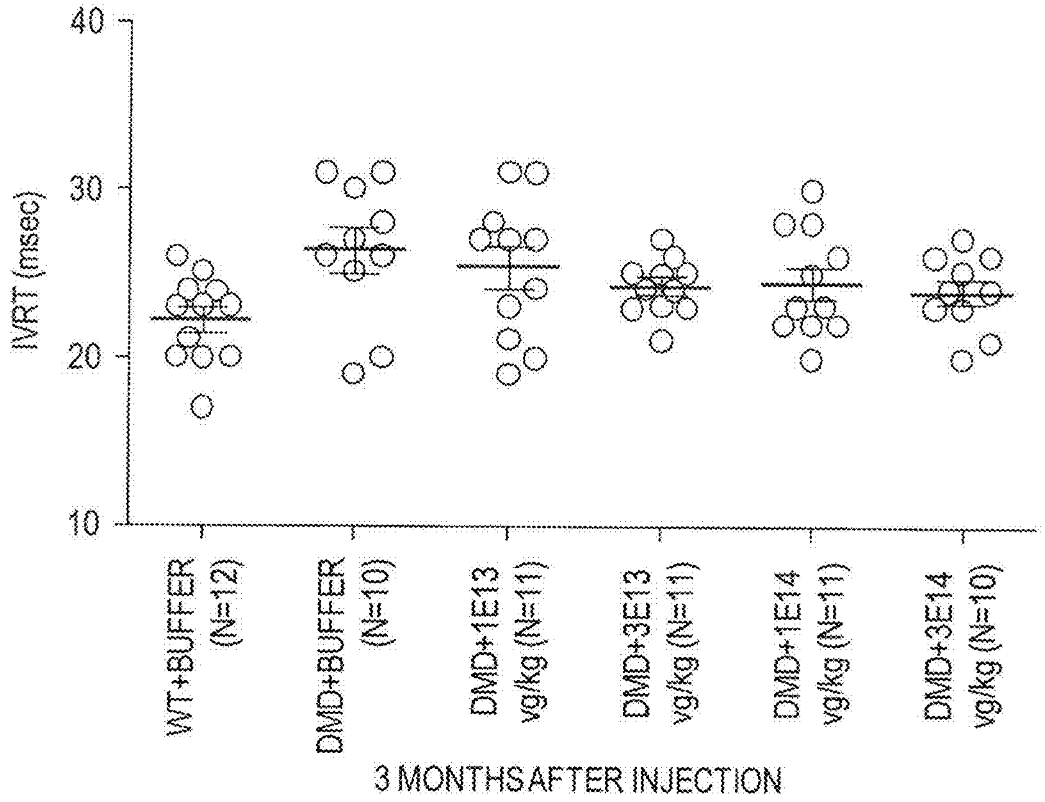
FIG. 46A provides isovolumetric relaxation time measured using pulsed Doppler with an apical four-chamber orientation 3 months post-injection in WT and Dmd$^{mdx}$ rats administered vehicle or AAV9.hCK.Hopti-Dys3978.spA vector. Descriptive statistics shown are mean±SEM.
Figure 46B:
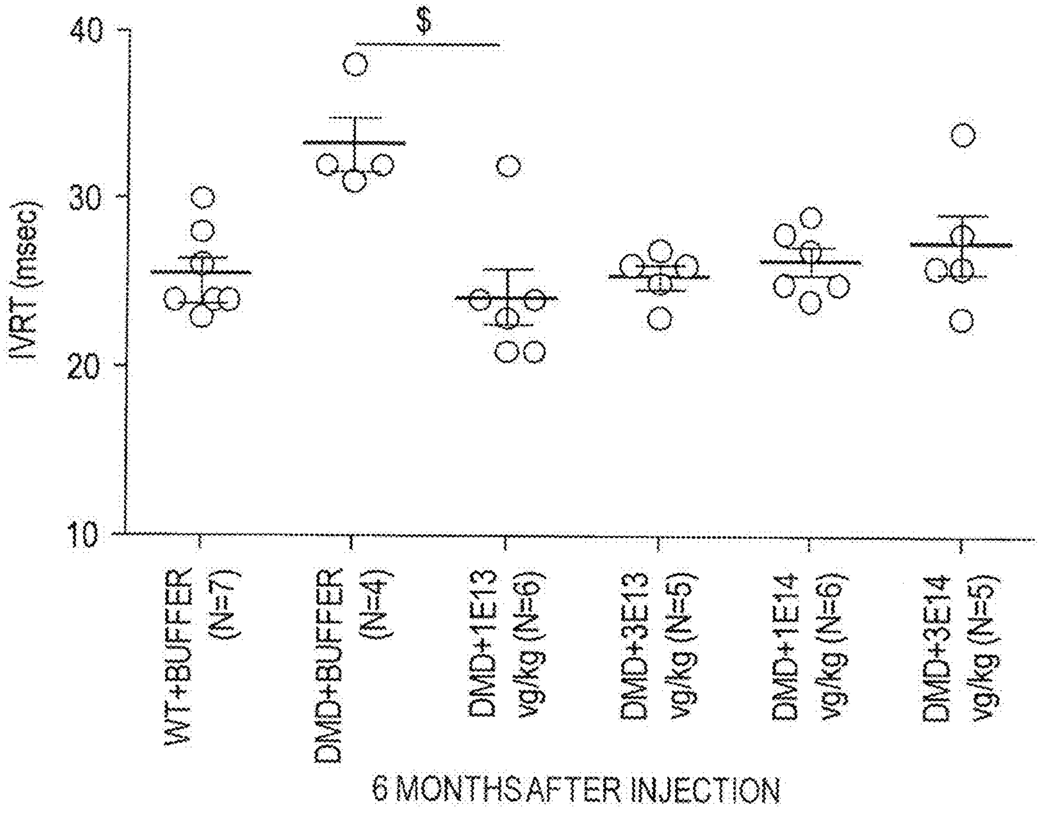
FIG. 46B provides isovolumetric relaxation time measured using pulsed Doppler with an apical four-chamber orientation 6 months post-injection in WT and Dmd$^{mdx}$ rats administered vehicle or AAV9.hCK.Hopti-Dys3978.spA vector. Descriptive statistics shown are mean±SEM, and the "$" symbol indicates a statistically significant difference between the data over which it is placed and the data for Dmd$^{mdx}$ rats treated with vehicle (buffer) (p<0.05).

At 3 months post-injection, IVRT was elevated in Dmd$^{mdx}$ rats treated with vehicle compared to WT controls, and there was a slight trend suggesting a dose responsive reduction in IVRT in Dmd$^{mdx}$ rats treated with vector, although none of the differences in the data reached statistical significance (FIG. 46A). At 6 months post-injection, Dmd$^{mdx}$ rats treated with vehicle had an IVRT that was significantly higher compared to WT controls, whereas vector treatment resulted in a strong trend suggesting return of IVRT to normal levels, which reached statistical significance at the lowest vector dose, $1\times10^{13}$ vg/kg (FIG. 46B).

Figure 47:
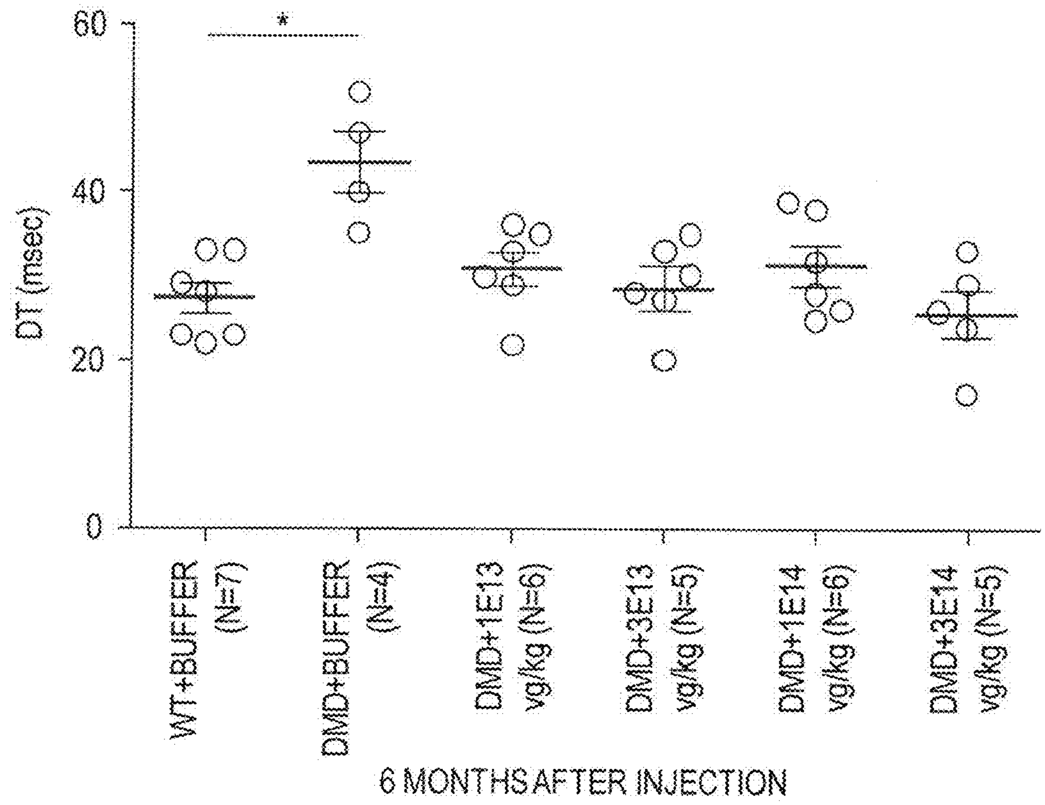
FIG. 47 provides deceleration time measured using pulsed Doppler with an apical four-chamber orientation 6 months post-injection in WT and Dmd$^{mdx}$ rats administered vehicle or AAV9.hCK.Hopti-Dys3978.spA vector. Descriptive statistics shown are mean±SEM, and the"*" symbol indicates a statistically significant difference between the data over which it is placed and the data for WT rats treated with vehicle (buffer) (p<0.05).

Finally, DT could only be measured in older rats due to technical difficulties with an anesthesia protocol. When examined at 6 months post-injection, however, DT was significantly elevated in Dmd$^{mdx}$ rats treated with vehicle compared to WT controls, and there was a strong trend toward restoration to normal values after vector treatment at all doses tested (FIG. 47).

Despite variability in the data, the results of these studies strongly suggest the existence of diastolic dysfunction in the hearts of 5 and 8 month old Dmd$^{mdx}$ rats, which could be at least partially reversed by treatment with AAV9.hCK.Hopti-Dys3978.spA vector.

Blood Chemistry

Prior to treatment and at the time of sacrifice, blood samples from the rats were taken and stored for eventual analysis. Tests were carried out to determine serum concentrations of urea, creatinine, alkaline phosphatase (ALK), alanine aminotransferase (ALT), aspartate aminotransferase (AST), lactate dehydrogenase (LDH), creatine kinase (CK), troponin I, and antibodies against the mini-dystrophin protein and AAV9 capsid. ALT, AST, CK, and LDH are all enzymes released into the blood from damaged muscle cells, and are known to be elevated in human DMD patients.

At 3 months and 6 months post-injection, the levels of urea, creatinine, ALK, total serum proteins, total bilirubin and troponin I were not significantly different between the different experimental groups. By contrast, AST, ALT, LDH and total CK levels were all elevated in vehicle treated Dmd$^{mdx}$ rats compared to WT rats and responded with varying degrees to vector treatment.

Figure 48A:
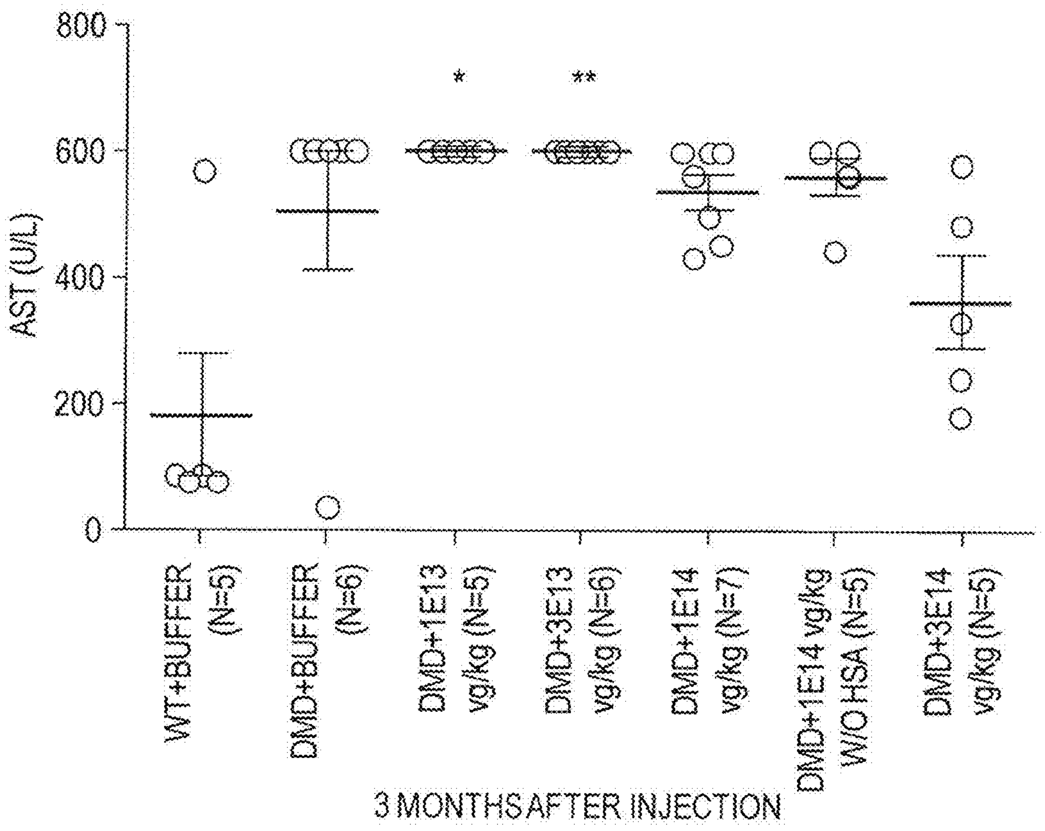
FIG. 48A shows effect in Dmd$^{mdx}$ rats of increasing doses of AAV9.hCK.Hopti-Dys3978.spA vector on blood AST levels 3 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (**p<0.01, *p<0.05).
Figure 48B:
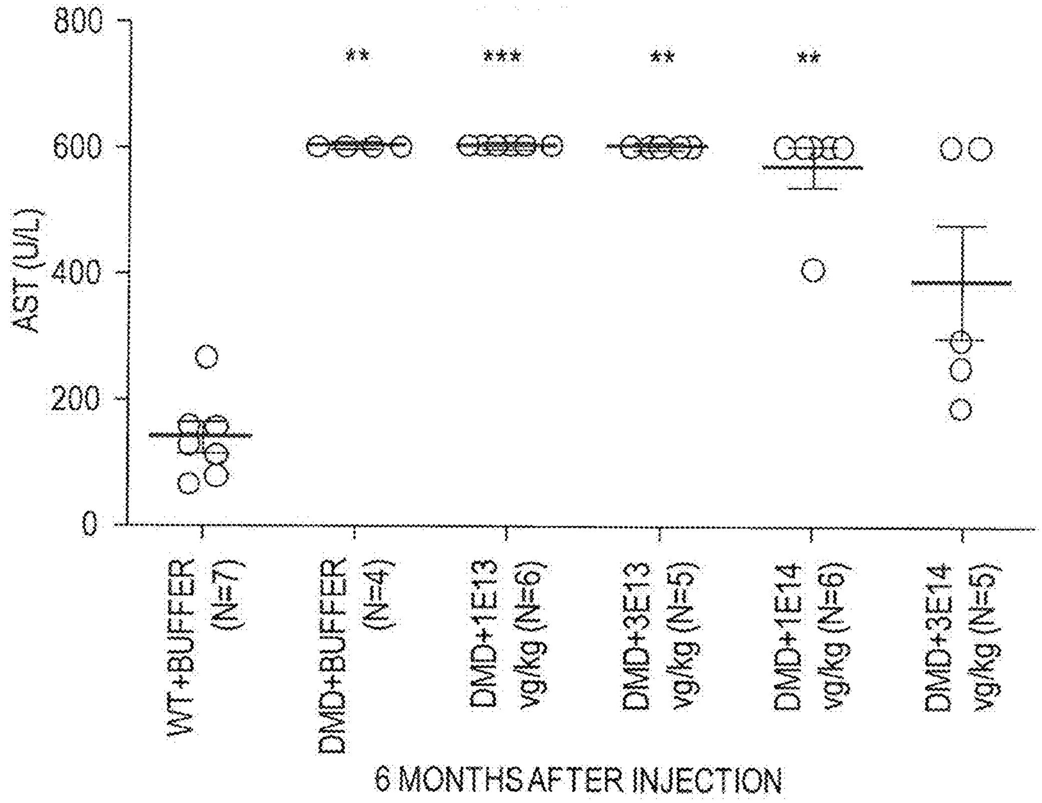
FIG. 48B shows effect in Dmd$^{mdx}$ rats of different doses of AAV9.hCK.Hopti-Dys3978.spA vector on blood AST levels 6 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (*p<0.001, p<0.01).

At both 3 and 6 months post-injection, AST levels were elevated in Dmd$^{mdx}$ rats treated with vehicle compared to WT rats, although due to variability in the data, significance existed only at the 6 month time point. When Dmd$^{mdx}$ rats were treated with vector, a trend towards lower AST levels (albeit with wide inter-individual variability) was observed in the $1\times10^{14}$ and $3\times10^{14}$ vg/kg dose groups at 3 months post-injection and in the $3\times10^{14}$ vg/kg dose group at 6 months post-injection. Again, due to variability in the data, these differences did not reach statistical significance. These results are shown in FIG. 48A and FIG. 48B, which reports data for the 3 month and 6 month post-injection time points, respectively.

Figure 49A:
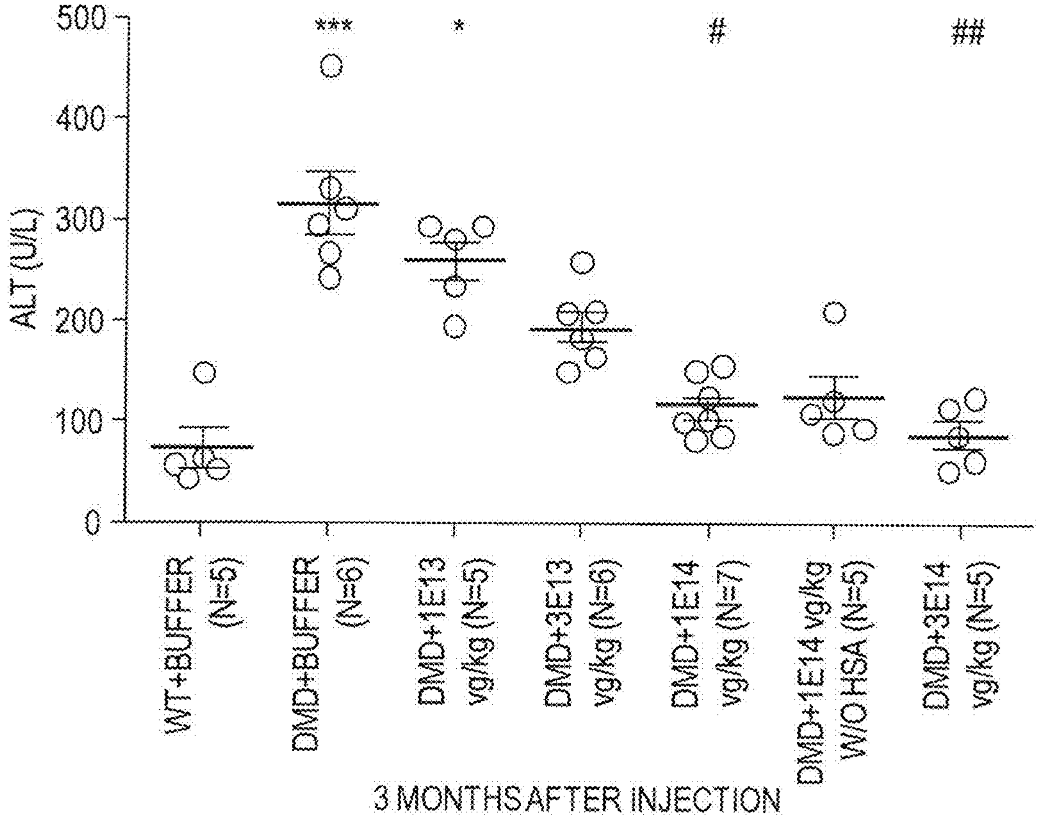
FIG. 49A shows effect in Dmd$^{mdx}$ rats of different doses of AAV9.hCK.Hopti-Dys3978.spA vector on blood ALT levels 3 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) (***p<0.001, *p<0.05), or against Dmd$^{mdx}$ rats that received buffer (##p<0.01, #p<0.05), as negative controls.
Figure 49B:
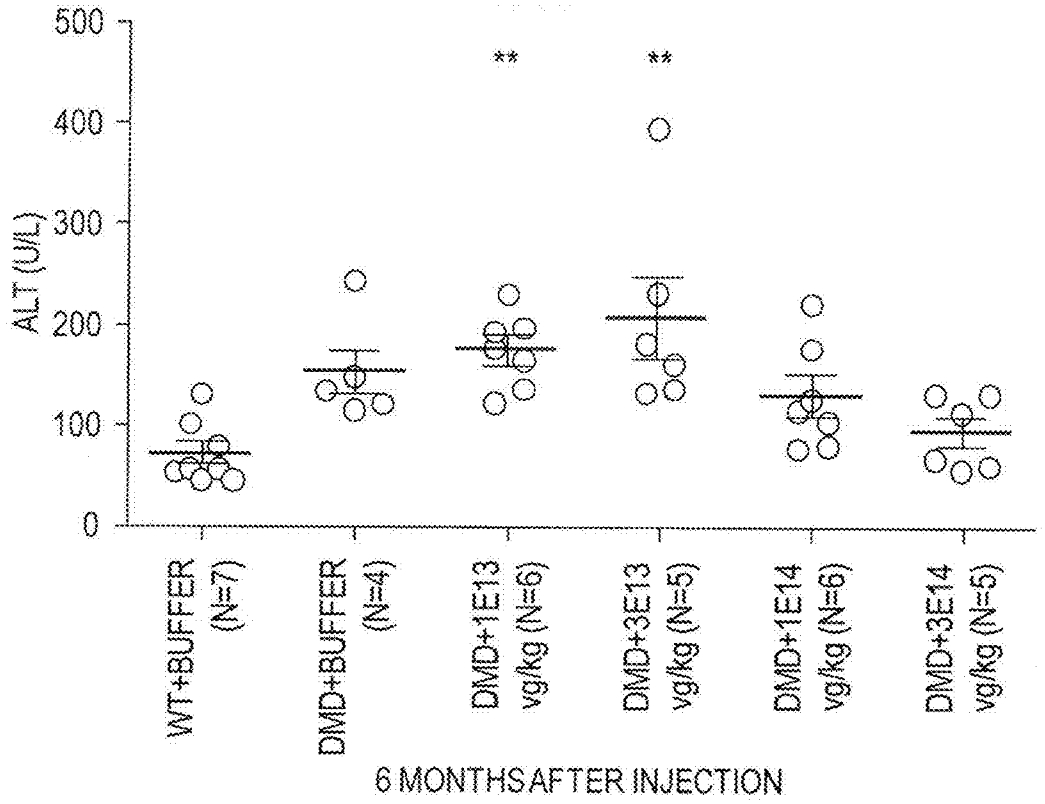
FIG. 49B shows effect in Dmd$^{mdx}$ rats of different doses of AAV9.hCK.Hopti-Dys3978.spA vector on blood ALT levels 6 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (**p<0.01).
Figure 50A:
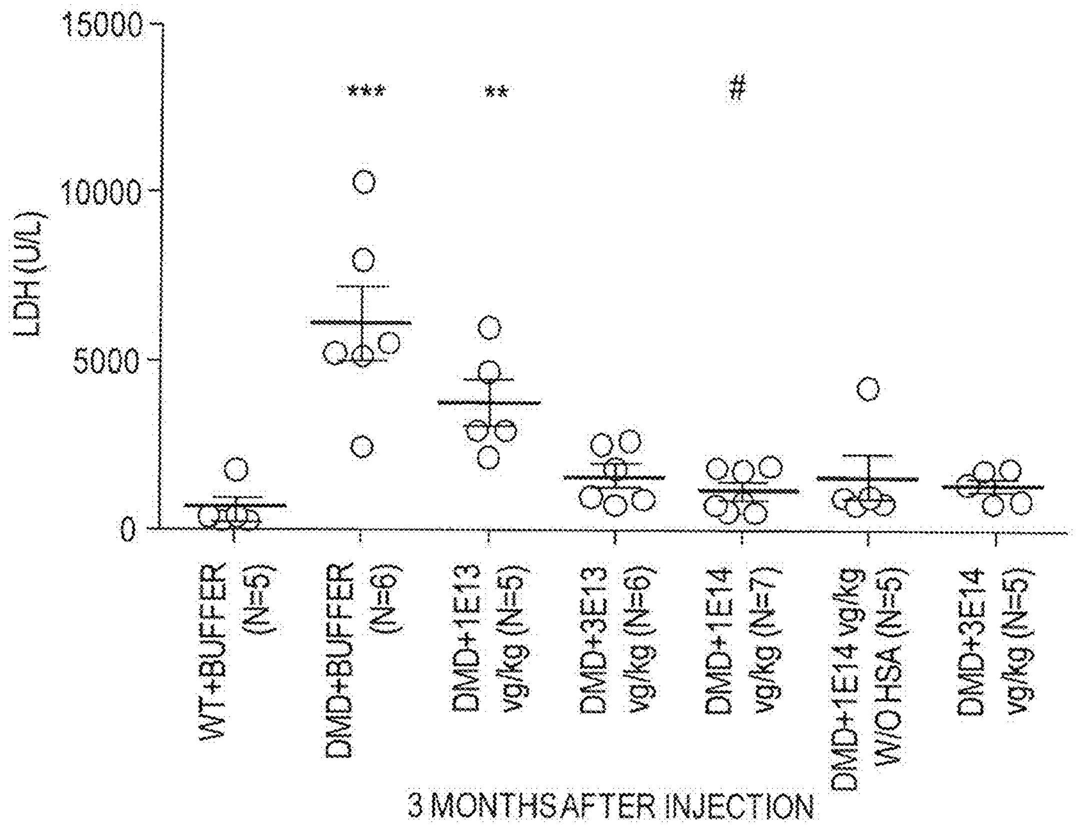
FIG. 50A shows effect in Dmd$^{mdx}$ rats of different doses of AAV9.hCK.Hopti-Dys3978.spA vector on blood LDH levels 3 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) (*p<0.001, p<0.01), or against Dmd$^{mdx}$ rats that received buffer (#p<0.05), as negative controls.
Figure 50B:
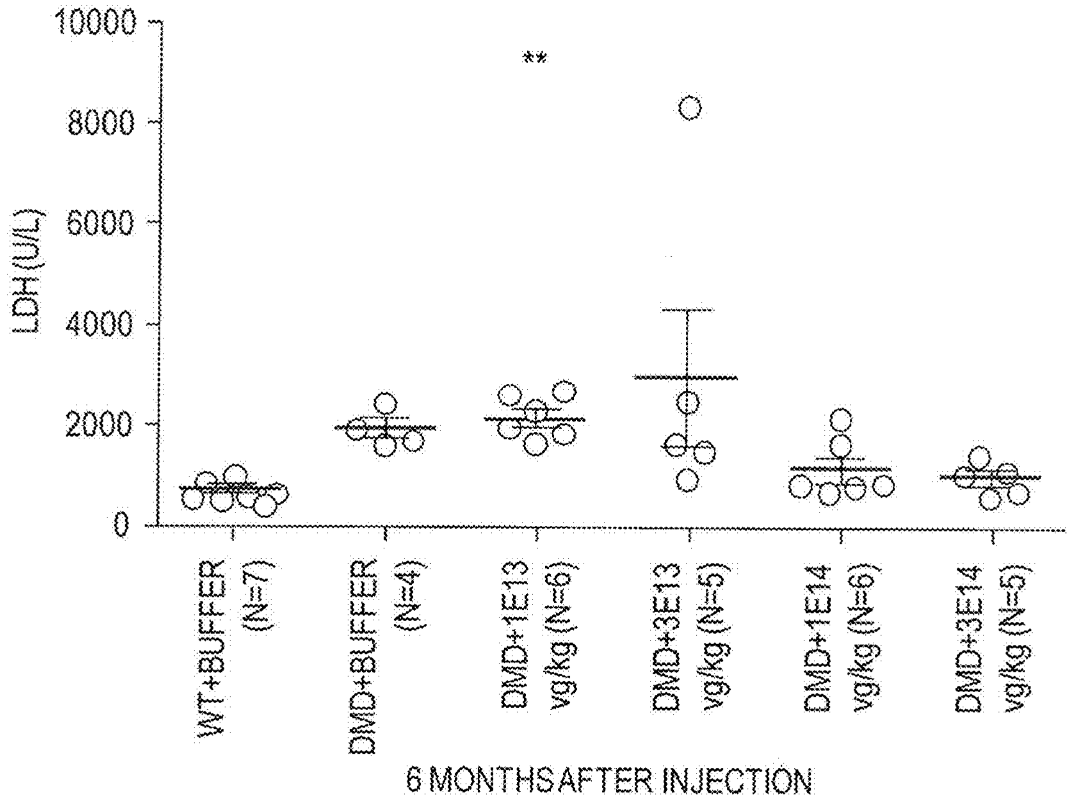
FIG. 50B shows effect in Dmd$^{mdx}$ rats of different doses of AAV9.hCK.Hopti-Dys3978.spA vector on blood LDH levels 6 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (**p<0.01).
Figure 51A:
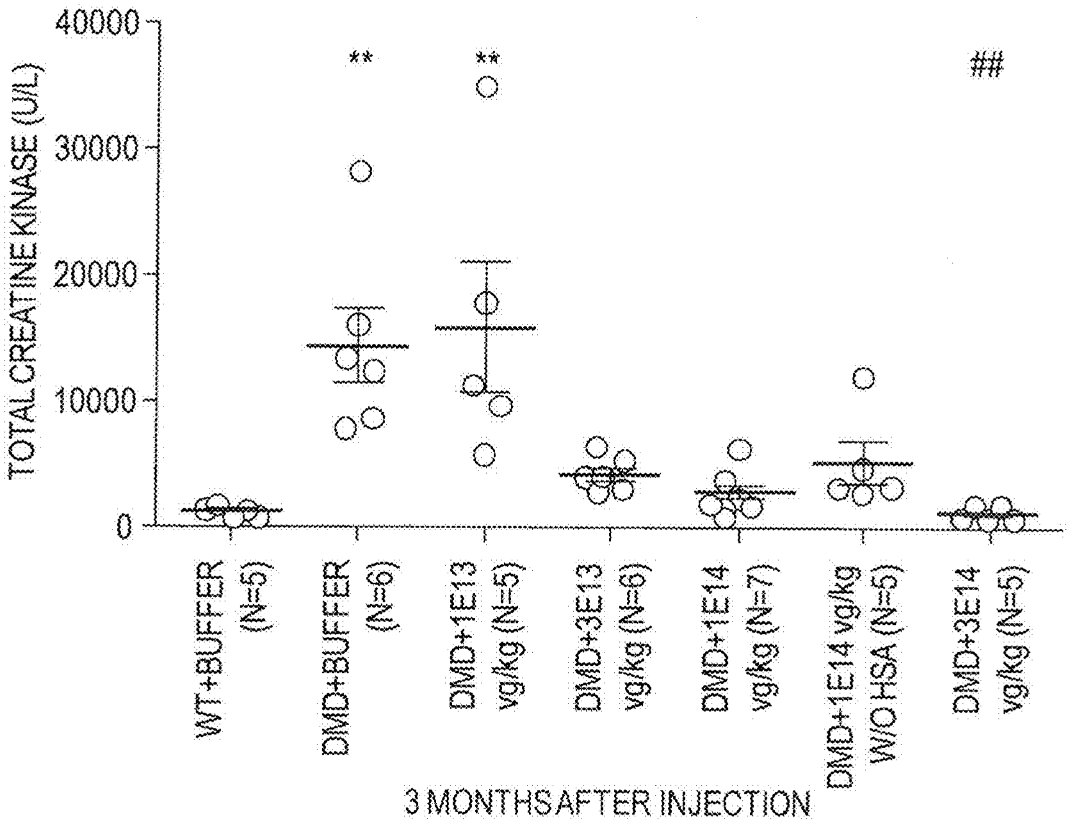
FIG. 51A shows effect in Dmd$^{mdx}$ rats of different doses of AAV9.hCK.Hopti-Dys3978.spA vector on blood total creatine kinase (CK) levels 3 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) (**$p<0.01$), or compare Dmd$^{mdx}$ rats dosed with $3\times10^{14}$ vg/kg vector against Dmd$^{mdx}$ rats that received buffer or $1\times10^{13}$ vg/kg vector (##$p<0.01$).
Figure 51B:
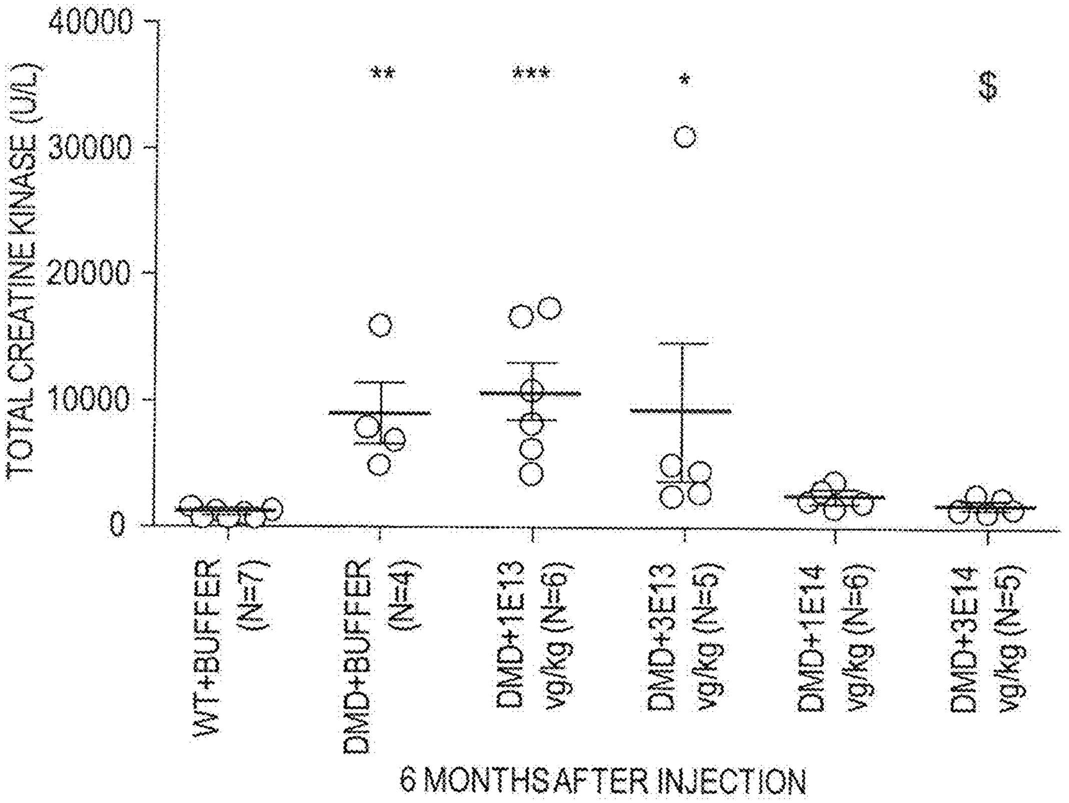
FIG. 51B shows effect in Dmd$^{mdx}$ rats of different doses of AAV9.hCK.Hopti-Dys3978.spA vector on blood total creatine kinase (CK) levels 6 months post-injection. Results are represented as mean±SEM. Statistical analyses were performed using the non-parametric Kruskal Wallis test and a post-hoc Dunn's multiple comparison test. Statistics compare Dmd$^{mdx}$ rats treated with vector against WT rats that received buffer (vehicle) as a negative control (*$p<0.001$, $p<0.01$, *$p<0.05$), or compare Dmd$^{mdx}$ rats dosed with $3\times10^{14}$ vg/kg vector against Dmd$^{mdx}$ rats that received $1\times10^{13}$ vg/kg vector ($$p<0.05$).

The pattern of ALT, LDH, and total CK levels all responded to age and vector treatment in similar ways. At 3 months post-injection, ALT, LDH and total CK levels were all significantly elevated in Dmd$^{mdx}$ rats treated with vehicle compared to WT rats. Treating the Dmd$^{mdx}$ rats with the mini-dystrophin vector resulted in a trend suggesting a dose responsive reduction in ALT, LDH and total CK levels relative to vehicle treated Dmd$^{mdx}$ rats, which in some cases achieved statistical significance. These results are shown in FIG. 49A, FIG. 50A, and FIG. 51A, respectively. At 6 months post-injection, there was a trend in the data suggesting elevated levels of ALT and LDH in Dmd$^{mdx}$ rats treated with vehicle compared to WT rats, which was reversed at highest vector dose tested, but none of the differences were statistically significant. These results are shown in FIG. 49B and FIG. 50B, respectively. In contrast, similar to the pattern seen at 3 months post-injection, total CK was significantly elevated in Dmd$^{mdx}$ rats treated with vehicle at 6 months post-injection compared to WT rats, and vector treatment resulted in a trend toward reduced levels that achieved statistical significance at the highest vector dose tested (FIG. 51B).

Figure 52A:
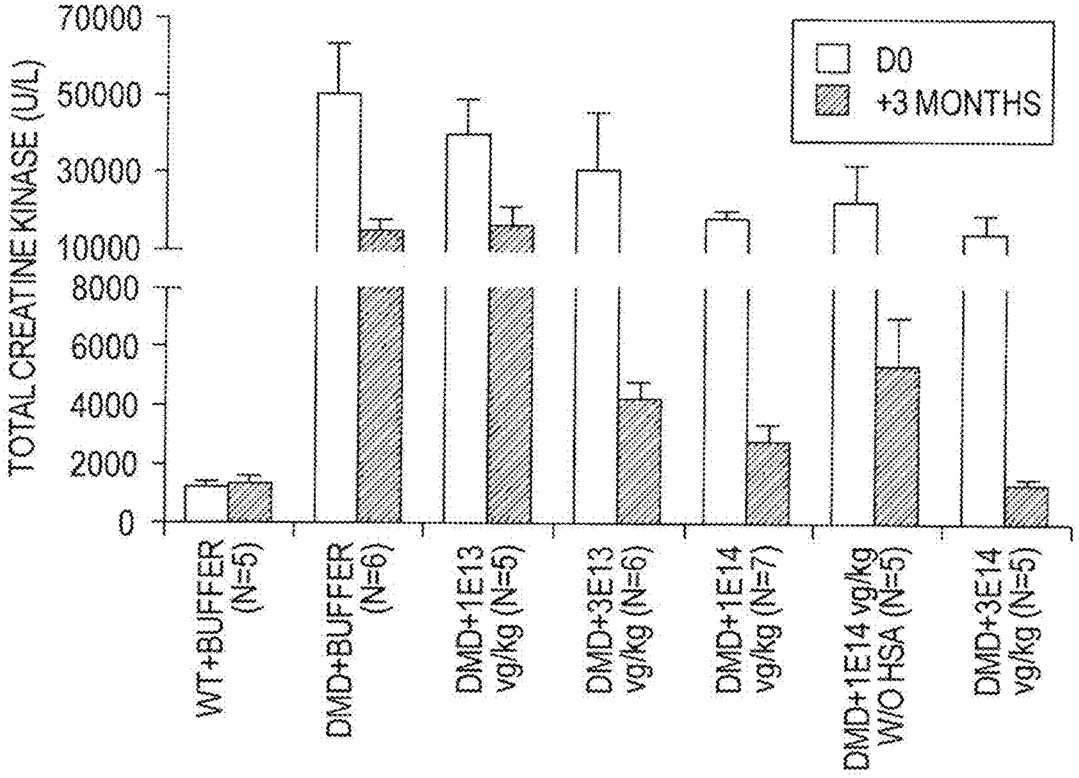
FIG. 52A provides total creatine kinase (CK) evolution between day of injection (DO) of vehicle of vector and sacrifice 3 months post-injection. Solid bars indicate data from DO, whereas hatched bars indicate data at 3 months. Results are represented as mean±SEM.
Figure 52B:
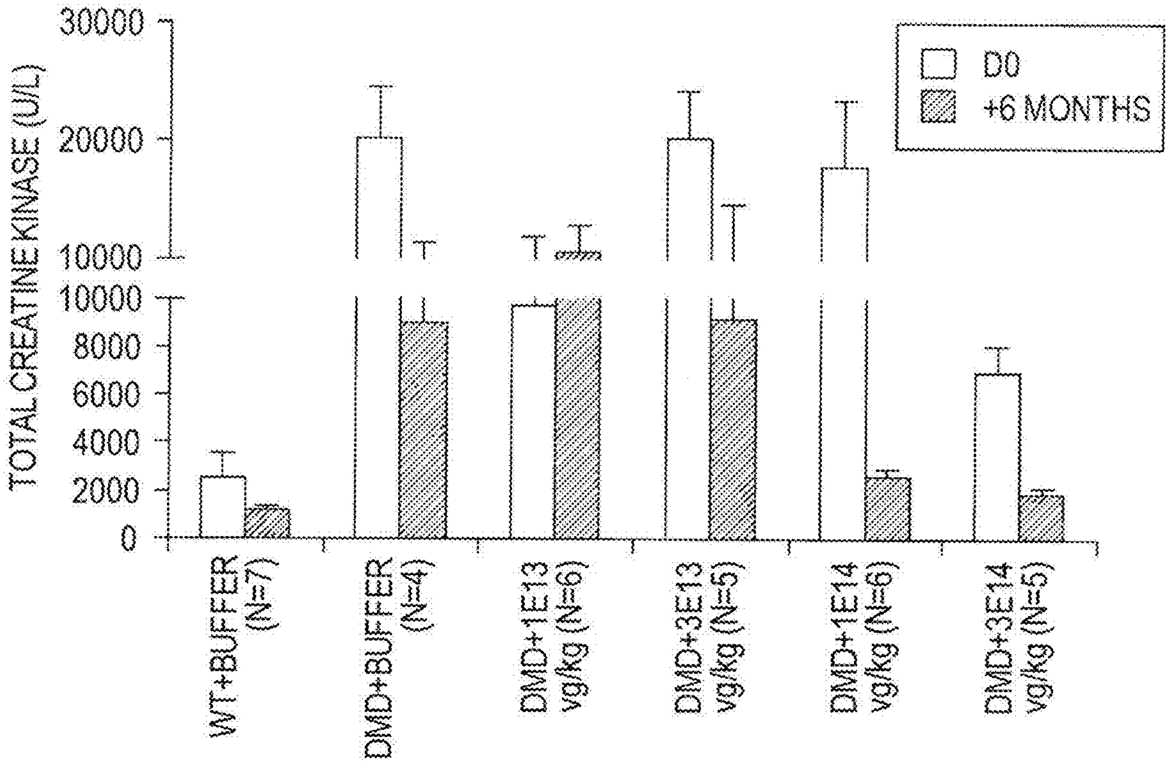
FIG. 52B provides total creatine kinase (CK) evolution between day of injection (DO) of vehicle of vector and sacrifice 6 months post-injection. Solid bars indicate data from DO, whereas hatched bars indicate data at 6 months. Results are represented as mean±SEM.

Total CK levels within treatment arms were also compared on the day of injection and 3 and 6 months after. As shown in FIG. 52A and FIG. 52B, blood total CK levels were consistently low in WT rats administered vehicle, while CK levels declined in all $Dmd^{mdx}$ rats, including those treated only with vehicle and the lowest vector dose. In contrast, the reduction of CK levels after 3 and 6 months was much greater for $Dmd^{mdx}$ rats treated with the three highest doses of vector. These observations are consistent with the natural course of DMD in humans, where CK levels, while elevated compared to controls, decline as the disease progresses due to replacement of muscle with adipose and fibrotic tissue, but also with a dose-responsive therapeutic effect at the higher vector doses tested.

Differences in CK isoenzymes were also observed. Before dosing, the CK-MM isoform predominated in $Dmd^{mdx}$ rats (mean >90%), whereas the CK-MM and CK—BB isoforms were comparable in WT rats (mean 40-60%), and CK-MB levels were higher in WT than in $Dmd^{mdx}$ rats (4-6% versus≈1%). At 3 and 6 months post-injection, $Dmd^{mdx}$ rats treated with vector doses above $1\times10^{13}$ vg/kg showed a slight increase in the proportion of the CK-BB isoform and a slight decrease in the proportion of the CK-MM isoform, with a trend towards a dose-related effect. No clear alteration in the proportion of the CK-MB isoform was observed in vector treated $Dmd^{mdx}$ rats.

Immunology

The humoral and cellular immune response in $Dmd^{mdx}$ rats treated with AAV9.hCK.Hopti-Dys3978.spA vector were measured before treatment and at 3 and 6 months post-injection and compared to negative and positive controls. Serum samples were obtained before injection of vehicle or vector, and at euthanasia 3 months post-injection. Splenocytes for analysis of T cell response were harvested at euthanasia at 3 and 6 months post-injection.

Humoral response to expression of the mini-dystrophin protein was assessed qualitatively by Western blot analysis of sera obtained from the test animals and diluted 1:500. Sera from all rats, whether WT or $Dmd^{mdx}$, were negative for antibodies against mini-dystrophin protein when administered vehicle, or prior to receiving vector. By contrast most $Dmd^{mdx}$ rats treated with vector, even at the lowest dose of $1\times10^{13}$ vg/kg, produced IgG antibodies that bound mini-dystrophin in Western blots. Between 80%-100% of $Dmd^{mdx}$ rats sacrificed at 3 months post-injection, and between 60%-100% of $Dmd^{mdx}$ rats sacrificed at 6 months post-injection produced IgG specific for the mini-dystrophin protein depending on dose.

Presence of antibodies to the AAV9 vector capsid was tested by ELISA. Serum from WT and $Dmd^{mdx}$ rats treated with vehicle had no detectable IgG that reacted with AAV9. By contrast, all rats treated with vector, regardless of dose or whether sacrificed 3 or 6 months post-injection, produced anti-AAV9 IgG with a titer higher than 1:10240, the highest dilution tested. Neutralizing antibodies against AAV9 were also tested with a cell transduction inhibition assay using a recombinant AAV9 vector that expresses LacZ reporter gene detected using a luminometer. The titer was defined as the lowest dilution that inhibited transduction >50%. Neutralizing antibodies against AAV9 were detected in the serum from all $Dmd^{mdx}$ rats that had received vector, regardless of dose or whether sacrificed 3 or 6 months post-injection, but not in the same animals prior to injection or WT and $Dmd^{mdx}$ rats that had received vehicle only. Titers ranged from 1:5000 to >1:500000 with no clear dose effect.

Presence of a cellular immune response to vector was evaluated using an IFNγ ELISpot assay on splenocytes isolated from vehicle treated WT and $Dmd^{mdx}$ rats, and $Dmd^{mdx}$ rats that had received vector. T cell response to the human mini-dystrophin protein expressed by the vector genome was tested using an overlapping peptide bank covering the whole sequence of opti-dys3978 protein (length of 15 amino acids, overlap of 10 amino acids, total of 263 peptides) and a rat specific IFNγ-$ELISpot^{BASIC}$ kit (Mabtech). Negative control consisted of unstimulated splenocytes and positive control consisted of cells stimulated with the mitogen concanavalin A. IFNγ secretion was quantified as the number of spot-forming cells (SFC) per $10^6$ cells, and a positive response was defined as >50 SFC/$10^6$ cells or at least 3-fold the value obtained for the negative control. No specific T cell response against any peptide sequences derived from the mini-dystrophin protein was found in splenocytes obtained from any of the test animals, at either 3 months or 6 months post-injection, including from $Dmd^{mdx}$ rats treated at the highest vector dose of $3\times10^{14}$ vg/kg.

T cell response against the AAV9 capsid was also tested using the IFNγ ELISpot assay screened against peptide sequences derived from AAV9 (15-mers overlapping by 10 amino acids divided into 3 pools). There was a positive IFNγ response in between 16%-60% of vector treated $Dmd^{mdx}$ rats sacrificed at 3 months post-injection, and between 16%-66% of vector treated $Dmd^{mdx}$ rats sacrificed at 6 months post-injection, that was positively correlated with vector dose. By contrast, all WT and $Dmd^{mdx}$ rats treated with vehicle were negative for T cell response against AAV9 capsid.

EXAMPLE 9

Grip Strength in Older $Dmd^{mdx}$ Rats Treated with AAV9.hCK.Hopti-Dys3978.spA The studies described in Example 8, above, were initiated in young rats 7-9 weeks of age. This example describes muscle function analysis of older $Dmd^{mdx}$ rats first treated with the AAV9.hCK.Hopti-Dys3978.spA vector when they were 4 months of age and 6 months of age, respectively. The average life span of Sprague Dawley rats is 24-36 months. The goal of these experiments was to determine if treatment with vector later in a $Dmd^{mdx}$ rat's life might be effective. Positive results would suggest that treating older human DMD patients, such as older children, adolescents, or even young adults, with vector might also improve their muscle function.

The experiments described in this example were conducted using similar materials and methods as those described in Example 8. More specifically, $Dmd^{mdx}$ rats at 4 and 6 months of age (n=6 for each age group) were separately treated with $1\times10^{14}$ vg/kg of AAV9.hCK.Hopti-Dys3978.spA vector. As negative controls, WT rats and $Dmd^{mdx}$ rats (n=6 for each age group) 4 months and 6 months of age were separately treated with vehicle only. At 3 months post-injection, rats were tested for grip strength as described previously. As with the younger rats, maximum forelimb grip strength and grip strength over multiple repeated trials with short latency periods between each trial were tested. The latter test was intended to measure muscle fatigue.

Figure 53A:
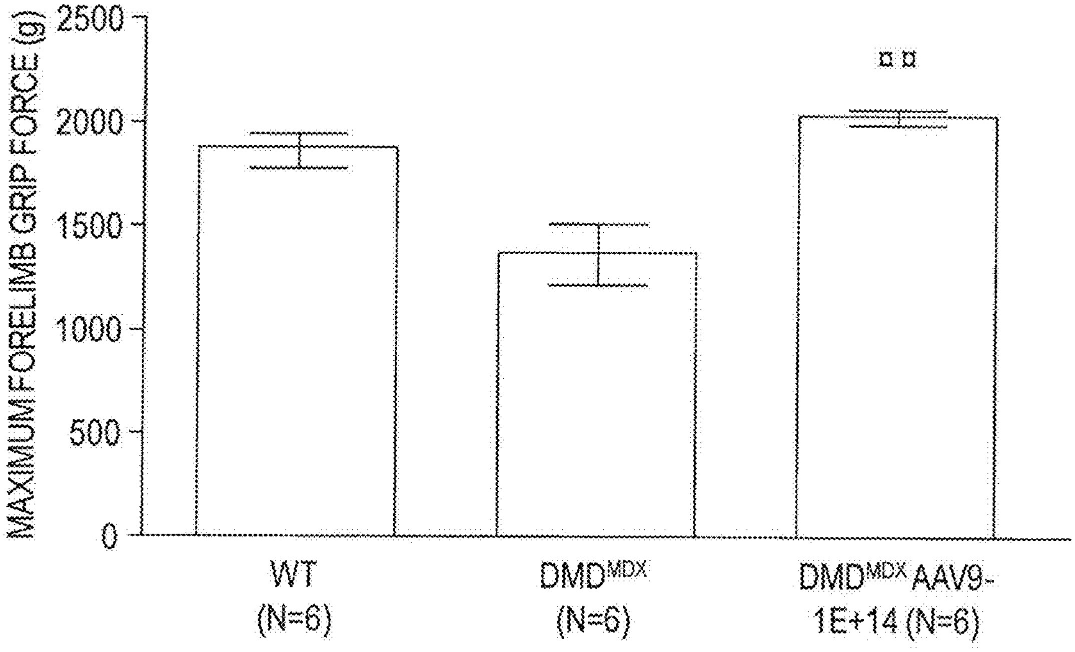
FIG. 53A provides average absolute maximum forelimb grip strength of older Dmd$^{mdx}$ rats treated with $1\times10^{14}$ vg/kg AAV9.hCK.Hopti-Dys3978.spA vector compared to Dmd$^{mdx}$ and WT rats treated with vehicle. Tests were conducted 3 months post-injection in rats injected at 4 months of age, or when the rats were approximately 7 months old. Results are represented as mean±SEM. Statistics compare Dmd$^{mdx}$ rats treated with vector against Dmd$^{mdx}$ rats treated with vehicle (*$p<0.01$).
Figure 53B:
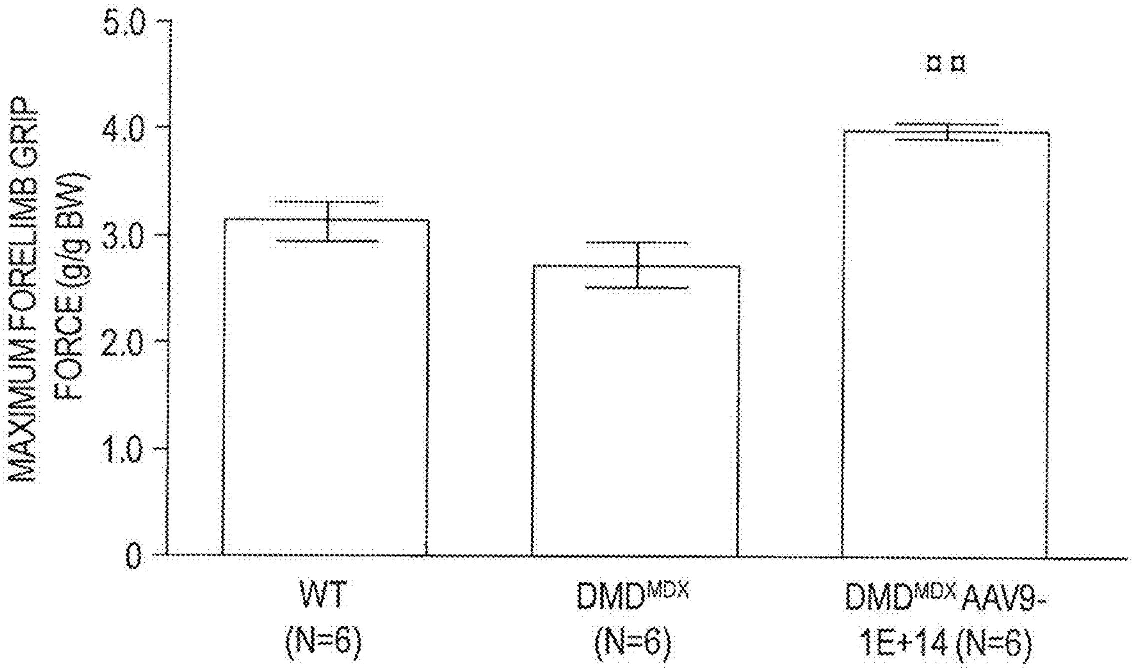
FIG. 53B provides average maximum forelimb grip strength relative to body weight of older Dmd$^{mdx}$ rats treated with $1\times10^{14}$ vg/kg AAV9.hCK.Hopti-Dys3978.spA vector compared to Dmd$^{mdx}$ and WT rats treated with vehicle. Tests were conducted 3 months post-injection in rats injected at 4 months of age, or when the rats were approximately 7 months old. Results are represented as mean±SEM. Statistics compare Dmd$^{mdx}$ rats treated with vector against Dmd$^{mdx}$ rats treated with vehicle (*$p<0.01$).

As shown in FIG. 53A, at 3 months post-injection, maximum forelimb grip strength of $Dmd^{mdx}$ rats treated with vehicle at 4 months of age was on average slightly lower compared to 4 month old WT rats treated with vehicle, although the difference did not reach statistical significance. By contrast, Dmd$^{mdx}$ rats injected with $1\times10^{14}$ vg/kg vector at 4 months of age had greater average maximum forelimb grip strength than Dmd$^{mdx}$ rats treated only with vehicle at the same age, a difference that did reach statistical significance. The strength of the vector treated rats was even greater than WT rats, although that difference was not statistically significant. The results were similar when the data was normalized for body weight, as shown in FIG. 53B. In FIG. 53A and FIG. 53B, the symbol "aa" indicates a statistically significant difference between vector versus vehicle treated Dmd$^{mdx}$ rats ($p<0.01$).

Figure 53C:
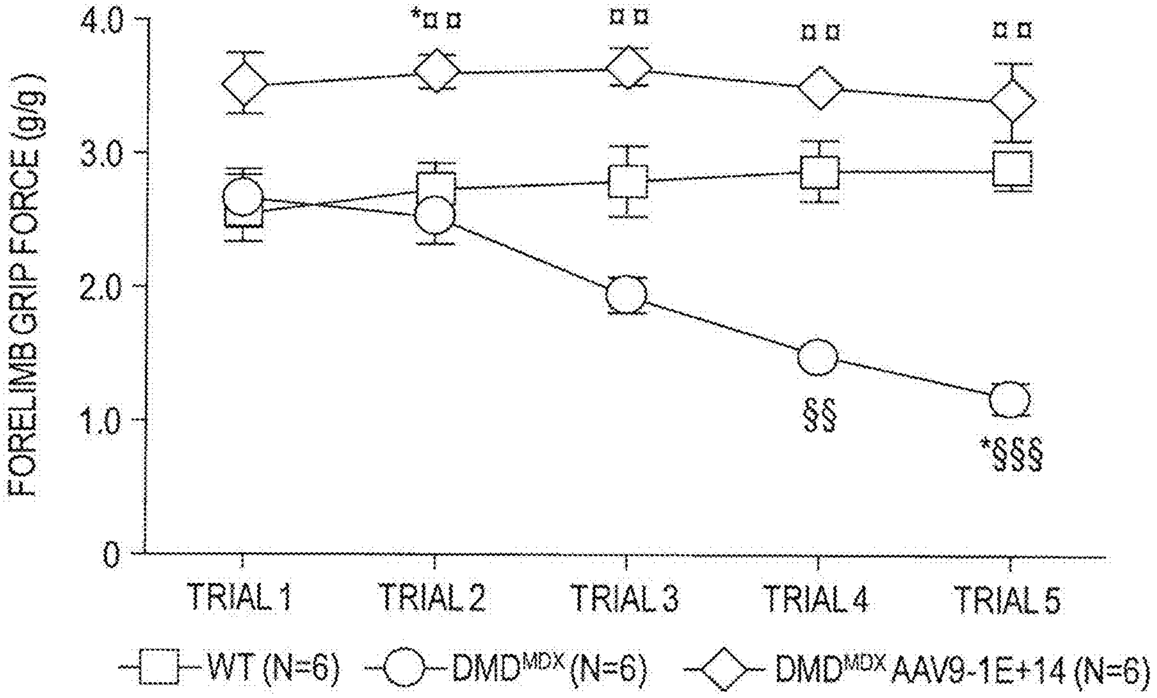
FIG. 53C shows evolution of forelimb grip force as a measure of muscle fatigue in older Dmd$^{mdx}$ rats treated with $1\times10^{14}$ vg/kg AAV9.hCK.Hopti-Dys3978.spA vector compared to Dmd$^{mdx}$ and WT rats treated with vehicle. Test was conducted by measuring average maximum grip force 5 times with short intervals between each trial. Tests were conducted 3 months post-injection in rats injected at 4 months of age, or when the rats were approximately 7 months old. Results are provided relative to body weight and as the mean±SEM. Statistics compare Dmd$^{mdx}$ rats treated with vector against WT rats receiving vehicle (*$p<0.05$) and Dmd$^{mdx}$ rats receiving vehicle (aa$p<0.01$), and compare later trials against trial 1 in vehicle treated Dmd$^{mdx}$ rats (§ § $p<0.01$, § § § $p<0.001$).

With respect to muscle fatigue, as shown in FIG. 53C, Dmd$^{mdx}$ rats treated with vehicle at 4 months exhibited fatigue after the 2nd grip test, whereas WT rats exhibited no fatigue even after 4 tests. By contrast, 4 month old Dmd$^{mdx}$ rats treated with vector exhibited minimal, if any, muscle fatigue between the 1st and 5th grip tests. The vector treated Dmd$^{mdx}$ rats also appeared stronger overall compared to WT rats treated with vehicle. In FIG. 53C, the symbol "*" indicates a statistically significant difference between vector treated Dmd$^{mdx}$ rats and WT rats treated with vehicle ($p<0.05$); "¤¤" indicates a statistically significant difference between vector versus vehicle treated Dmd$^{mdx}$ rats ($p<0.01$); and "§ §" and "§ § §" indicate a statistically significant difference between vehicle treated Dmd$^{mdx}$ rats at the 4th and 5th grip tests, respectively, compared to the 1st grip test (at $p<0.01$ and $p<0.001$, respectively).

Figure 54A:
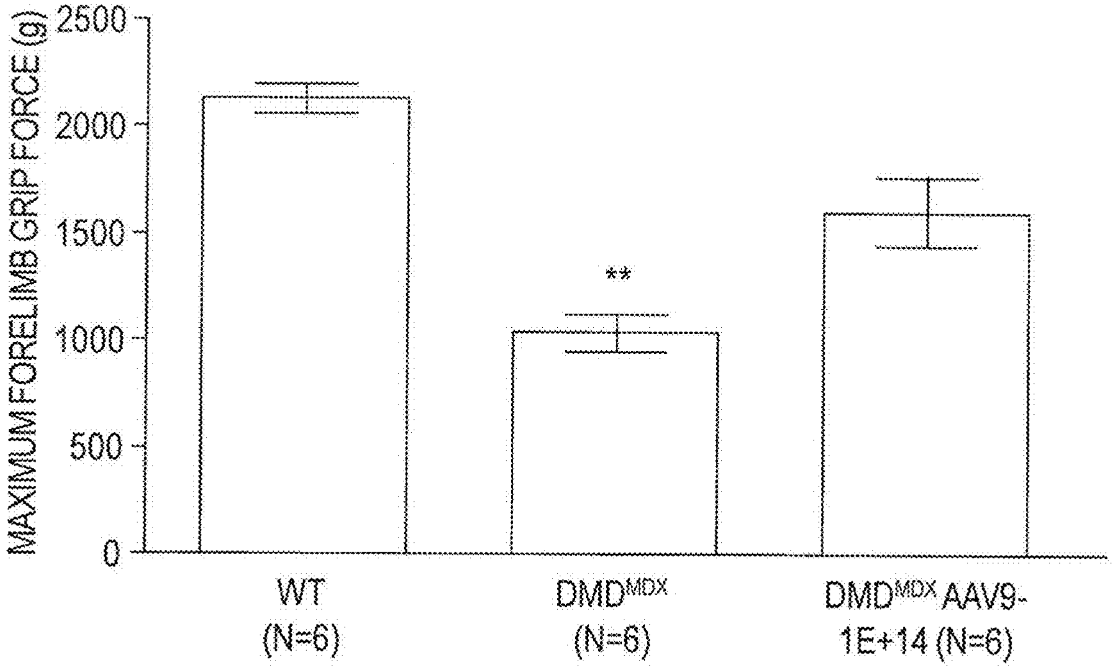
FIG. 54A provides average absolute maximum forelimb grip strength of older Dmd$^{mdx}$ rats treated with $1\times10^{14}$ vg/kg AAV9.hCK.Hopti-Dys3978.spA vector compared to Dmd$^{mdx}$ and WT rats treated with vehicle. Tests were conducted 3 months post-injection in rats injected at 6 months of age, or when the rats were approximately 9 months old. Results are represented as mean±SEM. Statistics compare Dmd$^{mdx}$ rats treated with vehicle against WT rats treated with vehicle (**$p<0.01$).
Figure 54B:
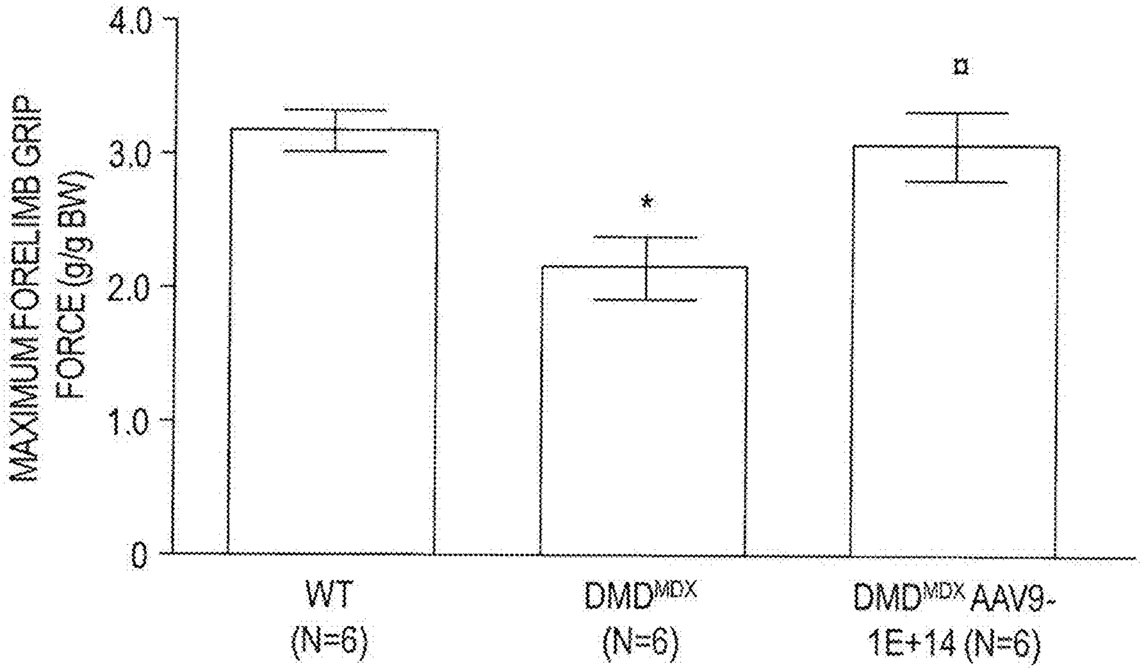
FIG. 54B provides average maximum forelimb grip strength relative to body weight of older Dmd$^{mdx}$ rats treated with $1\times10^{14}$ vg/kg AAV9.hCK.Hopti-Dys3978.spA vector compared to Dmd$^{mdx}$ and WT rats treated with vehicle. Tests were conducted 3 months post-injection in rats injected at 6 months of age, or when the rats were approximately 9 months old. Results are represented as mean±SEM. Statistics compare Dmd$^{mdx}$ rats treated with vehicle against WT rats treated with vehicle (*$p<0.05$) or Dmd$^{mdx}$ rats treated with vector against Dmd$^{mdx}$ rats treated with vehicle (¤$p<0.05$).

As shown in FIG. 54A, at 3 months post-injection, maximum forelimb grip strength of Dmd$^{mdx}$ rats treated with vehicle at 6 months of age was significantly lower compared to 6 month old WT rats treated with vehicle. This effect was maintained even when the results were normalized for body weight, as shown in FIG. 54B. Treating Dmd$^{mdx}$ rats with $1\times10^{14}$ vg/kg vector at 6 months of age increased the average maximum forelimb grip strength compared with Dmd$^{mdx}$ rats treated only with vehicle, a difference that reached statistical significance when normalized for body weight (FIG. 54B). In FIG. 54A and FIG. 54B, the symbols "*" and "**" indicate a statistically significant difference between vehicle treated Dmd$^{mdx}$ and WT rats (at $p<0.05$ and $p<0.01$, respectively); and "a" indicates a statistically significant difference between vector versus vehicle treated Dmd$^{mdx}$ rats ($p<0.05$).

Figure 54C:
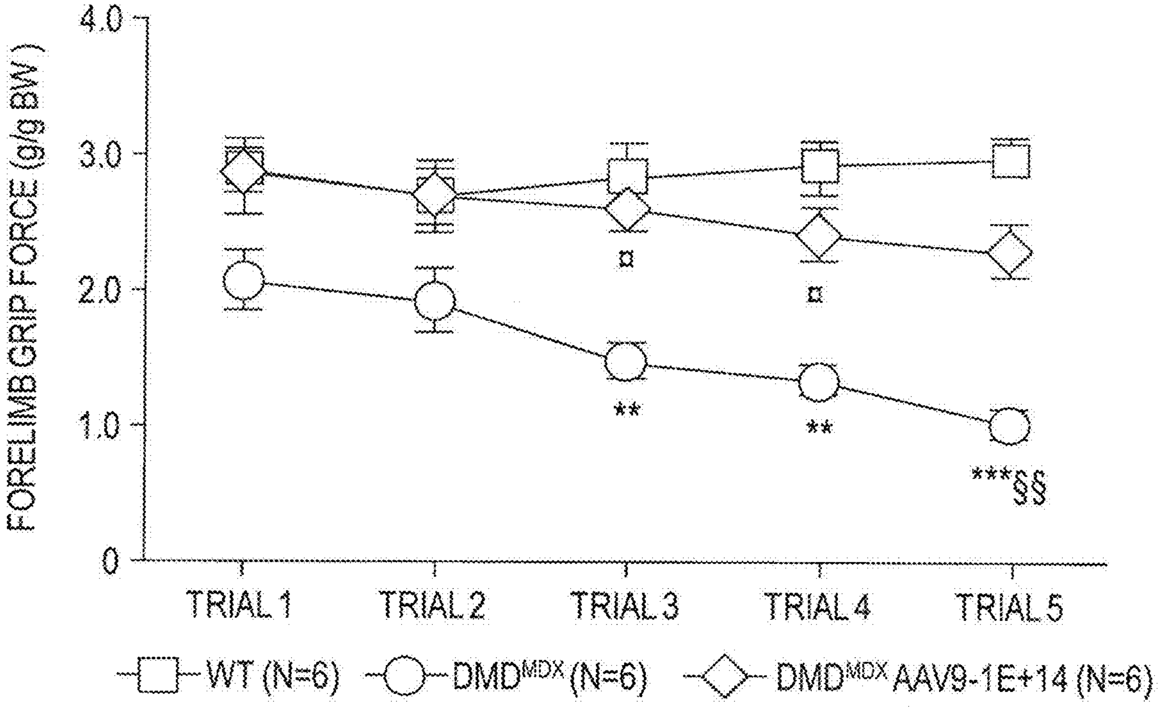
FIG. 54C shows evolution of forelimb grip force as a measure of muscle fatigue in older Dmd$^{mdx}$ rats treated with $1\times10^{14}$ vg/kg AAV9.hCK.Hopti-Dys3978.spA vector compared to Dmd$^{mdx}$ and WT rats treated with vehicle. Test was conducted by measuring average maximum grip force 5 times with short intervals between each trial. Tests were conducted 3 months post-injection in rats injected at 6 months of age, or when the rats were approximately 9 months old. Results are provided relative to body weight and as the mean±SEM. Statistics compare Dmd$^{mdx}$ rats treated with vector against Dmd$^{mdx}$ rats receiving vehicle (a$p<0.05$), Dmd$^{mdx}$ rats treated with vehicle against WT rats receiving vehicle ($p<0.01$, *$p<0.001$), and trial 5 against trial 1 in vehicle treated Dmd$^{mdx}$ rats (§ § $p<0.01$).

With respect to muscle fatigue, as shown in FIG. 54C, Dmd$^{mdx}$ rats treated with vehicle at 6 months exhibited fatigue after the 2nd grip test, whereas WT rats exhibited no fatigue even after 4 tests. In contrast with rats treated at 4 months, 6 month old Dmd$^{mdx}$ rats treated with vector exhibited some reduced strength over the multiple grip tests, although not to the same extent as that seen with vehicle treated control Dmd$^{mdx}$ rats. Also in contrast to the tests conducted with rats treated at 4 months of age, the strength of the WT rats appeared to be greater than that of Dmd$^{mdx}$ rats treated with vector at 6 months over the course of the experiment. In FIG. 54C, the symbols "" and "*" indicate a statistically significant difference between vector treated Dmd$^{mdx}$ rats and WT rats treated with vehicle (at $p<0.01$ and $p<0.001$, respectively); "¤" indicates a statistically significant difference between vector versus vehicle treated Dmd$^{mdx}$ rats ($p<0.05$); and "§ §" indicates a statistically significant difference between vehicle treated Dmd$^{mdx}$ rats at the 5th grip test compared to the 1st grip test ($p<0.01$).

TABLE 13

TABLE OF SEQUENCES

| SEQ ID NO | DESCRIPTION AND SEQUENCE | |
|---|---|---|
| SEQ ID NO: 1 | DNA sequence of human codon-optimized gene encoding human mini-dystrophin 3978 (Hopti-Dys3978) | |
| | atgctttggt gggaggaagt ggaggactgc tacgagagag aggacgtgca gaagaaaacc | 60 |
| | ttcaccaagt gggtgaacgc ccagttcagc aagttcggca agcagcacat cgagaacctg | 120 |
| | ttcagcgacc tgcaggatgg caggagactg ctggacctgc tggagggcct gaccggccag | 180 |
| | aagctgccca aggagaaggg cagcaccaga gtgcacgccc tgaacaacgt gaacaaggcc | 240 |
| | ctgagagtgc tgcagaacaa caacgtggac ctggtgaaca tcggcagcac cgacatcgtg | 300 |
| | gacggcaacc acaagctgac cctgggcctg atctggaaca tcatcctgca ctggcaggtg | 360 |
| | aagaacgtga tgaagaacat catggccggc ctgcagcaga ccaacagcga gaagatcctg | 420 |
| | ctgagctggg tgaggcagag caccagaaac taccccaagg tgaacgtgat caacttcacc | 480 |
| | acctcctgga gcgacggcct ggccctgaac gccctgatcc acagccacag acccgacctg | 540 |
| | ttcgactgga acagcgtggt gtgtcagcag agcgccaccc agagactgga gcacgccttc | 600 |
| | aacatcgcca gataccagct gggcatcgag aagctgctgg accccgagga cgtggacacc | 660 |
| | acctaccccg acaagaaaag catcctcatg tacattacca gcctgttcca ggtgctgccc | 720 |
| | cagcaggtgt ccatcgaggc catccaggaa gtggaaatgc tgcccaggcc ccccaaagtg | 780 |
| | accaaggagg agcacttcca gctgcaccac cagatgcact acagccagca gatcacagtg | 840 |
| | agcctggccc agggctatga gagaaccagc agccccaagc ccagattcaa gagctacgcc | 900 |
| | tacacccagg ccgcctacgt gaccacctcc gaccccacca gaagcccctt ccccagccag | 960 |
| | cacctggagg cccccgagga caagagcttc ggcagcagcc tgatggagag cgaagtgaac | 1020 |
| | ctggacagat accagaccgc cctggaggaa gtgctgtcct ggctgctgag cgccgaggac | 1080 |
| | accctgcagg cccagggcga gatcagcaac gacgtggaag tggtgaagga ccagttccac | 1140 |
| | acccacgagg gctacatgat ggatctgacc gcccaccagg gcagagtggg caatatcctg | 1200 |
| | cagctgggca gcaagctgat cggcaccggc aagctgagcg aggacgagga gaccgaagtg | 1260 |
| | caggagcaga tgaacctgct gaacagcaga tgggagtgcc tgagagtggc cagcatggag | 1320 |
| | aagcagagca acctgcacag agtgctgatg gacctgcaga accagaagct gaaggagctg | 1380 |
| | aacgactggc tgaccaagac cgaggagcgg accagaaaga tggaggagga gcccctgggc | 1440 |
| | cccgacctgg aggacctgaa gagacaggtg cagcagcaca aagtgctgca ggaggacctg | 1500 |
| | gagcaggagc aggtgcgcgt gaacagcctg acccacatgg tggtggtcgt ggacgagagc | 1560 |
| | agcggcgacc acgccacagc cgccctggaa gagcagctga aagtgctggg cgacagatgg | 1620 |
| | gccaatattt gtaggtggac cgaggacaga tgggtgctgc tgcaggacca gcccgacctg | 1680 |
| | gcccctggcc tgaccaccat cggcgccagc cccacccaga ccgtgaccct ggtgacccag | 1740 |
| | cccgtggtga caaaggagac cgccatcagc aagctggaga tgcccagctc cctgatgctg | 1800 |
| | gaagtgccca cccaccgcct gctccagcag ttcccccctgg acctggagaa gttcctggcc | 1860 |
| | tggctgaccg aggccgaaac caccgccaat gtgctccagg acgccactag aaaggagagg | 1920 |

TABLE 13-continued

| TABLE OF SEQUENCES | |
|---|---|
| SEQ ID NO | DESCRIPTION AND SEQUENCE |
| | ctgctggagg acagcaaggg cgtgaaagag ctgatgaagc agtggcagga tctgcagggc 1980<br>gaaatcgagg cccacaccga cgtgtaccac aacctggacg agaacagcca gaagattctg 2040<br>aggagcctgg agggcagcga cgacgccgtc ctgctccaga ggaggctgga caacatgaac 2100<br>ttcaagtgga gcgagctgcg gaagaagagc ctgaacatcc ggagccacct ggaagccagc 2160<br>agcgaccagt ggaagagact gcacctgagc ctgcaggagc tgctggtgtg gctgcagctg 2220<br>aaggacgacg agctgagcag acaggccccc atcggcggcg acttccccgc cgtgcagaag 2280<br>cagaacgacg tgcaccgggc cttcaagagg gagctgaaaa ccaaggaacc cgtgatcatg 2340<br>agcaccctgg agacagtgcg gatcttcctg accgagcagc cctggaggg actggagaag 2400<br>ctgtaccagg agcccagaga gctgcccccc gaggagagag cccagaacgt gaccaggctg 2460<br>ctgagaaagc aggccgagga agtgaatacc gagtgggaga agctgaatct gcacagcgcc 2520<br>gactggcaga gaaagatcga cgagaccctg gagagactcc aggaactgca ggaagccacc 2580<br>gacgagctgg acctgaagct gagacaggcc gaagtgatca agggcagctg gcagcctgtg 2640<br>ggcgatctgc tgatcgactc cctgcaggat cacctggaga aagtgaaggc cctgcggggc 2700<br>gagatcgccc ccctgaagga gaatgtgagc cacgtgaacg acctggccag acagctgacc 2760<br>accctgggca tccagctgag cccctacaac ctgagcacac tggaggatct gaacacccgg 2820<br>tggaaactgc tgcaggtggc cgtggaggat agagtgaggc agctgcacga agcccacaga 2880<br>gacttcggcc ctgcctccca gcacttcctg agcaccagcg tgcagggccc ctgggagaga 2940<br>gccatctccc ccaacaaagt gccctactac atcaaccacg agacccagac cacctgctgg 3000<br>gaccacccta agatgaccga gctgtatcag agcctggccg acctgaacaa tgtgcggttc 3060<br>agcgcctaca gaaccgccat gaagctgcgg agactgcaga aggccctgtg cctggatctg 3120<br>ctgagcctga gcgccgcctg cgacgccctg gaccagcaca acctgaagca gaatgaccag 3180<br>cccatggaca tcctgcagat catcaactgc ctgaccacaa tctacgaccg gctggaacag 3240<br>gagcacaaca acctggtgaa tgtgcccctg tgcgtggaca tgtgcctgaa ttggctgctg 3300<br>aacgtgtacg acaccggcag gaccggcaga atccgcgtgc tgagcttcaa gaccggcatc 3360<br>atcagcctgt gcaaggccca cctggaggat aagtaccgct acctgttcaa gcaggtggcc 3420<br>agcagcaccg gcttctgcga tcagaggaga ctgggcctgc tgctgcacga tagcatccag 3480<br>atccctaggc agctgggcga agtggccagc tttggcggca gcaacatcga gccctctgtg 3540<br>aggagctgct tccagttcgc caacaacaag cccgagatcg aggccgccct gttcctggac 3600<br>tggatgaggc tggagcctca gagcatggtg tggctgcctg tgctgcacag agtggccgcc 3660<br>gccgagaccg ccaagcacca ggccaagtgc aatatctgca aggagtgccc catcatcggc 3720<br>ttccggtaca ggagcctgaa gcacttcaac tacgacatct gccagagctg ctttttcagc 3780<br>ggcagagtgg ccaagggcca caaaatgcac taccccatgg tggagtactg cacccccacc 3840<br>acctccggcg aggatgtgag agacttcgcc aaagtgctga agaataagtt ccggaccaag 3900<br>cggtactttg ccaagcaccc caggatgggc tacctgcccg tgcagaccgt gctggaaggc 3960<br>gacaacatgg agacctga 3978 |
| SEQ ID NO: 2 | DNA sequence of human codon-optimized gene encoding human mini-dystrophin 3837 (Hopti-Dys3837)<br>atgctttggt gggaggaagt ggaggactgc tacgagagag aggacgtgca gaagaaaacc 60<br>ttcaccaagt gggtgaacgc ccagttcagc aagttcggca agcagcacat cgagaacctg 120<br>ttcagcgacc tgcaggatgg caggagactg ctggacctgc tggagggcct gaccggccag 180<br>aagctgccca aggagaaggg cagcaccaga gtgcacgccc tgaacaacgt gaacaaggcc 240<br>ctgagagtgc tgcagaacaa caacgtggac ctggtgaaca tcggcagcac cgacatcgtg 300<br>gacggcaacc acaagctgac cctgggcctg atctggaaca tcatcctgca ctggcaggtg 360<br>aagaacgtga tgaagaacat catggccggc ctgcagcaga ccaacagcga gaagatcctg 420<br>ctgagctggg tgaggcagag caccagaaac tacccccagg tgaacgtgat caacttcacc 480<br>acctcctgga gcgacggcct ggccctgaac gccctgatcc acagccacag acccgacctg 540<br>ttcgactgga acagcgtggt gtgtcagcag agcgccaccc agagactgga gcacgccttc 600<br>aacatcgcca gataccagct gggcatcgag aagctgctgg accccgagga cgtggacacc 660<br>acctaccccg acaagaaaag catcctcatg tacattacca gcctgttcca ggtgctgccc 720<br>cagcaggtgt ccatcgaggc catccaggaa gtggaaatgc tgcccaggcc ccccaaagtg 780<br>accaaggagg agcacttcca gctgcaccac cagatgcact acagccagca gatcacagtg 840<br>agcctggccc agggctatga gagaaccagc agccccaagc ccagattcaa gagctacgcc 900<br>tacacccagg ccgcctacgt gaccacctcc gaccccacca gaagcccctt ccccagccag 960<br>cacctggagg cccccgagga caagagcttc ggcagcagcc tgatggagag cgaagtgaac 1020<br>ctggacagat accagaccgc cctggaggaa gtgctgtcct ggctgctgag cgccgaggac 1080<br>accctgcagg cccagggcga gatcagcaac gacgtggaag tggtgaagga ccagttccac 1140<br>acccacgagg gctacatgat ggatctgacc gcccaccagg gcagagtggg caatatcctg 1200<br>cagctgggca gcaagctgat cggcaccggc aagctgagcg aggacgagga gaccgaagtg 1260<br>caggagcaga tgaacctgct gaacagcaga tgggagtgcc tgagagtggc cagcatggag 1320<br>aagcagagca acctgcacag agtgctgatg gacctgcaga accagaagct gaaggagctg 1380<br>aacgactggc tgaccaagac cgaggagcgg accagaaaga tggaggagga gcccctgggc 1440<br>cccgacctgg aggacctgaa gagacaggtg cagcagcaca aagtgctgca ggaggacctg 1500<br>gagcaggagc aggtgcgcgt gaacagcctg acccacatgg tggtggtcgt ggacgagagc 1560<br>agcggcgacc acgccacagc cgccctggaa gagcagctga aagtgctggg cgacagatgg 1620<br>gccaatattt gtaggtggac cgaggacaga tgggtgctgc tgcaggacac ccaccgcctg 1680<br>ctccagcagt tcccccctgga cctggagaag ttcctggcct ggctgaccga ggccgaaacc 1740<br>accgccaatg tgctccagga cgccactaga aaggagaggc tgctggagga cagcaagggc 1800<br>gtgaaagagc tgatgaagca gtggcaggat ctgcagggcg aaatcgaggc ccacaccgac 1860<br>gtgtaccaca acctggacga gaacagccag aagattctga ggagcctgga gggcagcgac 1920<br>gacgccgtcc tgctccagag gaggctggac aacatgaact tcaagtggag cgagctgcgg 1980<br>aagaagagcc tgaacatccg gagccacctg gaagccagca gcgaccagtg gaagagactg 2040<br>cacctgagcc tgcaggagct gctggtgtgg ctgcagctga aggacgacga gctgagcaga 2100<br>caggccccca tcggcggcga cttccccgcc gtgcagaagc agaacgacgt gcaccgggcc 2160<br>ttcaagaggg agctgaaaac caaggaaccc gtgatcatga gcaccctgga gacagtgcgg 2220<br>atcttcctga ccgagcagcc cctggaggga ctggagaagc tgtaccagga gcccagagag 2280 |

TABLE 13-continued

TABLE OF SEQUENCES

| SEQ ID NO | DESCRIPTION AND SEQUENCE | |
|---|---|---|
| | ctgcccccg aggagagagc ccagaacgtg accaggctgc tgagaaagca ggccgaggaa | 2340 |
| | gtgaataccg agtgggagaa gctgaatctg cacagcgccg actggcagag aaagatcgac | 2400 |
| | gagaccctgg agagactcca ggaactgcag gaagccaccg acgagctgga cctgaagctg | 2460 |
| | agacaggccg aagtgatcaa gggcagctgg cagcctgtgg gcgatctgct gatcgactcc | 2520 |
| | ctgcaggatc acctggagaa agtgaaggcc ctgcggggcg agatcgcccc cctgaaggag | 2580 |
| | aatgtgagcc acgtgaacga cctggccaga cagctgacca ccctgggcat ccagctgagc | 2640 |
| | ccctacaacc tgagcacact ggaggatctg aacacccggt ggaaactgct gcaggtggcc | 2700 |
| | gtggaggata gagtgaggca gctgcacgaa gcccacagag acttcggccc tgcctcccag | 2760 |
| | cacttcctga gcaccagcgt gcagggcccc tgggagagag ccatctcccc caacaaagtg | 2820 |
| | ccctactaca tcaaccacga gacccagacc acctgctggg accaccctaa gatgaccgag | 2880 |
| | ctgtatcaga gcctggccga cctgaacaat gtgcggttca gcgcctacag aaccgccatg | 2940 |
| | aagctgcgga gactgcagaa ggccctgtgc ctggatctgc tgagcctgag cgccgcctgc | 3000 |
| | gacgccctgg accagcacaa cctgaagcag aatgaccagc ccatggacat cctgcagatc | 3060 |
| | atcaactgcc tgaccacaat ctacgaccgg ctggaacagg agcacaacaa cctggtgaat | 3120 |
| | gtgcccctgt gcgtggacat gtgcctgaat tggctgctga acgtgtacga caccggcagg | 3180 |
| | accggcagaa tccgcgtgct gagcttcaag accggcatca tcagcctgtg caaggcccac | 3240 |
| | ctggaggata agtaccgcta cctgttcaag caggtggcca gcagcaccgg cttctgcgat | 3300 |
| | cagaggagac tgggcctgct gctgcacgat agcatccaga tccctaggca gctgggcgaa | 3360 |
| | gtggccagct ttggcggcag caacatcgag ccctctgtga ggagctgctt ccagttcgcc | 3420 |
| | aacaacaagc ccgagatcga ggccgccctg ttcctggact ggatgaggct ggagcctcag | 3480 |
| | agcatggtgt ggctgcctgt gctgcacaga gtggccgccg ccgagaccgc caagcaccag | 3540 |
| | gccaagtgca atatctgcaa ggagtgcccc atcatcggct tccggtacag gagcctgaag | 3600 |
| | cacttcaact acgacatctg ccagagctgc tttttcagcg gcagagtggc caagggccac | 3660 |
| | aaaatgcact accccatggt ggagtactgc accccccacca cctccggcga ggatgtgaga | 3720 |
| | gacttcgcca aagtgctgaa gaataagttc cggaccaagc ggtactttgc caagcacccc | 3780 |
| | aggatgggct acctgcccgt gcagaccgtg ctggaaggcg acaacatgga gacctga | 3837 |
| SEQ ID NO: 3 | DNA sequence of canine codon-optimized gene encoding human mini-dystrophin 3978 (Copti-Dys3978) | |
| | atgctttggt gggaggaagt ggaggactgc tacgagcggg aggacgtgca gaagaaaacc | 60 |
| | ttcaccaagt gggtgaacgc ccagttcagc aagttcggca agcagcacat cgagaacctg | 120 |
| | ttcagcgacc tgcaggacgg caggcggctg ctggacctcc tggaaggcct gaccggccag | 180 |
| | aagctgccca aagagaaggg cagcaccagg gtgcacgccc tgaacaacgt gaacaaggcc | 240 |
| | ctgagggtgc tgcagaacaa caacgtggac ctggtgaaca tcggcagcac cgacatcgtg | 300 |
| | gacggcaacc acaagctgac cctgggcctg atctggaaca tcatcctgca ctggcaggtc | 360 |
| | aagaacgtga tgaagaacat catggccggc ctgcagcaga ccaacagcga gaagatcctg | 420 |
| | ctgtcctggg tgcggcagag caccaggaac taccccccagg tcaacgtgat caacttcacc | 480 |
| | acctcttgga gcgacggcct ggccctgaac gccctgatcc acagccacag gcccgacctg | 540 |
| | ttcgactgga acagcgtggt gtgccagcag agcgccaccc agaggctgga acacgccttc | 600 |
| | aacatcgcca gataccagct gggcatcgag aagctgctgg atcccgagga cgtggacacc | 660 |
| | acctaccccg acaagaaaag catcctcatg tacatcacca gcctgttcca ggtgctgccc | 720 |
| | cagcaggtgt ccatcgaggc catccaggaa gtggagatgc tgcccaggcc ccccaaggtc | 780 |
| | accaaagagg aacacttcca gctgcaccac cagatgcact acagccagca gatcaccgtg | 840 |
| | agcctggccc agggctacga gaggaccagc agccccaagc ccaggttcaa gagctacgcc | 900 |
| | tacacccagg ccgcctacgt gaccacctcc gaccccacca ggtccccctt ccccagccag | 960 |
| | catctcgaag cccccgagga caagagcttc ggcagcagcc tgatggaaag cgaggtgaac | 1020 |
| | ctggacagat accagaccgc cctggaagaa gtgctgtctt ggctgctgtc cgccgaggac | 1080 |
| | accctgcagg cccagggcga gatcagcaac gacgtggagg tcgtgaagga ccagttccac | 1140 |
| | acccacgagg gctacatgat ggacctgacc gcccaccagg gcagagtggg caacatcctg | 1200 |
| | cagctgggca gcaagctgat cggcaccggc aagctgtccg aggacgagga aaccgaggtg | 1260 |
| | caggaacaga tgaacctgct gaacagcaga tgggagtgcc tgagggtggc cagcatggaa | 1320 |
| | aagcagagca acctgcacag ggtgctgatg gatctgcaga accagaagct caaagagctg | 1380 |
| | aacgactggc tgaccaagac cgaggaaagg acccggaaga tggaagagga accccctgggc | 1440 |
| | cccgatctcg aagatctgaa gaggcaggtg cagcagcaca aggtgctgca ggaagatctc | 1500 |
| | gaacaggaac aggtccgggt caacagcctg acccacatgg tcgtggtggt ggacgagagc | 1560 |
| | agcggcgacc acgccaccgc tgccctggaa gagcagctga aggtgctggg cgacagatgg | 1620 |
| | gccaacatct gccggtggac cgaggacaga tgggtcctcc tgcaggacca gcccgacctg | 1680 |
| | gcccctggcc tgacaaccat cggcgccagc cccacccaga ccgtgaccct ggtgacccag | 1740 |
| | cccgtggtga ccaaagagac cgccatcagc aagctggaaa tgcccagctc cctgatgctg | 1800 |
| | gaagtgccca cccacaggct cctccagcag ttccccctgg acctggaaaa gttcctggcc | 1860 |
| | tggctgaccg aggccgagac caccgccaac gtgctgcagg acgccaccag gaaagagagg | 1920 |
| | ctgctggaag atagcaaggg cgtgaaagag ctgatgaagc agtggcagga cctgcagggg | 1980 |
| | gagattgagg cccacaccga cgtgtaccac aacctggacg agaacagcca gaaaatcctg | 2040 |
| | agaagcctgg aaggcagcga cgacgccgtg ctgctgcaga ggcggctgga caacatgaac | 2100 |
| | ttcaagtgga gcgagctgag gaagaagagc ctgaacatca ggtcccatct ggaagccagc | 2160 |
| | agcgaccagt ggaagaggct gcacctgagc ctgcaggaac tgctcgtctg gctgcagctg | 2220 |
| | aaagacgacg agctgtccag gcaggccccc atcggcggcg acttccccgc cgtgcagaaa | 2280 |
| | cagaacgacg tgcacagggc cttcaagcgg gagctgaaaa ccaaagagcc cgtgatcatg | 2340 |
| | agcaccctgg aaaccgtgag gatcttcctg accgagcagc ccctggaagg actggaaaag | 2400 |
| | ctgtaccagg aacccagaga gctgccccccc gaggaacggg cccagaacgt gaccaggctg | 2460 |
| | ctgagaaagc aggccgagga agtgaacacc gagtgggaga agctgaacct gcactccgcc | 2520 |
| | gactggcaga ggaagatcga cgagaccctg gaaaggctcc aggaactgca ggaagccacc | 2580 |
| | gacgagctgg acctgaagct gagacaggcc gaggtgatca agggcagctg gcagcccgtg | 2640 |
| | ggcgacctgc tgatcgactc cctgcaggat cacctggaaa aagtgaaggc cctgcggggc | 2700 |
| | gagatcgccc ccctgaaaga gaacgtcagc cacgtcaacg acctggccag gcagctgacc | 2760 |
| | accctgggca tccagctgtc cccctacaac ctgtccaccc tggaagatct gaacacaagg | 2820 |

TABLE 13-continued

TABLE OF SEQUENCES

| SEQ ID NO | DESCRIPTION AND SEQUENCE | |
|---|---|---|
| | tggaagctgc tgcaggtggc cgtggaggac agagtgaggc agctgcacga ggcccacagg | 2880 |
| | gacttcggcc ctgcctccca gcacttcctg agcaccagcg tgcagggccc ctgggagagg | 2940 |
| | gccatctccc ccaacaaggt gccctactac atcaaccacg agacccagac cacctgctgg | 3000 |
| | gaccacccta agatgaccga gctgtaccag tccctggccg acctgaacaa tgtgcggttc | 3060 |
| | agcgcctacc ggaccgccat gaagctgagg cggctgcaga aagccctgtg cctggatctg | 3120 |
| | ctgtccctga gcgccgcctg cgacgccctg gaccagcaca acctgaagca gaacgaccag | 3180 |
| | cccatggata tcctgcagat catcaactgt ctgaccacca tctacgacag gctggaacag | 3240 |
| | gaacacaaca acctggtcaa cgtgcccctg tgcgtggaca tgtgcctgaa ctggctgctg | 3300 |
| | aacgtgtacg acaccggcag gaccggccgg atcagggtgc tgtccttcaa gaccggcatc | 3360 |
| | atcagcctgt gcaaggccca cctggaagat aagtaccgct acctgttcaa gcaggtggcc | 3420 |
| | agctctaccg gcttctgcga ccagcggagg ctgggcctgc tgctgcacga cagcatccag | 3480 |
| | atcccccggc agctgggcga ggtggcctcc ttcggcggca gcaacatcga gcccagcgtg | 3540 |
| | cggagctgct tccagttcgc caacaacaag cccgagatcg aggccgccct gttcctggac | 3600 |
| | tggatgcggc tggaacccca gagcatggtc tggctgcccg tgctgcacag agtggctgcc | 3660 |
| | gccgagaccg ccaagcacca ggccaagtgc aacatctgca aagagtgccc catcatcggc | 3720 |
| | ttcaggtaca gaagcctgaa gcacttcaac tacgacatct gccagagctg tttcttcagc | 3780 |
| | ggcagggtgg ccaagggcca caaaatgcac taccccatgg tggagtactg cacccccacc | 3840 |
| | acctccggcg aggacgtgag ggacttcgcc aaggtgctga agaataagtt ccggaccaag | 3900 |
| | cggtacttcg ccaaacaccc caggatgggc tacctgcccg tgcagaccgt gctggaaggc | 3960 |
| | gacaacatgg aaacctga | 3978 |
| SEQ ID | DNA sequence of synthetic hybrid muscle-specific promoter hCK | |
| NO: 4 | gaattcggta ccccactacg ggtttaggct gcccatgtaa ggaggcaagg cctggggaca | 60 |
| | cccgagatgc ctggttataa ttaacccaga catgtggctg cccccccccc ccccaacacc | 120 |
| | tgctgcctct aaaaataacc ctgtccctgg tggatcccct gcatgcgaag atcttcgaac | 180 |
| | aaggctgtgg gggactgagg gcaggctgta acaggcttgg gggccagggc ttatacgtgc | 240 |
| | ctgggactcc caaagtatta ctgttccatg ttcccggcga agggccagct gtcccccgcc | 300 |
| | agctagactc agcacttagt ttaggaacca gtgagcaagt cagcccttgg ggcagcccat | 360 |
| | acaaggccat ggggctgggc aagctgcacg cctgggtccg gggtgggcac ggtgcccggg | 420 |
| | caacgagctg aaagctcatc tgctctcagg ggcccctccc tggggacagc ccctcctggc | 480 |
| | tagtcacacc ctgtaggctc ctctatataa cccaggggca caggggctgc cctcattcta | 540 |
| | ccaccacctc cacagcacag acagacactc aggagccagc cagcgtcgag cggccgatcc | 600 |
| | gccacc | 606 |
| SEQ ID | DNA sequence of synthetic hybrid muscle-specific promoter hCKplus | |
| NO: 5 | gaattcggta ccccactacg ggtctaggct gcccatgtaa ggaggcaagg cctggggaca | 60 |
| | cccgagatgc ctggttataa ttaaccccaa cacctgctgc cccccccccc ccaacacctg | 120 |
| | ctgcctctaa aaataaccct gtccctggtg gatcccctgc atgccccact acgggtttag | 180 |
| | gctgcccatg taaggaggca aggcctgggg acacccgaga tgcctggtta taattaaccc | 240 |
| | agacatgtgg ctgccccccc cccccccaac acctgctgcc tctaaaaata accctgtccc | 300 |
| | tggtggatcc cctgcatgcg aagatcttcg aacaaggctg tgggggactg agggcaggct | 360 |
| | gtaacaggct tgggggccag ggcttatacg tgcctgggac tcccaaagta ttactgttcc | 420 |
| | atgttcccgg cgaagggcca gctgtccccc gccagctaga ctcagcactt agtttaggaa | 480 |
| | ccagtgagca agtcagccct tggggcagcc catacaaggc catggggctg ggcaagctgc | 540 |
| | acgcctgggt ccggggtggg cacggtgccc gggcaacgag ctgaaagctc atctgctctc | 600 |
| | aggggcccct ccctggggac agcccctcct ggctagtcac accctgtagg ctcctctata | 660 |
| | taacccaggg gcacaggggc tgccctcatt ctaccaccac ctccacagca cagacagaca | 720 |
| | ctcaggagcc agccagcgtc gagcggccga tccgccacc | 759 |
| SEQ ID | DNA sequence of small synthetic polyadenylation element | |
| NO: 6 | tgaggagctc gagaggccta ataaagagct cagatgcatc gatcagagtg tgttggtttt | 60 |
| | ttgtgtg | 67 |
| SEQ ID | Amino acid sequence encoded by Hopti-Dys3978 gene (Dys3978 protein) | |
| NO: 7 | MLWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDQPDL APGLTTIGAS PTQTVTLVTQ PVVTKETAIS KLEMPSSLML | 600 |
| | EVPTHRLLQQ FPLDLEKFLA WLTEAETTAN VLQDATRKER LLEDSKGVKE LMKQWQDLQG | 660 |
| | EIEAHTDVYH NLDENSQKIL RSLEGSDDAV LLQRRLDNMN FKWSELRKKS LNIRSHLEAS | 720 |
| | SDQWKRLHLS LQELLVWLQL KDDELSRQAP IGGDFPAVQK QNDVHRAFKR ELKTKEPVIM | 780 |
| | STLETVRIFL TEQPLEGLEK LYQEPRELPP EERAQNVTRL LRKQAEEVNT EWEKLNLHSA | 840 |
| | DWQRKIDETL ERLQELQEAT DELDLKLRQA EVIKGSWQPV GDLLIDSLQD HLEKVKALRG | 900 |
| | EIAPLKENVS HVNDLARQLT TLGIQLSPYN LSTLEDLNTR WKLLQVAVED RVRQLHEAHR | 960 |
| | DFGPASQHFL STSVQGPWER AISPNKVPYY INHETQTTCW DHPKMTELYQ SLADLNNVRF | 1020 |
| | SAYRTAMKLR RLQKALCLDL LSLSAACDAL DQHNLKQNDQ PMDILQIINC LTTIYDRLEQ | 1080 |
| | EHNNLVNVPL CVDMCLNWLL NVYDTGRTGR IRVLSFKTGI ISLCKAHLED KYRYLFKQVA | 1140 |
| | SSTGFCDQRR LGLLLHDSIQ IPRQLGEVAS FGGSNIEPSV RSCFQFANNK PEIEAALFLD | 1200 |
| | WMRLEPQSMV WLPVLHRVAA AETAKHQAKC NICKECPIIG FRYRSLKHFN YDICQSCFFS | 1260 |

TABLE 13-continued

TABLE OF SEQUENCES

| SEQ ID NO | DESCRIPTION AND SEQUENCE | |
|---|---|---|
| | GRVAKGHKMH YPMVEYCTPT TSGEDVRDFA KVLKNKFRTK RYFAKHPRMG YLPVQTVLEG | 1320 |
| | DNMET | 1325 |
| SEQ ID | Amino acid sequence encoded by Hopti-Dys3837 gene (Dys3837 protein) | |
| NO: 8 | MLWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDTHRL LQQFPLDLEK FLAWLTEAET TANVLQDATR KERLLEDSKG | 600 |
| | VKELMKQWQD LQGEIEAHTD VYHNLDENSQ KILRSLEGSD DAVLLQRRLD NMNFKWSELR | 660 |
| | KKSLNIRSHL EASSDQWKRL HLSLQELLVW LQLKDDELSR QAPIGGDFPA VQKQNDVHRA | 720 |
| | FKRELKTKEP VIMSTLETVR IFLTEQPLEG LEKLYQEPRE LPPEERAQNV TRLLRKQAEE | 780 |
| | VNTEWEKLNL HSADWQRKID ETLERLQELQ EATDELDLKL RQAEVIKGSW QPVGDLLIDS | 840 |
| | LQDHLEKVKA LRGEIAPLKE NVSHVNDLAR QLTTLGIQLS PYNLSTLEDL NTRWKLLQVA | 900 |
| | VEDRVRQLHE AHRDFGPASQ HFLSTSVQGP WERAISPNKV PYYINHETQT TCWDHPKMTE | 960 |
| | LYQSLADLNN VRFSAYRTAM KLRRLQKALC LDLLSLSAAC DALDQHNLKQ NDQPMDILQI | 1020 |
| | INCLTTIYDR LEQEHNNLVN VPLCVDMCLN WLLNVYDTGR TGRIRVLSFK TGIISLCKAH | 1080 |
| | LEDKYRYLFK QVASSTGFCD QRRLGLLLHD SIQIPRQLGE VASFGGSNIE PSVRSCFQFA | 1140 |
| | NNKPEIEAAL FLDWMRLEPQ SMVWLPVLHR VAAAETAKHQ AKCNICKECP IIGFRYRSLK | 1200 |
| | HFNYDICQSC FFSGRVAKGH KMHYPMVEYC TPTTSGEDVR DFAKVLKNKF RTKRYFAKHP | 1260 |
| | RMGYLPVQTV LEGDNMET | 1278 |
| SEQ ID | DNA sequence of a human-codon optimized human mini-dystrophin 3978 (Hopti-Dys3978) gene | |
| NO: 9 | expression cassette | |
| | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctagatc tgaattcggt accccactac gggtttaggc | 180 |
| | tgcccatgta aggaggcaag gcctggggac acccgagatg cctggttata attaacccag | 240 |
| | acatgtggct gccccccccc cccccaacac ctgctgcctc taaaaataac cctgtccctg | 300 |
| | gtggatcccc tgcatgcgaa gatcttcgaa caaggctgtg ggggactgag ggcaggctgt | 360 |
| | aacaggcttg gggccagggg cttatacgtg cctgggactc ccaaagtatt actgttccat | 420 |
| | gttcccggcg aagggccagc tgtcccccgc cagctagact cagcacttag tttaggaacc | 480 |
| | agtgagcaag tcagcccttg gggcagccca tacaaggcca tggggctggg caagctgcac | 540 |
| | gcctgggtcc ggggtgggca cggtgcccgg gcaacgagct gaaagctcat ctgctctcag | 600 |
| | gggcccctcc ctggggacag cccctcctgg ctagtcacac cctgtaggct cctctatata | 660 |
| | acccaggggc acaggggctg ccctcattct accaccacct ccacagcaca gacagacact | 720 |
| | caggagccag ccagcgtcga gcggccgatc cgccaccatg ctttggtggg aggaagtgga | 780 |
| | ggactgctac gagagagagg acgtgcagaa gaaaaccttc accaagtggg tgaacgccca | 840 |
| | gttcagcaag ttcggcaagc agcacatcga gaacctgttc agcgacctgc aggatggcag | 900 |
| | gagactgctg gacctgctgg agggcctgac cggccagaag ctgcccaagg agaagggcag | 960 |
| | caccagagtg cacgccctga acaacgtgaa caaggccctg agagtgctgc agaacaacaa | 1020 |
| | cgtggacctg gtgaacatcg gcagcaccga catcgtggac ggcaaccaca agctgaccct | 1080 |
| | gggcctgatc tggaacatca tcctgcactg gcaggtgaag aacgtgatga agaacatcat | 1140 |
| | ggccggcctg cagcagacca acagcgagaa gatcctgctg agctgggtga ggcagagcac | 1200 |
| | cagaaactac ccccaggtga acgtgatcaa cttcaccacc tcctggagcg acggcctggc | 1260 |
| | cctgaacgcc ctgatccaca gccacagacc cgacctgttc gactggaaca gcgtggtgtg | 1320 |
| | tcagcagagc gccacccaga gactggagca cgccttcaac atcgccagat accagctggg | 1380 |
| | catcgagaag ctgctggacc ccgaggacgt ggacaccacc taccccgaca agaaaagcat | 1440 |
| | cctcatgtac attaccagcc tgttccaggt gctgccccag caggtgtcca tcgaggccat | 1500 |
| | ccaggaagtg gaaatgctgc ccaggccccc caaagtgacc aaggaggagc acttccagct | 1560 |
| | gcaccaccag atgcactaca gccagcagat cacagtgagc ctggcccagg gctatgagag | 1620 |
| | aaccagcagc cccaagccca gattcaagag ctacgcctac acccaggccg cctacgtgac | 1680 |
| | cacctccgac cccaccagaa gccccttccc cagccagcac ctggaggccc ccgaggacaa | 1740 |
| | gagcttcggc agcagcctga tggagagcga agtgaacctg gacagatacc agaccgccct | 1800 |
| | ggaggaagtg ctgtcctggc tgctgagcgc cgaggacacc ctgcaggccc agggcgagat | 1860 |
| | cagcaacgac gtggaagtgg tgaaggacca gttccacacc cacgagggct acatgatgga | 1920 |
| | tctgaccgcc caccagggca gagtgggcaa tatcctgcag ctgggcagca agctgatcgg | 1980 |
| | caccggcaag ctgagcgagg acgaggagac cgaagtgcag gagcagatga acctgctgaa | 2040 |
| | cagcagatgg gagtgcctga gagtggccag catggagaag cagagcaacc tgcacagagt | 2100 |
| | gctgatggac ctgcagaacc agaagctgaa ggagctgaac gactggctga ccaagaccga | 2160 |
| | ggagcggacc agaaagatgg aggaggagcc cctgggcccc gacctggagg acctgaagag | 2220 |
| | acaggtgcag cagcacaaag tgctgcagga ggacctggag caggagcagg tgcgcgtgaa | 2280 |
| | cagcctgacc cacatggtgg tggtcgtgga cgagagcagc ggcgaccacg ccacagccgc | 2340 |
| | cctggaagag cagctgaaag tgctgggcga cagatgggcc aatatttgta ggtggaccga | 2400 |
| | ggacagatgg gtgctgctgc aggaccagcc cgacctggcc cctggcctga ccaccatcgg | 2460 |
| | cgccagcccc acccagaccg tgaccctggt gacccagccc gtggtgacaa aggagaccgc | 2520 |
| | catcagcaag ctggagatgc ccagctccct gatgctggaa gtgcccaccc accgcctgct | 2580 |
| | ccagcagttc cccctggacc tggagaagtt cctggcctgg ctgaccgagg ccgaaaccac | 2640 |
| | cgccaatgtg ctccaggacg ccactagaaa ggagaggctg ctggaggaca gcaagggcgt | 2700 |
| | gaaagagctg atgaagcagt ggcaggatct gcagggcgaa atcgaggccc acaccgacgt | 2760 |

TABLE 13-continued

TABLE OF SEQUENCES

| SEQ ID NO | DESCRIPTION AND SEQUENCE | |
|---|---|---|
| | gtaccacaac ctggacgaga acagccagaa gattctgagg agcctggagg gcagcgacga | 2820 |
| | cgccgtcctg ctccagagga ggctggacaa catgaacttc aagtggagcg agctgcggaa | 2880 |
| | gaagagcctg aacatccgga gccacctgga agccagcagc gaccagtgga agagactgca | 2940 |
| | cctgagcctg caggagctgc tggtgtggct gcagctgaag gacgacgagc tgagcagaca | 3000 |
| | ggcccccatc ggcggcgact tccccgccgt gcagaagcag aacgacgtgc accgggcctt | 3060 |
| | caagagggag ctgaaaacca aggaacccgt gatcatgagc accctggaga cagtgcggat | 3120 |
| | cttcctgacc gagcagcccc tggagggact ggagaagctg taccaggagc ccagagagct | 3180 |
| | gcccccccgag gagagagccc agaacgtgac caggctgctg agaaagcagg ccgaggaagt | 3240 |
| | gaataccgag tgggagaagc tgaatctgca cagcgccgac tggcagagaa agatcgacga | 3300 |
| | gaccctggag agactccagg aactgcagga agccaccgac gagctggacc tgaagctgag | 3360 |
| | acaggccgaa gtgatcaagg gcagctggca gcctgtgggc gatctgctga tcgactccct | 3420 |
| | gcaggatcac ctggagaaag tgaaggccct gcggggcgag atcgcccccc tgaaggagaa | 3480 |
| | tgtgagccac gtgaacgacc tggccagaca gctgaccacc ctgggcatcc agctgagccc | 3540 |
| | ctacaacctg agcacactgg aggatctgaa cacccggtgg aaactgctgc aggtggccgt | 3600 |
| | ggaggataga gtgaggcagc tgcacgaagc ccacagagac ttcggccctg cctcccagca | 3660 |
| | cttcctgagc accagcgtgc agggcccctg ggagagagcc atctccccca acaaagtgcc | 3720 |
| | ctactacatc aaccacgaga cccagaccac ctgctgggac caccctaaga tgaccgagct | 3780 |
| | gtatcagagc ctggccgacc tgaacaatgt gcggttcagc gcctacagaa ccgccatgaa | 3840 |
| | gctgcggaga ctgcagaagg ccctgtgcct ggatctgctg agcctgagcg ccgcctgcga | 3900 |
| | cgccctggac cagcacaacc tgaagcagaa tgaccagccc atggacatcc tgcagatcat | 3960 |
| | caactgcctg accacaatct acgaccggct ggaacaggag cacaacaacc tggtgaatgt | 4020 |
| | gcccctgtgc gtggacatgt gcctgaattg gctgctgaac gtgtacgaca ccggcaggac | 4080 |
| | cggcagaatc cgcgtgctga gcttcaagac cggcatcatc agcctgtgca aggcccacct | 4140 |
| | ggaggataag taccgctacc tgttcaagca ggtggccagc agcaccggct tctgcgatca | 4200 |
| | gaggagactg ggcctgctgc tgcacgatag catccagatc cctaggcagc tgggcgaagt | 4260 |
| | ggccagcttt ggcggcagca acatcgagcc ctctgtgagg agctgcttcc agttcgccaa | 4320 |
| | caacaagccc gagatcgagg ccgccctgtt cctggactgg atgaggctgg agcctcagag | 4380 |
| | catggtgtgg ctgcctgtgc tgcacagagt ggccgccgcc gagaccgcca agcaccaggc | 4440 |
| | caagtgcaat atctgcaagg agtgccccat catcggcttc cggtacagga gcctgaagca | 4500 |
| | cttcaactac gacatctgcc agagctgctt tttcagcggc agagtggcca agggccacaa | 4560 |
| | aatgcactac cccatggtgg agtactgcac ccccaccacc tccggcgagg atgtgagaga | 4620 |
| | cttcgccaaa gtgctgaaga ataagttccg gaccaagcgg tactttgcca agcaccccag | 4680 |
| | gatgggctac ctgcccgtgc agaccgtgct ggaaggcgac aacatggaga cctgatgagg | 4740 |
| | agctcgagag gcctaataaa gagctcagat gcatcgatca gagtgtgttg gttttttgtg | 4800 |
| | tgagatctag gaacccctag tgatggagtt ggccactccc tctctgcgcg ctcgctcgct | 4860 |
| | cactgaggcc gcccgggcaa agcccgggcg tcgggcgacc tttggtcgcc cggcctcagt | 4920 |
| | gagcgagcga gcgcgcagag agggagtggc caa | 4953 |
| SEQ ID NO: 10 | DNA sequence of AAV-hCK-Hopti-Dys3837 gene expression cassette | |
| | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctagatc tgaattcggt accccactac gggtttaggc | 180 |
| | tgcccatgta aggaggcaag gcctggggac acccgagatg cctggttata attaacccag | 240 |
| | acatgtggct gcccccccccc cccccaacac ctgctgcctc taaaaataac cctgtccctg | 300 |
| | gtggatcccc tgcatgcgaa gatcttcgaa caaggctgtg ggggactgag ggcaggctgt | 360 |
| | aacaggcttg ggggccaggg cttatacgtg cctgggactc ccaaagtatt actgttccat | 420 |
| | gttcccggcg aagggccagc tgtcccccgc cagctagact cagcacttag tttaggaacc | 480 |
| | agtgagcaag tcagcccttg gggcagccca tacaaggcca tggggctggg caagctgcac | 540 |
| | gcctgggtcc ggggtgggca cggtgcccgg gcaacgagct gaaagctcat ctgctctcag | 600 |
| | gggcccctcc ctggggacag cccctcctgg ctagtcacac cctgtaggct cctctatata | 660 |
| | acccaggggc acaggggctg ccctcattct accaccacct ccacagcaca gacagacact | 720 |
| | caggagccag ccagcgtcga gcggccgatc cgccaccatg ctttggtggg aggaagtgga | 780 |
| | ggactgctac gagagagagg acgtgcagaa gaaaaccttc accaagtggg tgaacgccca | 840 |
| | gttcagcaag ttcggcaagc agcacatcga gaacctgttc agcgacctgc aggatggcag | 900 |
| | gagactgctg gacctgctgg agggcctgac cggccagaag ctgcccaagg agaagggcag | 960 |
| | caccagagtg cacgccctga acaacgtgaa caaggccctg agagtgctgc agaacaacaa | 1020 |
| | cgtggacctg gtgaacatcg gcagcaccga catcgtggac ggcaaccaca agctgaccct | 1080 |
| | gggcctgatc tggaacatca tcctgcactg gcaggtgaag aacgtgatga agaacatcat | 1140 |
| | ggccggcctg cagcagacca acagcgagaa gatcctgctg agctgggtga ggcagagcac | 1200 |
| | cagaaactac ccccaggtga acgtgatcaa cttcaccacc tcctggagcg acggcctggc | 1260 |
| | cctgaacgcc ctgatccaca gccacagacc cgacctgttc gactggaaca gcgtggtgtg | 1320 |
| | tcagcagagc gccacccaga gactggagca cgccttcaac atcgccagat accagctggg | 1380 |
| | catcgagaag ctgctggacc ccgaggacgt ggacaccacc taccccgaca agaaaagcat | 1440 |
| | cctcatgtac attaccagcc tgttccaggt gctgccccag caggtgtcca tcgaggccat | 1500 |
| | ccaggaagtg gaaatgctgc ccaggccccc caaagtgacc aaggaggagc acttccagct | 1560 |
| | gcaccaccag atgcactaca gccagcagat cacagtgagc ctggcccagg gctatgagag | 1620 |
| | aaccagcagc cccaagccca gattcaagag ctacgcctac acccaggccg cctacgtgac | 1680 |
| | cacctccgac cccaccagaa gccccttccc cagccagcac ctggaggccc ccgaggacaa | 1740 |
| | gagcttcggc agcagcctga tggagagcga agtgaacctg gacagatacc agaccgccct | 1800 |
| | ggaggaagtg ctgtcctggc tgctgagcgc cgaggacacc ctgcaggccc agggcgagat | 1860 |
| | cagcaacgac gtggaagtgg tgaaggacca gttccacacc cacgagggct acatgatgga | 1920 |
| | tctgaccgcc caccagggca gagtgggcaa tatcctgcag ctgggcagca agctgatcgg | 1980 |
| | caccggcaag ctgagcgagg acgaggagac cgaagtgcag gagcagatga acctgctgaa | 2040 |
| | cagcagatgg gagtgcctga gagtggccag catggagaag cagagcaacc tgcacagagt | 2100 |
| | gctgatggac ctgcagaacc agaagctgaa ggagctgaac gactggctga ccaagaccga | 2160 |

TABLE 13-continued

TABLE OF SEQUENCES

| SEQ ID NO | DESCRIPTION AND SEQUENCE |
|---|---|
| | ggagcggacc agaaagatgg aggaggagcc cctgggcccc gacctggagg acctgaagag 2220 |
| | acaggtgcag cagcacaaag tgctgcagga ggacctggag caggagcagg tgcgcgtgaa 2280 |
| | cagcctgacc cacatggtgg tggtcgtgga cgagagcagc ggcgaccacg ccacagccgc 2340 |
| | cctggaagag cagctgaaag tgctgggcga cagatgggcc aatatttgta ggtggaccga 2400 |
| | ggacagatgg gtgctgctgc aggacaccca ccgcctgctc cagcagttcc ccctggacct 2460 |
| | ggagaagttc ctggcctggc tgaccgaggc cgaaaccacc gccaatgtgc tccaggacgc 2520 |
| | cactagaaag gagaggctgc tggaggacag caagggcgtg aaagagctga tgaagcagtg 2580 |
| | gcaggatctg cagggcgaaa tcgaggccca caccgacgtg taccacaacc tggacgagaa 2640 |
| | cagccagaag attctgagga gcctggaggg cagcgacgac gccgtcctgc tccagaggag 2700 |
| | gctggacaac atgaacttca agtggagcga gctgcggaag aagagcctga acatccggag 2760 |
| | ccacctggaa gccagcagcg accagtggaa gagactgcac ctgagcctgc aggagctgct 2820 |
| | ggtgtggctg cagctgaagg acgacgagct gagcagacag gcccccatcg gcggcgactt 2880 |
| | ccccgccgtg cagaagcaga acgacgtgca ccgggccttc aagagggagc tgaaaaccaa 2940 |
| | ggaacccgtg atcatgagca ccctggagac agtgcggatc ttcctgaccg agcagcccct 3000 |
| | ggagggactg gagaagctgt accaggagcc cagagagctg ccccccgagg agagagccca 3060 |
| | gaacgtgacc aggctgctga gaaagcaggc cgaggaagtg aataccgagt gggagaagct 3120 |
| | gaatctgcac agcgccgact ggcagagaaa gatcgacgag accctggaga gactccagga 3180 |
| | actgcaggaa gccaccgacg agctggacct gaagctgaga caggccgaag tgatcaaggg 3240 |
| | cagctggcag cctgtgggcg atctgctgat cgactccctg caggatcacc tggagaaagt 3300 |
| | gaaggccctg cggggcgaga tcgcccccct gaaggagaat gtgagccacg tgaacgacct 3360 |
| | ggccagacag ctgaccaccc tgggcatcca gctgagcccc tacaacctga gcacactgga 3420 |
| | ggatctgaac acccggtgga aactgctgca ggtggccgtg gaggatagag tgaggcagct 3480 |
| | gcacgaagcc cacagagact tcggccctgc ctcccagcac ttcctgagca ccagcgtgca 3540 |
| | gggcccctgg gagagagcca tctcccccaa caaagtgccc tactacatca accacgagac 3600 |
| | ccagaccacc tgctgggacc accctaagat gaccgagctg tatcagagcc tggccgacct 3660 |
| | gaacaatgtg cggttcagcg cctacagaac cgccatgaag ctgcggagac tgcagaaggc 3720 |
| | cctgtgcctg gatctgctga gcctgagcgc cgcctgcgac gccctggacc agcacaacct 3780 |
| | gaagcagaat gaccagccca tggacatcct gcagatcatc aactgcctga ccacaatcta 3840 |
| | cgaccggctg gaacaggagc acaacaacct ggtgaatgtg cccctgtgcg tggacatgtg 3900 |
| | cctgaattgg ctgctgaacg tgtacgacac cggcaggacc ggcagaatcc gcgtgctgag 3960 |
| | cttcaagacc ggcatcatca gcctgtgcaa ggcccacctg gaggataagt accgctacct 4020 |
| | gttcaagcag gtggccagca gcaccggctt ctgcgatcag aggagactgg gcctgctgct 4080 |
| | gcacgatagc atccagatcc ctaggcagct gggcgaagtg gccagctttg gcggcagcaa 4140 |
| | catcgagccc tctgtgagga gctgcttcca gttcgccaac aacaagcccg agatcgaggc 4200 |
| | cgccctgttc ctggactgga tgaggctgga gcctcagagc atggtgtggc tgcctgtgct 4260 |
| | gcacagagtg gccgccgccg agaccgccaa gcaccaggcc aagtgcaata tctgcaagga 4320 |
| | gtgccccatc atcggcttcc ggtacaggag cctgaagcac ttcaactacg acatctgcca 4380 |
| | gagctgcttt ttcagcggca gagtggccaa gggccacaaa atgcactacc ccatggtgga 4440 |
| | gtactgcacc cccaccacct ccggcgagga tgtgagagac ttcgccaaag tgctgaagaa 4500 |
| | taagttccgg accaagcggt actttgccaa gcaccccagg atgggctacc tgcccgtgca 4560 |
| | gaccgtgctg gaaggcgaca acatggagac ctgatgagga gctcgagagg cctaataaag 4620 |
| | agctcagatg catcgatcag agtgtgttgg ttttttgtgt gagatctagg aacccctagt 4680 |
| | gatggagttg gccactccct ctctgcgcgc tcgctcgctc actgaggccg cccgggcaaa 4740 |
| | gcccgggcgt cgggcgacct ttggtcgccc ggcctcagtg agcgagcgag cgcgcagaga 4800 |
| | gggagtggcc aa 4812 |
| SEQ ID NO: 11 | DNA sequence of AAV-hCKplus-Hopti-Dys3837 gene expression cassette |
| | ttggccactc cctctctgcg cgctcgctcg ctcactgagg ccgggcgacc aaaggtcgcc 60 |
| | cgacgcccgg gctttgcccg ggcggcctca gtgagcgagc gagcgcgcag agagggagtg 120 |
| | gccaactcca tcactagggg ttcctagatc tgaattcggt accccactac gggtctaggc 180 |
| | tgcccatgta aggaggcaag gcctggggac acccgagatg cctggttata attaacccca 240 |
| | acacctgctg cccccccccc cccaacacct gctgcctcta aaaataaccc tgtccctggt 300 |
| | ggatcccctg catgccccac tacgggttta ggctgcccat gtaaggaggc aaggcctggg 360 |
| | gacacccgag atgcctggtt ataattaacc cagacatgtg gctgcccccc cccccccaa 420 |
| | cacctgctgc ctctaaaaat aaccctgtcc ctggtggatc ccctgcatgc gaagatcttc 480 |
| | gaacaaggct gtgggggact gagggcaggc tgtaacaggc ttgggggcca gggcttatac 540 |
| | gtgcctggga ctcccaaagt attactgttc catgttcccg gcgaagggcc agctgtcccc 600 |
| | cgccagctag actcagcact tagtttagga accagtgagc aagtcagccc ttggggcagc 660 |
| | ccatacaagg ccatggggct gggcaagctg cacgcctggg tccggggtgg gcacggtgcc 720 |
| | cgggcaacga gctgaaagct catctgctct caggggcccc tccctgggga cagcccctcc 780 |
| | tggctagtca caccctgtag gctcctctat ataacccagg ggcacagggg ctgccctcat 840 |
| | tctaccacca cctccacagc acagacagac actcaggagc cagccagcgt cgagcggccg 900 |
| | atccgccacc atgctttggt gggaggaagt ggaggactgc tacgagagag aggacgtgca 960 |
| | gaagaaaacc ttcaccaagt gggtgaacgc ccagttcagc aagttcggca agcagcacat 1020 |
| | cgagaacctg ttcagcgacc tgcaggatgg caggagactg ctggacctgc tggagggcct 1080 |
| | gaccggccag aagctgccca aggagaaggg cagcaccaga gtgcacgccc tgaacaacgt 1140 |
| | gaacaaggcc ctgagagtgc tgcagaacaa caacgtggac ctggtgaaca tcggcagcac 1200 |
| | cgacatcgtg gacggcaacc acaagctgac cctgggcctg atctggaaca tcatcctgca 1260 |
| | ctggcaggtg aagaacgtga tgaagaacat catggccggc ctgcagcaga ccaacagcga 1320 |
| | gaagatcctg ctgagctggg tgaggcagag caccagaaac taccccccagg tgaacgtgat 1380 |
| | caacttcacc acctcctgga gcgacggcct ggccctgaac gccctgatcc acagccacag 1440 |
| | acccgacctg ttcgactgga acagcgtggt gtgtcagcag agcgccaccc agagactgga 1500 |
| | gcacgccttc aacatcgcca gataccagct gggcatcgag aagctgctgg accccgagga 1560 |
| | cgtggacacc acctaccccg acaagaaaag catcctcatg tacattacca gcctgttcca 1620 |
| | ggtgctgccc cagcaggtgt ccatcgaggc catccaggaa gtggaaatgc tgcccaggcc 1680 |

TABLE 13-continued

| SEQ ID NO | DESCRIPTION AND SEQUENCE | |
|---|---|---|
| | TABLE OF SEQUENCES | |
| | ccccaaagtg accaaggagg agcacttcca gctgcaccac cagatgcact acagccagca | 1740 |
| | gatcacagtg agcctggccc agggctatga gagaaccagc agccccaagc ccagattcaa | 1800 |
| | gagctacgcc tacacccagg ccgcctacgt gaccacctcc gaccccacca gaagcccctt | 1860 |
| | ccccagccag cacctggagg cccccgagga caagagcttc ggcagcagcc tgatggagag | 1920 |
| | cgaagtgaac ctggacagat accagaccgc cctggaggaa gtgctgtcct ggctgctgag | 1980 |
| | cgccgaggac accctgcagg cccagggcga gatcagcaac gacgtggaag tggtgaagga | 2040 |
| | ccagttccac acccacgagg gctacatgat ggatctgacc gcccaccagg gcagagtggg | 2100 |
| | caatatcctg cagctgggca gcaagctgat cggcaccggc aagctgagcg aggacgagga | 2160 |
| | gaccgaagtg caggagcaga tgaacctgct gaacagcaga tgggagtgcc tgagagtggc | 2220 |
| | cagcatggag aagcagagca acctgcacag agtgctgatg gacctgcaga accagaagct | 2280 |
| | gaaggagctg aacgactggc tgaccaagac cgaggagcgg accagaaaga tggaggagga | 2340 |
| | gcccctgggc cccgacctgg aggacctgaa gagacaggtg cagcagcaca aagtgctgca | 2400 |
| | ggaggacctg gagcaggagc aggtgcgcgt gaacagcctg acccacatgg tggtggtcgt | 2460 |
| | ggacgagagc agcggcgacc acgccacagc cgccctggaa gagcagctga aagtgctggg | 2520 |
| | cgacagatgg gccaatattt gtaggtggac cgaggacaga tgggtgctgc tgcaggacac | 2580 |
| | ccaccgcctg ctccagcagt tcccccctgga cctggagaag ttcctggcct ggctgaccga | 2640 |
| | ggccgaaacc accgccaatg tgctccagga cgccactaga aaggagaggc tgctggagga | 2700 |
| | cagcaagggc gtgaaagagc tgatgaagca gtggcaggat ctgcagggcg aaatcgaggc | 2760 |
| | ccacaccgac gtgtaccaca acctggacga gaacagccag aagattctga ggagcctgga | 2820 |
| | gggcagcgac gacgccgtcc tgctccagag gaggctggac aacatgaact tcaagtggag | 2880 |
| | cgagctgcgg aagaagagcc tgaacatccg gagccacctg gaagccagca gcgaccagtg | 2940 |
| | gaagagactg cacctgagcc tgcaggagct gctggtgtgg ctgcagctga aggacgacga | 3000 |
| | gctgagcaga caggccccca tcggcggcga cttccccgcc gtgcagaagc agaacgacgt | 3060 |
| | gcaccgggcc ttcaagaggg agctgaaaac caaggaaccc gtgatcatga gcaccctgga | 3120 |
| | gacagtgcgg atcttcctga ccgagcagcc cctggaggga ctggagaagc tgtaccagga | 3180 |
| | gcccagagag ctgccccccg aggagagagc ccagaacgtg accaggctgc tgagaaagca | 3240 |
| | ggccgaggaa gtgaataccg agtgggagaa gctgaatctg cacagcgccg actggcagag | 3300 |
| | aaagatcgac gagaccctgg agagactcca ggaactgcag gaagccaccg acgagctgga | 3360 |
| | cctgaagctg agacaggccg aagtgatcaa gggcagctgg cagcctgtgg gcgatctgct | 3420 |
| | gatcgactcc ctgcaggatc acctggagaa agtgaaggcc ctgcggggcg agatcgcccc | 3480 |
| | cctgaaggag aatgtgagcc acgtgaacga cctggccaga cagctgacca ccctgggcat | 3540 |
| | ccagctgagc ccctacaacc tgagcacact ggaggatctg aacacccggt ggaaactgct | 3600 |
| | gcaggtggcc gtggaggata gagtgaggca gctgcacgaa gcccacagag acttcggccc | 3660 |
| | tgcctcccag cacttcctga gcaccagcgt gcagggcccc tgggagagag ccatctcccc | 3720 |
| | caacaaagtg ccctactaca tcaaccacga gacccagacc acctgctggg accaccctaa | 3780 |
| | gatgaccgag ctgtatcaga gcctggccga cctgaacaat gtgcggttca gcgcctacag | 3840 |
| | aaccgccatg aagctgcgga gactgcagaa ggccctgtgc ctggatctgc tgagcctgag | 3900 |
| | cgccgcctgc gacgccctgg accagcacaa cctgaagcag aatgaccagc ccatggacat | 3960 |
| | cctgcagatc atcaactgcc tgaccacaat ctacgaccgg ctggaacagg agcacaacaa | 4020 |
| | cctggtgaat gtgcccctgt gcgtggacat gtgcctgaat tggctgctga acgtgtacga | 4080 |
| | caccggcagg accggcagaa tccgcgtgct gagcttcaag accggcatca tcagcctgtg | 4140 |
| | caaggcccac ctggaggata agtaccgcta cctgttcaag caggtggcca gcagcaccgg | 4200 |
| | cttctgcgat cagaggagac tgggcctgct gctgcacgat agcatccaga tccctaggca | 4260 |
| | gctgggcgaa gtggccagct ttggcggcag caacatcgag ccctctgtga ggagctgctt | 4320 |
| | ccagttcgcc aacaacaagc ccgagatcga ggccgccctg ttcctggact ggatgaggct | 4380 |
| | ggagcctcag agcatggtgt ggctgcctgt gctgcacaga gtggccgccg ccgagaccgc | 4440 |
| | caagcaccag gccaagtgca atatctgcaa ggagtgcccc atcatcggct tccggtacag | 4500 |
| | gagcctgaag cacttcaact acgacatctg ccagagctgc tttttcagcg gcagagtggc | 4560 |
| | caagggccac aaaatgcact accccatggt ggagtactgc acccccacca cctccggcga | 4620 |
| | ggatgtgaga gacttcgcca aagtgctgaa gaataagttc cggaccaagc ggtactttgc | 4680 |
| | caagcacccc aggatgggct acctgcccgt gcagaccgtg ctggaaggcg acaacatgga | 4740 |
| | gacctgatga ggagctcgag aggcctaata aagagctcag atgcatcgat cagagtgtgt | 4800 |
| | tggttttttg tgtgagatct aggaacccct agtgatggag ttggccactc cctctctgcg | 4860 |
| | cgctcgctcg ctcactgagg ccgcccgggc aaagcccggg cgtcgggcga cctttggtcg | 4920 |
| | cccggcctca gtgagcgagc gagcgcgcag agagggagtg gccaa | 4965 |
| SEQ ID NO: 12 | DNA sequence of AAV-hCK-Copti-Dys3978 gene expression cassette | |
| | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctcagat ctgaattcgg taccccacta cgggtttagg | 180 |
| | ctgcccatgt aaggaggcaa ggcctgggga cacccgagat gcctggttat aattaaccca | 240 |
| | gacatgtggc tgcccccccc ccccccaaca cctgctgcct ctaaaaataa ccctgtccct | 300 |
| | ggtggatccc ctgcatgcga agatcttcga acaaggctgt gggggactga gggcaggctg | 360 |
| | taacaggctt gggggccagg gcttatacgt gcctgggact cccaaagtat tactgttcca | 420 |
| | tgttcccggc gaagggccag ctgtcccccg ccagctagac tcagcactta gtttaggaac | 480 |
| | cagtgagcaa gtcagccctt ggggcagccc atacaaggcc atggggctgg gcaagctgca | 540 |
| | cgcctgggtc cggggtgggc acggtgcccg ggcaacgagc tgaaagctca tctgctctca | 600 |
| | ggggcccctc cctggggaca gcccctcctg gctagtcaca ccctgtaggc tcctctatat | 660 |
| | aacccagggg cacaggggct gccctcattc taccaccacc tccacagcac agacagacac | 720 |
| | tcaggagcca gccagcgtcg agcggccgcc accatgcttt ggtgggagga agtggaggac | 780 |
| | tgctacgagc gggaggacgt gcagaagaaa accttcacca agtgggtgaa cgcccagttc | 840 |
| | agcaagttcg gcaagcagca catcgagaac ctgttcagcg acctgcagga cggcaggcgg | 900 |
| | ctgctggacc tcctggaagg cctgaccggc cagaagctgc ccaaagagaa gggcagcacc | 960 |
| | agggtgcacg ccctgaacaa cgtgaacaag gccctgaggg tgctgcagaa caacaacgtg | 1020 |
| | gacctggtga acatcggcag caccgacatc gtggacggca accacaagct gaccctgggc | 1080 |

TABLE 13-continued

TABLE OF SEQUENCES

| SEQ ID NO | DESCRIPTION AND SEQUENCE |
|---|---|
| | ctgatctgga acatcatcct gcactggcag gtcaagaacg tgatgaagaa catcatggcc 1140 |
| | ggcctgcagc agaccaacag cgagaagatc ctgctgtcct gggtgcggca gagcaccagg 1200 |
| | aactaccccc aggtcaacgt gatcaacttc accacctctt ggagcgacgg cctggccctg 1260 |
| | aacgccctga tccacagcca caggcccgac ctgttcgact ggaacagcgt ggtgtgccag 1320 |
| | cagagcgcca cccagaggct ggaacacgcc ttcaacatcg ccagatacca gctgggcatc 1380 |
| | gagaagctgc tggatcccga ggacgtggac accacctacc ccgacaagaa aagcatcctc 1440 |
| | atgtacatca ccagcctgtt ccaggtgctg ccccagcagg tgtccatcga ggccatccag 1500 |
| | gaagtggaga tgctgcccag gcccccccaag gtcaccaaag aggaacactt ccagctgcac 1560 |
| | caccagatgc actacagcca gcagatcacc gtgagcctgg cccagggcta cgagaggacc 1620 |
| | agcagcccca agcccaggtt caagagctac gcctacaccc aggccgccta cgtgaccacc 1680 |
| | tccgacccca ccaggtcccc cttccccagc cagcatctcg aagcccccga ggacaagagc 1740 |
| | ttcggcagca gcctgatgga aagcgaggtg aacctggaca gataccagac cgccctggaa 1800 |
| | gaagtgctgt cttggctgct gtccgccgag gacaccctgc aggcccaggg cgagatcagc 1860 |
| | aacgacgtgg aggtcgtgaa ggaccagttc cacacccacg agggctacat gatggacctg 1920 |
| | accgcccacc agggcagagt gggcaacatc ctgcagctgg gcagcaagct gatcggcacc 1980 |
| | ggcaagctgt ccgaggacga ggaaaccgag gtgcaggaac agatgaacct gctgaacagc 2040 |
| | agatgggagt gcctgagggt ggccagcatg gaaaagcaga gcaacctgca cagggtgctg 2100 |
| | atggatctgc agaaccagaa gctcaaagag ctgaacgact ggctgaccaa gaccgaggaa 2160 |
| | aggacccgga agatggaaga ggaacccctg ggccccgatc tcgaagatct gaagaggcag 2220 |
| | gtgcagcagc acaaggtgct gcaggaagat ctcgaacagg aacaggtccg ggtcaacagc 2280 |
| | ctgacccaca tggtcgtggt ggtggacgag agcagcggcg accacgccac cgctgccctg 2340 |
| | gaagagcagc tgaaggtgct gggcgacaga tgggccaaca tctgccggtg gaccgaggac 2400 |
| | agatgggtcc tcctgcagga ccagcccgac ctggcccctg gcctgacaac catcggcgcc 2460 |
| | agccccaccc agaccgtgac cctggtgacc cagcccgtgg tgaccaaaga gaccgccatc 2520 |
| | agcaagctgg aaatgcccag ctccctgatg ctggaagtgc ccacccacag gctcctccag 2580 |
| | cagttccccc tggacctgga aaagttcctg gcctggctga ccgaggccga gaccaccgcc 2640 |
| | aacgtgctgc aggacgccac caggaaagag aggctgctgg aagatagcaa gggcgtgaaa 2700 |
| | gagctgatga agcagtggca ggacctgcag gggagattgg aggcccacac cgacgtgtac 2760 |
| | cacaacctgg acgagaacag ccagaaaatc ctgagaagcc tggaaggcag cgacgacgcc 2820 |
| | gtgctgctgc agaggcggct ggacaacatg aacttcaagt ggagcgagct gaggaagaag 2880 |
| | agcctgaaca tcaggtccca tctggaagcc agcagcgacc agtggaagag gctgcacctg 2940 |
| | agcctgcagg aactgctcgt ctggctgcag ctgaaagacg acgagctgtc caggcaggcc 3000 |
| | cccatcggcg gcgacttccc cgccgtgcag aaacagaacg acgtgcacag ggccttcaag 3060 |
| | cgggagctga aaaccaaaga gcccgtgatc atgagcaccc tggaaaccgt gaggatcttc 3120 |
| | ctgaccgagc agcccctgga aggactggaa aagctgtacc aggaacccag agagctgccc 3180 |
| | cccgaggaac gggcccagaa cgtgaccagg ctgctgagaa agcaggccga ggaagtgaac 3240 |
| | accgagtggg agaagctgaa cctgcactcc gccgactggc agaggaagat cgacgagacc 3300 |
| | ctggaaaggc tccaggaact gcaggaagcc accgacgagc tggacctgaa gctgagacag 3360 |
| | gccgaggtga tcaagggcag ctggcagccc gtgggcgacc tgctgatcga ctccctgcag 3420 |
| | gatcacctgg aaaaagtgaa ggccctgcgg ggcgagatcg cccccctgaa agagaacgtc 3480 |
| | agccacgtca acgacctggc caggcagctg accaccctgg gcatccagct gtccccctac 3540 |
| | aacctgtcca ccctggaaga tctgaacaca aggtggaagc tgctgcaggt ggccgtggag 3600 |
| | gacagagtga ggcagctgca cgaggcccac agggacttcg gccctgcctc ccagcacttc 3660 |
| | ctgagcacca gcgtgcaggg cccctgggag agggcccatct cccccaacaa ggtgccctac 3720 |
| | tacatcaacc acgagaccca gaccacctgc tgggaccacc ctaagatgac cgagctgtac 3780 |
| | cagtccctgg ccgacctgaa caatgtgcgg ttcagcgcct accggaccgc catgaagctg 3840 |
| | aggcggctgc agaaagccct gtgcctggat ctgctgtccc tgagcgccgc ctgcgacgcc 3900 |
| | ctggaccagc acaacctgaa gcagaacgac cagcccatgg atatcctgca gatcatcaac 3960 |
| | tgtctgacca ccatctacga caggctggaa caggaacaca acaacctggt caacgtgccc 4020 |
| | ctgtgcgtgg acatgtgcct gaactggctg ctgaacgtgt acgacaccgg caggaccggc 4080 |
| | cggatcaggg tgctgtcctt caagaccggc atcatcagcc tgtgcaaggc ccacctggaa 4140 |
| | gataagtacc gctacctgtt caagcaggtg gccagctcta ccggcttctg cgaccagcgg 4200 |
| | aggctgggcc tgctgctgca cgacagcatc cagatccccc ggcagctggg cgaggtggcc 4260 |
| | tccttcggcg gcagcaacat cgagcccagc gtgcggagct gcttccagtt cgccaacaac 4320 |
| | aagcccgaga tcgaggccgc cctgttcctg gactggatgc ggctggaacc ccagagcatg 4380 |
| | gtctggctgc ccgtgctgca cagagtggct gccgccgaga ccgccaagca ccaggccaag 4440 |
| | tgcaacatct gcaaagagtg ccccatcatc ggcttcaggt acagaagcct gaagcacttc 4500 |
| | aactacgaca tctgccagag ctgtttcttc agcggcaggg tggccaaggg ccacaaaatg 4560 |
| | cactacccca tggtggagta ctgcaccccc accacctccg gcgaggacgt gagggacttc 4620 |
| | gccaaggtgc tgaagaataa gttccggacc aagcggtact tcgccaaaca ccccaggatg 4680 |
| | ggctacctgc ccgtgcagac cgtgctggaa ggcgacaaca tggaaacctg ataacacgcg 4740 |
| | tcgactcgag aggcctaata aagagctcag atgcatcgat cagagtgtgt tggttttttg 4800 |
| | tgtgagatct aggaacccct agtgatggag ttggccactc cctctctgcg cgctcgctcg 4860 |
| | ctcactgagg ccgcccgggc aaagcccggg cgtcggggcga cctttggtcg cccggcctca 4920 |
| | gtgagcgagc gagcgcgcag agagggagtg gccaa 4955 |
| SEQ ID NO: 13 | Amino acid sequence of AAV9 capsid VP1 protein |
| | MAADGYLPDW LEDNLSEGIR EWWALKPGAP QPKANQQHQD NARGLVLPGY KYLGPGNGLD 60 |
| | KGEPVNAADA AALEHDKAYD QQLKAGDNPY LKYNHADAEF QERLKEDTSF GGNLGRAVFQ 120 |
| | AKKRLLEPLG LVEEAAKTAP GKKRPVEQSP QEPDSSAGIG KSGAQPAKKR LNFGQTGDTE 180 |
| | SVPDPQPIGE PPAAPSGVGS LTMASGGGAP VADNNEGADG VGSSSGNWHC DSQWLGDRVI 240 |
| | TTSTRTWALP TYNNHLYKQI SNSTSGGSSN DNAYFGYSTP WGYFDFNRFH CHFSPRDWQR 300 |
| | LINNNWGFRP KRLNFKLFNI QVKEVTDNNG VKTIANNLTS TVQVFTDSDY QLPYVLGSAH 360 |
| | EGCLPPFPAD VFMIPQYGYL TLNDGSQAVG RSSFYCLEYF PSQMLRTGNN FQFSYEFENV 420 |
| | PFHSSYAHSQ SLDRLMNPLI DQYLYYLSKT INGSGQNQQT LKFSVAGPSN MAVQGRNYIP 480 |

TABLE 13-continued

TABLE OF SEQUENCES

| SEQ ID NO | DESCRIPTION AND SEQUENCE | |
|---|---|---|
| | GPSYRQQRVS TTVTQNNNSE FAWPGASSWA LNGRNSLMNP GPAMASHKEG EDRFFPLSGS | 540 |
| | LIFGKQGTGR DNVDADKVMI TNEEEIKTTN PVATESYGQV ATNHQSAQAQ AQTGWVQNQG | 600 |
| | ILPGMVWQDR DVYLQGPIWA KIPHTDGNFH PSPLMGGFGM KHPPPQILIK NTPVPADPPT | 660 |
| | AFNKDKLNSF ITQYSTGQVS VEIEWELQKE NSKRWNPEIQ YTSNYYKSNN VEFAVNTEGV | 720 |
| | YSEPRPIGTR YLTRNL | 736 |
| SEQ ID | Left AAV2 ITR | |
| NO: 14 | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcct | 145 |
| SEQ ID | Right AAV2 ITR | |
| NO: 15 | aggaacccct agtgatggag ttggccactc cctctctgcg cgctcgctcg ctcactgagg | 60 |
| | ccgcccgggc aaagcccggg cgtcgggcga cctttggtcg cccggcctca gtgagcgagc | 120 |
| | gagcgcgcag agagggagtg gccaa | 145 |
| SEQ ID | DNA sequence of synthetic muscle-specific enhancer and promoter | |
| NO: 16 | ccactacggg tctaggctgc ccatgtaagg aggcaaggcc tggggacacc cgagatgcct | 60 |
| | ggttataatt aacccagaca tgtggctgcc cccccccccc ccaacacctg ctgcctctaa | 120 |
| | aaataaccct gtccctggtg gatcccctgc atgcgaagat cttcgaacaa ggctgtgggg | 180 |
| | gactgagggc aggctgtaac aggcttgggg gccagggctt atacgtgcct gggactccca | 240 |
| | aagtattact gttccatgtt cccggcgaag ggccagctgt cccccgccag ctagactcag | 300 |
| | cacttagttt aggaaccagt gagcaagtca gcccttgggg cagcccatac aaggccatgg | 360 |
| | ggctgggcaa gctgcacgcc tgggtccggg gtgggcacgg tgcccgggca acgagctgaa | 420 |
| | agctcatctg ctctcagggg cccctccctg gggacagccc ctcctggcta gtcacaccct | 480 |
| | gtaggctcct ctatataacc caggggcaca ggggctgccc tcattctacc accacctcca | 540 |
| | cagcacagac agacactcag gagccagcca gcgtcga | 577 |
| SEQ ID | DNA sequence of transcription terminator | |
| NO: 17 | aggcctaata aagagctcag atgcatcgat cagagtgtgt tggttttttg tgtg | 54 |
| SEQ ID | DNA sequence of AAV9.hCK.Hopti-Dys3978.spA vector genome | |
| NO: 18 | ttggccactc cctctctgcg cgctcgctcg ctcactgagg ccgggcgacc aaaggtcgcc | 60 |
| | cgacgcccgg gctttgcccg ggcggcctca gtgagcgagc gagcgcgcag agagggagtg | 120 |
| | gccaactcca tcactagggg ttcctcagat ctgaattcgg taccccacta cgggtctagg | 180 |
| | ctgcccatgt aaggaggcaa ggcctgggga cacccgagat gcctggttat aattaaccca | 240 |
| | gacatgtggc tgcccccccc cccccaaca cctgctgcct ctaaaaataa ccctgtccct | 300 |
| | ggtggatccc ctgcatgcga agatcttcga acaaggctgt gggggactga gggcaggctg | 360 |
| | taacaggctt gggggccagg gcttatacgt gcctgggact cccaaagtat tactgttcca | 420 |
| | tgttcccggc gaagggccag ctgtcccccg ccagctagac tcagcactta gtttaggaac | 480 |
| | cagtgagcaa gtcagccctt ggggcagccc atacaaggcc atggggctgg gcaagctgca | 540 |
| | cgcctgggtc cggggtgggc acggtgcccg ggcaacgagc tgaaagctca tctgctctca | 600 |
| | ggggcccctc cctggggaca gcccctcctg gctagtcaca ccctgtaggc tcctctatat | 660 |
| | aacccagggg cacaggggct gccctcattc taccaccacc tccacagcac agacagacac | 720 |
| | tcaggagcca gccagcgtcg agcggccgat ccgccaccat gctttggtgg gaggaagtgg | 780 |
| | aggactgcta cgagagagag gacgtgcaga agaaaacctt caccaagtgg gtgaacgccc | 840 |
| | agttcagcaa gttcggcaag cagcacatcg agaacctgtt cagcgacctg caggatggca | 900 |
| | ggagactgct ggacctgctg gagggcctga ccggccagaa gctgcccaag gagaagggca | 960 |
| | gcaccagagt gcacgccctg aacaacgtga acaaggccct gagagtgctg cagaacaaca | 1020 |
| | acgtggacct ggtgaacatc ggcagcaccg acatcgtgga cggcaaccac aagctgaccc | 1080 |
| | tgggcctgat ctggaacatc atcctgcact ggcaggtgaa gaacgtgatg aagaacatca | 1140 |
| | tggccggcct gcagcagacc aacagcgaga agatcctgct gagctgggtg aggcagagca | 1200 |
| | ccagaaacta cccccaggtg aacgtgatca acttcaccac ctcctggagc gacggcctgg | 1260 |
| | ccctgaacgc cctgatccac agccacagac ccgacctgtt cgactggaac agcgtggtgt | 1320 |
| | gtcagcagag cgccacccag agactggagc acgccttcaa catcgccaga taccagctgg | 1380 |
| | gcatcgagaa gctgctggac cccgaggacg tggacaccac ctaccccgac aagaaaagca | 1440 |
| | tcctcatgta cattaccagc ctgttccagg tgctgcccca gcaggtgtcc atcgaggcca | 1500 |
| | tccaggaagt ggaaatgctg cccaggcccc ccaaagtgac caaggaggag cacttccagc | 1560 |
| | tgcaccacca gatgcactac agccagcaga tcacagtgag cctggcccag ggctatgaga | 1620 |
| | gaaccagcag ccccaagccc agattcaaga gctacgccta cacccaggcc gcctacgtga | 1680 |
| | ccacctccga ccccaccaga agccccttcc ccagccagca cctggaggcc cccgaggaca | 1740 |
| | agagcttcgg cagcagcctg atggagagcg aagtgaacct ggacagatac cagaccgccc | 1800 |
| | tggaggaagt gctgtcctgg ctgctgagcg ccgaggacac cctgcaggcc cagggcgaga | 1860 |
| | tcagcaacga cgtggaagtg gtgaaggacc agttccacac ccacgagggc tacatgatgg | 1920 |
| | atctgaccgc ccaccagggc agagtgggca atatcctgca gctgggcagc aagctgatcg | 1980 |
| | gcaccggcaa gctgagcgag gacgaggaga ccgaagtgca ggagcagatg aacctgctga | 2040 |
| | acagcagatg ggagtgcctg agagtggcca gcatggagaa gcagagcaac ctgcacagag | 2100 |
| | tgctgatgga cctgcagaac cagaagctga aggagctgaa cgactggctg accaagaccg | 2160 |
| | aggagcggac cagaaagatg gaggaggagc ccctgggccc cgacctggag gacctgaaga | 2220 |
| | gacaggtgca gcagcacaaa gtgctgcagg aggacctgga gcaggagcag gtgcgcgtga | 2280 |
| | acagcctgac ccacatggtg gtggtcgtgg acgagagcag cggcgaccac gccacagccg | 2340 |
| | ccctggaaga gcagctgaaa gtgctgggcg acagatgggc caatatttgt aggtggaccg | 2400 |
| | aggacagatg ggtgctgctg caggaccagc ccgacctggc ccctggcctg accaccatcg | 2460 |
| | gcgccagccc cacccagacc gtgaccctgg tgacccagcc cgtggtgaca aaggagaccg | 2520 |
| | ccatcagcaa gctggagatg cccagctccc tgatgctgga agtgcccacc caccgcctgc | 2580 |

TABLE 13-continued

TABLE OF SEQUENCES

| SEQ ID NO | DESCRIPTION AND SEQUENCE | |
|---|---|---|
| | tccagcagtt ccccctggac ctggagaagt tcctggcctg gctgaccgag gccgaaacca | 2640 |
| | ccgccaatgt gctccaggac gccactagaa aggagaggct gctggaggac agcaagggcg | 2700 |
| | tgaaagagct gatgaagcag tggcaggatc tgcagggcga aatcgaggcc cacaccgacg | 2760 |
| | tgtaccacaa cctggacgag aacagccaga agattctgag gagcctggag ggcagcgacg | 2820 |
| | acgccgtcct gctccagagg aggctggaca acatgaactt caagtggagc gagctgcgga | 2880 |
| | agaagagcct gaacatccgg agccacctgg aagccagcag cgaccagtgg aagagactgc | 2940 |
| | acctgagcct gcaggagctg ctggtgtggc tgcagctgaa ggacgacgag ctgagcagac | 3000 |
| | aggcccccat cggcggcgac ttccccgccg tgcagaagca gaacgacgtg caccgggcct | 3060 |
| | tcaagaggga gctgaaaacc aaggaacccg tgatcatgag caccctggag acagtgcgga | 3120 |
| | tcttcctgac cgagcagccc ctggagggac tggagaagct gtaccaggag cccagagagc | 3180 |
| | tgccccccga ggagagagcc cagaacgtga ccaggctgct gagaaagcag gccgaggaag | 3240 |
| | tgaataccga gtgggagaag ctgaatctgc acagcgccga ctggcagaga aagatcgacg | 3300 |
| | agaccctgga gagactccag gaactgcagg aagccaccga cgagctggac ctgaagctga | 3360 |
| | gacaggccga agtgatcaag ggcagctggc agcctgtggg cgatctgctg atcgactccc | 3420 |
| | tgcaggatca cctggagaaa gtgaaggccc tgcggggcga gatcgccccc ctgaaggaga | 3480 |
| | atgtgagcca cgtgaacgac ctggccagac agctgaccac cctgggcatc cagctgagcc | 3540 |
| | cctacaacct gagcacactg gaggatctga acacccggtg gaaactgctg caggtggccg | 3600 |
| | tggaggatag agtgaggcag ctgcacgaag cccacagaga cttcggccct gcctcccagc | 3660 |
| | acttcctgag caccagcgtg cagggcccct gggagagagc catctccccc aacaaagtgc | 3720 |
| | cctactacat caaccacgag acccagacca cctgctggga ccaccctaag atgaccgagc | 3780 |
| | tgtatcagag cctggccgac ctgaacaatg tgcggttcag cgcctacaga accgccatga | 3840 |
| | agctgcggag actgcagaag gccctgtgcc tggatctgct gagcctgagc gccgcctgcg | 3900 |
| | acgccctgga ccagcacaac ctgaagcaga atgaccagcc catggacatc ctgcagatca | 3960 |
| | tcaactgcct gaccacaatc tacgaccggc tggaacagga gcacaacaac ctggtgaatg | 4020 |
| | tgcccctgtg cgtggacatg tgcctgaatt ggctgctgaa cgtgtacgac accggcagga | 4080 |
| | ccggcagaat ccgcgtgctg agcttcaaga ccggcatcat cagcctgtgc aaggcccacc | 4140 |
| | tggaggataa gtaccgctac ctgttcaagc aggtggccag cagcaccggc ttctgcgatc | 4200 |
| | agaggagact gggcctgctg ctgcacgata gcatccagat ccctaggcag ctgggcgaag | 4260 |
| | tggccagctt tggcggcagc aacatcgagc cctctgtgag gagctgcttc cagttcgcca | 4320 |
| | acaacaagcc cgagatcgag gccgccctgt tcctggactg gatgaggctg gagcctcaga | 4380 |
| | gcatggtgtg gctgcctgtg ctgcacagag tggccgccgc cgagaccgcc aagcaccagg | 4440 |
| | ccaagtgcaa tatctgcaag gagtgcccca tcatcggctt ccggtacagg agcctgaagc | 4500 |
| | acttcaacta cgacatctgc cagagctgct ttttcagcgg cagagtggcc aagggccaca | 4560 |
| | aaatgcacta ccccatggtg gagtactgca cccccaccac ctccggcgag gatgtgagag | 4620 |
| | acttcgccaa agtgctgaag aataagttcc ggaccaagcg gtactttgcc aagcacccca | 4680 |
| | ggatgggcta cctgcccgtg cagaccgtgc tggaaggcga caacatggag acctgatgag | 4740 |
| | gagctcgaga ggcctaataa agagctcaga tgcatcgatc agagtgtgtt ggttttttgt | 4800 |
| | gtgagatctg aggaacccct agtgatggag ttggccactc cctctctgcg cgctcgctcg | 4860 |
| | ctcactgagg ccgcccgggc aaagcccggg cgtcgggcga cctttggtcg cccggcctca | 4920 |
| | gtgagcgagc gagcgcgcag agagggagtg gccaa | 4955 |
| SEQ ID NO: 19 | DNA sequence of PCR forward primer for mini-dystrophin gene<br>ccaacaaagt gccctactac atc | 23 |
| SEQ ID NO: 20 | DNA sequence of PCR reverse primer for mini-dystrophin gene<br>ggttgtgctg gtccagggcg t | 21 |
| SEQ ID NO: 21 | DNA sequence of probe for mini-dystrophin gene<br>ccgagctgta tcagagcctg gcc | 23 |
| SEQ ID NO: 22 | DNA sequence of PCR forward primer for rat HPRT1 gene<br>gcgaaagtgg aaaagccaag t | 21 |
| SEQ ID NO: 23 | DNA sequence of PCR reverse primer for rat HPRT1 gene<br>gccacatcaa caggactctt gtag | 24 |
| SEQ ID NO: 24 | DNA sequence of probe for rat HPRT1 gene<br>caaagcctaa aagacagcgg caagttgaat | 30 |
| SEQ ID NO: 25 | Amino acid sequence of human muscle dystrophin (Dp427m isoform)<br>MLWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDILLK WQRLTEEQCL FSAWLSEKED AVNKIHTTGF KDQNEMLSSL | 600 |
| | QKLAVLKADL EKKKQSMGKL YSLKQDLLST LKNKSVTQKT EAWLDNFARC WDNLVQKLEK | 660 |
| | STAQISQAVT TTQPSLTQTT VMETVITVIT REQILVKHAQ EELPPPPPQK KRQITVDSEI | 720 |
| | RKRLDVDITE LHSWITRSEA VLQSPEFAIF RKEGNFSDLK EKVNAIEREK AEKFRKLQDA | 780 |
| | SRSAQALVEQ MVNEGVNADS IKQASEQLNS RWIEFCQLLS ERLNWLEYQN NIIAFYNQLQ | 840 |
| | QLEQMTTTAE NWLKIQPTTP SEPTAIKSQL KICKDEVNRL SGLQPQIERL KIQSIALKEK | 900 |

TABLE 13-continued

TABLE OF SEQUENCES

| SEQ ID NO | DESCRIPTION AND SEQUENCE |
|---|---|
| | GQGPMFLDAD FVAFTNHFKQ VFSDVQAREK ELQTIFDTLP PMRYQETMSA IRTWVQQSET 960 |
| | KLSIPQLSVT DYEIMEQRLG ELQALQSSLQ EQQSGLYYLS TTVKEMSKKA PSEISRKYQS 1020 |
| | EFEEIEGRWK KLSSQLVEHC QKLEEQMNKL RKIQNHIQTL KKWMAEVDVF LKEEWPALGD 1080 |
| | SEILKKQLKQ CRLLVSDIQT IQPSLNSVNE GGQKIKNEAE PEFASRLETE LKELNTQWDH 1140 |
| | MCQQVYARKE ALKGGLEKTV SLQKDLSEMH EWMTQAEEEY LERDFEYKTP DELQKAVEEM 1200 |
| | KRAKEEAQQK EAKVKLLTES VNSVIAQAPP VAQEALKKEL ETLTTNYQWL CTRLNGKCKT 1260 |
| | LEEVWACWHE LLSYLEKANK WLNEVEFKLK TTENIPGGAE EISEVLDSLE NLMRHSEDNP 1320 |
| | NQIRILAQTL TDGGVMDELI NEELETFNSR WRELHEEAVR RQKLLEQSIQ SAQETEKSLH 1380 |
| | LIQESLTFID KQLAAYIADK VDAAQMPQEA QKIQSDLTSH EISLEEMKKH NQGKEAAQRV 1440 |
| | LSQIDVAQKK LQDVSMKFRL FQKPANFEQR LQESKMILDE VKMHLPALET KSVEQEVVQS 1500 |
| | QLNHCVNLYK SLSEVKSEVE MVIKTGRQIV QKKQTENPKE LDERVTALKL HYNELGAKVT 1560 |
| | ERKQQLEKCL KLSRKMRKEM NVLTEWLAAT DMELTKRSAV EGMPSNLDSE VAWGKATQKE 1620 |
| | IEKQKVHLKS ITEVGEALKT VLGKKETLVE DKLSLLNSNW IAVTSRAEEW LNLLLEYQKH 1680 |
| | METFDQNVDH ITKWIIQADT LLDESEKKKP QQKEDVLKRL KAELNDIRPK VDSTRDQAAN 1740 |
| | LMANRGDHCR KLVEPQISEL NHRFAAISHR IKTGKASIPL KELEQFNSDI QKLLEPLEAE 1800 |
| | IQQGVNLKEE DFNKDMNEDN EGTVKELLQR GDNLQQRITD ERKREEIKIK QQLLQTKHNA 1860 |
| | LKDLRSQRRK KALEISHQWY QYKRQADDLL KCLDDIEKKL ASLPEPRDER KIKEIDRELQ 1920 |
| | KKKEELNAVR RQAEGLSEDG AAMAVEPTQI QLSKRWREIE SKFAQFRRLN FAQIHTVREE 1980 |
| | TMMVMTEDMP LEISYVPSTY LTEITHVSQA LLEVEQLLNA PDLCAKDFED LFKQEESLKN 2040 |
| | IKDSLQQSSG RIDIIHSKKT AALQSATPVE RVKLQEALSQ LDFQWEKVNK MYKDRQGRFD 2100 |
| | RSVEKWRRFH YDIKIFNQWL TEAEQFLRKT QIPENWEHAK YKWYLKELQD GIGQRQTVVR 2160 |
| | TLNATGEEII QQSSKTDASI LQEKLGSLNL RWQEVCKQLS DRKKRLEEQK NILSEFQRDL 2220 |
| | NEFVLWLEEA DNIASIPLEP GKEQQLKEKL EQVKLLVEEL PLRQGILKQL NETGGPVLVS 2280 |
| | APISPEEQDK LENKLKQTNL QWIKVSRALP EKQGEIEAQI KDLGQLEKKL EDLEEQLNHL 2340 |
| | LLWLSPIRNQ LEIYNQPNQE GPFDVQETEI AVQAKQPDVE EILSKGQHLY KEKPATQPVK 2400 |
| | RKLEDLSSEW KAVNRLLQEL RAKQPDLAPG LTTIGASPTQ TVTLVTQPVV TKETAISKLE 2460 |
| | MPSSLMLEVP ALADFNRAWT ELTDWLSLLD QVIKSQRVMV GDLEDINEMI IKQKATMQDL 2520 |
| | EQRRPQLEEL ITAAQNLKNK TSNQEARTII TDRIERIQNQ WDEVQEHLQN RRQQLNEMLK 2580 |
| | DSTQWLEAKE EAEQVLGQAR AKLESWKEGP YTVDAIQKKI TETKQLAKDL RQWQTNVDVA 2640 |
| | NDLALKLLRD YSADDTRKVH MITENINASW RSIHKRVSER EAALEETHRL LQQFPLDLEK 2700 |
| | FLAWLTEAET TANVLQDATR KERLLEDSKG VKELMKQWQD LQGEIEAHTD VYHNLDENSQ 2760 |
| | KILRSLEGSD DAVLLQRRLD NMNFKWSELR KKSLNIRSHL EASSDQWKRL HLSLQELLVW 2820 |
| | LQLKDDELSR QAPIGGDFPA VQKQNDVHRA FKRELKTKEP VIMSTLETVR IFLTEQPLEG 2880 |
| | LEKLYQEPRE LPPEERAQNV TRLLRKQAEE VNTEWEKLNL HSADWQRKID ETLERLQELQ 2940 |
| | EATDELDLKL RQAEVIKGSW QPVGDLLIDS LQDHLEKVKA LRGEIAPLKE NVSHVNDLAR 3000 |
| | QLTTLGIQLS PYNLSTLEDL NTRWKLLQVA VEDRVRQLHE AHRDFGPASQ HFLSTSVQGP 3060 |
| | WERAISPNKV PYYINHETQT TCWDHPKMTE LYQSLADLNN VRFSAYRTAM KLRRLQKALC 3120 |
| | LDLLSLSAAC DALDQHNLKQ NDQPMDILQI INCLTTIYDR LEQEHNNLVN VPLCVDMCLN 3180 |
| | WLLNVYDTGR TGRIRVLSFK TGIISLCKAH LEDKYRYLFK QVASSTGFCD QRRLGLLLHD 3240 |
| | SIQIPRQLGE VASFGGSNIE PSVRSCFQFA NNKPEIEAAL FLDWMRLEPQ SMVWLPVLHR 3300 |
| | VAAAETAKHQ AKCNICKECP IIGFRYRSLK HFNYDICQSC FFSGRVAKGH KMHYPMVEYC 3360 |
| | TPTTSGEDVR DFAKVLKNKF RTKRYFAKHP RMGYLPVQTV LEGDNMETPV TLINFWPVDS 3420 |
| | APASSPQLSH DDTHSRIEHY ASRLAEMENS NGSYLNDSIS PNESIDDEHL LIQHYCQSLN 3480 |
| | QDSPLSQPRS PAQILISLES EERGELERIL ADLEEENRNL QAEYDRLKQQ HEHKGLSPLP 3540 |
| | SPPEMMPTSP QSPRDAELIA EAKLLRQHKG RLEARMQILE DHNKQLESQL HRLRQLLEQP 3600 |
| | QAEAKVNGTT VSSPSTSLQR SDSSQPMLLR VVGSQTSDSM GEEDLLSPPQ DTSTGLEEVM 3660 |
| | EQLNNSFPSS RGRNTPGKPM REDTM 3685 |
| SEQ ID NO: 26 | DNA sequence of non-codon-optimized gene encoding human mini-dystrophin Dys3987 |
| | atgctttggt gggaagaagt agaggactgt tatgaaagag aagatgttca aaagaaaaca 60 |
| | ttcacaaaat gggtaaatgc acaattttct aagtttggga agcagcatat tgagaacctc 120 |
| | ttcagtgacc tacaggatgg gaggcgcctc ctagacctcc tcgaaggcct gacagggcaa 180 |
| | aaactgccaa aagaaaaagg atccacaaga gttcatgccc tgaacaatgt caacaaggca 240 |
| | ctgcgggttt tgcagaacaa taatgttgat ttagtgaata ttggaagtac tgacatcgta 300 |
| | gatggaaatc ataaactgac tcttggtttg atttggaata taatcctcca ctggcaggtc 360 |
| | aaaaatgtaa tgaaaaatat catggctgga ttgcaacaaa ccaacagtga aaagattctc 420 |
| | ctgagctggg tccgacaatc aactcgtaat tatccacagg ttaatgtaat caacttcacc 480 |
| | accagctggt ctgatggcct ggctttgaat gctctcatcc atagtcatag gccagaccta 540 |
| | tttgactgga atagtgtggt ttgccagcag tcagccacac aacgactgga acatgcattc 600 |
| | aacatcgcca gatatcaatt aggcatagag aaactactcg atcctgaaga tgttgatacc 660 |
| | acctatccag ataagaagtc catcttaatg tacatcacat cactcttcca agttttgcct 720 |
| | caacaagtga gcattgaagc catccaggaa gtggaaatgt tgccaaggcc acctaaagtg 780 |
| | actaaagaag aacattttca gttacatcat caaatgcact attctcaaca gatcacggtc 840 |
| | agtctagcac agggatatga gagaacttct tcccctaagc ctcgattcaa gagctatgcc 900 |
| | tacacacagg ctgcttatgt caccacctct gaccctacac ggagcccatt tccttcacag 960 |
| | catttggaag ctcctgaaga caagtcattt ggcagttcat tgatggagag tgaagtaaac 1020 |
| | ctggaccgtt atcaaacagc tttagaagaa gtattatcgt ggcttctttc tgctgaggac 1080 |
| | acattgcaag cacaaggaga gatttctaat gatgtggaag tggtgaaaga ccagtttcat 1140 |
| | actcatgagg ggtacatgat ggatttgaca gcccatcagg gccgggttgg taatattcta 1200 |
| | caattgggaa gtaagctgat tggaacagga aaattatcag aagatgaaga aactgaagta 1260 |
| | caagagcaga tgaatctcct aaattcaaga tgggaatgcc tcagggtagc tagcatggaa 1320 |
| | aaacaaagca atttacatag agttttaatg gatctccaga atcagaaact gaaagagttg 1380 |
| | aatgactggc taacaaaaac agaagaaaga acaaggaaaa tggaggaaga gcctcttgga 1440 |
| | cctgatcttg aagacctaaa acgccaagta caacaacata aggtgcttca agaagatcta 1500 |
| | gaacaagaac aagtcagggt caattctctc actcacatgg tggtggtagt tgatgaatct 1560 |

TABLE 13-continued

TABLE OF SEQUENCES

| SEQ ID NO | DESCRIPTION AND SEQUENCE | |
|---|---|---|
| | agtggagatc acgcaactgc tgctttggaa gaacaactta aggtattggg agatcgatgg | 1620 |
| | gcaaacatct gtagatggac agaagaccgc tgggttcttt tacaagacca gcctgaccta | 1680 |
| | gctcctggac tgaccactat tggagcctct cctactcaga ctgttactct ggtgacacaa | 1740 |
| | cctgtggtta ctaaggaaac tgccatctcc aaactagaaa tgccatcttc cttgatgttg | 1800 |
| | gaggtaccta ctcatagatt actgcaacag ttccccctgg acctggaaaa gtttcttgcc | 1860 |
| | tggcttacag aagctgaaac aactgccaat gtcctacagg atgctacccg taaggaaagg | 1920 |
| | ctcctagaag actccaaggg agtaaaagag ctgatgaaac aatggcaaga cctccaaggt | 1980 |
| | gaaattgaag ctcacacaga tgtttatcac aacctggatg aaaacagcca aaaaatcctg | 2040 |
| | agatccctgg aaggttccga tgatgcagtc ctgttacaaa gacgtttgga taacatgaac | 2100 |
| | ttcaagtgga gtgaacttcg gaaaaagtct ctcaacatta ggtcccattt ggaagccagt | 2160 |
| | tctgaccagt ggaagcgtct gcacctttct ctgcaggaac ttctggtgtg gctacagctg | 2220 |
| | aaagatgatg aattaagccg gcaggcacct attggaggcg actttccagc agttcagaag | 2280 |
| | cagaacgatg tacatagggc cttcaagagg gaattgaaaa ctaaagaacc tgtaatcatg | 2340 |
| | agtactcttg agactgtacg aatatttctg acagagcagc ctttggaagg actagagaaa | 2400 |
| | ctctaccagg agcccagaga gctgcctcct gaggagagag cccagaatgt cactcggctt | 2460 |
| | ctacgaaagc aggctgagga ggtcaatact gagtgggaaa aattgaacct gcactccgct | 2520 |
| | gactggcaga gaaaaataga tgagaccctt gaaagactcc aggaacttca agaggccacg | 2580 |
| | gatgagctgg acctcaagct gcgccaagct gaggtgatca agggatcctg gcagcccgtg | 2640 |
| | ggcgatctcc tcattgactc tctccaagat cacctcgaga aagtcaaggc acttcgagga | 2700 |
| | gaaattgcgc ctctgaaaga gaacgtgagc cacgtcaatg accttgctcg ccagcttacc | 2760 |
| | actttgggca ttcagctctc accgtataac ctcagcactc tggaagacct gaacaccaga | 2820 |
| | tggaagcttc tgcaggtggc cgtcgaggac cgagtcaggc agctgcatga agcccacagg | 2880 |
| | gactttggtc cagcatctca gcactttctt tccacgtctg tccagggtcc ctgggagaga | 2940 |
| | gccatctcgc caaacaaagt gccctactat atcaaccacg agactcaaac aacttgctgg | 3000 |
| | gaccatccca aaatgacaga gctctaccag tctttagctg acctgaataa tgtcagattc | 3060 |
| | tcagcttata ggactgccat gaaactccga agactgcaga aggccctttg cttggatctc | 3120 |
| | ttgagcctgt cagctgcatg tgatgccttg gaccagcaca acctcaagca aaatgaccag | 3180 |
| | cccatggata tcctgcagat tattaattgt ttgaccacta tttatgaccg cctggagcaa | 3240 |
| | gagcacaaca atttggtcaa cgtccctctc tgcgtggata tgtgtctgaa ctggctgctg | 3300 |
| | aatgtttatg atacgggacg aacagggagg atccgtgtcc tgtcttttaa aactggcatc | 3360 |
| | atttccctgt gtaaagcaca tttggaagac aagtacagat acctttttcaa gcaagtggca | 3420 |
| | agttcaacag gattttgtga ccagcgcagg ctgggcctcc ttctgcatga ttctatccaa | 3480 |
| | attccaagac agttgggtga agttgcatcc tttgggggca gtaacattga gccaagtgtc | 3540 |
| | cggagctgct tccaatttgc taataataag ccagagatcg aagcggccct cttcctagac | 3600 |
| | tggatgagac tggaacccca gtccatggtg tggctgcccg tcctgcacag agtggctgct | 3660 |
| | gcagaaactg ccaagcatca ggccaaatgt aacatctgca aagagtgtcc aatcattgga | 3720 |
| | ttcaggtaca ggagtctaaa gcactttaat tatgacatct gccaaagctg cttttttttct | 3780 |
| | ggtcgagttg caaaaggcca taaaatgcac tatcccatgg tggaatattg cactccgact | 3840 |
| | acatcaggag aagatgttcg agactttgcc aaggtactaa aaaacaaatt tcgaaccaaa | 3900 |
| | aggtattttg cgaagcatcc ccgaatgggc tacctgccag tgcagactgt cttagagggg | 3960 |
| | gacaacatgg aaacttag | 3978 |
| SEQ ID NO: 27 | Amino acid sequence of human mini-dystrophin protein Δ3990 | |
| | MVWWEEVEDC YEREDVQKKT FTKWVNAQFS KFGKQHIENL FSDLQDGRRL LDLLEGLTGQ | 60 |
| | KLPKEKGSTR VHALNNVNKA LRVLQNNNVD LVNIGSTDIV DGNHKLTLGL IWNIILHWQV | 120 |
| | KNVMKNIMAG LQQTNSEKIL LSWVRQSTRN YPQVNVINFT TSWSDGLALN ALIHSHRPDL | 180 |
| | FDWNSVVCQQ SATQRLEHAF NIARYQLGIE KLLDPEDVDT TYPDKKSILM YITSLFQVLP | 240 |
| | QQVSIEAIQE VEMLPRPPKV TKEEHFQLHH QMHYSQQITV SLAQGYERTS SPKPRFKSYA | 300 |
| | YTQAAYVTTS DPTRSPFPSQ HLEAPEDKSF GSSLMESEVN LDRYQTALEE VLSWLLSAED | 360 |
| | TLQAQGEISN DVEVVKDQFH THEGYMMDLT AHQGRVGNIL QLGSKLIGTG KLSEDEETEV | 420 |
| | QEQMNLLNSR WECLRVASME KQSNLHRVLM DLQNQKLKEL NDWLTKTEER TRKMEEEPLG | 480 |
| | PDLEDLKRQV QQHKVLQEDL EQEQVRVNSL THMVVVVDES SGDHATAALE EQLKVLGDRW | 540 |
| | ANICRWTEDR WVLLQDQPDL APGLTTIGAS PTQTVTLVTQ PVVTKETAIS KLEMPSSLML | 600 |
| | EVPTHRLLQQ FPLDLEKFLA WLTEAETTAN VLQDATRKER LLEDSKGVKE LMKQWQDLQG | 660 |
| | EIEAHTDVYH NLDENSQKIL RSLEGSDDAV LLQRRLDNMN FKWSELRKKS LNIRSHLEAS | 720 |
| | SDQWKRLHLS LQELLVWLQL KDDELSRQAP IGGDFPAVQK QNDVHRAFKR ELKTKEPVIM | 780 |
| | STLETVRIFL TEQPLEGLEK LYQEPRELPP EERAQNVTRL LRKQAEEVNT EWEKLNLHSA | 840 |
| | DWQRKIDETL ERLQELQEAT DELDLKLRQA EVIKGSWQPV GDLLIDSLQD HLEKVKALRG | 900 |
| | EIAPLKENVS HVNDLARQLT TLGIQLSPYN LSTLEDLNTR WKLLQVAVED RVRQLHEAHR | 960 |
| | DFGPASQHFL STSVQGPWER AISPNKVPYY INHETQTTCW DHPKMTELYQ SLADLNNVRF | 1020 |
| | SAYRTAMKLR RLQKALCLDL LSLSAACDAL DQHNLKQNDQ PMDILQIINC LTTIYDRLEQ | 1080 |
| | EHNNLVNVPL CVDMCLNWLL NVYDTGRTGR IRVLSFKTGI ISLCKAHLED KYRYLFKQVA | 1140 |
| | SSTGFCDQRR LGLLLHDSIQ IPRQLGEVAS FGGSNIEPSV RSCFQFANNK PEIEAALFLD | 1200 |
| | WMRLEPQSMV WLPVLHRVAA AETAKHQAKC NICKECPIIG FRYRSLKHFN YDICQSCFFS | 1260 |
| | GRVAKGHKMH YPMVEYCTPT TSGEDVRDFA KVLKNKFRTK RYFAKHPRMG YLPVQTVLEG | 1320 |
| | DNMETPDTM | 1329 |
| SEQ ID NO: 28 | DNA sequence of human mini-dystrophin gene Δ3990 | |
| | atggtttggt gggaagaagt agaggactgt tatgaaagag aagatgttca aaagaaaaca | 60 |
| | ttcacaaaat gggtaaatgc acaattttct aagtttggga agcagcatat tgagaacctc | 120 |
| | ttcagtgacc tacaggatgg gaggcgcctc ctagacctcc tcgaaggcct gacagggcaa | 180 |
| | aaactgccaa aagaaaaagg atccacaaga gttcatgccc tgaacaatgt caacaaggca | 240 |
| | ctgcgggttt tgcagaacaa taatgttgat ttagtgaata ttggaagtac tgacatcgta | 300 |
| | gatggaaatc ataaactgac tcttggtttg atttggaata taatcctcca ctggcaggtc | 360 |
| | aaaaatgtaa tgaaaaatat catggctgga ttgcaacaaa ccaacagtga aaagattctc | 420 |

TABLE 13-continued

| TABLE OF SEQUENCES | |
|---|---|
| SEQ ID NO | DESCRIPTION AND SEQUENCE |
| | ctgagctggg tccgacaatc aactcgtaat tatccacagg ttaatgtaat caacttcacc 480 |
| | accagctggt ctgatggcct ggctttgaat gctctcatcc atagtcatag gccagaccta 540 |
| | tttgactgga atagtgtggt ttgccagcag tcagccacac aacgactgga acatgcattc 600 |
| | aacatcgcca gatatcaatt aggcatagag aaactactcg atcctgaaga tgttgatacc 660 |
| | acctatccag ataagaagtc catcttaatg tacatcacat cactcttcca agttttgcct 720 |
| | caacaagtga gcattgaagc catccaggaa gtggaaatgt tgccaaggcc acctaaagtg 780 |
| | actaaagaag aacattttca gttacatcat caaatgcact attctcaaca gatcacggtc 840 |
| | agtctagcac agggatatga gagaacttct tcccctaagc ctcgattcaa gagctatgcc 900 |
| | tacacacagg ctgcttatgt caccacctct gaccctacac ggagcccatt tccttcacag 960 |
| | catttggaag ctcctgaaga caagtcattt ggcagttcat tgatggagag tgaagtaaac 1020 |
| | ctggaccgtt atcaaacagc tttagaagaa gtattatcgt ggcttctttc tgctgaggac 1080 |
| | acattgcaag cacaaggaga gatttctaat gatgtggaag tggtgaaaga ccagtttcat 1140 |
| | actcatgagg ggtacatgat ggatttgaca gcccatcagg gccgggttgg taatattcta 1200 |
| | caattgggaa gtaagctgat tggaacagga aaattatcag aagatgaaga aactgaagta 1260 |
| | caagagcaga tgaatctcct aaattcaaga tgggaatgcc tcagggtagc tagcatggaa 1320 |
| | aaacaaagca atttacatag agttttaatg gatctccaga atcagaaact gaaagagttg 1380 |
| | aatgactggc taacaaaaac agaagaaaga acaaggaaaa tggaggaaga gcctcttgga 1440 |
| | cctgatcttg aagacctaaa acgccaagta caacaacata aggtgcttca agaagatcta 1500 |
| | gaacaagaac aagtcagggt caattctctc actcacatgg tggtggtagt tgatgaatct 1560 |
| | agtggagatc acgcaactgc tgctttggaa gaacaactta aggtattggg agatcgatgg 1620 |
| | gcaaacatct gtagatggac agaagaccgc tgggttcttt tacaagacca gcctgaccta 1680 |
| | gctcctggac tgaccactat tggagcctct cctactcaga ctgttactct ggtgacacaa 1740 |
| | cctgtggtta ctaaggaaac tgccatctcc aaactagaaa tgccatcttc cttgatgttg 1800 |
| | gaggtaccta ctcatagatt actgcaacag ttccccctgg acctggaaaa gtttcttgcc 1860 |
| | tggcttacag aagctgaaac aactgccaat gtcctacagg atgctacccg taaggaaagg 1920 |
| | ctcctagaag actccaaggg agtaaaagag ctgatgaaac aatggcaaga cctccaaggt 1980 |
| | gaaattgaag ctcacacaga tgtttatcac aacctggatg aaaacagcca aaaaatcctg 2040 |
| | agatccctgg aaggttccga tgatgcagtc ctgttacaaa gacgtttgga taacatgaac 2100 |
| | ttcaagtgga gtgaacttcg gaaaaagtct ctcaacatta ggtcccattt ggaagccagt 2160 |
| | tctgaccagt ggaagcgtct gcacctttct ctgcaggaac ttctggtgtg gctacagctg 2220 |
| | aaagatgatg aattaagccg gcaggcacct attggaggcg actttccagc agttcagaag 2280 |
| | cagaacgatg tacatagggc cttcaagagg gaattgaaaa ctaaagaacc tgtaatcatg 2340 |
| | agtactcttg agactgtacg aatatttctg acagagcagc ctttggaagg actagagaaa 2400 |
| | ctctaccagg agcccagaga gctgcctcct gaggagagag cccagaatgt cactcggctt 2460 |
| | ctacgaaagc aggctgagga ggtcaatact gagtgggaaa aattgaacct gcactccgct 2520 |
| | gactggcaga gaaaaataga tgagaccctt gaaagactcc aggaacttca agaggccacg 2580 |
| | gatgagctgg acctcaagct gcgccaagct gaggtgatca agggatcctg gcagcccgtg 2640 |
| | ggcgatctcc tcattgactc tctccaagat cacctcgaga aagtcaaggc acttcgagga 2700 |
| | gaaattgcgc ctctgaaaga gaacgtgagc cacgtcaatg accttgctcg ccagcttacc 2760 |
| | actttgggca ttcagctctc accgtataac ctcagcactc tggaagacct gaacaccaga 2820 |
| | tggaagcttc tgcaggtggc cgtcgaggac cgagtcaggc agctgcatga agcccacagg 2880 |
| | gactttggtc cagcatctca gcactttctt tccacgtctg tccagggtcc ctgggagaga 2940 |
| | gccatctcgc caaacaaagt gccctactat atcaaccacg agactcaaac aacttgctgg 3000 |
| | gaccatccca aaatgacaga gctctaccag tctttagctg acctgaataa tgtcagattc 3060 |
| | tcagcttata ggactgccat gaaactccga agactgcaga aggccctttg cttggatctc 3120 |
| | ttgagcctgt cagctgcatg tgatgccttg gaccagcaca acctcaagca aaatgaccag 3180 |
| | cccatggata tcctgcagat tattaattgt ttgaccacta tttatgaccg cctggagcaa 3240 |
| | gagcacaaca atttggtcaa cgtccctctc tgcgtggata tgtgtctgaa ctggctgctg 3300 |
| | aatgtttatg atacgggacg aacagggagg atccgtgtcc tgtcttttaa aactggcatc 3360 |
| | atttccctgt gtaaagcaca tttggaagac aagtacagat acctttcaa gcaagtggca 3420 |
| | agttcaacag gattttgtga ccagcgcagg ctgggcctcc ttctgcatga ttctatccaa 3480 |
| | attccaagac agttgggtga agttgcatcc tttgggggca gtaacattga gccaagtgtc 3540 |
| | cggagctgct tccaatttgc taataataag ccagagatcg aagcggccct cttcctagac 3600 |
| | tggatgagac tggaacccca gtccatggtg tggctgcccg tcctgcacag agtggctgct 3660 |
| | gcagaaactg ccaagcatca ggccaaatgt aacatctgca aagagtgtcc aatcattgga 3720 |
| | ttcaggtaca ggagtctaaa gcactttaat tatgacatct gccaaagctg ctttttttct 3780 |
| | ggtcgagttg caaaaggcca taaaatgcac tatcccatgg tggaatattg cactccgact 3840 |
| | acatcaggag aagatgttcg agactttgcc aaggtactaa aaaacaaatt tcgaaccaaa 3900 |
| | aggtattttg cgaagcatcc ccgaatgggc tacctgccag tgcagactgt cttagagggg 3960 |
| | gacaacatgg aaactcccga cacaatgtag 3990 |

The foregoing is illustrative of the present invention, and is not to be construed as limiting thereof. The invention is defined by the following claims, with equivalents of the claims to be included therein.

That which is claimed is:

1. A method for treating a human subject in need of treatment for Duchenne muscular dystrophy (DMD) comprising administering to said subject a composition comprising a therapeutically effective amount of recombinant AAV (rAAV) particles comprising an AAV9 capsid and a vector genome, said genome comprising a first AAV2 inverted terminal repeat (ITR), a muscle-specific transcriptional regulatory element operably linked to a nucleotide sequence encoding a human mini-dystrophin protein consisting of the amino acid sequence of SEQ ID NO: 7, a transcription termination sequence, and a second AAV2 ITR, wherein the therapeutically effective amount of rAAV particles is administered in a dose of at least $1\times10^{14}$ vg/kg subject body weight.

2. The method of claim 1, wherein the therapeutically effective amount of rAAV particles is administered in a dose ranging from $1\times10^{14}$ vg/kg to $5\times10^{14}$ vg/kg subject body weight.

3. The method of claim 1, wherein said method is effective to reduce the average total creatine kinase (CK) level in the blood of treated subjects to within fold of the average total CK level in the blood of healthy controls.

4. The method of claim 1, wherein said method is effective to reduce the average fat fraction in the lower extremities of treated subjects by at least 5% compared to the average fat fraction in the lower extremities of untreated DMD controls.

5. The method of claim 1, wherein said method is effective to cause an average of at least 20% of the muscle fibers in skeletal muscle biopsies from treated subjects to produce detectable levels of said mini-dystrophin protein.

6. The method of treatment of claim 1, wherein the therapeutically effective amount of rAAV particles is administered in a dose of at least $2\times10^{14}$ vg/kg subject body weight.

7. The method of treatment of claim 1, wherein the therapeutically effective amount of rAAV particles is administered in a dose of at least $3\times10^{14}$ vg/kg subject body weight.

8. The method of treatment of claim 1, wherein the therapeutically effective amount of rAAV particles is administered in a dose of about $1\times10^{14}$ vg/kg subject body weight.

9. The method of treatment of claim 1, wherein the therapeutically effective amount of rAAV particles is administered in a dose of about $2\times10^{14}$ vg/kg subject body weight.

10. The method of treatment of claim 1, wherein the therapeutically effective amount of rAAV particles is administered in a dose of about $3\times10^{14}$ vg/kg subject body weight.

11. The method of treatment of claim 1, wherein quantitative PCR (qPCR) is used to determine a titer of the rAAV particles.

12. The method of treatment of claim 11, wherein the titer of rAAV particles is determined by qPCR using primers against ITR sequence.

13. The method of treatment of claim 11, wherein the titer of rAAV particles is determined by qPCR using primers against sequence encoding the mini-dystrophin protein.

14. The method of treatment of claim 1, wherein said vector genome is single-stranded DNA.

15. The method of treatment of claim 1, wherein said nucleotide sequence encoding human mini-dystrophin protein is codon-optimized.

16. The method of treatment of claim 15, wherein codon-optimization increases GC content relative to wild-type coding sequence.

17. The method of treatment of claim 16, wherein the GC content of said nucleotide sequence is at least 60%.

18. The method of treatment of claim 15, wherein said nucleotide sequence encoding human mini-dystrophin protein is human codon-optimized.

19. The method of treatment of claim 1, wherein said muscle-specific transcriptional regulatory element confers muscle tissue-specific expression in skeletal and cardiac muscle.

20. The method of treatment of claim 19, wherein said muscle-specific transcriptional regulatory element is a synthetic enhancer and promoter derived from a muscle creatinine kinase gene.

21. The method of treatment of claim 15, wherein said nucleotide sequence encoding human mini-dystrophin protein is at least 90% identical to the nucleotide sequence of SEQ ID NO: 1.

22. The method of treatment of claim 21, wherein said muscle-specific transcriptional regulatory element comprises the nucleotide sequence of SEQ ID NO: 16.

23. The method of treatment of claim 22, wherein said transcription termination sequence comprises the nucleotide sequence of SEQ ID NO: 17.

24. The method of treatment of claim 23, wherein said vector genome comprises the nucleotide sequence of SEQ ID NO: 18, or the reverse complement thereof.

25. The method of treatment of claim 2, wherein quantitative PCR (qPCR) is used to determine a titer of the rAAV particles.

26. The method of treatment of claim 25, wherein the titer of rAAV particles is determined by qPCR using primers against ITR sequence.

27. The method of treatment of claim 25, wherein the titer of rAAV particles is determined by qPCR using primers against sequence encoding the mini-dystrophin protein.

28. The method of treatment of claim 6, wherein quantitative PCR (qPCR) is used to determine a titer of the rAAV particles.

29. The method of treatment of claim 28, wherein the titer of rAAV particles is determined by qPCR using primers against ITR sequence.

30. The method of treatment of claim 28, wherein the titer of rAAV particles is determined by qPCR using primers against sequence encoding the mini-dystrophin protein.

31. The method of treatment of claim 7, wherein quantitative PCR (qPCR) is used to determine a titer of the rAAV particles.

32. The method of treatment of claim 31, wherein the titer of rAAV particles is determined by qPCR using primers against ITR sequence.

33. The method of treatment of claim 31, wherein the titer of rAAV particles is determined by qPCR using primers against sequence encoding the mini-dystrophin protein.

34. The method of treatment of claim 8, wherein quantitative PCR (qPCR) is used to determine a titer of the rAAV particles.

35. The method of treatment of claim 34, wherein the titer of rAAV particles is determined by qPCR using primers against ITR sequence.

36. The method of treatment of claim 34, wherein the titer of rAAV particles is determined by qPCR using primers against sequence encoding the mini-dystrophin protein.

37. The method of treatment of claim 9, wherein quantitative PCR (qPCR) is used to determine a titer of the rAAV particles.

38. The method of treatment of claim 37, wherein the titer of rAAV particles is determined by qPCR using primers against ITR sequence.

39. The method of treatment of claim 37, wherein the titer of rAAV particles is determined by qPCR using primers against sequence encoding the mini-dystrophin protein.

40. The method of treatment of claim 10, wherein quantitative PCR (qPCR) is used to determine a titer of the rAAV particles.

41. The method of treatment of claim 40, wherein the titer of rAAV particles is determined by qPCR using primers against ITR sequence.

42. The method of treatment of claim 40, wherein the titer of rAAV particles is determined by qPCR using primers against sequence encoding the mini-dystrophin protein.

43. The method of treatment of claim 2, wherein the therapeutically effective amount of rAAV particles is administered in a dose ranging from about $2\times10^{14}$ vg/kg to about $3\times10^{14}$ vg/kg subject body weight.

44. The method of treatment of claim 43, wherein quantitative PCR (qPCR) is used to determine a titer of the rAAV particles.

45. The method of treatment of claim 44, wherein the titer of rAAV particles is determined by qPCR using primers against ITR sequence.

46. The method of treatment of claim 44, wherein the titer of rAAV particles is determined by qPCR using primers against sequence encoding the mini-dystrophin protein.

* * * * *

UNITED STATES PATENT AND TRADEMARK OFFICE

CERTIFICATE OF CORRECTION

PATENT NO. : 11,547,765 B2
APPLICATION NO. : 16/787938
DATED : January 10, 2023
INVENTOR(S) : Xiao et al.

It is certified that error appears in the above-identified patent and that said Letters Patent is hereby corrected as shown below:

On the Title Page

(56) References Cited, OTHER PUBLICATIONS, Page 3, Column 2, Line 59, Watchko et al. cite: Please correct “in dystrophin” to read --Minidystrophin--

(56) References Cited, OTHER PUBLICATIONS, Page 4, Column 1, Line 10, Xiao et al. cite: Please correct “Production Production of High-Titer” to read --Production of High-Titer--

(56) References Cited, OTHER PUBLICATIONS, Page 4, Column 2, Line 18, Li, Juan et al. cite: Please correct “AAV9-Minidystraphin” to read --AAV9-Minidystrophin--

In the Specification

Column 12, Line 8: Please insert a paragraph break between “E114.” and “A method”

Column 20, Line 7: Please correct “the“*”” to read --the “*”--

Column 21, Line 18: Please correct “(DO)” to read --(D0)--

Column 21, Line 20: Please correct “(DO)” to read --(D0)--

Column 21, Line 23: Please correct “(DO)” to read --(D0)--

Column 21, Line 25: Please correct “(DO)” to read --(D0)--

Column 21, Line 56: Please correct “(aap<0.01)” to read --(¤¤p<0.01)--

Column 21, Line 57-58: Please correct “(§ § p<0.01, § § §p<0.001).” to read --(§§p<0.01, §§§p<0.001).--

Signed and Sealed this
Twenty-seventh Day of August, 2024

Katherine Kelly Vidal
*Director of the United States Patent and Trademark Office*

CERTIFICATE OF CORRECTION (continued) 
U.S. Pat. No. 11,547,765 B2

Column 22, Line 23: Please correct "(ap<0.05)" to read --(¤p<0.05)--

Column 22, Line 26: Please correct "(§ § p<0.01)" to read --(§§p<0.01)--

Column 22, Line 66: Please correct "*Patent In*" to read --*PatentIn*--

Column 23, Line 51: Please correct "Hut," to read --Hu1,--

Column 23, Line 56: Please correct "Hub," to read --Hu6,--

Column 35, Line 43: Please correct "essentially or," to read --essentially of,--

Column 47, Line 8: Please correct "MRCS," to read --MRC5,--

Column 51, Line 40: Please correct "28," to read --58,--

Column 51, Line 66: Please correct "MM" to read --MRI--

Column 59, Line 22-23: Please correct "administration" to read --administration.)--

Column 64, Line 16: Please correct "MM" to read --MRI--

Column 73, Line 48: Please correct "diaphragm" to read --≈ diaphragm ≈--

Column 74, Line 60: Please correct "heart diaphragm" to read --heart ≈ diaphragm--

Column 77, Line 18: Please correct "DRAQS" to read --DRAQ5--

Column 80, Line 41: Please correct "regardless dose" to read --regardless of dose--

Column 82, Line 60: Please correct "of$1\times10^{14}$" to read --of $1\times10^{14}$--

Column 91, Line 12: Please correct ""aa"" to read --"¤¤"--

Column 91, Line 27: Please correct ""§ §"" to read --"§§"--

Column 91, Line 27: Please correct ""§ § §"" to read --"§§§"--

Column 92, Line 11: Please correct ""a"" to read --"¤"--

Column 92, Line 30: Please correct ""§ §"" to read --"§§"--